United States Patent
Chen et al.

(10) Patent No.: US 11,117,899 B2
(45) Date of Patent: Sep. 14, 2021

(54) [1,2,4]TRIAZOLO[1,5-C]PYRIMIDINE DERIVATIVE AS $A_{2A}$ RECEPTOR INHIBITOR

(71) Applicant: MEDSHINE DISCOVERY INC., Jiangsu (CN)

(72) Inventors: Kevin X Chen, Shanghai (CN); Yanxin Yu, Shanghai (CN); Xinde Chen, Shanghai (CN); Li Zhang, Shanghai (CN); Zhaoguo Chen, Shanghai (CN); Cheng Xie, Shanghai (CN); Xiaofei Wang, Shanghai (CN); Linghui Wu, Shanghai (CN); Guoping Hu, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 0 days.

(21) Appl. No.: 16/500,901

(22) PCT Filed: Apr. 8, 2018

(86) PCT No.: PCT/CN2018/082119
§ 371 (c)(1),
(2) Date: Oct. 4, 2019

(87) PCT Pub. No.: WO2018/184590
PCT Pub. Date: Oct. 11, 2018

(65) Prior Publication Data
US 2020/0131184 A1  Apr. 30, 2020

(30) Foreign Application Priority Data

Apr. 7, 2017 (CN) .......................... 201710224553.9
Aug. 24, 2017 (CN) .......................... 201710737871.5
Feb. 8, 2018 (CN) .......................... 201810129208.1

(51) Int. Cl.
*C07D 487/04* (2006.01)
*A61P 25/16* (2006.01)
*A61P 35/00* (2006.01)

(52) U.S. Cl.
CPC ............ *C07D 487/04* (2013.01); *A61P 25/16* (2018.01); *A61P 35/00* (2018.01)

(58) Field of Classification Search
CPC ...... A61K 31/519; C07D 487/04; A61P 35/00
USPC .................................. 514/259.31; 544/263
See application file for complete search history.

(56) References Cited

FOREIGN PATENT DOCUMENTS

CN             109535162 A        3/2019

*Primary Examiner* — Jeffrey H Murray
(74) *Attorney, Agent, or Firm* — McDermott Will & Emery LLP

(57) ABSTRACT

Provided are a compound represented by formula (I), an isomer or a pharmaceutically acceptable salt thereof, and an application of the same in preparing a drug for treating a disease related to $A_{2A}$ receptor. The $R_1$, $R_2$, $R_3$, ring A, ring B, n, and m are as defined in the specification.

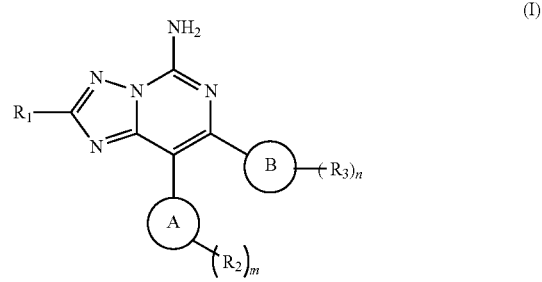

(I)

23 Claims, No Drawings

[1,2,4]TRIAZOLO[1,5-C]PYRIMIDINE DERIVATIVE AS $A_{2A}$ RECEPTOR INHIBITOR

CROSS REFERENCE TO RELATED APPLICATIONS

The present application is a national state filing under 35 U.S.C § 371 of International Application No. PCT/CN2018/082119, filed Apr. 8, 2019, which claims the benefit of the Chinese Patent Application No. 201710224553.9 filed on Apr. 7, 2017 with the National Intellectual Property Administration of the People's Republic of China, No. 201710737871.5 filed on Aug. 24, 2017 with the National Intellectual Property Administration of the People's Republic of China and No. 201810129208.1 filed on on Feb. 8, 2018 with the National Intellectual Property Administration of the People's Republic of China, the contents of each of which are incorporated herein by reference in their entireties.

TECHNICAL FIELD

The present disclosure relates to a compound represented by formula (I), an isomer thereof or a pharmaceutically acceptable salt thereof, and to the use thereof in the preparation of a medicament for treating a disease associated with $A_{2A}$ receptor.

BACKGROUND OF THE INVENTION

The adenosine $A_{2A}$ receptor is widely distributed in human tissues. This receptor is highly expressed in tissues such as spleen, thymus, white blood cell, platelet, GABA-type neuron and olfactory bulb. It is also expressed in other parts such as heart, lung, blood vessel, and brain. Adenosine $A_{2A}$ receptors generally coexist with other GPCRs and bind together to form heterodimers, for example, $A_{2A}$ receptor may form a heterodimer with dopamine $D_2$, cannabinoid $CB_1$, glutamic acid mGluR5 or the like. The adenosine $A_{2A}$ receptor plays an important role in life activities such as regulating vasodilation, supporting the formation of new blood vessels, and protecting body tissues from damage caused by inflammation; and the adenosine $A_{2A}$ receptor also affects the degree of activity of the basal ganglia indirect pathway.

In solid tumors, decomposition of cell tissue and hypoxic environment cause a large amount of ATP decomposed, leading to extracellular adenosine enrichment to an abnormally high concentration, which is 10-20 times the normal value. Binding of the adenosine and the $A_{2A}$ receptor in high concentration may activate the adenosine signaling pathway. This signaling pathway is a mechanism that protects body's tissues through immunosuppression in the event of damage to the body's tissues. Activation of the adenosine signaling pathway results in long-term inhibition of innate immune response, which may produce immune tolerance, and in turn leads to uncontrolled growth of malignant tumors. The binding of adenosine and the $A_{2A}$ receptor in white blood cells (such as lymphocytes, T lymphocytes, natural killer cells, dendritic cells, etc.) inhibits the effector functions that these white blood cells should have in the immune system. The binding of adenosine and the $A_{2A}$ receptor increases the expression of CD39, CD73 and CTLA4 (T cell checkpoints), resulting in more $T_{reg}$ cells with stronger immuno-suppressive activity. Blocking the $A_{2A}$ receptor's adenosine signaling pathway can reduce the inhibitory effect on the immune system and enhance the immune function of T cells, and is therefore considered to be a promising negative feedback mechanism for inhibiting tumor growth.

Literature J. Med. Chem. 2012, 55, 1898-1903 reports compound A as an adenosine $A_{2A}$ receptor antagonist for the treatment of Parkinson's disease.

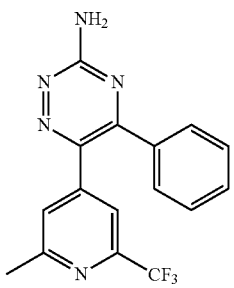

SUMMARY OF THE INVENTION

The present disclosure provides a compound represented by formula (I) or a pharmaceutically acceptable salt thereof,

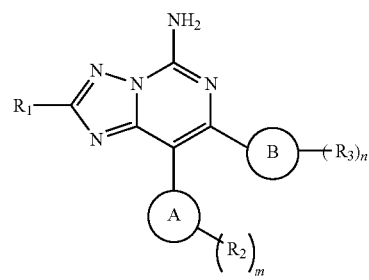

wherein $R_1$ is selected from the group consisting of H, or is selected from the group consisting of $C_{1-3}$ alkyl, $C_{1-3}$ alkyl-O—$C_{1-3}$ alkyl-, $C_{3-6}$ cycloalkyl, and $C_{1-3}$ alkyl-C(=O)NH—, each of which is optionally substituted by 1, 2 or 3 R;

$R_2$ is each independently selected from the group consisting of H, F, Cl, Br, I, OH, $NH_2$, and CN, or is independently selected from the group consisting of $C_{3-6}$ cycloalkyl, $C_{1-6}$ alkyl, and $C_{1-6}$ heteroalkyl, each of which is optionally substituted by 1, 2 or 3 R;

$R_3$ is each independently selected from the group consisting of H, F, Cl, Br, I, OH, $NH_2$, and CN, or is independently selected from the group consisting of $C_{1-6}$ alkyl and $C_{1-6}$ heteroalkyl, each of which is optionally substituted by 1, 2 or 3 R;

n is 0, 1, 2 or 3;

m is 0, 1, 2 or 3;

ring A is selected from the group consisting of 6- to 10-membered aryl, 5- to 10-membered heteroaryl, 5- to 10-membered heterocycloalkyl and 5- to 10-membered heterocycloalkenyl;

ring B is selected from the group consisting of phenyl and 5- to 6-membered heteroaryl;

R is selected from the group consisting of F, Cl, Br, I, OH, $NH_2$, and CN, or is selected from the group consisting of $C_{1-3}$ alkyl, $C_{3-6}$ cycloalkyl, $C_{3-6}$ cycloalkyl-NH—, and phenyl, each of which is optionally substituted by 1, 2 or 3 R';

R' is selected from the group consisting of F, Cl, Br, I, OH, NH$_2$, and

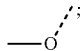;

the heteroatom or the heteroatom group of the C$_{1-6}$ heteroalkyl, 5- to 10-membered heteroaryl, 5- to 10-membered heterocycloalkyl or 5- to 10-membered heterocycloalkenyl is each independently selected from the group consisting of N, O, S, NH, —C(=O)—, —C(=O)O— and —C(=O)NH—;

the number of the heteroatom or the heteroatom group is each independently 1, 2, 3 or 4.

In some embodiments disclosed herein, the above R is selected from the group consisting of F, Cl, Br, I, OH, NH$_2$, and CN, or is selected from the group consisting of Me, Et,

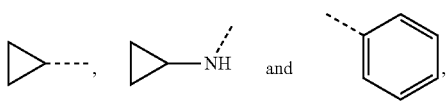

each of which is optionally substituted by 1, 2 or 3 R'.

In some embodiments disclosed herein, the above R is selected from the group consisting of F, Cl, Br, I, OH, NH$_2$, CN, Me, Et,

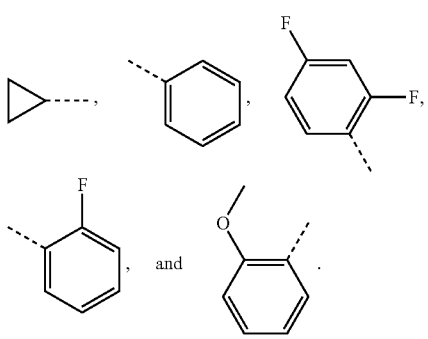

In some embodiments disclosed herein, the above R$_1$ H or is selected from the group consisting of Me, Et,

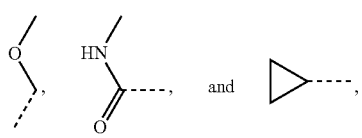

each of which is optionally substituted by 1, 2 or 3 R.

In some embodiments disclosed herein, the above R$_1$ is selected from the group consisting of H, Me, Et, CF$_3$,

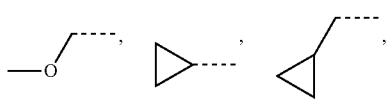

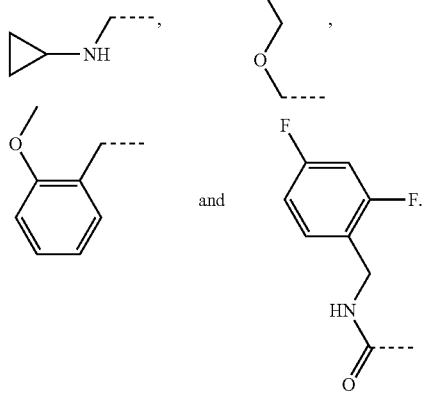

In some embodiments disclosed herein, the above R$_2$ is each independently selected from the group consisting of H, F, Cl, Br, I, OH, NH$_2$, and CN, or is independently selected from the group consisting of C$_{3-6}$ cycloalkyl, C$_{1-3}$ alkyl and C$_{1-3}$ alkoxy, each of which is optionally substituted by 1, 2 or 3 R.

In some embodiments disclosed herein, the above R$_2$ is each independently selected from the group consisting of H, F, Cl, Br, I, OH, NH$_2$, CN, Me, Et, CF$_3$,

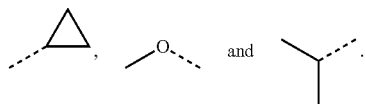

In some embodiments disclosed herein, the above R$_3$ is each independently selected from the group consisting of H, F, Cl, Br, I, OH, NH$_2$, and CN, or is independently selected from the group consisting of C$_{1-3}$ alkyl and C$_{1-3}$ alkoxy, each of which is optionally substituted by 1, 2 or 3 R.

In some embodiments disclosed herein, the above R$_3$ is each independently selected from the group consisting of H, F, Cl, Br, I, OH, NH$_2$, CN, Me, Et, CF$_3$ and

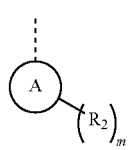

In some embodiments disclosed herein, the above ring A is selected from the group consisting of phenyl, pyridyl, tetrahydropyranyl, 3,6-dihydro-2H-pyranyl, piperidinyl, 1,2,3,6-tetrahydropyridyl, 1H-indolyl, 1H-indazolyl, 1H-benzo[d]imidazolyl, benzo[d][1,3 dioxolyl, indolin-2-onyl, 1H-benzo[d][1,2,3]triazolyl, quinolinyl and 1,2,3,4-tetrahydroquinolinyl.

In some embodiments disclosed herein, the above moiety is selected from the group consisting of
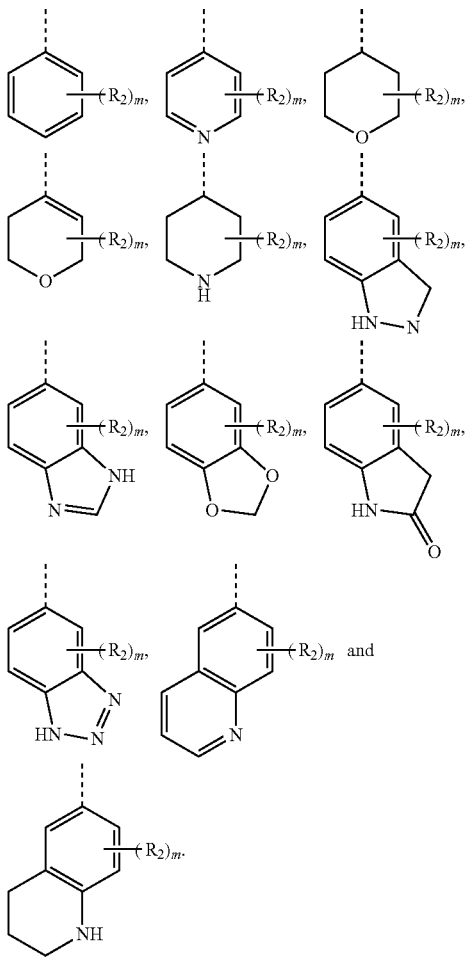
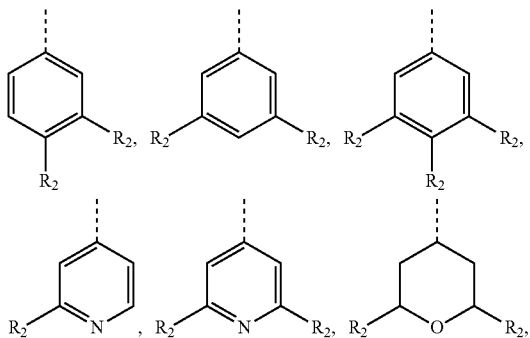
In some embodiments disclosed herein, the above moiety
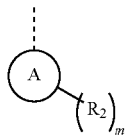
is selected from the group consisting of
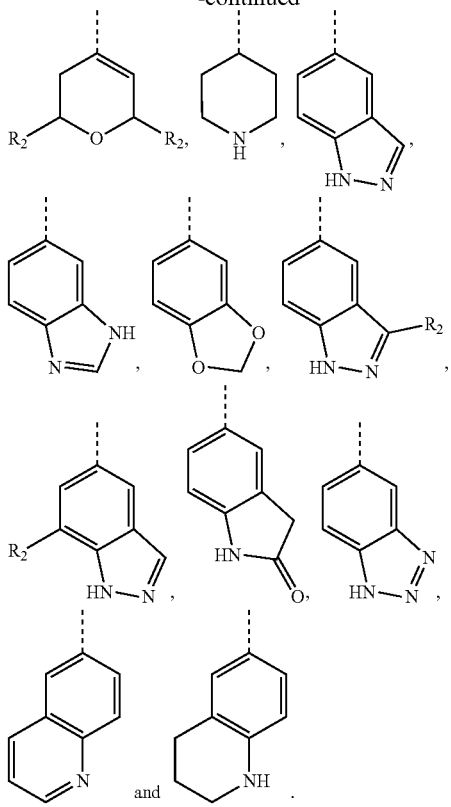
In some embodiments disclosed herein, the above moiety
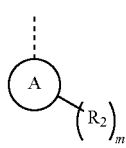
is selected from the group consisting of
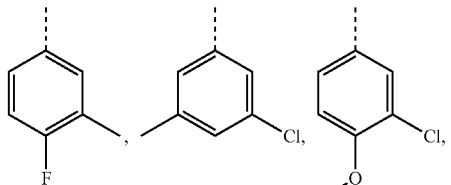
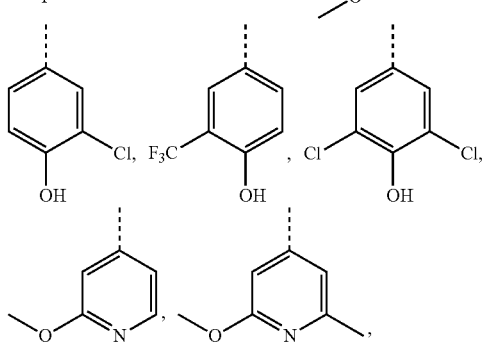

-continued

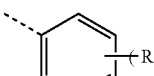

In some embodiments disclosed herein, the above ring B is selected from the group consisting of phenyl, pyridyl, imidazolyl, pyrazolyl, furyl, thienyl, and thiazolyl.

In some embodiments disclosed herein, the above moiety

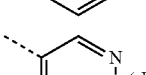

is selected from the group consisting of

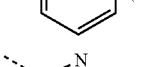

In some embodiments disclosed herein, the above moiety

is selected from the group consisting of

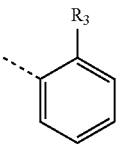

In some embodiments disclosed herein, the above moiety

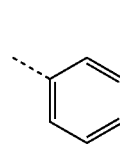

is selected from the group consisting of

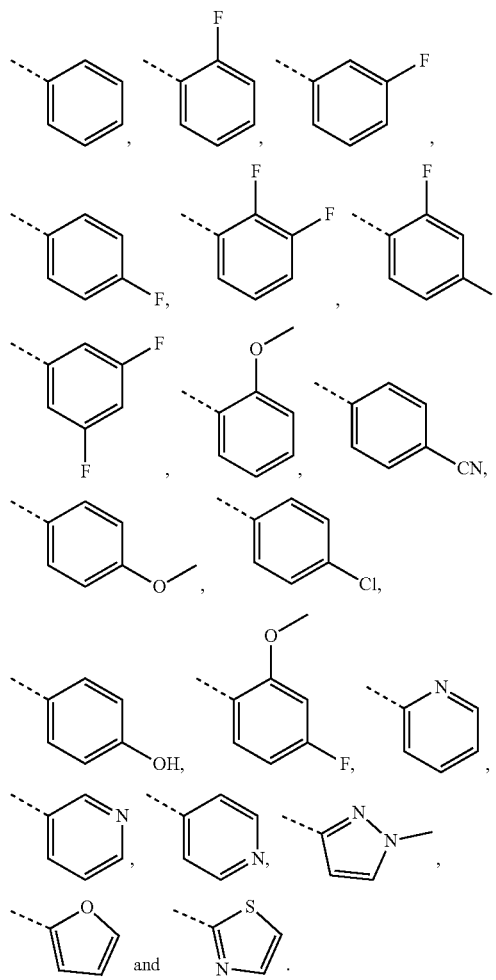

In some embodiments disclosed herein, the above R is selected from the group consisting of F, Cl, Br, I, OH, $NH_2$, and CN, or is selected from the group consisting of Me, Et,

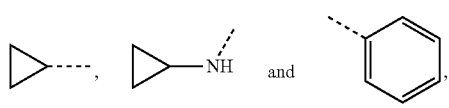

each of which is optionally substituted by 1, 2 or 3 R', and other variables are as defined above.

In some embodiments disclosed herein, the above R is selected from the group consisting of F, Cl, Br, I, OH, $NH_2$, CN, Me, Et,

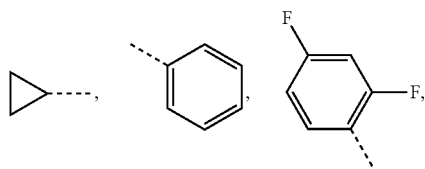

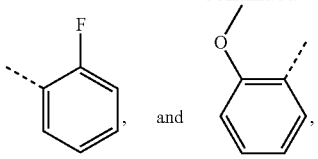

and other variables are as defined above.

In some embodiments disclosed herein, the above $R_1$ is H, or is selected from the group consisting of Me, Et,

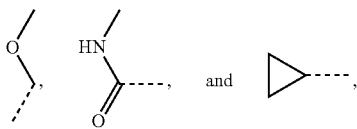

each of which is optionally substituted by 1, 2 or 3 R, and other variables are as defined above.

In some embodiments disclosed herein, the above $R_1$ is selected from the group consisting of H, Me, Et, $CF_3$,

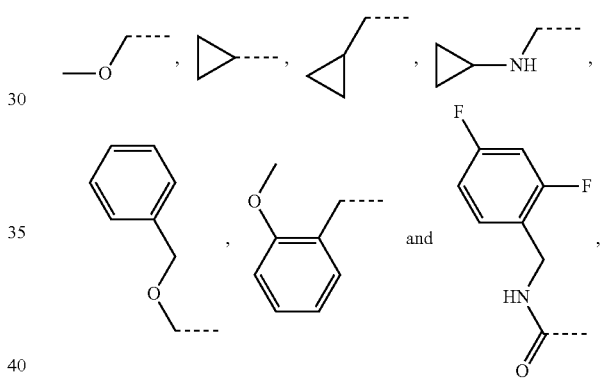

and other variables are as defined above.

In some embodiments disclosed herein, the above $R_2$ is each independently selected from the group consisting of H, F, Cl, Br, I, OH, $NH_2$, and CN, or is independently selected from the group consisting of $C_{3-6}$ cycloalkyl, $C_{1-3}$ alkyl and $C_{1-3}$ alkoxy, each of which is optionally substituted by 1, 2 or 3 R, and other variables are as defined above.

In some embodiments disclosed herein, the above $R_2$ is each independently selected from the group consisting of H, F, Cl, Br, I, OH, $NH_2$, CN, Me, Et, $CF_3$,

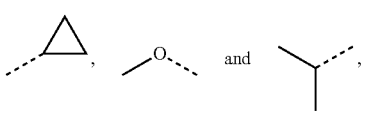

and other variables are as defined above.

In some embodiments disclosed herein, the above $R_3$ is each independently selected from the group consisting of H, F, Cl, Br, I, OH, $NH_2$, and CN, or is independently selected from the group consisting of $C_{1-3}$ alkyl and $C_{1-3}$ alkoxy, each of which is optionally substituted by 1, 2 or 3 R, and other variables are as defined above.

In some embodiments disclosed herein, the above $R_3$ is each independently selected from the group consisting of H, F, Cl, Br, I, OH, $NH_2$, CN, Me, Et, $CF_3$ and

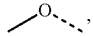

and other variables are as defined above.

In some embodiments disclosed herein, the above ring A is selected from the group consisting of phenyl, pyridyl, tetrahydropyranyl, 3,6-dihydro-2H-pyranyl, piperidinyl, 1,2,3,6-tetrahydropyridyl, 1H-indolyl, 1H-indazolyl, 1H-benzo[d]imidazolyl, benzo[d][1,3]dioxolyl, indolin-2-onyl, 1H-benzo[d][1,2,3]triazolyl, quinolinyl and 1,2,3,4-tetrahydroquinolinyl, and other variables are as defined above.

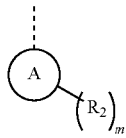

In some embodiments disclosed herein, the above moiety is selected from the group consisting of

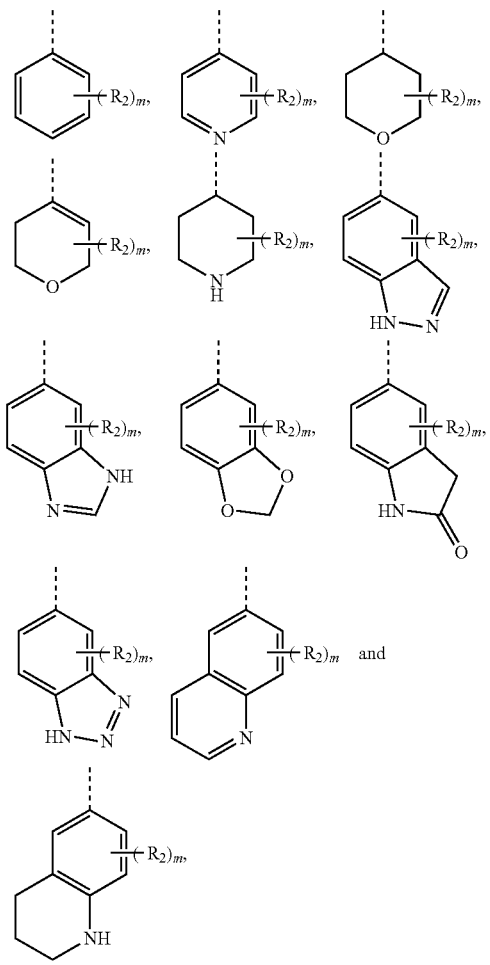

and other variables are as defined above.

In some embodiments disclosed herein, the above moiety

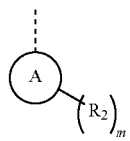

is selected from the group consisting of

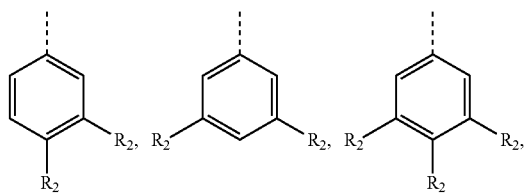
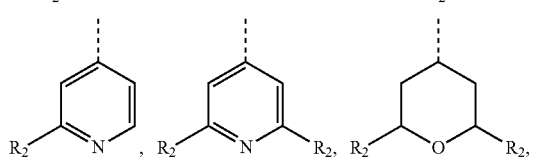
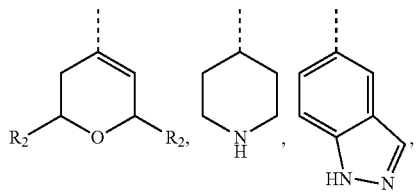
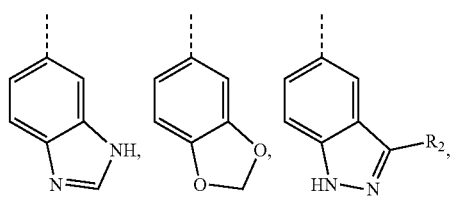
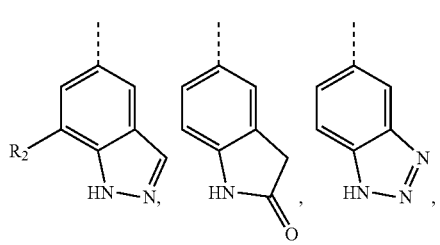
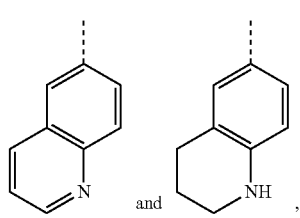

and other variables are as defined above.

In some embodiments disclosed herein, the above moiety

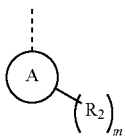

is selected from the group consisting of

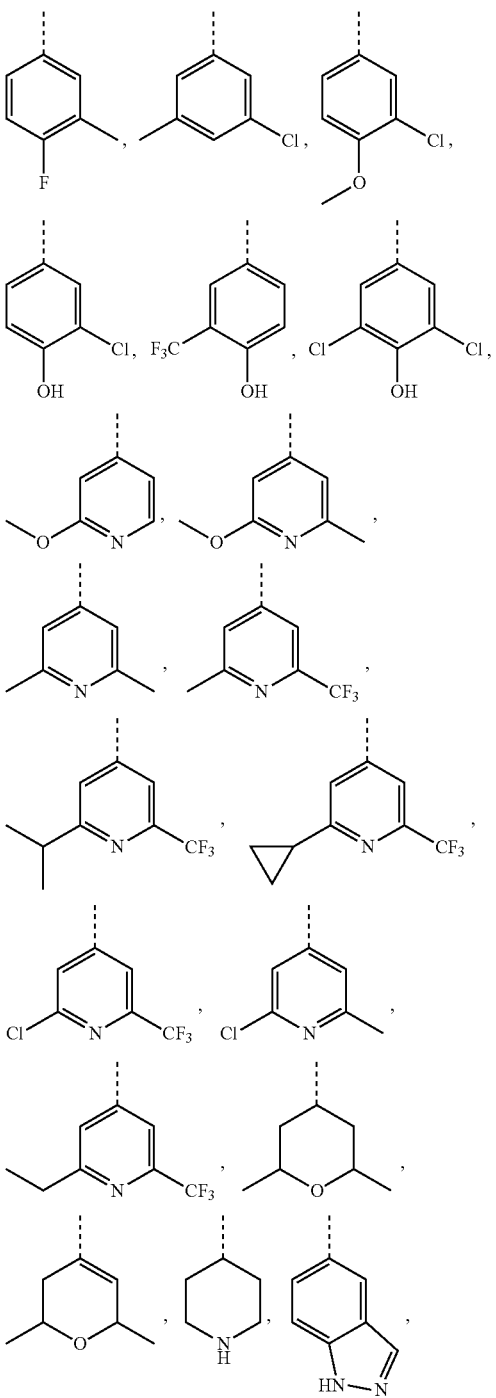

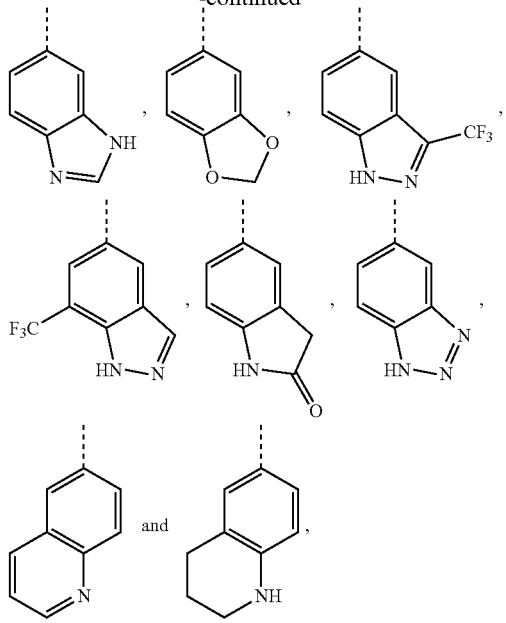

and other variables are as defined above.

In some embodiments disclosed herein, the ring B is selected from the group consisting of phenyl, pyridyl, imidazolyl, pyrazolyl, furyl, thienyl, and thiazolyl, and other variables are as defined above.

In some embodiments disclosed herein, the above moiety

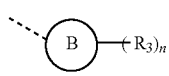

is selected from the group consisting of

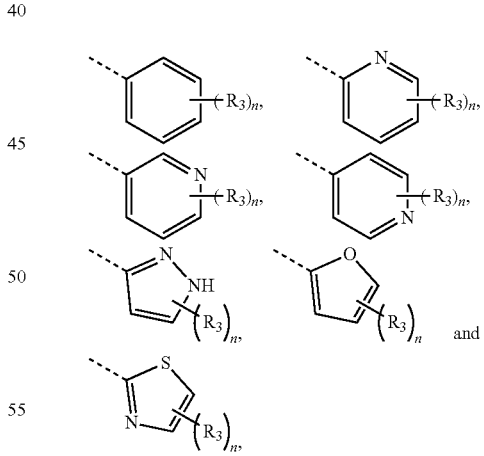

and other variables are as defined above.

In some embodiments disclosed herein, the above moiety

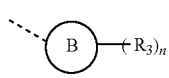

is selected from the group consisting of

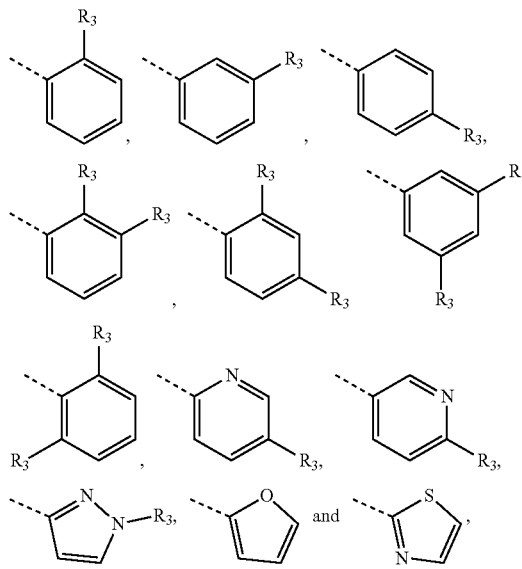

and other variables are as defined above.

In some embodiments disclosed herein, the above moiety

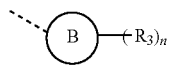

is selected from the group consisting of

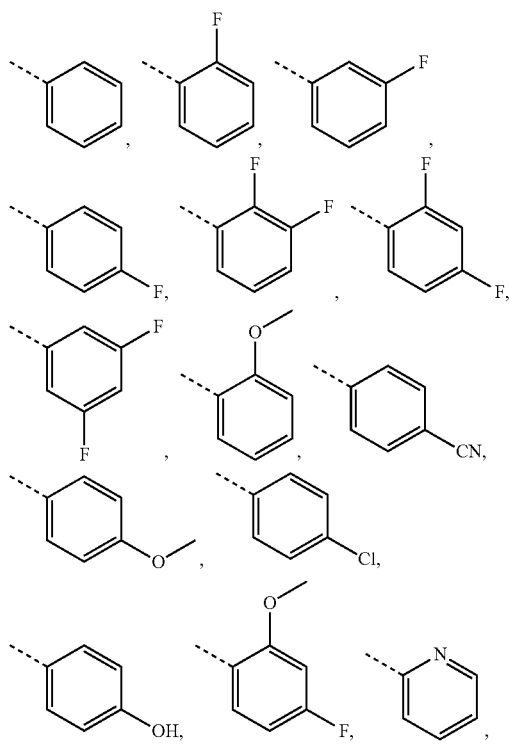

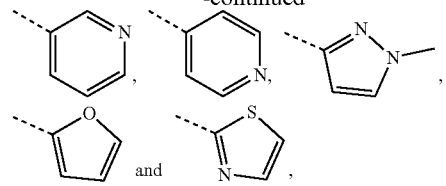

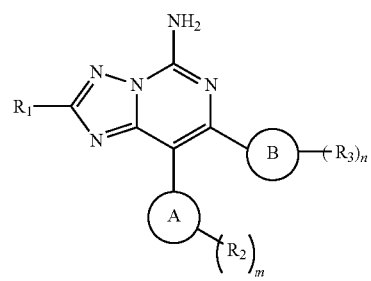

and other variables are as defined above.

The present disclosure provides a compound represented by formula (I) or a pharmaceutically acceptable salt thereof, (I)

wherein
$R_1$ is H, or is selected from the group consisting of $C_{1-3}$ alkyl, $C_{1-3}$ alkyl-O—$C_{1-3}$ alkyl-, $C_{3-6}$ cycloalkyl, and $C_{1-3}$ alkyl-C(=O)NH—, each of which is optionally substituted by 1, 2 or 3 R;

$R_2$ is each independently selected from the group consisting of H, F, Cl, Br, I, OH, $NH_2$, and CN, or is independently selected from the group consisting of $C_{3-6}$ cycloalkyl, $C_{1-6}$ alkyl and $C_{1-6}$ heteroalkyl, each of which is optionally substituted by 1, 2 or 3 R;

$R_3$ is each independently selected from the group consisting of H, F, Cl, Br, I, OH, $NH_2$, and CN, or is independently selected from the group consisting of $C_{1-6}$ alkyl or $C_{1-6}$ heteroalkyl, each of which is optionally substituted by 1, 2 or 3 R;

n is 0, 1, 2 or 3;
m is 0, 1, 2 or 3;
ring A is selected from the group consisting of 6- to 10-membered aryl, 5- to 10-membered heteroaryl, 5- to 10-membered heterocycloalkyl and 5- to 10-membered heterocycloalkenyl;
ring B is selected from the group consisting of phenyl and 5- to 6-membered heteroaryl;
R is selected from the group consisting of F, Cl, Br, I, OH, $NH_2$, and CN, or is selected from the group consisting of $C_{1-3}$ alkyl, $C_{3-6}$ cycloalkyl, $C_{3-6}$ cycloalkyl-NH—, and phenyl, each of which is optionally substituted by 1, 2 or 3 R';
R' is selected from the group consisting of F, Cl, Br, I, OH, $NH_2$, and

the heteroatom or the heteroatom group of the $C_{1-6}$ heteroalkyl, 5- to 10-membered heteroaryl, 5- to 10-membered heterocycloalkyl or 5- to 10-membered heterocycloalkenyl is each independently selected from the group consisting of N, O, S, NH, —C(=O)—, —C(=O)O— and —C(=O)NH—;

the number of the heteroatom or the heteroatom group is each independently 1, 2, 3 or 4.

In some embodiments disclosed herein, the above R is selected from the group consisting of F, Cl, Br, I, OH, NH$_2$, and CN, or is selected from the group consisting of Me, Et,

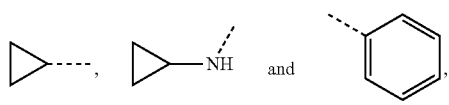

each of which is optionally substituted by 1, 2 or 3 R'.

In some embodiments disclosed herein, the above R is selected from the group consisting of F, Cl, Br, I, OH, NH$_2$, CN, Me, Et,

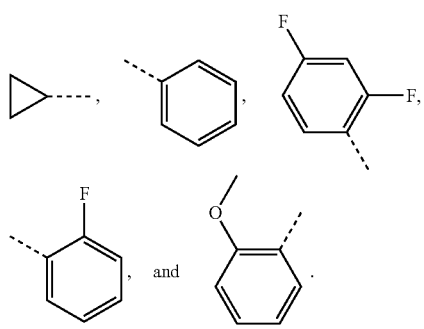

In some embodiments disclosed herein, the above R$_1$ is H, or is selected from the group consisting of Me, Et,

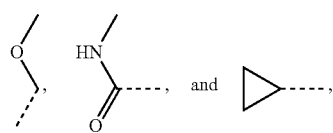

each of which is optionally substituted by 1, 2 or 3 R.

In some embodiments disclosed herein, the above R$_1$ is selected from the group consisting of H, Me, Et, CF$_3$,

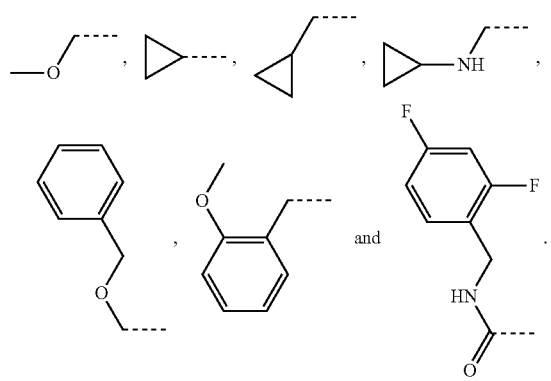

In some embodiments disclosed herein, the above R$_2$ is each independently selected from the group consisting of H, F, Cl, Br, I, OH, NH$_2$, and CN, or is independently selected from the group consisting of C$_{3-6}$ cycloalkyl, C$_{1-3}$ alkyl and C$_{1-3}$ alkoxy, each of which is optionally substituted by 1, 2 or 3 R.

In some embodiments disclosed herein, the above R$_2$ is each independently selected from the group consisting of H, F, Cl, Br, I, OH, NH$_2$, CN, Me, Et, CF$_3$,

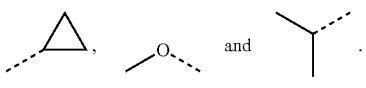

In some embodiments disclosed herein, the above R$_3$ is each independently selected from the group consisting of H, F, Cl, Br, I, OH, NH$_2$, and CN, or is independently selected from the group consisting of C$_{1-3}$ alkyl and C$_{1-3}$ alkoxy, each of which is optionally substituted by 1, 2 or 3 R.

In some embodiments disclosed herein, the above R$_3$ is each independently selected from the group consisting of H, F, Cl, Br, I, OH, NH$_2$, CN, Me, Et, CF$_3$ and

In some embodiments disclosed herein, the ring A is selected from the group consisting of phenyl, pyridyl, tetrahydropyranyl, 3,6-dihydro-2H-pyranyl, piperidinyl, 1,2,3,6-tetrahydropyridyl, 1H-indolyl, 1H-indazolyl, 1H-benzo[d]imidazolyl, benzo[d][1,3]dioxolyl, indolin-2-onyl, 1H-benzo[d][1,2,3]triazolyl, quinolinyl and 1,2,3,4-tetrahydroquinolinyl.

In some embodiments disclosed herein, the above moiety

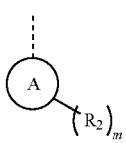

is selected from the group consisting of

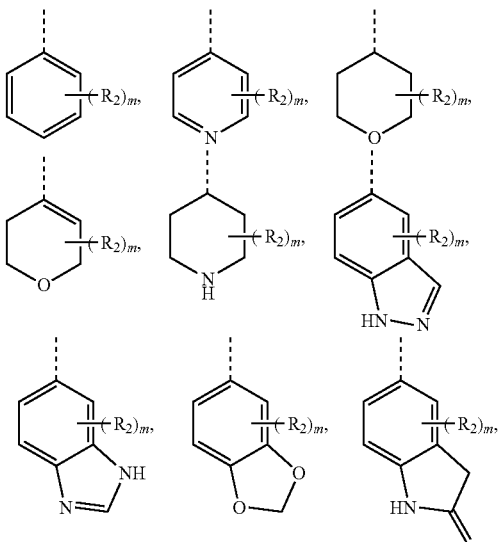

-continued
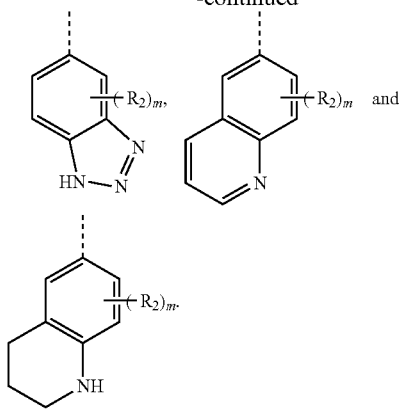
In some embodiments disclosed herein, the above moiety
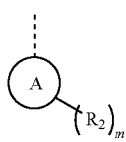
is selected from the group consisting of
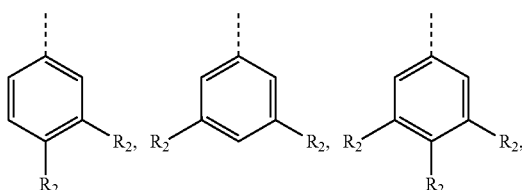
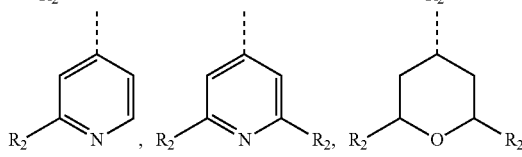
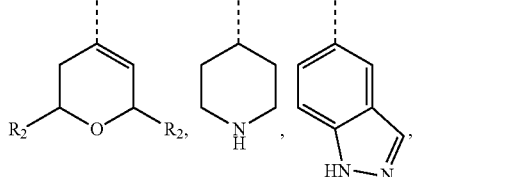
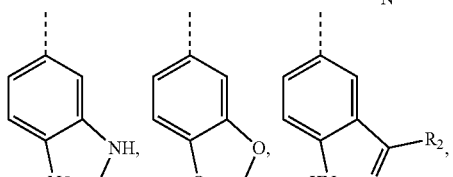
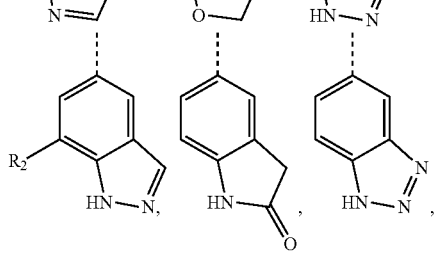
-continued
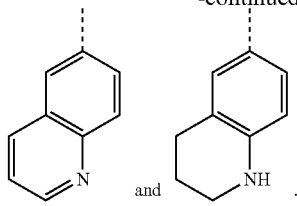
In some embodiments disclosed herein, the above moiety
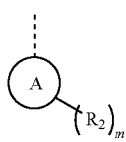
is selected from the group consisting of
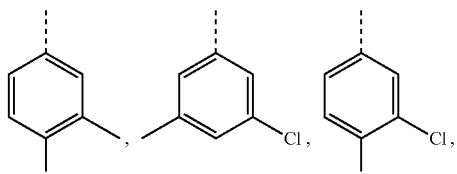
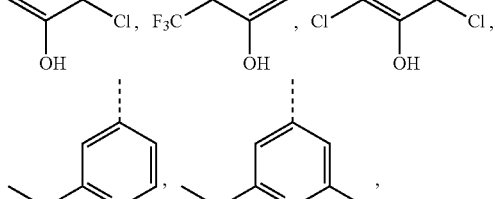
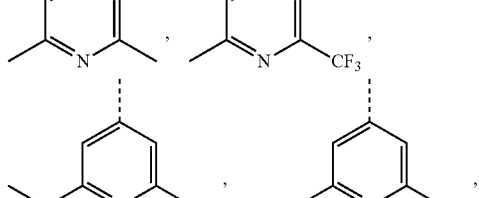
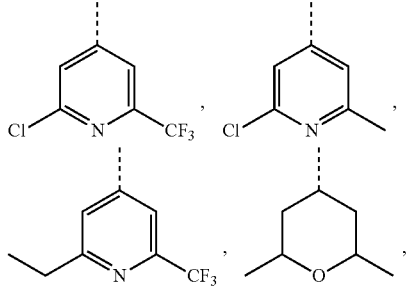

-continued

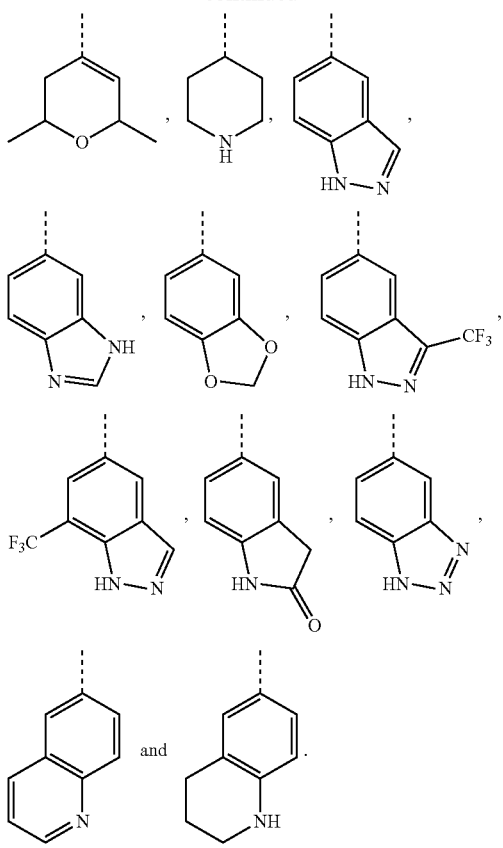

In some embodiments disclosed herein, the above ring B is selected from the group consisting of phenyl, pyridyl, imidazolyl, pyrazolyl, furyl, thienyl, and thiazolyl.

In some embodiments disclosed herein, the above moiety

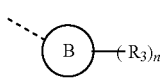

is selected from the group consisting of

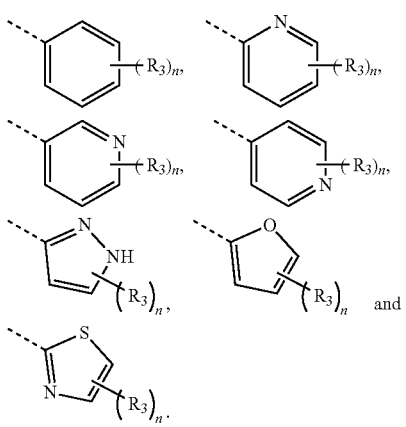

In some embodiments disclosed herein, the above moiety

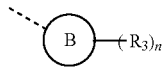

is selected from the group consisting of

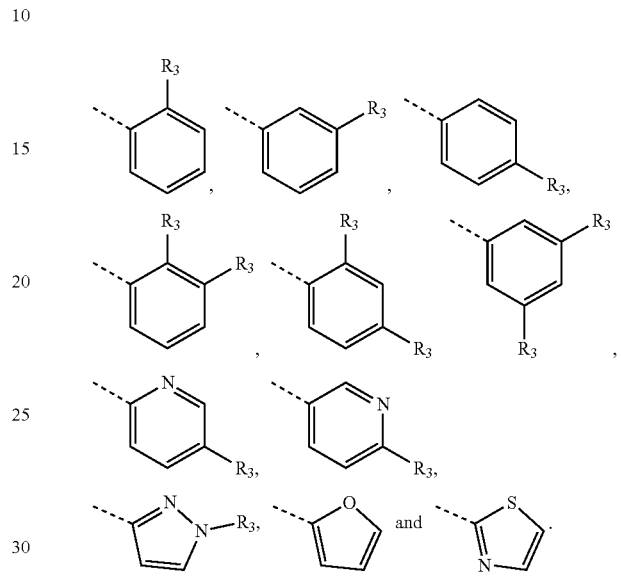

In some embodiments disclosed herein, the above moiety

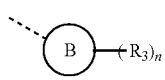

is selected from the group consisting of

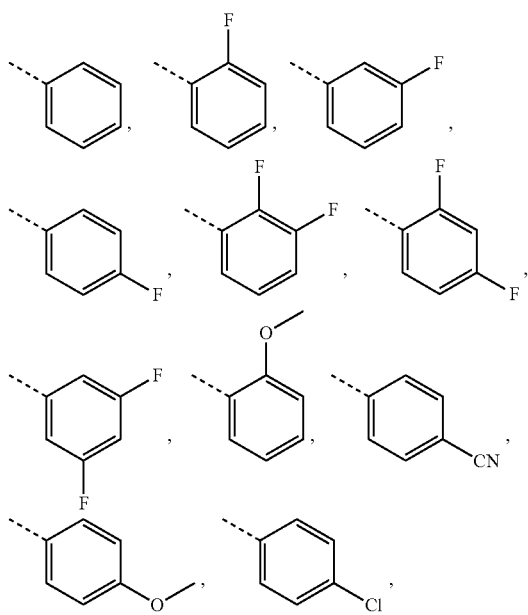

-continued

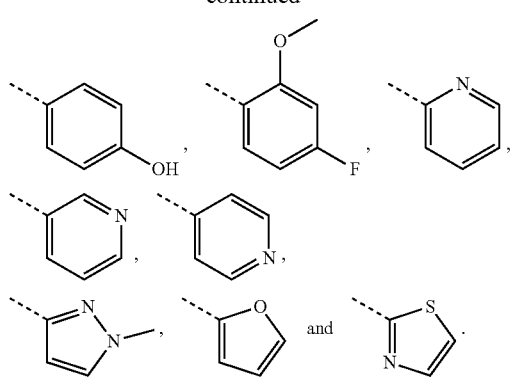

In some embodiments disclosed herein, the above R is selected from the group consisting of F, Cl, Br, I, OH, NH$_2$, and CN, or is selected from the group consisting of Me, Et,

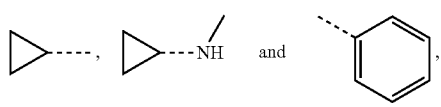

each of which is optionally substituted by 1, 2 or 3 R', and other variables are as defined above.

In some embodiments disclosed herein, the above R is selected from the group consisting of F, Cl, Br, I, OH, NH$_2$, CN, Me, Et,

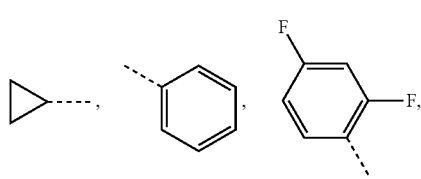

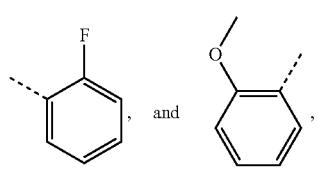

and other variables are as defined above.

In some embodiments disclosed herein, the above R$_1$ is selected from the group consisting of H or is selected from the group consisting of Me, Et,

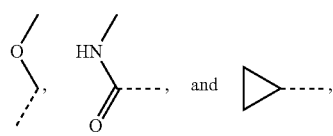

each of which is optionally substituted by 1, 2 or 3 R, and other variables are as defined above.

In some embodiments disclosed herein, the above R$_1$ is selected from the group consisting of H, Me, Et, CF$_3$.

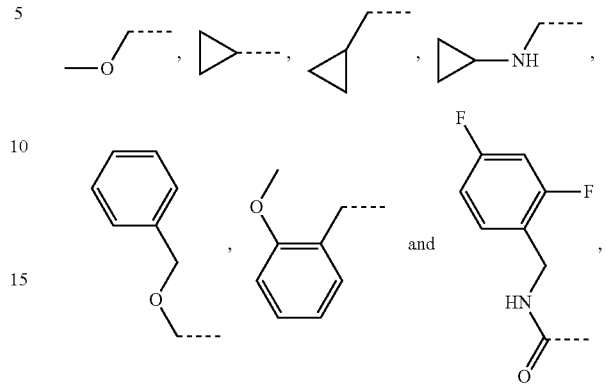

and other variables are as defined above.

In some embodiments disclosed herein, the above R$_2$ is each independently selected from the group consisting of H, F, Cl, Br, I, OH, NH$_2$, and CN, or is independently selected from the group consisting of C$_{3-6}$ cycloalkyl, C$_{1-3}$ alkyl and C$_{1-3}$ alkoxy, each of which is optionally substituted by 1, 2 or 3 R, and other variables are as defined above.

In some embodiments disclosed herein, the above R$_2$ is each independently selected from the group consisting of H, F, Cl, Br, I, OH, NH$_2$, CN, Me, Et, CF$_3$,

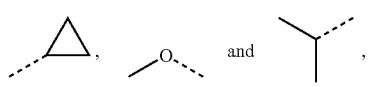

and other variables are as defined above.

In some embodiments disclosed herein, the above R$_3$ is each independently selected from the group consisting of H, F, Cl, Br, I, OH, NH$_2$, and CN, or is independently selected from the group consisting of C$_{1-3}$ alkyl and C$_{1-3}$ alkoxy, each of which is optionally substituted by 1, 2 or 3 R, and other variables are as defined above.

In some embodiments disclosed herein, the above R$_3$ is each independently selected from the group consisting of H, F, Cl, Br, I, OH, NH$_2$, CN, Me, Et, CF$_3$ and

and other variables are as defined above.

In some embodiments disclosed herein, the above ring A is selected from the group consisting of phenyl, pyridyl, tetrahydropyranyl, 3,6-dihydro-2H-pyranyl, piperidinyl, 1,2,3,6-tetrahydropyridyl, 1H-indolyl, 1H-indazolyl, 1H-benzo[d] imidazolyl, benzo[d][1,3]dioxolyl, indolin-2-onyl, 1H-benzo[d][1,2,3]triazolyl, quinolinyl and 1,2,3,4-tetrahydroquinolinyl, and other variables are as defined above.

In some embodiments disclosed herein, the above moiety
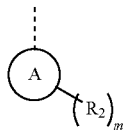
is selected from the group consisting of
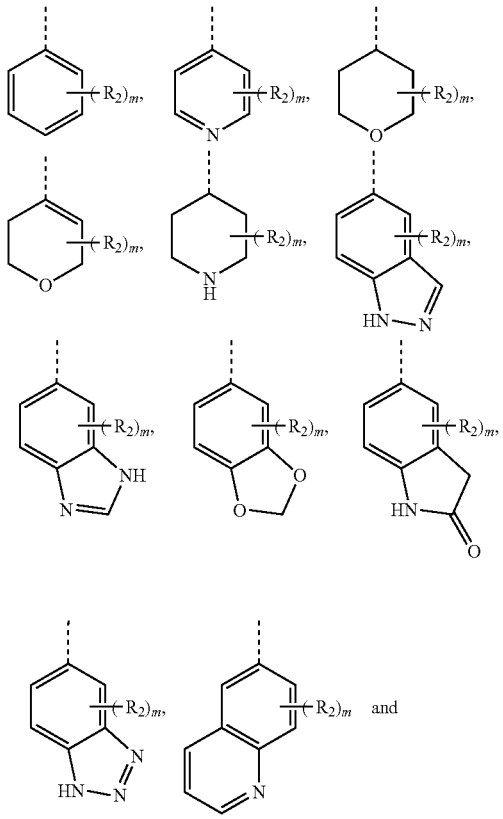
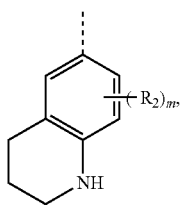
and other variables are as defined above.
In some embodiments disclosed herein, the above moiety
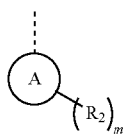
is selected from the group consisting of
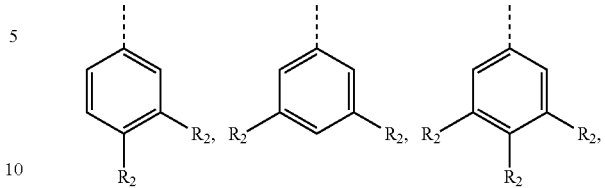
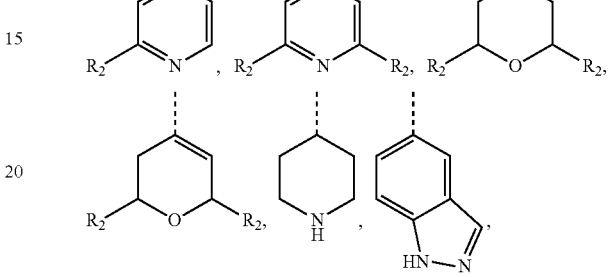
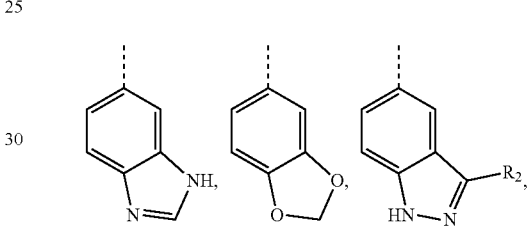
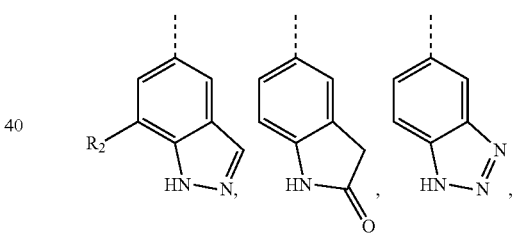
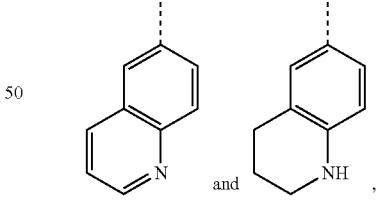
and other variables are as defined above.
In some embodiments disclosed herein, the above moiety
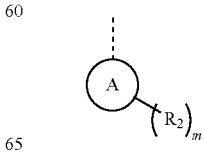

is selected from the group consisting of

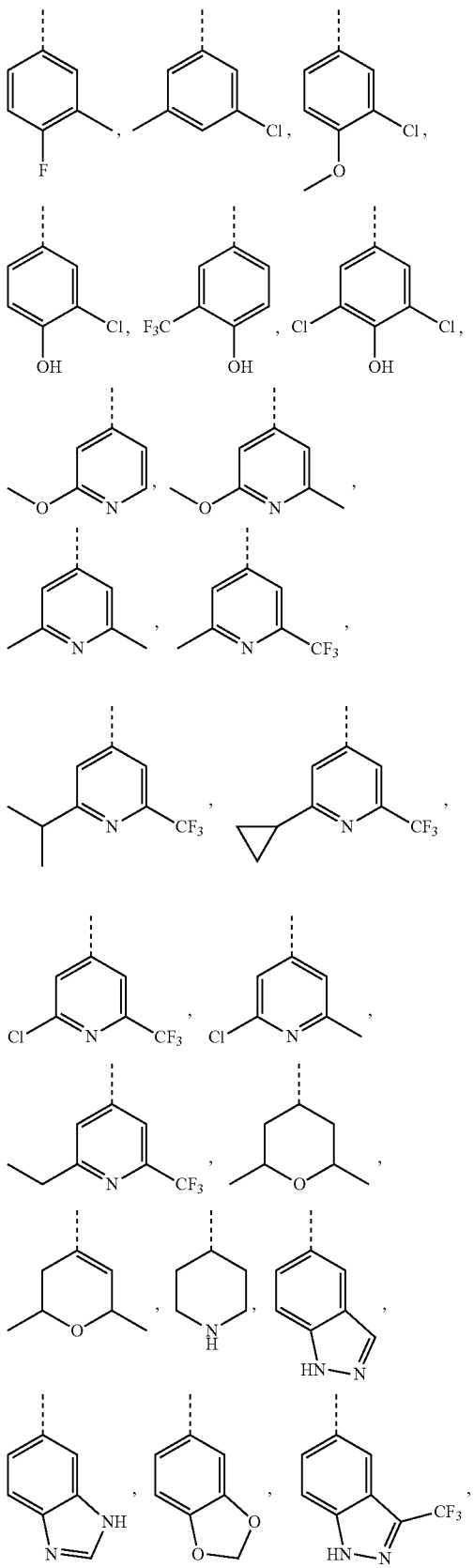

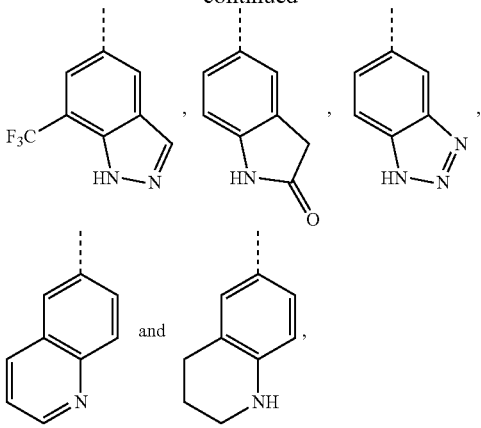

and other variables are as defined above.

In some embodiments disclosed herein, the above ring B is selected from the group consisting of phenyl, pyridyl, imidazolyl, pyrazolyl, furyl, thienyl, thiazolyl, and other variables are as defined above.

In some embodiments disclosed herein, the above moiety

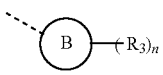

is selected from the group consisting of

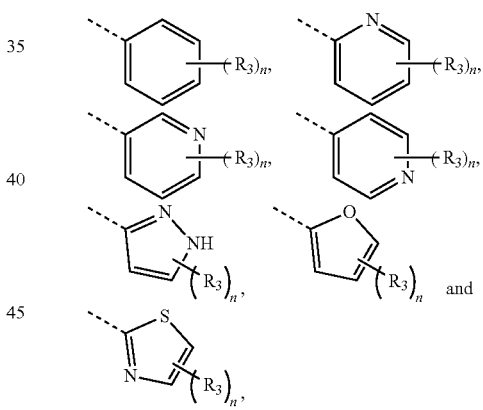

and other variables are as defined above.

In some embodiments disclosed herein, the above moiety

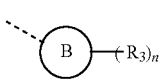

is selected from the group consisting of

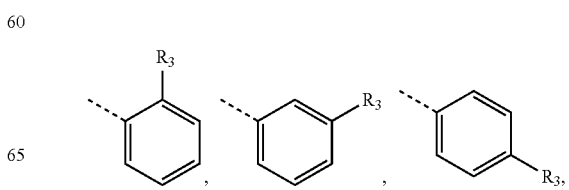

29
-continued

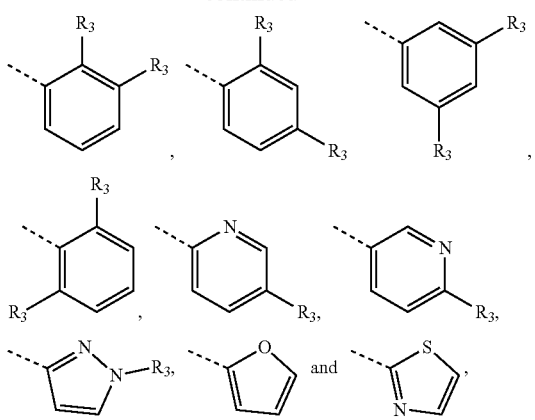

and other variables are as defined above.

In some embodiments disclosed herein, the above moiety

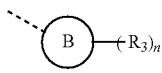

is selected from the group consisting of

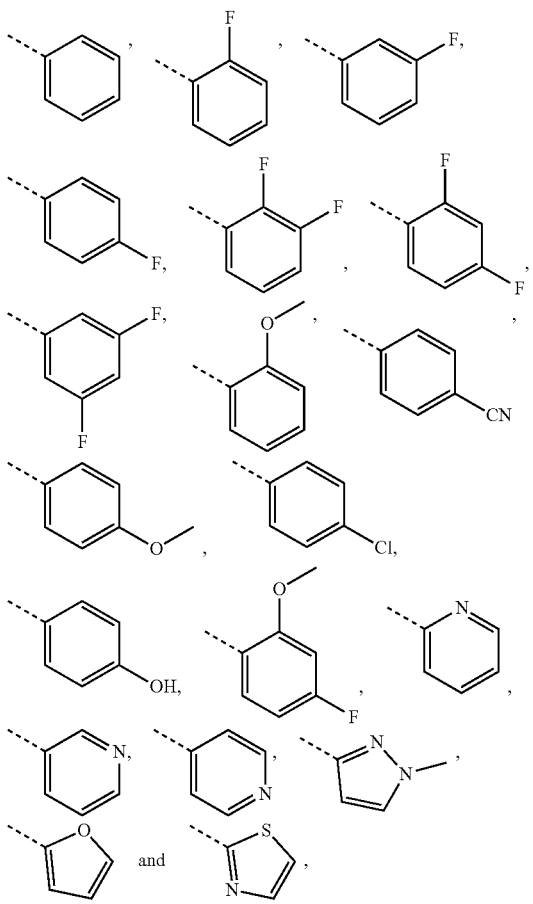

and other variables are as defined above.

30

The present disclosure provides a compound represented by formula (I) or a pharmaceutically acceptable salt thereof,

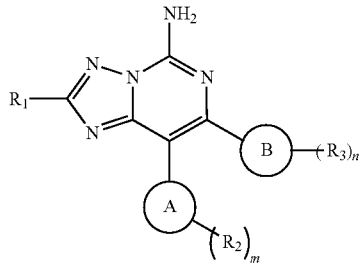

(I)

wherein $R_1$ is selected from the group consisting of H, CN, and

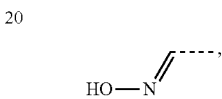

or is selected from the group consisting of $C_{1-3}$ alkyl, $C_{1-3}$ alkyl-O—$C_{1-3}$ alkyl-, $C_{3-6}$ cycloalkyl, and $C_{1-3}$ alkyl-C(=O)NH—, each of which is optionally substituted by 1, 2 or 3 R;

$R_2$ is each independently selected from the group consisting of H, F, Cl, Br, I, OH, $NH_2$, and CN, or is independently selected from the group consisting of $C_{3-6}$ cycloalkyl, $C_{1-6}$ alkyl and $C_{1-6}$ heteroalkyl, each of which is optionally substituted by 1, 2 or 3 R;

$R_3$ is each independently selected from the group consisting of H, F, Cl, Br, I, OH, $NH_2$, and CN, or is independently selected from the group consisting of $C_{1-6}$ alkyl or $C_{1-6}$ heteroalkyl, each of which is optionally substituted by 1, 2 or 3 R;

n is 0, 1, 2 or 3;

m is 0, 1, 2 or 3;

ring A is selected from the group consisting of 6- to 10-membered aryl, 5- to 10-membered heteroaryl, 5- to 10-membered heterocycloalkyl and 5- to 10-membered heterocycloalkenyl;

ring B is selected from the group consisting of phenyl and 5- to 6-membered heteroaryl;

R is selected from the group consisting of F, Cl, Br, I, OH, $NH_2$, and CN, or is selected from the group consisting of $C_{1-3}$ alkyl, $C_{1-3}$ alkylamino, $C_{1-3}$ alkoxy, $C_{3-6}$ cycloalkyl, $C_{3-6}$ cycloalkyl-NH—, 3- to 6-membered heterocycloalkyl, 3- to 6-membered heterocycloalkyl-O—, and phenyl, each of which is optionally substituted by 1, 2 or 3 R';

R' is selected from the group consisting of F, Cl, Br, I, OH, $NH_2$, and

the heteroatom or the heteroatom group of the $C_{1-6}$ heteroalkyl, 5- to 10-membered heteroaryl, 5- to 10-membered heterocycloalkyl, 3- to 6-membered heterocycloalkyl or 5- to 10-membered heterocycloalkenyl group is each independently selected from the group consisting of N, O, S, NH, —C(=O)—, —C(=O)O— and —C(=O)NH—;

the number of the heteroatom or the heteroatom group is each independently 1, 2, 3 or 4.

In some embodiments disclosed herein, the above R is selected from the group consisting of F, Cl, Br, I, OH, NH$_2$, and CN, or is selected from the group consisting of Me, Et,

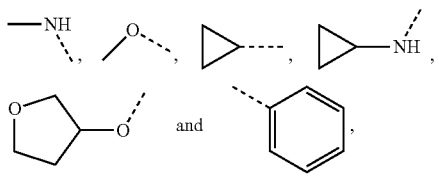

each of which is optionally substituted by 1, 2 or 3 R', and other variables are as defined above.

In some embodiments disclosed herein, the above R is selected from the group consisting of F, Cl, Br, I, OH, NH$_2$, CN, Me, Et,

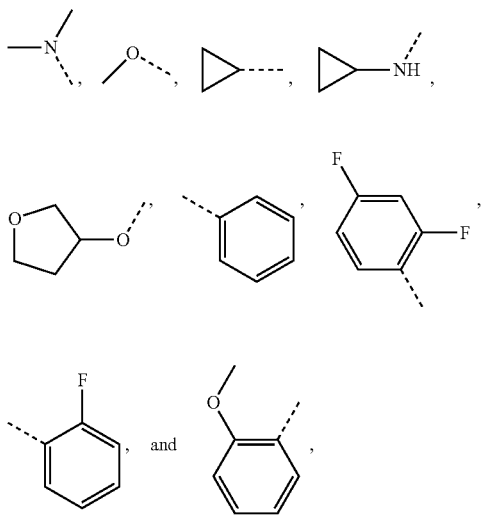

and other variables are as defined herein.

In some embodiments disclosed herein, the above R$_1$ is selected from the group consisting of H, CN, and

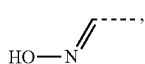

or is selected from the group consisting of Me, Et,

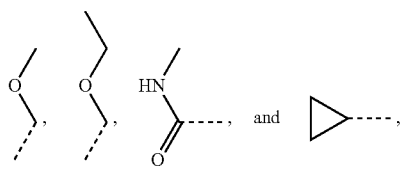

each of which is optionally substituted by 1, 2 or 3 R, and other variables are as defined above.

In some embodiments disclosed herein, the above R$_1$ is selected from the group consisting of H, CN,

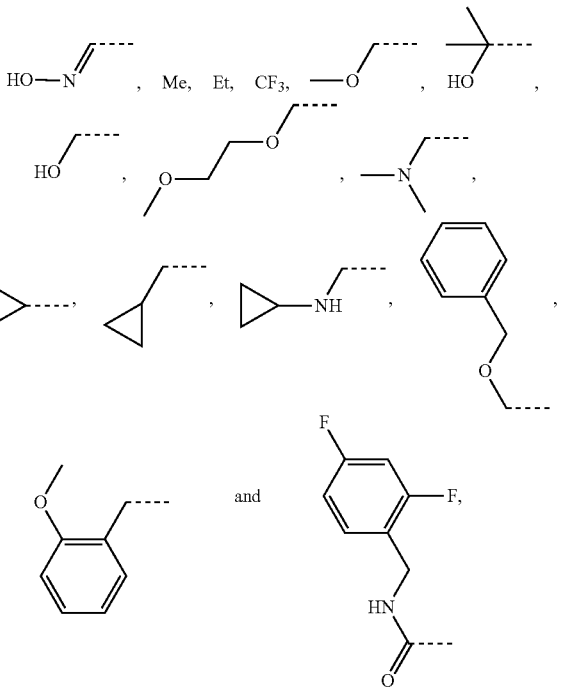

and other variables are as defined herein.

In some embodiments disclosed herein, the above R$_2$ is each independently selected from the group consisting of H, F, Cl, Br, I, OH, NH$_2$, and CN, or is independently selected from the group consisting of C$_{3-6}$ cycloalkyl, C$_{1-3}$ alkyl and C$_{1-3}$ alkoxy, each of which is optionally substituted by 1, 2 or 3 R, and other variables are as defined above.

In some embodiments disclosed herein, the above R$_2$ is each independently selected from the group consisting of H, F, Cl, Br, I, OH, NH$_2$, CN, Me, Et, CF$_3$,

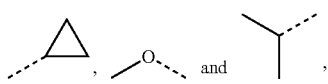

and other variables are as defined herein.

In some embodiments disclosed herein, the above R$_3$ is each independently selected from the group consisting of H, F, Cl, Br, I, OH, NH$_2$, and CN, or is independently selected from the group consisting of C$_{1-3}$ alkyl and C$_{1-3}$ alkoxy, each of which is optionally substituted by 1, 2 or 3 R, and other variables are as defined above.

In some embodiments disclosed herein, the above R$_3$ is each independently selected from the group consisting of H, F, Cl, Br, I, OH, NH$_2$, CN, Me, Et, CF$_3$ and

and other variables are as defined herein.

In some embodiments disclosed herein, the ring A is selected from the group consisting of phenyl, pyridyl, tetrahydropyranyl, 3,6-dihydro-2H-pyranyl, piperidinyl, 1,2,3, 6-tetrahydropyridyl, 1H-indolyl, 1H-indazolyl, 1H-benzo[d]imidazolyl, benzo[d][1,3]dioxolyl, indolin-2-onyl, 1H-benzo[d][1,2,3]triazolyl, quinolinyl and 1,2,3,4-tetrahydroquinolinyl, and other variables are as defined herein.

In some embodiments disclosed herein, the above moiety

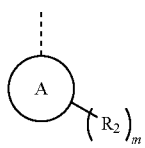

is selected from the group consisting of

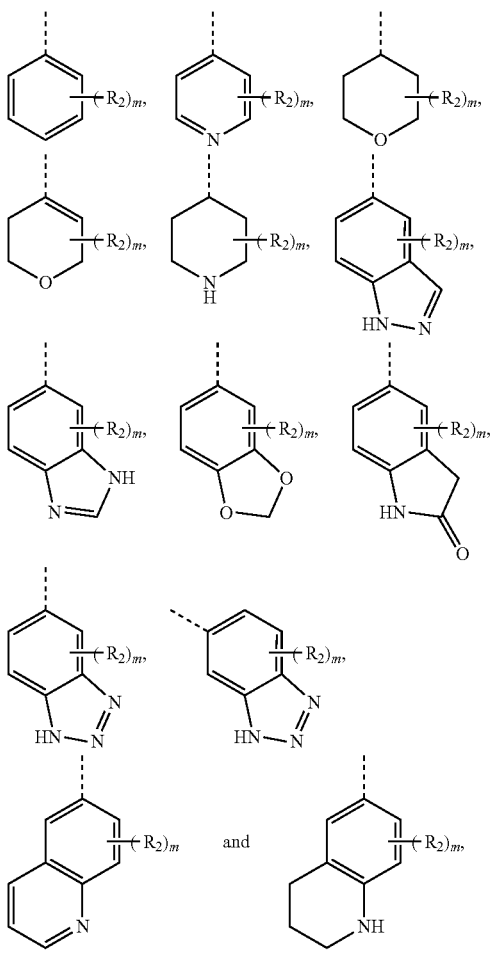

and other variables are as defined herein.

In some embodiments disclosed herein, the above moiety

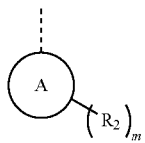

is selected from the group consisting of

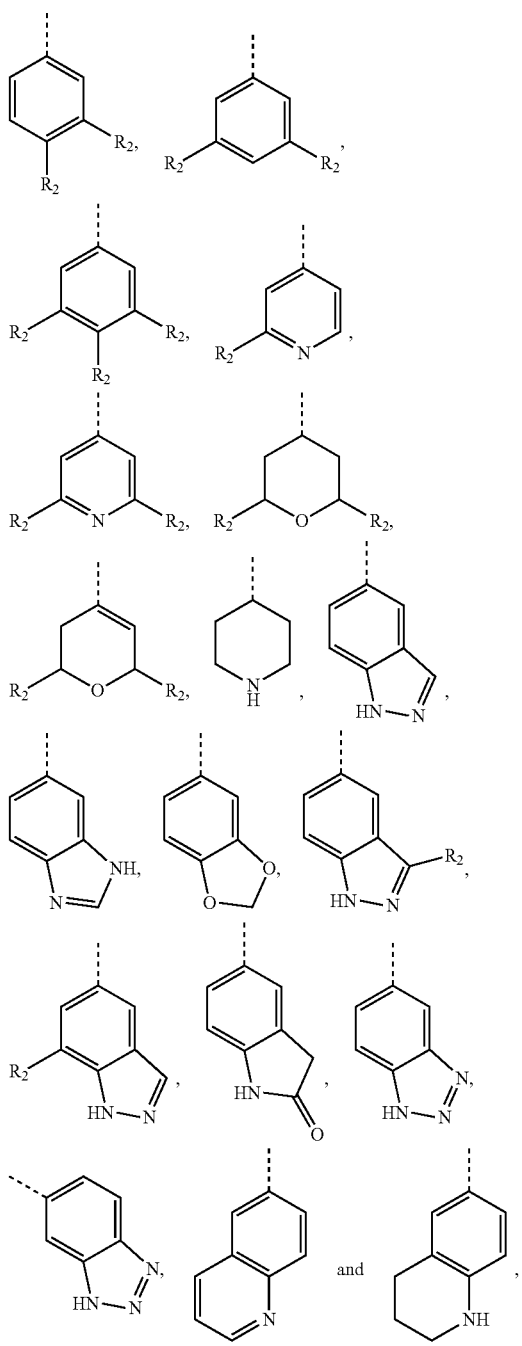

and other variables are as defined herein.

In some embodiments disclosed herein, the above moiety

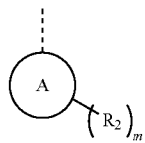

is selected from the group consisting of

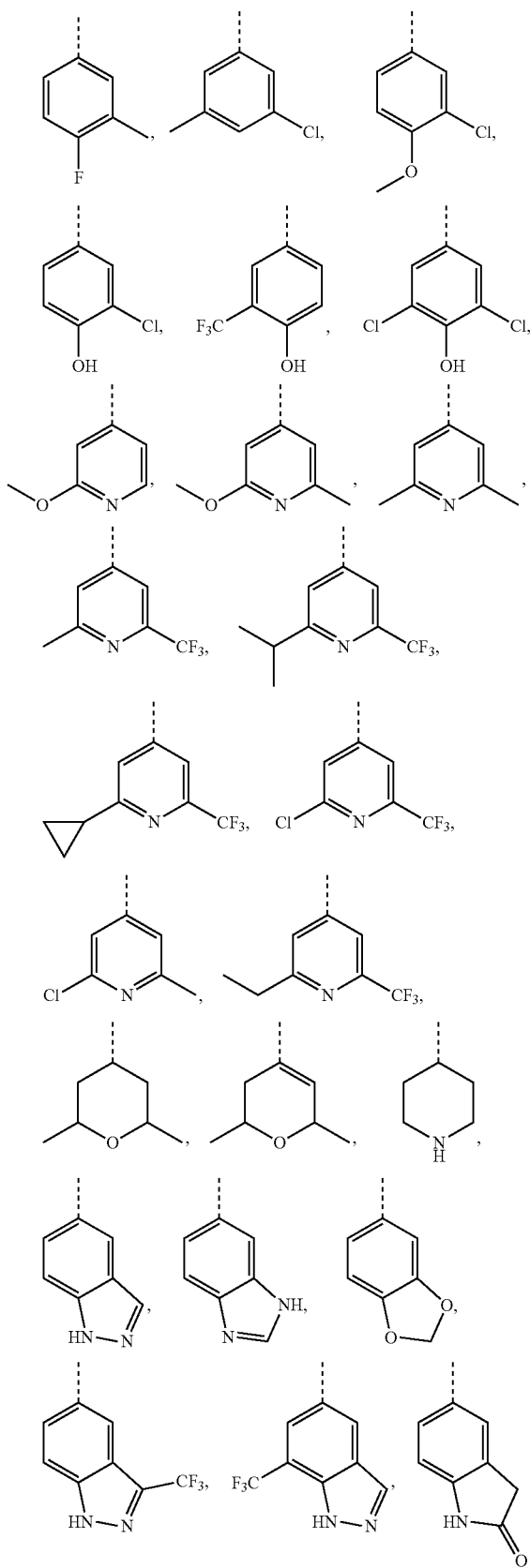

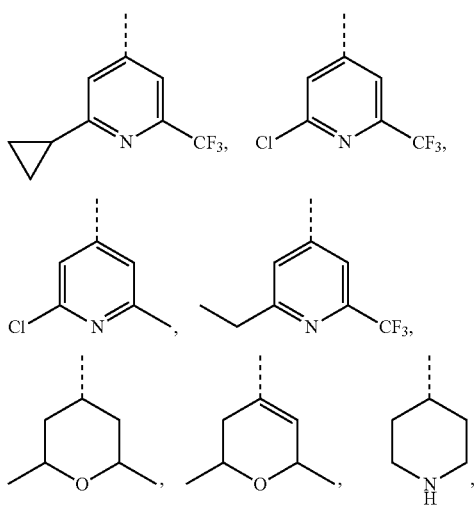

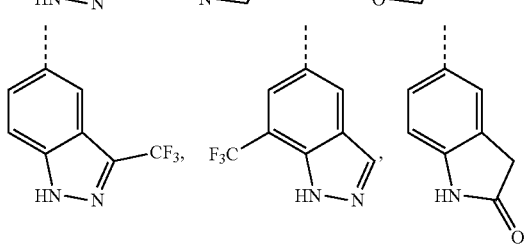

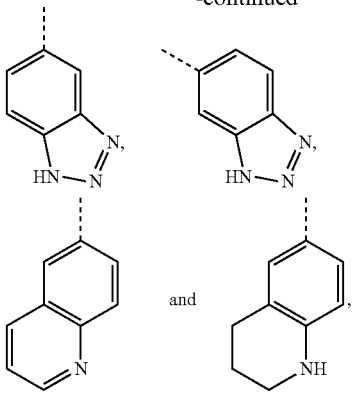

and other variables are as defined herein.

In some embodiments disclosed herein, the above ring B is selected from the group consisting of phenyl, pyridyl, imidazolyl, pyrazolyl, furyl, thienyl, thiazolyl, and other variables are as defined herein.

In some embodiments disclosed herein, the above moiety

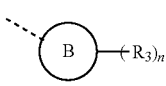

is selected from the group consisting of

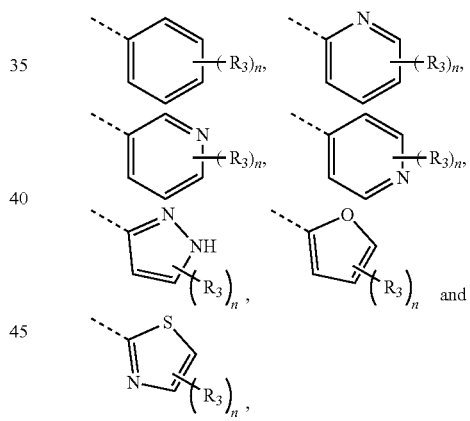

and other variables are as defined herein.

In some embodiments disclosed herein, the above moiety

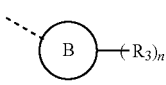

is selected from the group consisting of

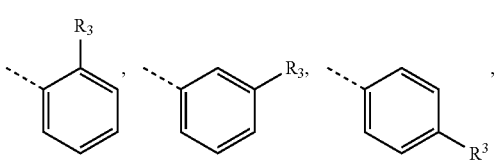

-continued

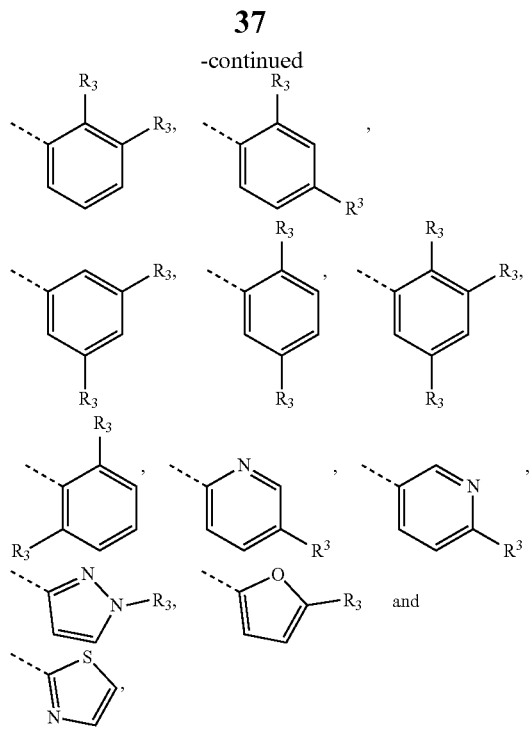

and other variables are as defined herein.

In some embodiments disclosed herein, the above moiety

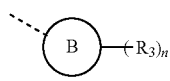

is selected from the group consisting of

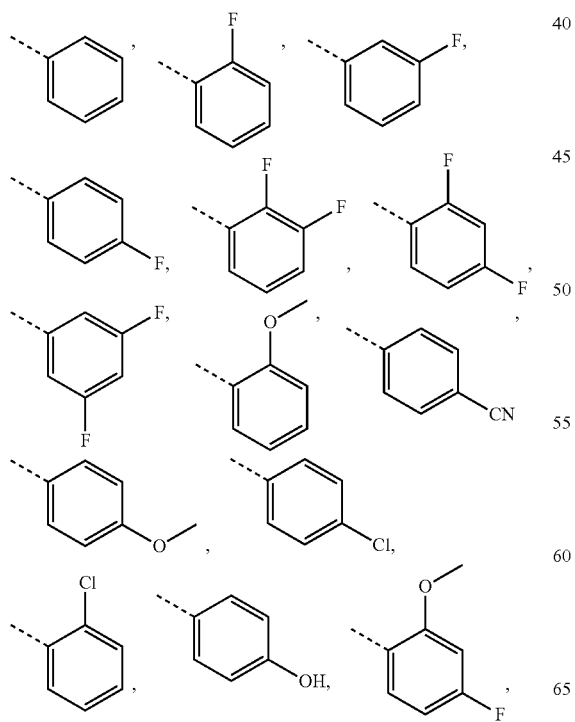

-continued

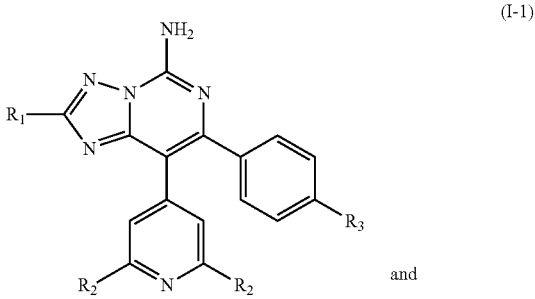

and other variables are as defined herein.

In some embodiments disclosed herein, the above compound, or a pharmaceutically acceptable salt thereof, is selected from the group consisting of

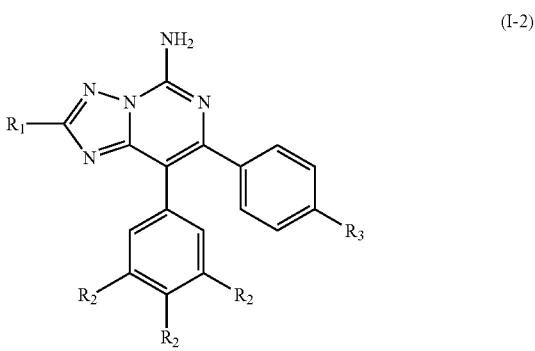

wherein $R_1$, $R_2$, $R_3$ are as defined herein.

The present disclosure provides a compound represented by formula (I), an isomer thereof or a pharmaceutically acceptable salt thereof,

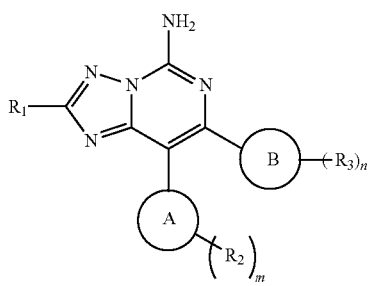

(I)

wherein

R₁ is selected from the group consisting of H, CN, COOH, and

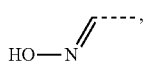

or is selected from the group consisting of $C_{1-3}$ alkyl, $C_{1-3}$ alkyl-O—$C_{1-3}$ alkyl-, $C_{3-6}$ cycloalkyl, and $C_{1-3}$ alkyl-C(=O)NH—, each of which is optionally substituted by 1, 2 or 3 R;

R₂ is each independently selected from the group consisting of H, F, Cl, Br, I, OH, NH₂, and CN, or is independently selected from the group consisting of $C_{3-6}$ cycloalkyl, $C_{1-6}$ alkyl or $C_{1-6}$ heteroalkyl, each of which is optionally substituted by 1, 2 or 3 R;

R₃ is each independently selected from the group consisting of H, F, Cl, Br, I, OH, NH₂, and CN, or is independently selected from the group consisting of $C_{1-6}$ alkyl and $C_{1-6}$ heteroalkyl, each of which is optionally substituted by 1, 2 or 3 R;

n is 0, 1, 2 or 3;

m is 0, 1, 2 or 3;

ring A is selected from the group consisting of 6- to 10-membered aryl, 5- to 10-membered heteroaryl, 5- to 10-membered heterocycloalkyl and 5- to 10-membered heterocycloalkenyl;

ring B is selected from the group consisting of phenyl and 5- to 6-membered heteroaryl;

R is selected from the group consisting of F, Cl, Br, I, OH, NH₂, and CN, or is selected from the group consisting of $C_{1-3}$ alkyl, $C_{1-3}$ alkylamino, $C_{1-3}$ alkoxy, $C_{3-6}$ cycloalkyl, $C_{3-6}$ cycloalkyl-NH—, 3- to 6-membered heterocycloalkyl, 3- to 6-membered heterocycloalkyl-O—, and phenyl, each of which is optionally substituted by 1, 2 or 3 R';

R' is selected from the group consisting of F, Cl, Br, I, OH, NH₂, and

the heteroatom or the heteroatom group of the $C_{1-6}$ heteroalkyl, 5- to 10-membered heteroaryl, 5- to 10-membered heterocycloalkyl, 3- to 6-membered heterocycloalkyl or 5- to 10-membered heterocycloalkenyl group is each independently selected from the group consisting of N, O, S, NH, —C(=O)—, —C(=O)O— and —C(=O)NH—;

The number of the heteroatom or the heteroatom group is each independently 1, 2, 3 or 4.

In some embodiments disclosed herein, the above R is selected from the group consisting of F, Cl, Br, I, OH, NH₂, and CN, or is selected from the group consisting of Me, Et,

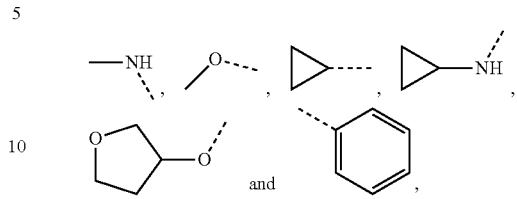

and each of which is optionally substituted by 1, 2 or 3 R', and other variables are as defined above.

In some embodiments disclosed herein, the above R is selected from the group consisting of F, Cl, Br, I, OH, NH₂, CN, Me, Et,

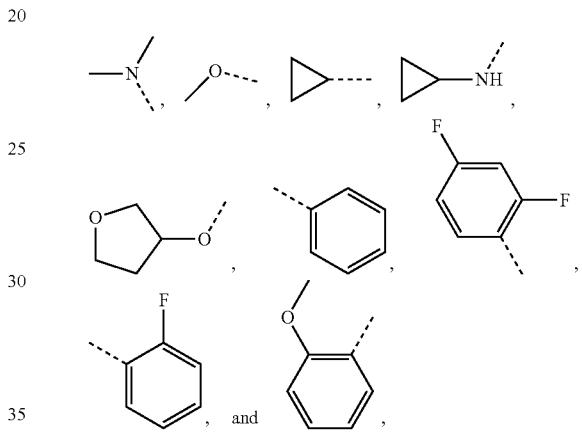

, and and other variables are as defined herein.

In some embodiments disclosed herein, the above R₁ is selected from the group consisting of H, CN, COOH, and

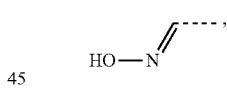

or is selected from the group consisting of Me, Et,

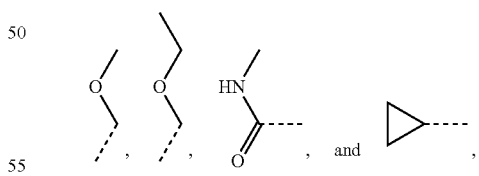

each of which is optionally substituted by 1, 2 or 3 R, and other variables are as defined above.

In some embodiments disclosed herein, the above R₁ is selected from the group consisting of H, CN, COOH,

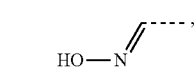

Me, Et, CF$_3$,

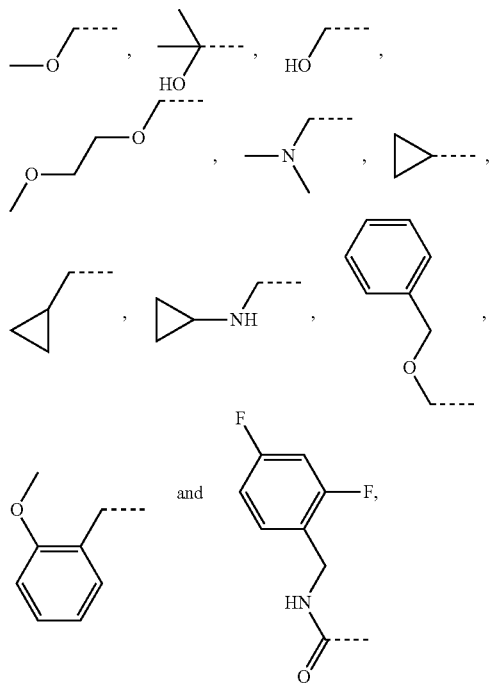

and other variables are as defined herein.

In some embodiments disclosed herein, the above R$_2$ is each independently selected from the group consisting of H, F, Cl, Br, I, OH, NH$_2$, and CN, or is independently selected from the group consisting of C$_{3-6}$ cycloalkyl, C$_{1-3}$ alkyl and C$_{1-3}$ alkoxy, each of which is optionally substituted by 1, 2 or 3 R, and other variables are as defined above.

In some embodiments disclosed herein, the above R$_2$ is each independently selected from the group consisting of H, F, Cl, Br, I, OH, NH$_2$, CN, Me, Et, CF$_3$,

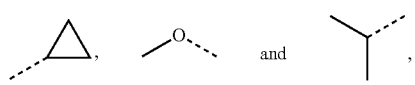

and other variables are as defined herein.

In some embodiments disclosed herein, the above R$_3$ is each independently selected from the group consisting of H, F, Cl, Br, I, OH, NH$_2$, and CN, or is independently selected from the group consisting of C$_{1-3}$ alkyl and C$_{1-3}$ alkoxy, each of which is optionally substituted by 1, 2 or 3 R, and other variables are as defined above.

In some embodiments disclosed herein, the above R$_3$ is each independently selected from the group consisting of H, F, Cl, Br, I, OH, NH$_2$, CN, Me, Et, CF$_3$ and

and other variables are as defined herein.

In some embodiments disclosed herein, the above ring A is selected from the group consisting of phenyl, pyridyl, tetrahydropyranyl, 3,6-dihydro-2H-pyranyl, piperidinyl, 1,2,3,6-tetrahydropyridyl, 1H-indolyl, 1H-indazolyl, 1H-benzo[d]imidazolyl, benzo[d][1,3]dioxolyl, indolin-2-onyl, 1H-benzo[d][1,2,3]triazolyl, quinolinyl and 1,2,3,4-tetrahydroquinolinyl, and other variables are as defined herein.

In some embodiments disclosed herein, the above moiety

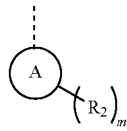

is selected from the group consisting of

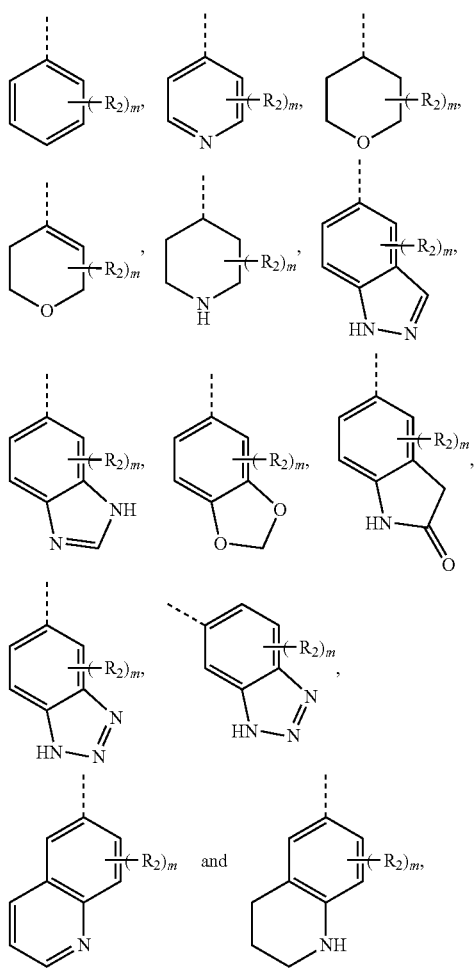

and other variables are as defined herein.

In some embodiments disclosed herein, the above moiety

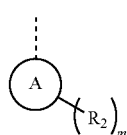

43
is selected from the group consisting of
44
is selected from the group consisting of
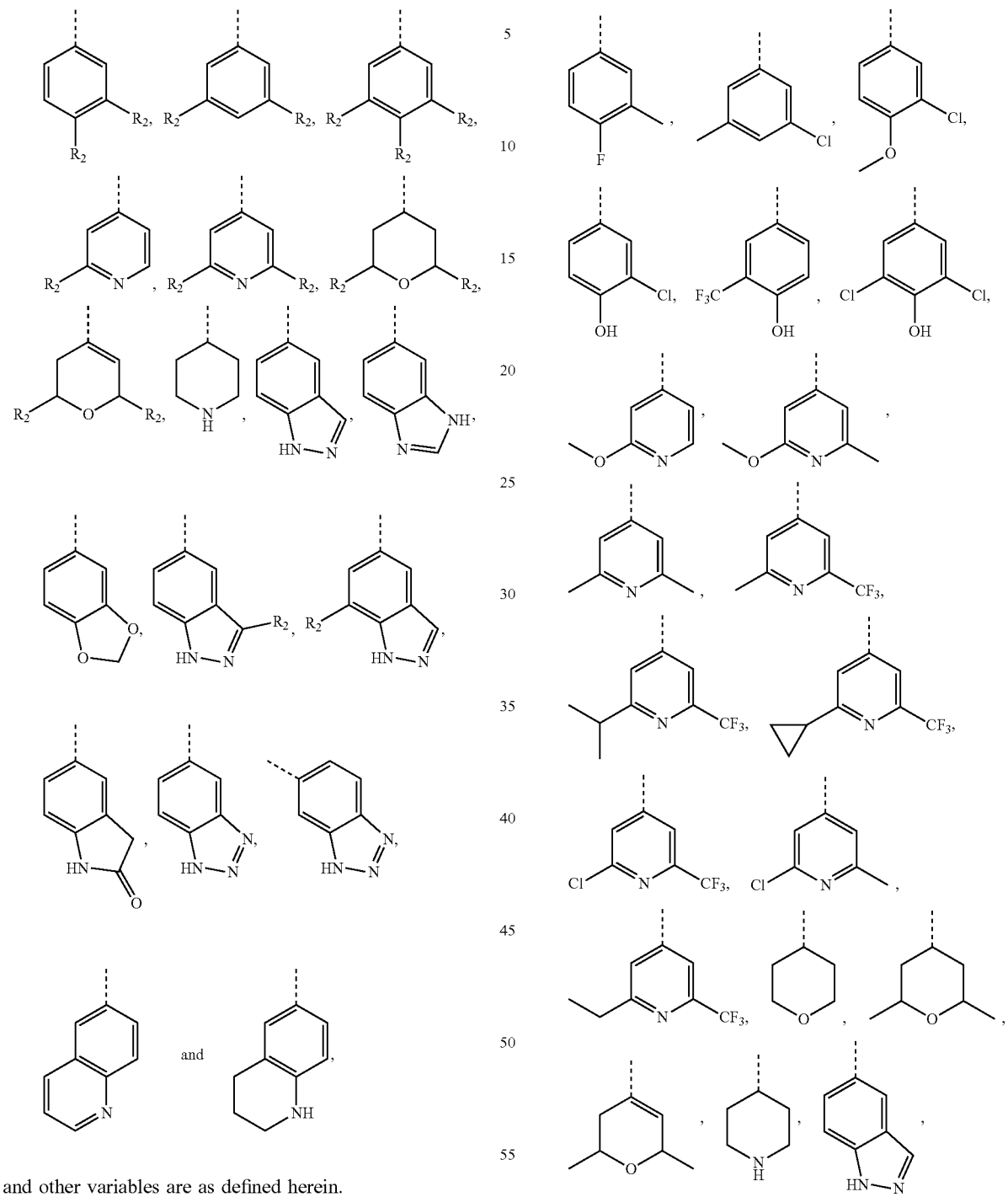
and other variables are as defined herein.
In some embodiments disclosed herein, the above moiety
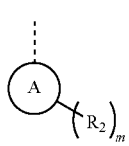

-continued

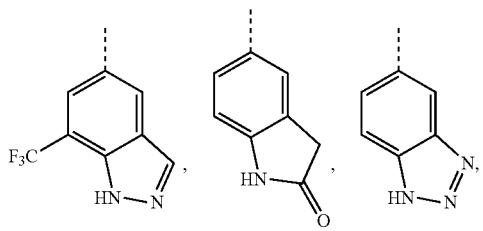

and other variables are as defined herein.

In some embodiments disclosed herein, the above ring B is selected from the group consisting of phenyl, pyridyl, imidazolyl, pyrazolyl, furyl, thienyl, thiazolyl, and other variables are as defined herein.

In some embodiments disclosed herein, the above moiety

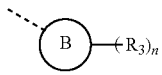

is selected from the group consisting of

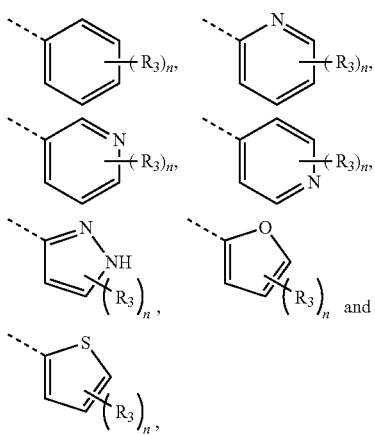

and other variables are as defined herein.

In some embodiments disclosed herein, the above moiety

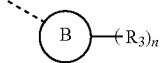

is selected from the group consisting of

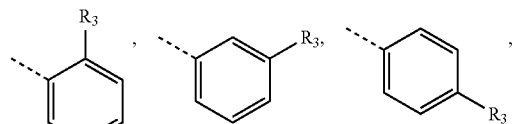

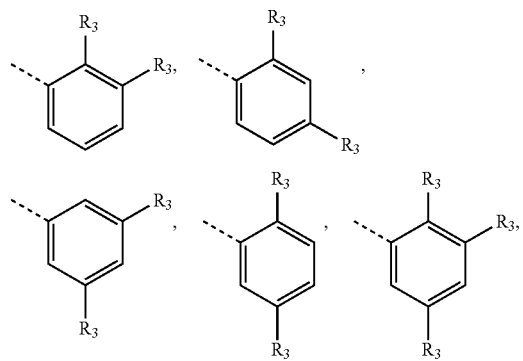

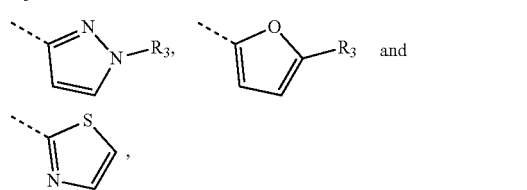

and other variables are as defined herein.

In some embodiments disclosed herein, the above moiety

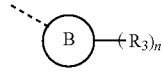

is selected from the group consisting of

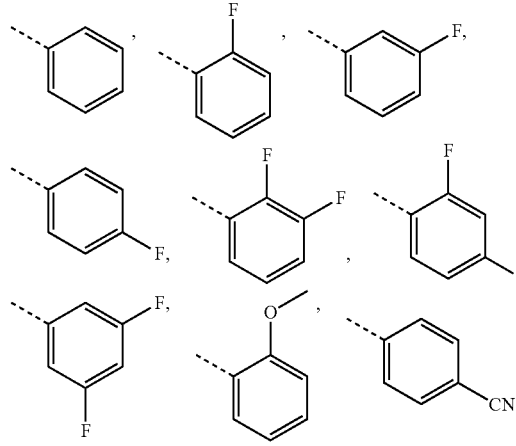

-continued

[structures: 4-methoxyphenyl, 4-chlorophenyl, 2-chlorophenyl, 4-hydroxyphenyl, 2-methoxy-4-fluorophenyl, 2-methoxy-4-fluorophenyl, 2-methoxy-4,5-difluorophenyl, 2-pyridyl, 3-pyridyl, 4-pyridyl, N-pyrazolyl, 2-furyl, 5-methyl-2-furyl, and 2-thiazolyl]

and other variables are as defined herein.

In some embodiments disclosed herein, the above compound, an isomer thereof, or a pharmaceutically acceptable salt thereof, is selected from the group consisting of (I-1)

[structure with R₁, R₂, R₂, R₃]

and (I-2)

[structure with R₁, R₂, R₂, R₂, R₃]

wherein
R₁, R₂, R₃ are as defined herein.

The present disclosure also includes some embodiments that are obtained by combining any of the above definitions for the above variables.

The present disclosure provides a compound represented by the following formula, an isomer thereof or a pharmaceutically acceptable salt thereof, which is selected from the group consisting of

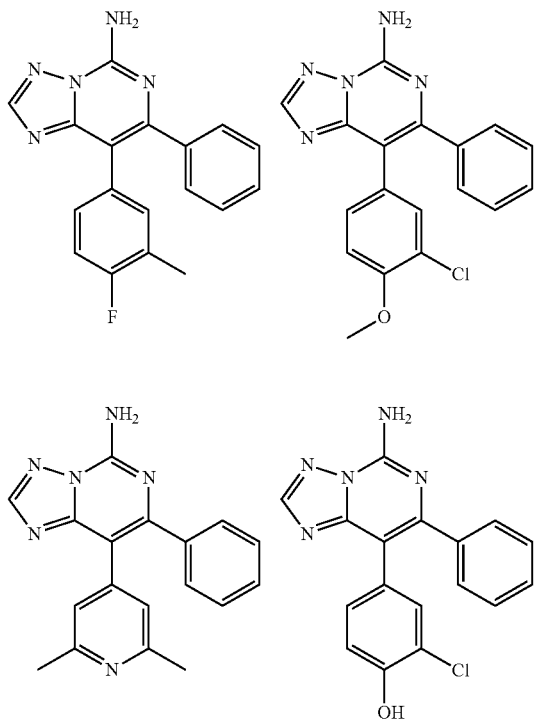

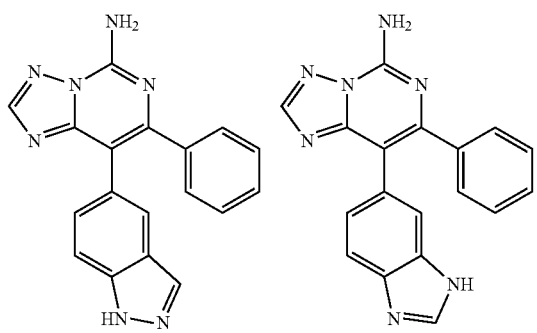

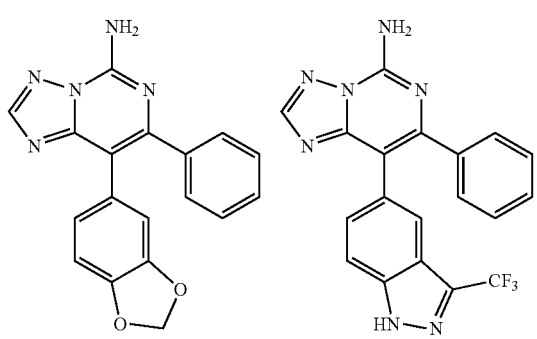

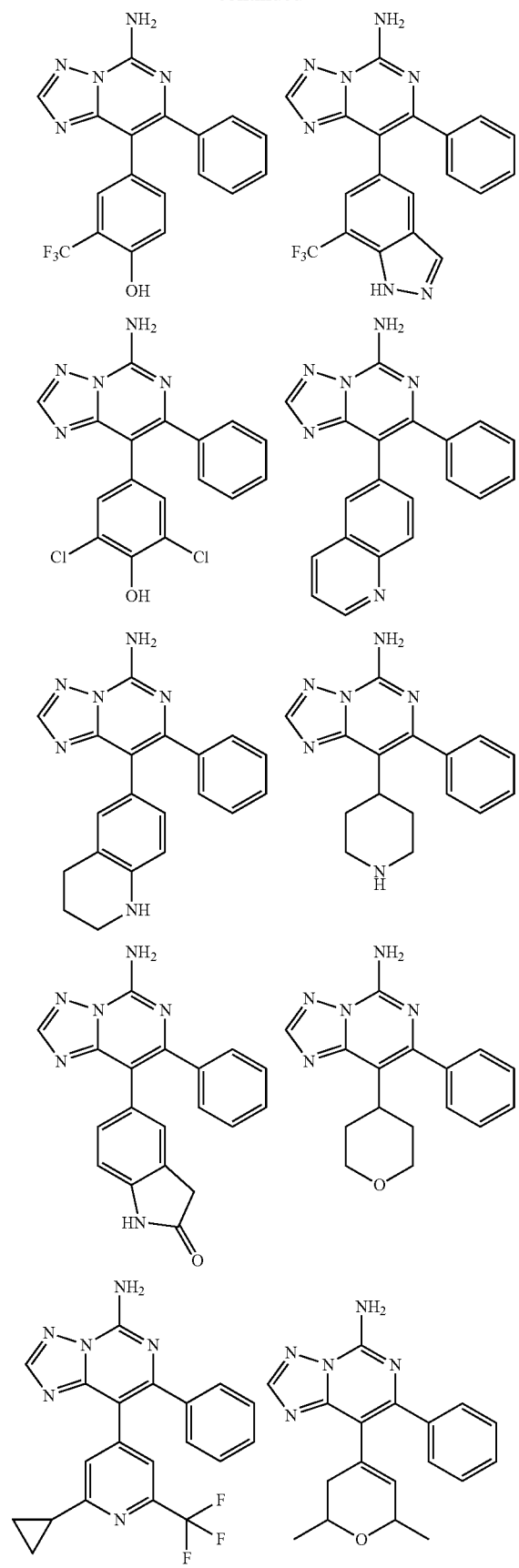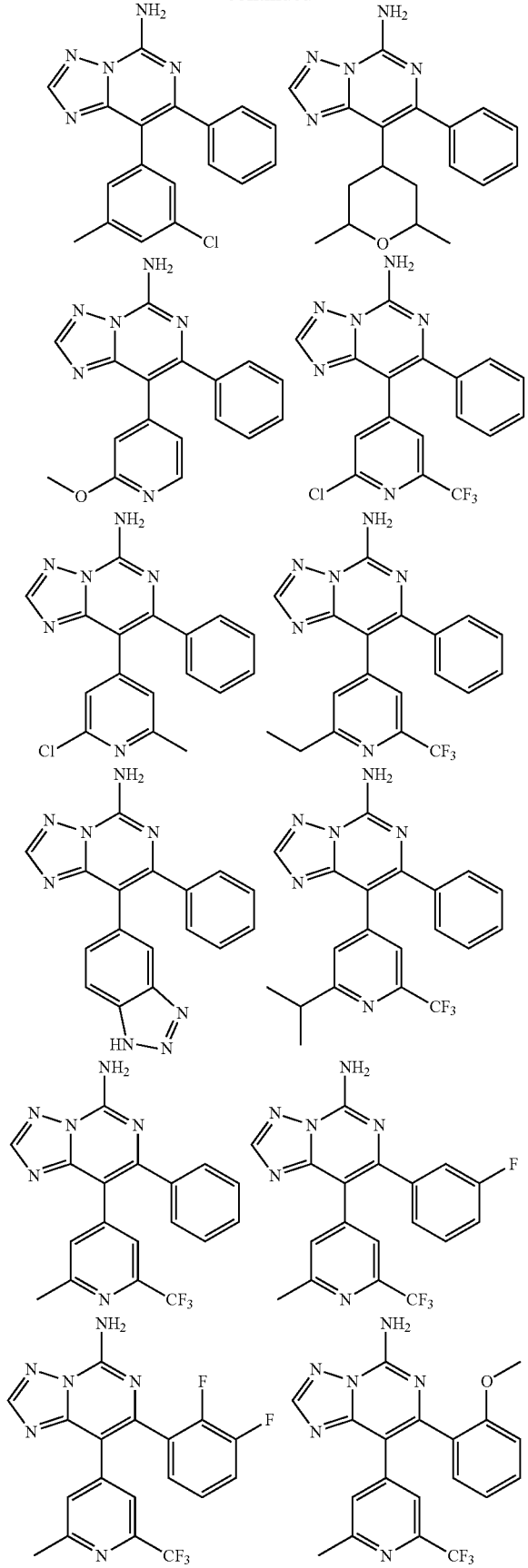

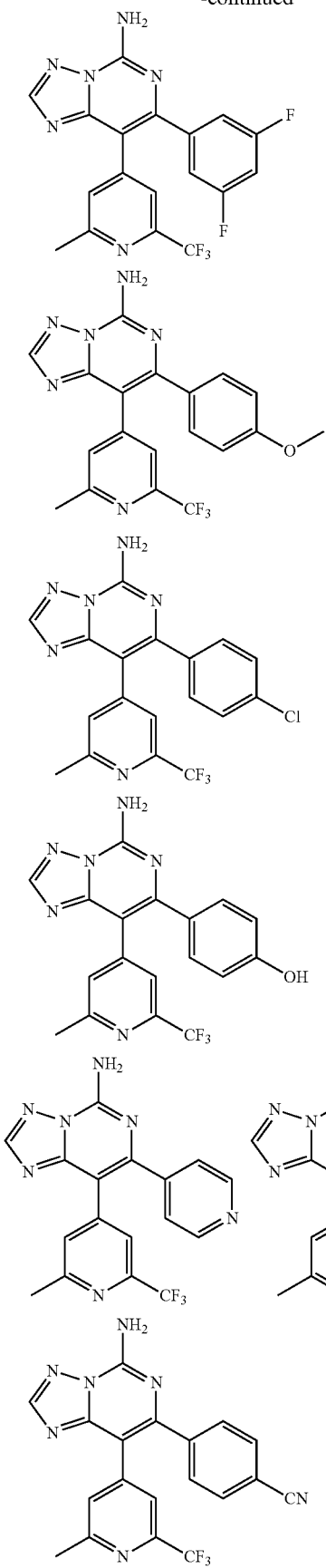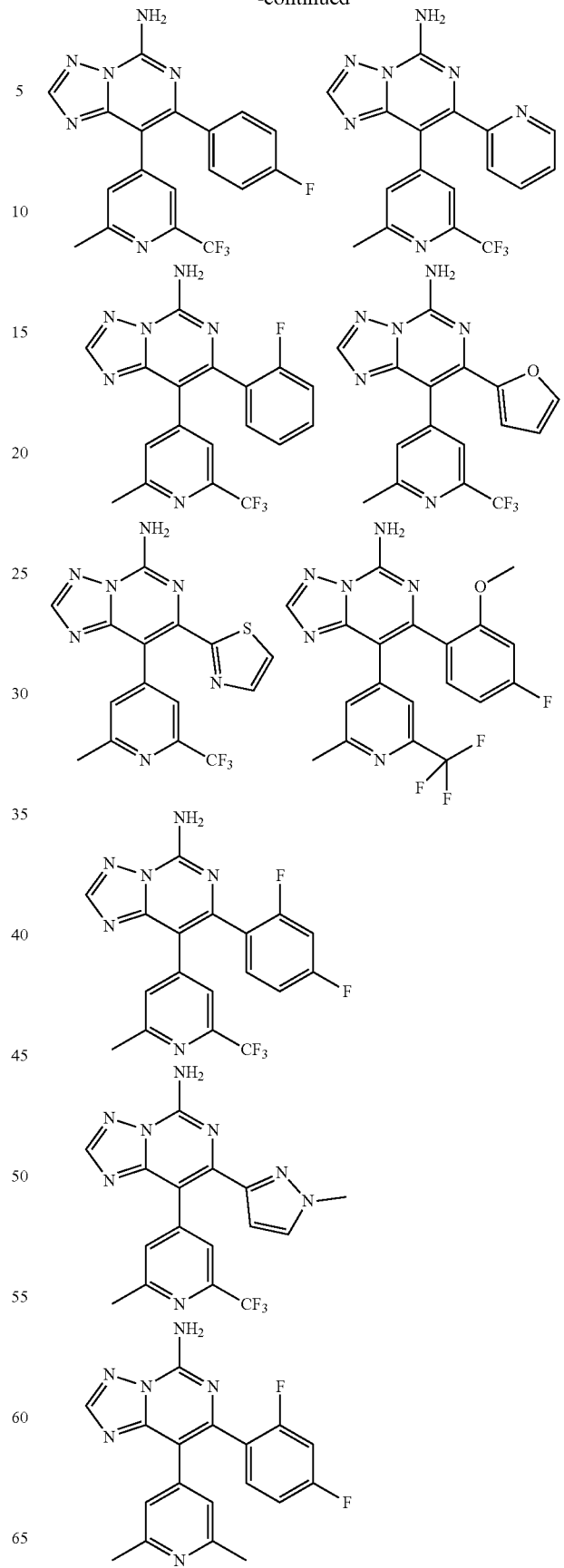

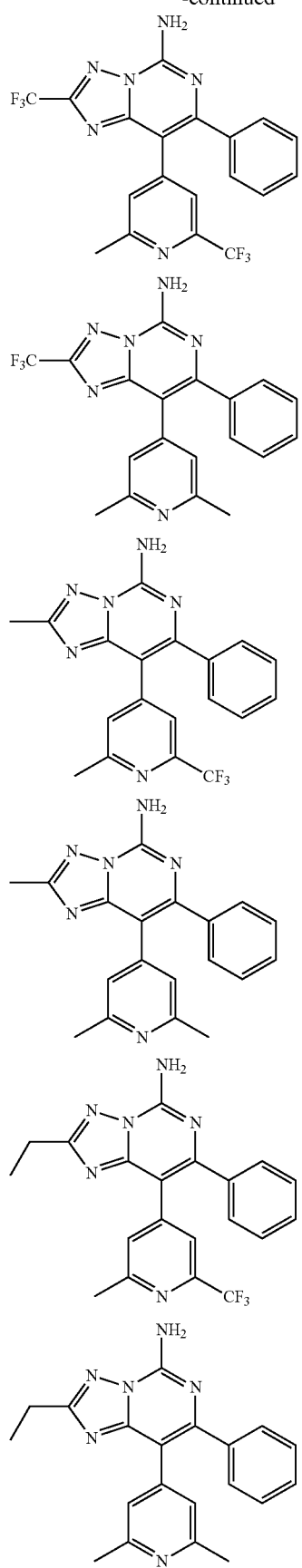
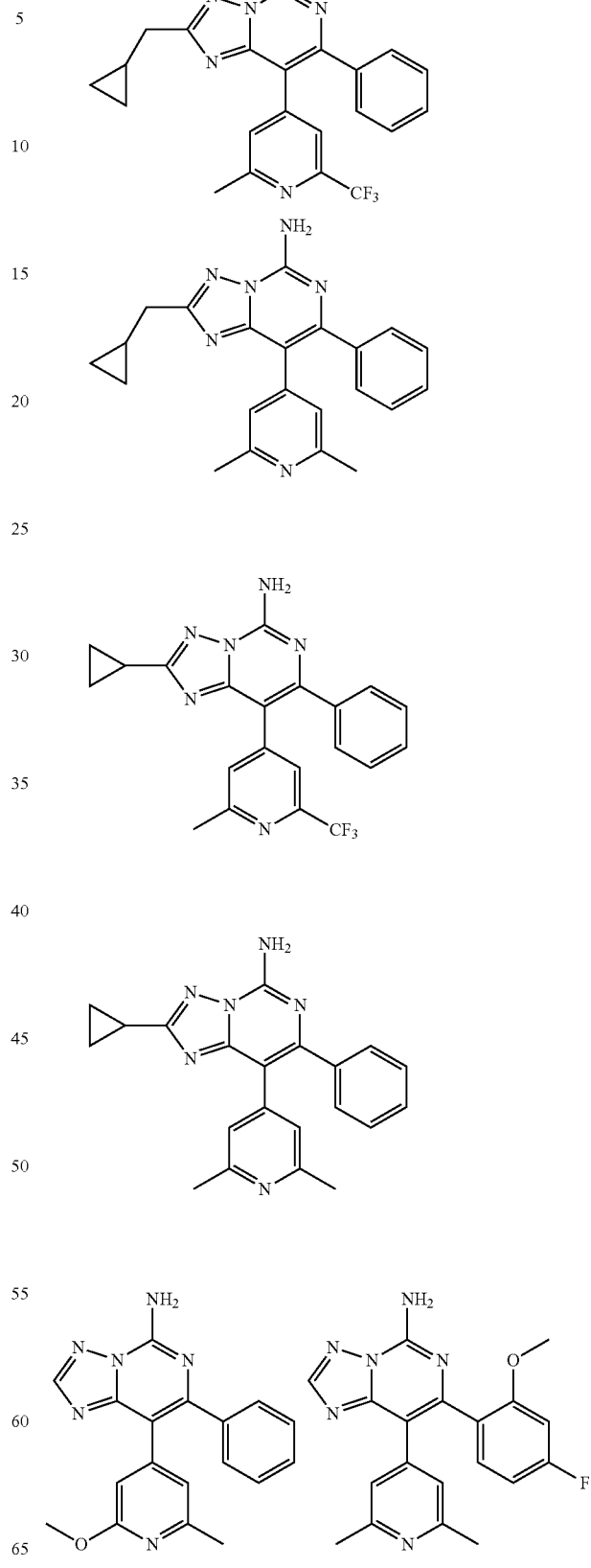

55
-continued
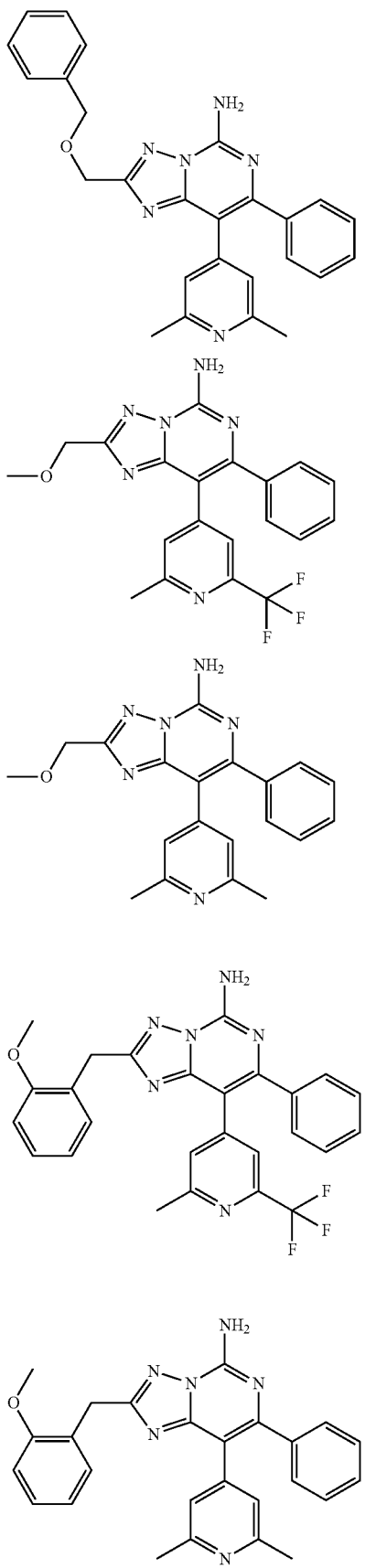
56
-continued
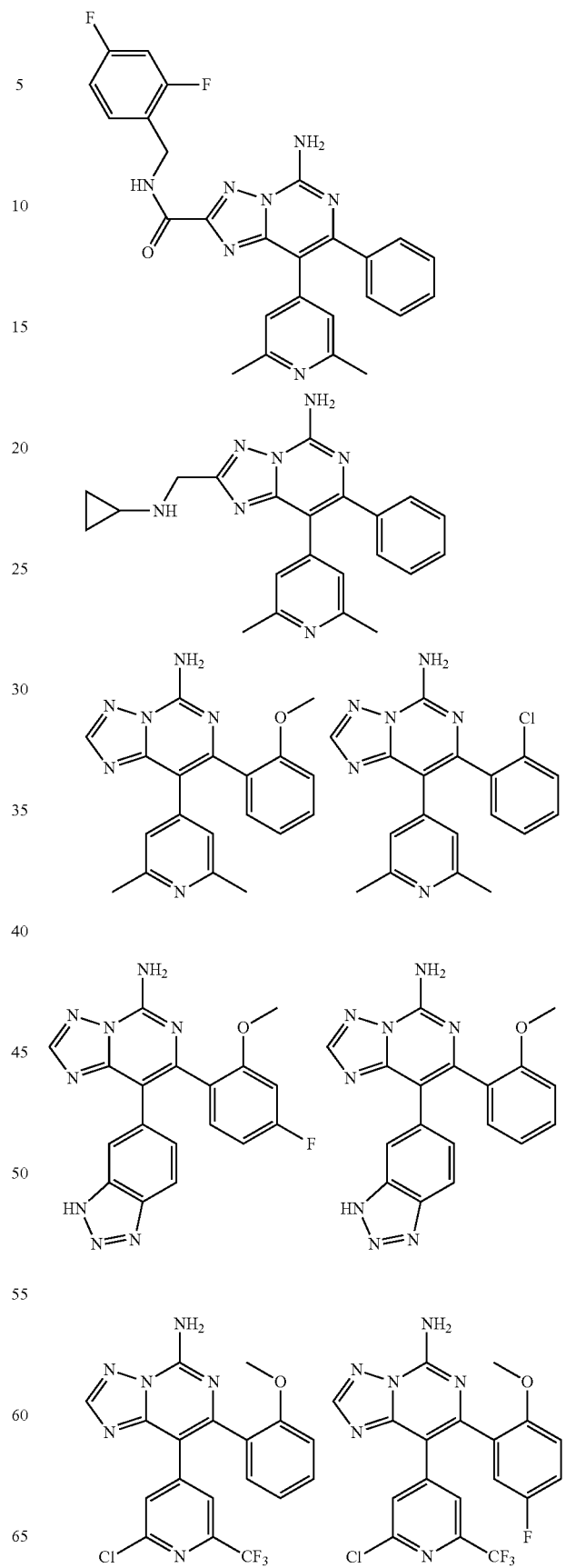

-continued
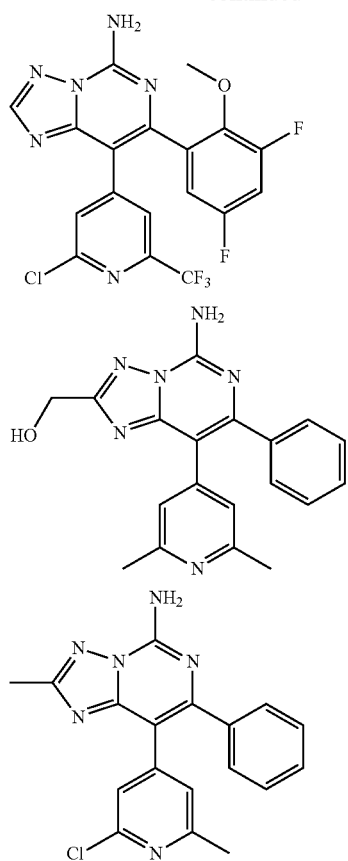
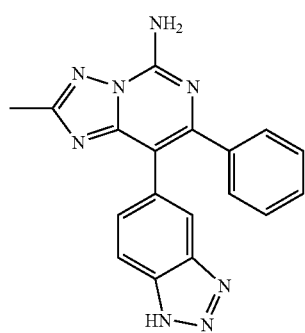
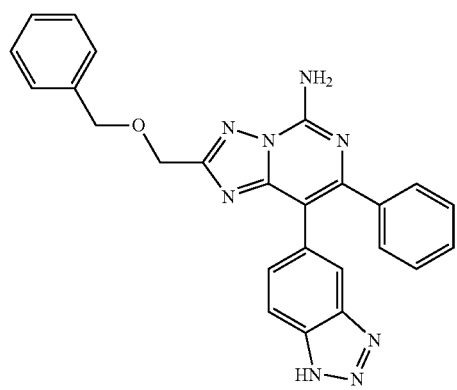
-continued
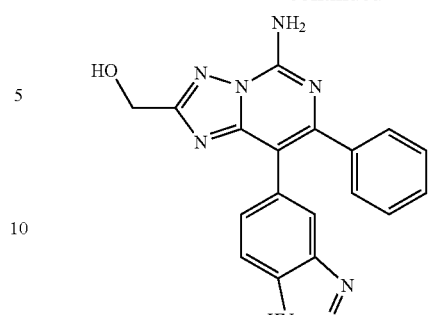
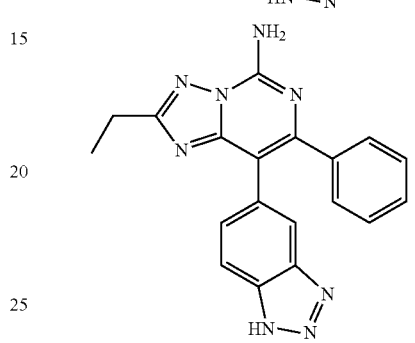
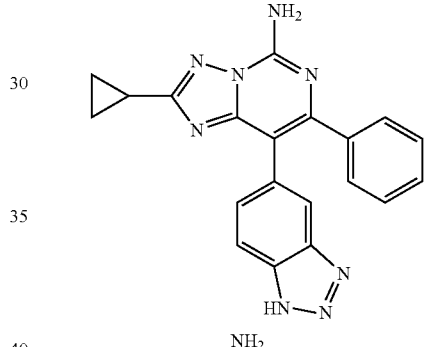
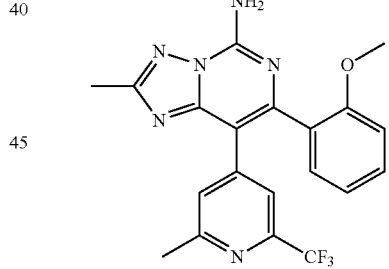
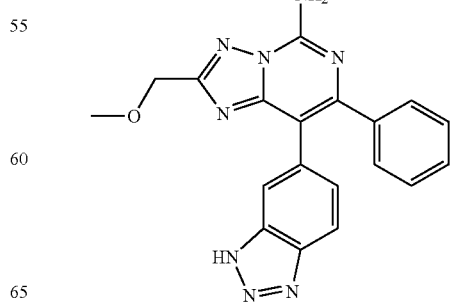

-continued
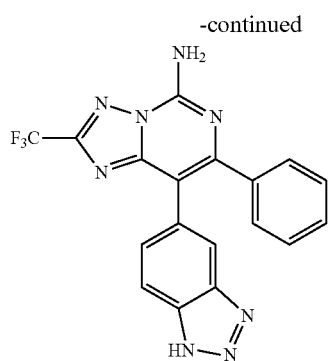
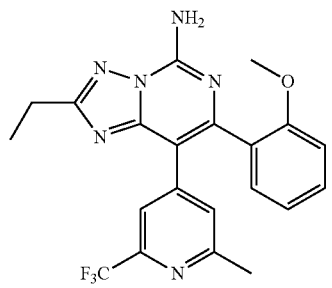
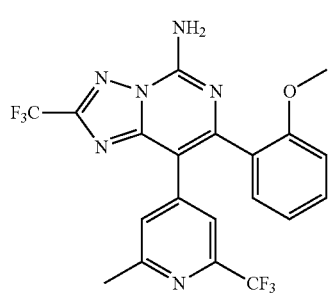
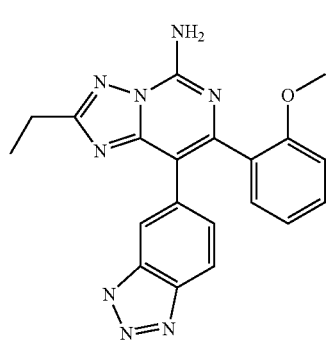
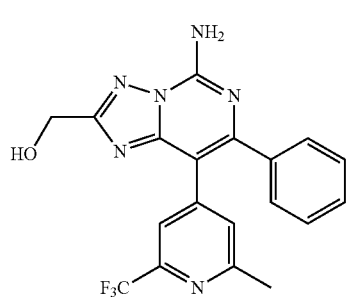
-continued
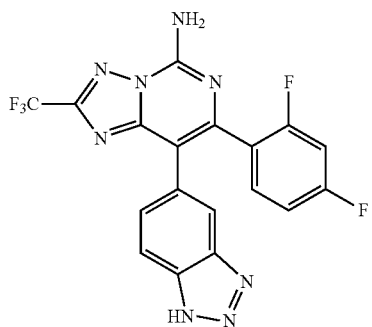
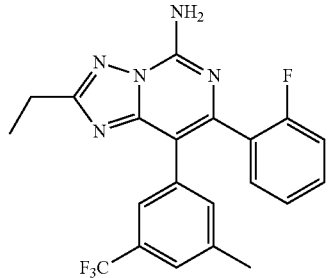
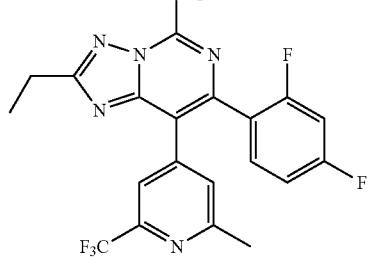
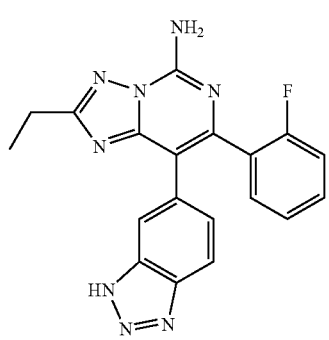
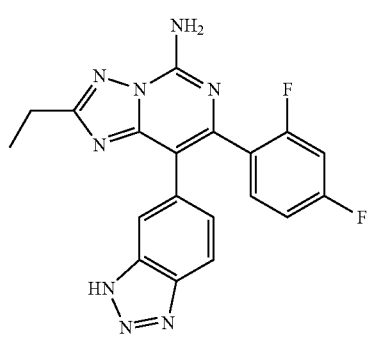

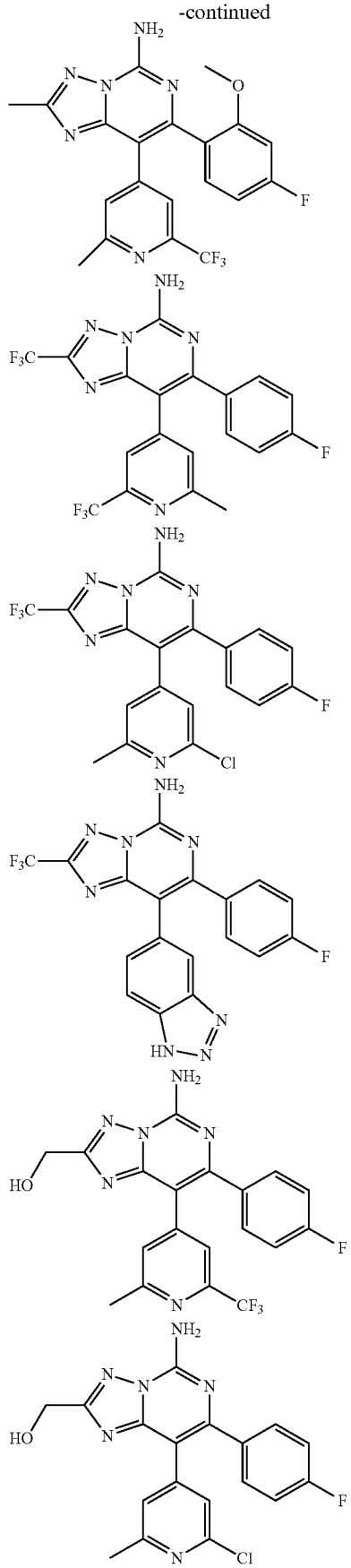
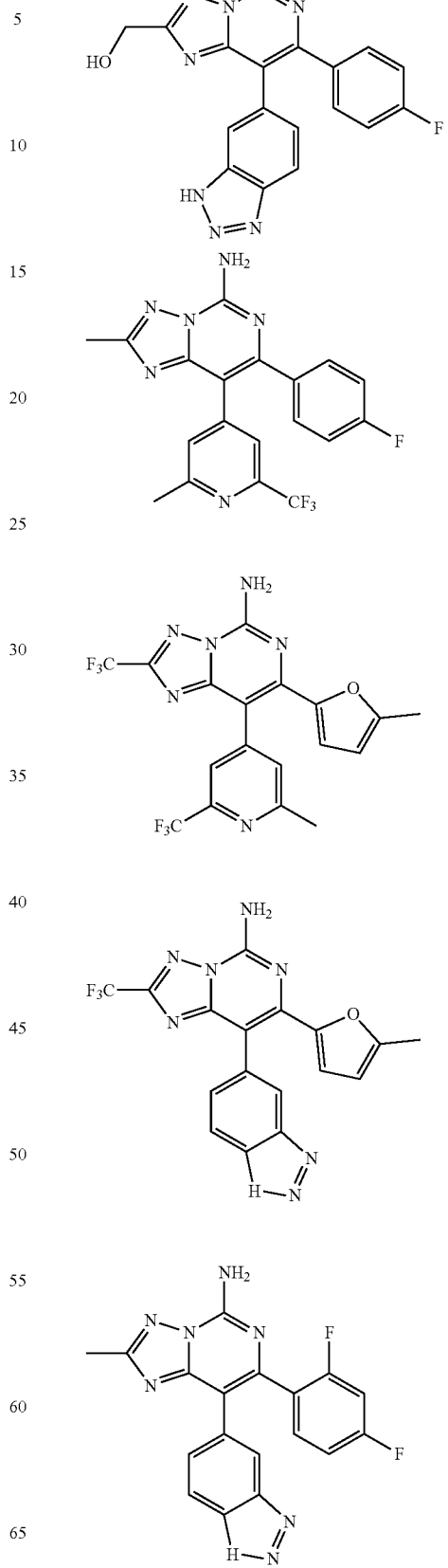

63
-continued
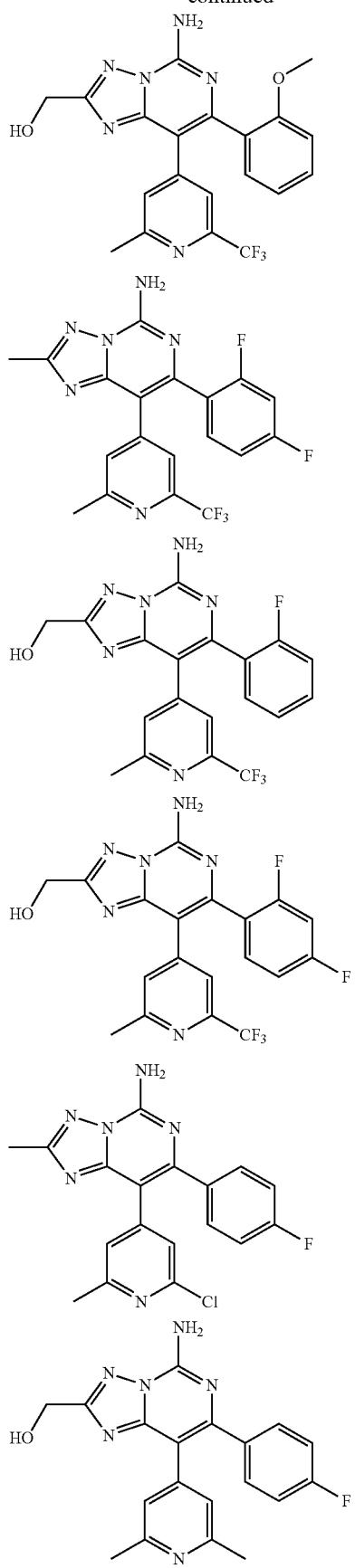
64
-continued
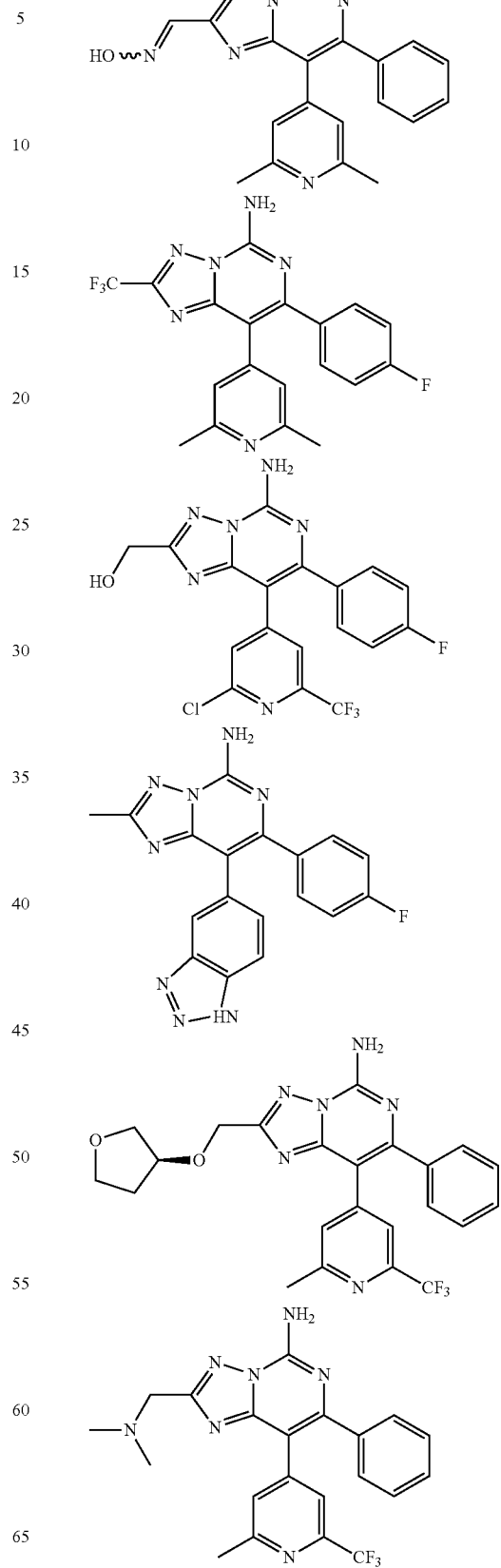

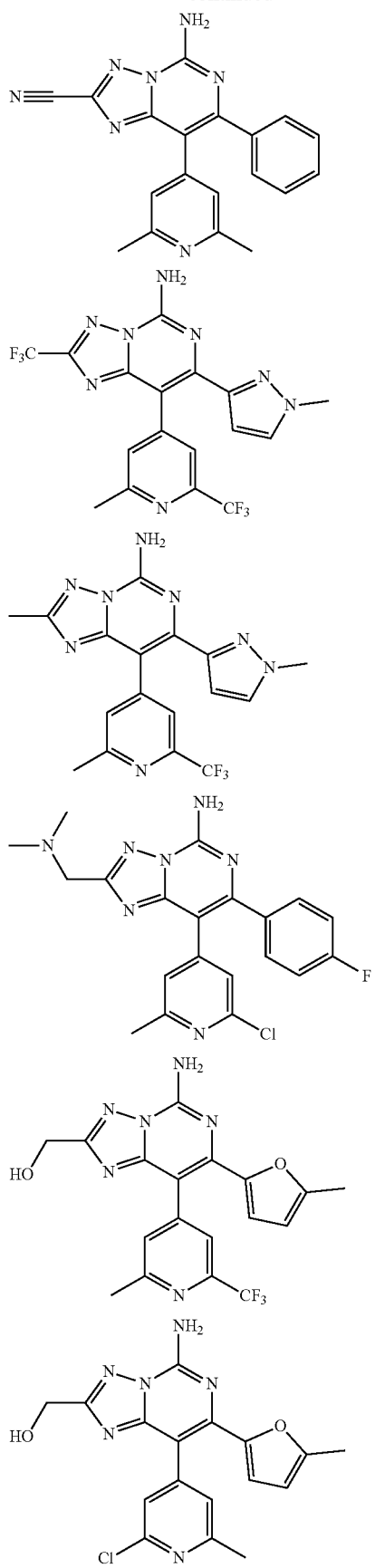
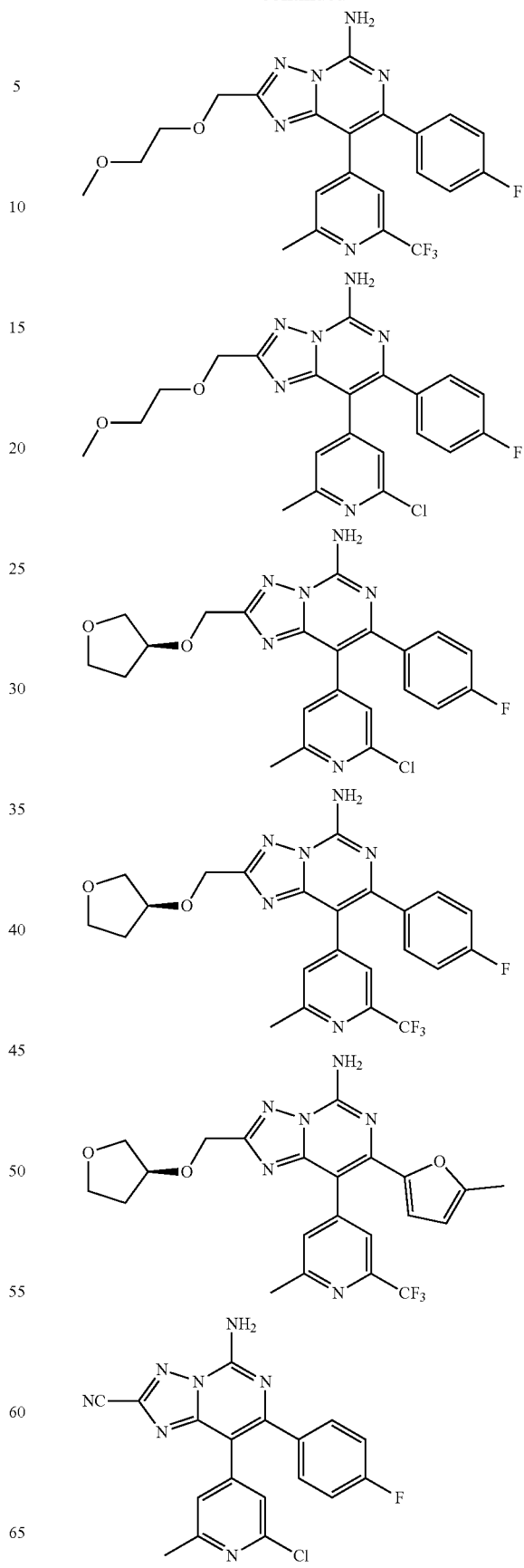

-continued

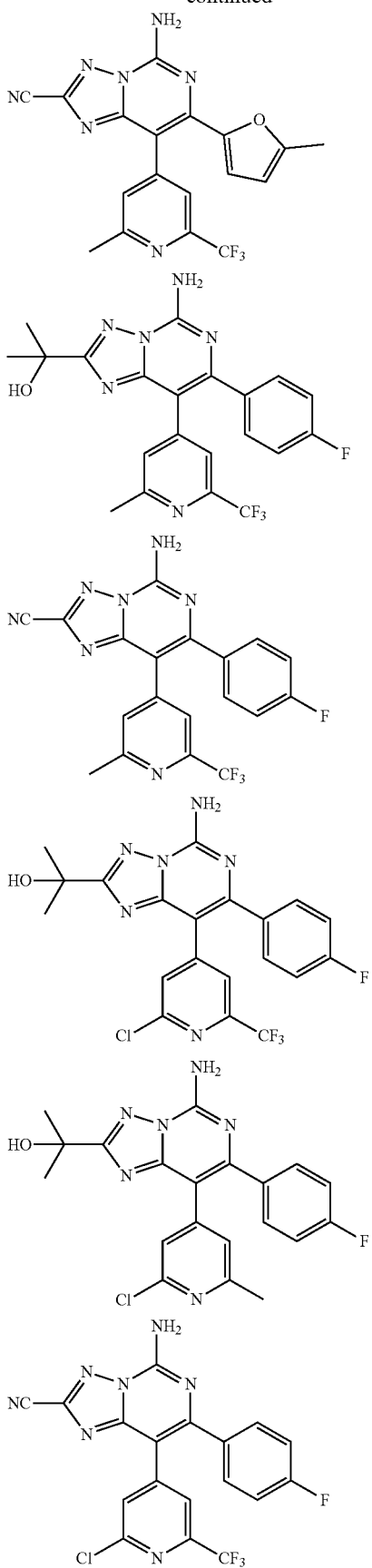

-continued

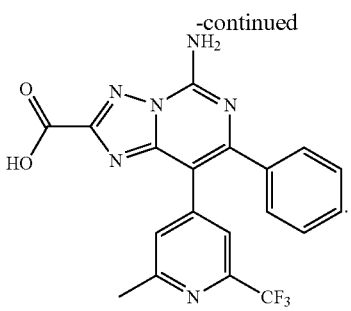

The present disclosure also provides a pharmaceutical composition including a therapeutically effective amount of the above compound, an isomer thereof, or a pharmaceutically acceptable salt thereof, and pharmaceutically acceptable carrier(s).

The present disclosure also provides use of the above compound, an isomer thereof or a pharmaceutically acceptable salt thereof in the preparation of a medicament for treating a disease associated with $A_{2A}$ receptor.

The present disclosure also provides use of the above pharmaceutical composition in the preparation of a medicament for treating a disease associated with $A_{2A}$ receptor.

Technical Effects

The present disclosure synthesizes a compound of formula (I) as a novel class of adenosine $A_{2A}$ antagonist, which is used alone or in combination with an antibody for tumor immunotherapy. The solubility of compounds is increased in the present disclosure while the pharmacokinetic profile is significantly improved.

Definitions and Terms

Unless otherwise specified, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound disclosed herein that is prepared by reacting the compound having a specific substituent disclosed herein with a relatively non-toxic acid or base. When the compound disclosed herein contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound disclosed herein contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds disclosed herein contain both basic and acidic functional groups and can be converted to any base or acid addition salt.

The pharmaceutically acceptable salt disclosed herein can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

In addition to the salt form, the compound provided herein also exists in prodrug form. The prodrug of the compound described herein is the compound that readily undergoes chemical change under physiological condition to be converted into the compound disclosed herein. Additionally, the prodrug can be converted to the compound disclosed herein by a chemical or biochemical method in vivo environment.

Certain compounds disclosed herein can exist in an unsolvated form or a solvated form, including a hydrated form. Generally, the solvated form is equivalent to the unsolvated form, and both are encompassed within the scope disclosed herein.

The compound disclosed herein may be present in a specific geometric or stereoisomeric form. The present disclosure contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope disclosed herein. The substituent such as alkyl may have an additional asymmetric carbon atom. All these isomers and mixtures thereof are encompassed within the scope disclosed herein.

Unless otherwise specified, the term "enantiomer" or "optical isomer" refers to stereoisomers that are in a mirrored relationship with each other.

Unless otherwise specified, the term "cis-trans isomer" or "geometric isomer" is produced by the inability of a double bond or a single bond between ring-forming carbon atoms to rotate freely.

Unless otherwise specified, the term "diastereomer" refers to a stereoisomer in which two or more chiral centers of are contained in a molecule and is in a non-mirrored relationship between molecules.

Unless otherwise specified, "(D)" or "(+)" means dextroisomer, "(L)" or "(−)" means levoisomer, and "(DL)" or "(±)" means racemate.

Unless otherwise specified, a wedged solid bond ( ) and a wedged dashed bond ( ) indicate the absolute configuration of a stereocenter; a straight solid bond ( ) and a straight dashed bond ( ) indicate the relative configuration of a stereocenter; a wavy line ( ) indicates a wedged solid bond ( ) or a wedged dashed bond ( ); or a wavy line ( ) indicates a straight solid bond ( ) and a straight dashed bond ( ).

The compounds disclosed herein may be present in a particular form. Unless otherwise specified, the terms "tautomer" or "tautomeric form" means that different functional groups are in dynamic equilibrium at room temperature and can be rapidly converted into each other. If tautomers are possible (as in solution), a chemical equilibrium of tautomers can be achieved. For example, proton tautomers (also known as prototropic tautomers) include interconversions by proton transfer, such as keto-enol isomerization and imine-enamine isomerization. Valence tautomers include interconversions by recombination of some bonding electrons. A specific example of keto-enol tautomerization is interconversion between two tautomers pentane-2,4-dione and 4-hydroxypent-3-en-2-one.

Unless otherwise specified, the term "enriched in one isomer", "isomer enriched", "enriched in one enantiomer" or "enantiomeric enriched" means that the content of one isomer or enantiomer is less than 100%, and the content of the isomer or enantiomer is 60% or more, or 70% or more, or 80% or more, or 90% or more, or 95% or more, or 96% or more, or 97% or more, 98% or more, 99% or more, 99.5% or more, 99.6% or more, 99.7% or more, 99.8% or more, or 99.9% or more.

Unless otherwise specified, the term "isomer excess" or "enantiomeric excess" refers to the difference between the relative percentages of two isomers or two enantiomers. For example, if one isomer or enantiomer is present in an amount of 90% and the other isomer or enantiomer is present in an amount of 10%, the isomer or enantiomeric excess (ee value) is 80%.

Optically active (R)- and (S)-isomer, or D and L isomer can be prepared using chiral synthesis or chiral reagents or other conventional techniques. If one kind of enantiomer of certain compound disclosed herein is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (for example, carbamate generated from amine).

The compounds disclosed herein may contain an unnatural proportion of atomic isotopes at one or more of the atoms that make up the compounds. For example, a compound may be labeled with a radioisotope such as tritium ($^3$H), iodine-125 ($^{125}$I) or C-14($^{14}$C). For another example, hydrogen can be replaced by heavy hydrogen to form a deuterated drug. The bond between deuterium and carbon is stronger than that between ordinary hydrogen and carbon. Compared with undeuterated drugs, deuterated drugs have advantages of reduced toxic side effects, increased drug stability, enhanced efficacy, and prolonged biological half-life of drugs. All changes in the isotopic composition of compounds disclosed herein, regardless of radioactivity, are included within the scope of the present disclosure.

The term "pharmaceutically acceptable carrier" refers to any formulation or carrier medium that is capable of delivering an effective amount of an active substance disclosed herein, which does not interfere with the biological activity of an active substance, and has no toxic side effects to the host or patient. Representative carriers include water, oil, vegetables, minerals, cream bases, lotion bases, ointment bases and the like. These bases include suspending agents, tackifiers, transdermal enhancers, etc. Their formulations are well known to those skilled in cosmetic or topical pharmaceutical arts.

The term "excipient" generally refers to the carrier, diluent and/or vehicle required to formulate an effective pharmaceutical composition.

The term "effective amount" or "therapeutically effective amount" with respect to a pharmaceutically or pharmacologically active agent refers to a sufficient amount of a drug or agent that is non-toxic but that can achieve the desired effect. For oral dosage forms in the present disclosure, an "effective amount" of an active substance in a composition refers to the amount required to achieve the desired effect when it is used in combination with another active substance in the composition. The determination of the effective amount will vary from person to person, depending on the age and general condition of the recipient, and also on the particular active substance. A suitable effective amount in a case can be determined by one skilled in the art based on routine experimentation.

The term "active ingredient", "therapeutic agent", "active substance" or "active agent" refers to a chemical entity that is effective in treating a target disorder, disease or condition.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted by a substituent, including deuterium and hydrogen variants, as long as the valence of the specific atom is normal and the substituted compound is stable. When the substituent is oxo (i.e. =O), it means two hydrogen atoms are substituted. Positions on an aromatic ring cannot be substituted by oxo. The term "optionally substituted" means an atom can be substituted by a substituent or not, unless otherwise specified, the species and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variable is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a substituent can be linked to more than one atoms on a ring, such substituent can be bonded to any atom on the ring. For example, a moiety

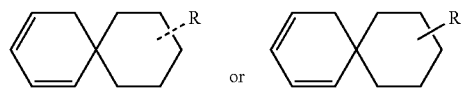

indicates that the substituent R can be positioned at any position on the cyclohexyl group or cyclohexadiene. When an enumerative substituent does not indicate through which atom it is linked to the substituted group, such substituent can be bonded through any of its atoms. For example, a pyridyl group as a substituent may be linked to the substituted group through any one of carbon atoms on the pyridine ring. When an enumerative linking group does not indicate its linking direction, its linking direction is arbitrary. For example, when the linking group L in

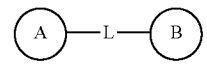

is -M-W-, the -M-W- can be linked to the ring A and the ring B in the same direction as the reading order from left to right to constitute

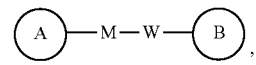, or can be linked to the ring A and the ring B in the reverse direction as the reading order from left to right to constitute

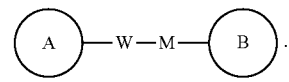.

A combination of the linking groups, substituents and/or variants thereof is allowed only when such combination can result in a stable compound.

Unless otherwise specified, the term "hetero" represents a heteroatom or a heteroatom group (e.g., an atom group containing a heteroatom), including the atom except carbon (C) and hydrogen (H) and the atom group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O)—, —S(=O)$_2$—, and the group consisting of —C(=O)N(H)—, —N(H)—, —C(=NH)—, —S(=O)$_2$ N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a ring assembly, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidyl; on the other hand, the term "5-7 membered heterocycloalkyl ring" includes pyridyl and piperidyl, but excluding phenyl. The term "ring" also includes a ring system containing at least one ring, wherein each ring independently meets the above definition.

Unless otherwise specified, the term "heterocycle" or "heterocyclyl" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from the group consisting of N, O and S, wherein any of the above heterocycle can be fused to a benzene ring to form a bicyclic ring. Nitrogen and sulfur heteroatoms can optionally be oxidized (i.e., NO and $S(O)_p$, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from the group consisting of N, O and S. Nitrogen atom can be substituted or unsubstituted (i.e., N or NR, wherein R is H or other substituents already defined herein). Nitrogen and sulfur heteroatoms may optionally be oxidized (i.e., NO and $S(O)_p$, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuryl, benzomercaptofuryl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-bltetrahydrofuryl, furyl, furazanyl, imidazolidinyl, imidazolinyl, imidazolyl, 1H-indazolyl, indolenyl, indolinyl, indolizinyl, indolyl, 3H-indolyl, isobenzofuryl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1H-1, 2,3-triazolyl, 2H-1,2,3-triazolyl, 1H-1,2,4-triazolyl, 4H-1,2, 4-triazolyl and xanthenyl. Fused-ring compounds and spiro compounds are also included.

Unless otherwise specified, the term "hydrocarbyl" or its hyponyms (e.g. alkyl, alkenyl, alkynyl, and aryl, etc.), by itself or as part of another substituent, refers to a linear, branched chain or cyclic hydrocarbon radical or any combination thereof They can be fully saturated (e.g. alkyl), mono- or polyunsaturated (e.g. alkenyl, alkynyl, and aryl), can be mono-, di- or poly-substituted, can be monovalent (e.g. methyl), divalent (e.g. methylene) or multivalent (e.g. methenyl), can also include a divalent or multivalent group, have a specified number of carbon atom (for example, $C_1$-$C_{12}$ indicates 1 to 12 carbon atoms, $C_{1-12}$ is selected from the group consisting of $C_1$, $C_2$, $C_3$, $C_4$, $C_5$, $C_6$, $C_7$, $C_8$, $C_9$, $C_{10}$, $C_{11}$ and $C_{13}$; $C_{3-12}$ is selected from the group consisting of $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, isobutyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1, 4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from the group consisting of B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —$CH_2$—CH=N—$OCH_3$ and —CH=CH—N($CH_3$)—$CH_3$. Up to two consecutive heteroatoms can be present, such as, —$CH_2$—NH—$OCH_3$.

Unless otherwise specified, the term "cyclohydrocarbyl", "heterocyclohydrocarbyl" or hyponyms thereof (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g. heteroalkyl, and heterocycloalkyl), one heteroatom can occupy the position where the heterocycle attaches to the remainder position of the molecule. Examples of the cyclohydrocarbyl include, but are not limited to, cyclopentyl, cyclohexyl, 1-cyclohexenyl, 3-cyclohexenyl, cycloheptyl and the like. Non-limiting examples of heterocyclohydrocarbyl include 1-(1,2,5,6-tetrahydropyridyl), 1-piperidyl, 2-piperidyl, 3-piperidyl, 4-morpholinyl, 3-morpholinyl, tetrahydrofuran-2-yl, tetrahydrofuran-3-yl, tetrahydrothiophen-2-yl, tetrahydrothiophen-3-yl, 1-piperazinyl and 2-piperazinyl.

Unless otherwise specified, the term "alkyl" refers to a linear chain or branched saturated hydrocarbon group, can be mono-substituted (e.g. —$CH_2F$) or poly-substituted (e.g. —$CF_3$), can be monovalent (e.g. methyl), divalent (e.g. methylene) or multivalent (e.g. methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, and the like.

Unless otherwise specified, cycloalkyl includes any stable cyclic or polycyclic hydrocarbyl, and any carbon atom thereof is saturated. Cycloalkyl can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon double bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and s-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from the group consisting of B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyloxazolyl, isoxazolyl, thiazolyl, furyl, thienyl, pyridyl, pyrimidinyl, benzothiazolyl, purinyl, benzimidazolyl, indolyl, isoquinolinyl, quinoxalinyl, quinolinyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl and 6-quinolinyl. The substituent of any of the above aryl and heteroaryl ring system is selected from the group consisting of the acceptable substituents described below.

Unless otherwise specified, when combined with other terms (such as aryloxy, arylthio, arylalkyl), the aryl includes the aryl and heteroaryl ring as defined above. Thus, the term "aralkyl" is meant to include the group (e.g. benzyl, phenethyl, pyridylmethyl, etc.) where an aryl is attached to an alkyl, including an alkyl where the carbon atom (e.g. methylene) has been replaced by an atom such as oxygen, for example, phenoxymethyl, 2-pyridyloxymethyl, 3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonate and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl)methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound disclosed herein can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment disclosed herein.

All of the solvents used in the present disclosure are commercially available. The present disclosure employs the following abbreviations: aq represents water; HATU represents O-(7-azabenzotriazol-1-yl)-N,N,N',N'-tetramethyluronium hexafluorophosphate; EDC represents N-(3-dimethylaminopropyl)-N'-ethylcarbodiimide hydrochloride; m-CPBA represents 3-chloroperoxybenzoic acid; eq represents equivalent or equivalence; CDI represents carbonyl diimidazole; DCM represents dichloromethane; PE represents petroleum ether; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amino protecting group; BOC represents tert-butylcarbonyl, which is an amino protecting group; HOAc represents acetic acid; NaCNBH$_3$ represents sodium cyanoborohydride; r.t. represents room temperature; O/N represents overnight; THF represents tetrahydrofuran; Boc$_2$O represents di-tert-butyldicarbonate; TFA represents trifluoroacetic acid; DIPEA represents diisopropylethylamine; SOCl$_2$ represents thionyl chloride; CS$_2$ represents carbon disulfide; TsOH represents p-toluenesulfonic acid; NFSI represents N-fluoro-N-(phenylsulfonyl)benzenesulfonamide; NCS represents 1-chloropyrrolidine-2,5-dione; n-Bu$_4$NF represents tetrabutylammonium fluoride; iPrOH represents 2-propanol; mp represents melting point; LDA represents lithium diisopropylamide; EDCI represents carbodiimide; HOBt represents 1-hydroxybenzotriazole; and Pd(dppf)Cl$_2$ represents [1,1'-bis(diphenylphosphino)ferrocene] palladium dichloride.

Compounds are named manually or by ChemDraw® software, and the commercially available compounds use their vendor directory names.

DETAILED DESCRIPTION

The present disclosure is described in detail below by means of examples. However, it is not intended that these examples have any disadvantageous limitations to the present disclosure. The present disclosure has been described in detail herein, and the embodiments are also disclosed herein. It will be apparent to those skilled in the art that various changes and modifications may be made to the embodiments disclosed herein without departing from the spirit and scope disclosed herein.

Example A-1

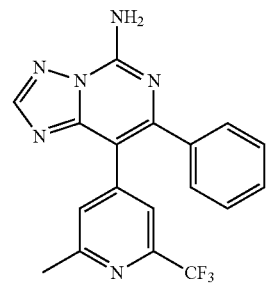 [SMILES: Cc1cc(-c2c(-c3ccccc3F)nc(N)n3ncnc23)cc(C(F)(F)F)n1]

Synthesis of compound A-1 using (A-1-1) as starting material, and the detailed synthetic route 1 as follows:

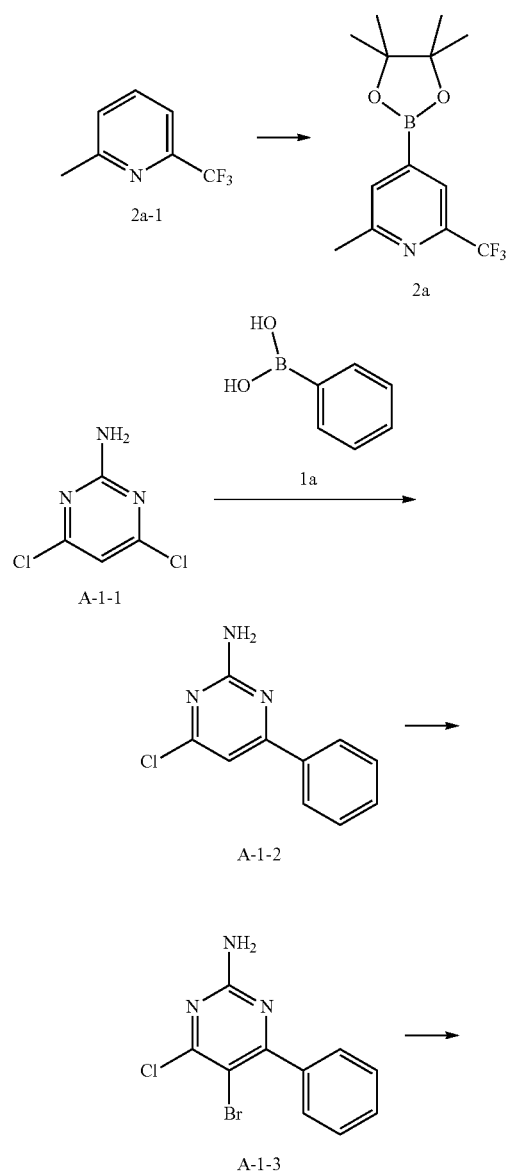

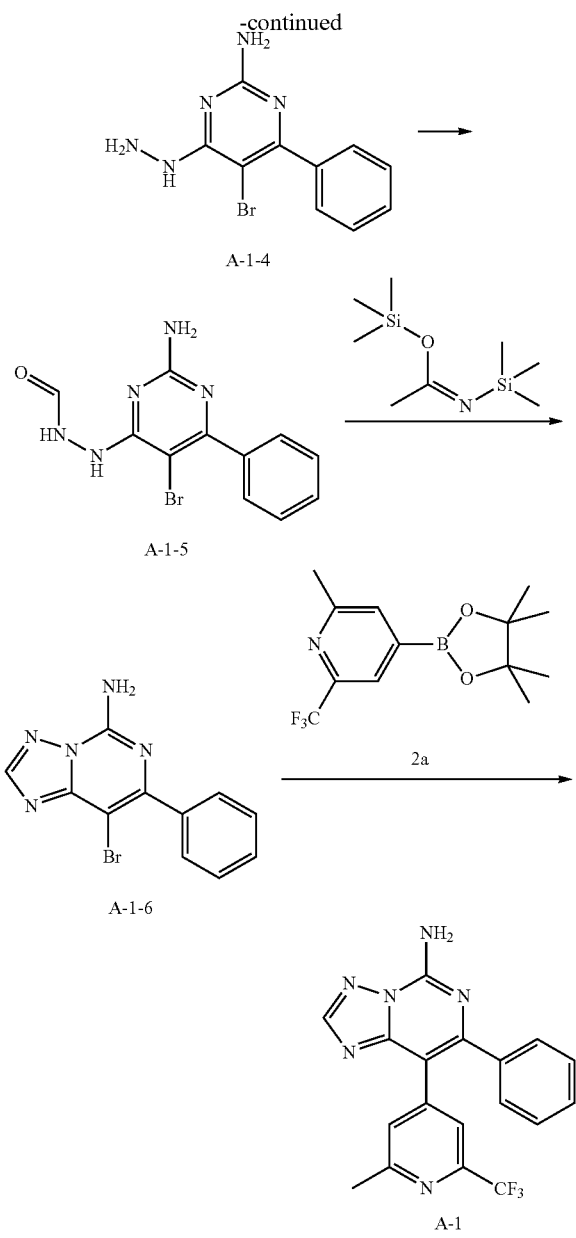

The First Step (Synthesis of Compound 2a)

Bis(pinacolato)diboron (25.61 g, 100.85 mmol, 0.65 eq), (1,5)-cyclooctadiene methoxy iridium dimer (308.56 mg, 465.48 0.003 eq) and 4,4'-di-tert-butyl-2,2'-bipyridine (249.88 mg, 930.96 μmol, 0.006 eq) were dissolved in n-hexane (250 mL). The reaction solution was stirred at 50° C. under nitrogen atmosphere until the reaction solution became dark red. Compound 2a-1 was added to the above solution, and the reaction solution was stirred at 50° C. for 3 hours under nitrogen atmosphere. LC-MS showed the hydrolysis product of borate compound 2a, indicating a total conversion to the borate. The reaction solution was concentrated under reduced pressure to afford a crude compound 2a, which was used directly in the next step without purification.

The relevant characterization data was as follows: LCMS m/z: 206.1 [M+H] (showing the boric acid which is hydrolysed from the borate ester).

$^1$H NMR (400 MHz, CDCl$_3$): δ 7.83 (s, 1H), 7.70 (s, 1H), 1.37 (s, 12H).

The Second Step (Synthesis of Compound A-1-2)

Compound A-1-1 (5 g, 30.49 mmol, 1.00 eq) was dissolved in a mixture solvent of anhydrous dioxane (80 mL) and water (15 mL). phenylboronic acid 1a (2.97 g, 24.39 mmol, 0.80 eq), sodium bicarbonate (5.12 g, 60.98 mmol, 2.37 mL, 2.00 eq), and tetrakis(triphenylphosphine)palladium (1.76 g, 1.52 mmol, 0.05 eq) were added to the reaction solution. The reaction solution was stirred at 100° C. for 12 hours under nitrogen atmosphere. When LC-MS showed the completion of the reaction, the reaction solution was concentrated under reduced pressure. 100 mL of water was added to the residue and the mixture was extracted with ethyl acetate (50 mL×3). The organic layer was washed with saturated brine. The organic phases were combined, dried over anhydrous sodium sulfate and filtered. The filtrate was concentrated under reduced pressure and subjected to column chromatography (petroleum ether:ethyl acetate: dichloromethane=20:1:1-5:1:1) to afford the compound A-1-2.

The relevant characterization data was as follows: LCMS m/z: 206.0 [M+H].

$^1$HNMR (400 MHz, DMSO-d$_6$): δ 8.12-8.14 (m, 2H), 7.53-7.57 (m, 3H), 7.29 (s, 1H), 7.23 (brs, 2H).

The Third Step (Synthesis of Compound A-1-3)

Compound A-1-2 (3.00 g, 14.59 mmol, 1.00 eq) was dissolved in acetonitrile (80.00 mL), and then NBS (5.19 g, 29.18 mmol, 2.00 eq) was added. The reaction solution was stirred at 80° C. for 2 hours. When LC-MS showed the completion of the reaction, the reaction solution was concentrated under reduced pressure. 100 mL of water was added to the residue and the mixture was extracted with ethyl acetate (50 mL×3). The organic layer was washed with saturated brine. The organic phases were combined, dried over anhydrous sodium sulfate and filtered. The filtrate was concentrated under reduced pressure and subjected to column chromatography (petroleum ether:ethyl acetate=30:1-15:1) to afford the compound A-1-3.

The relevant characterization data was as follows: LCMS m/z: 283.9 [M+H].

$^1$H NMR (400 MHz, DMSO-d$_6$): δ 7.62-7.67 (m, 2H), 7.52-7.54 (m, 3H), 7.43 (brs, 2H).

The Fourth Step (Synthesis of Compound A-1-4)

Compound A-1-3 (2.18 g, 7.66 mmol, 1.00 eq) was dissolved in water (40.00 mL), and then hydrazine hydrate (1.92 g, 38.31 mmol, 1.86 mL, 5.00 eq) was added. The reaction solution was stirred at 100° C. for 12 hour. When LC-MS showed the completion of the reaction, the reaction solution was concentrated under reduced pressure to afford a crude compound A-1-4, which was used directly in the next step.

The relevant characterization data was as follows: LCMS m/z: 280.0 [M+H].

The Fifth Step (Synthesis of Compound A-1-5)

Compound A-1-4 (4.00 g, 14.28 mmol, 1.00 eq) was dissolved in formic acid (50.00 mL), and the reaction solution was stirred at 100° C. for 12 hours. When LC-MS showed the completion of the reaction, the reaction solution was concentrated under reduced pressure to afford a crude compound A-1-5, which was used directly in the next step.

The relevant characterization data was as follows: LCMS m/z: 309.9 [M+H].

The Sixth Step (Synthesis of Compound A-1-6)

Compound A-1-5 (4.00 g, 12.98 mmol, 1.00 eq) was dissolved in BSTA (30.00 mL), and the reaction solution was stirred at 100° C. for 12 hours. When LC-MS showed the completion of the reaction, the reaction solution was concentrated under reduced pressure. 50 mL of water was added to the residue and the mixture was extracted with ethyl acetate (50 mL×3). The organic layer was washed with saturated brine. The organic phases were combined, dried over anhydrous sodium sulfate and filtered. The filtrate was concentrated under reduced pressure and subjected to column chromatography (petroleum ether:ethyl acetate=20:1-2:1) to afford the compound A-1-6.

The relevant characterization data was as follows: LCMS m/z: 289.9 [M+H].

$^1$H NMR (400 MHz, DMSO-d$_6$): δ 8.61 (s, 1H), 7.76-7.74 (m, 2H), 7.51-7.43 (m, 5H).

The Seventh Step (Synthesis of Compound A-1)

Compound A-1-6 (500.00 mg, 1.72 mmol, 1.00 eq), and compound 2a (602.43 mg, 2.10 mmol, 1.22 eq) were dissolved in tetrahydrofuran (3 mL). K$_3$PO$_4$ (2 M, 1.77 mL, 2.05 eq) and XPHOS-PD-G2 (297.73 mg, 378.40 μmol, 0.22 eq) were added to the solution. The atmosphere of the reaction was vented and purged with nitrogen, and the reaction solution was stirred at 70° C. for 12 hours. LCMS monitored and showed a large amount of raw material remaining and a trace of the product was detected. The reaction solution was rotary concentrated to dryness, and the residue was diluted with 1,4-dioxane (5.00 mL). Pd(dppf)Cl$_2$.CH$_2$Cl$_2$ (294.97 mg, 361.20 μmol, 0.21 eq) and K$_2$CO$_3$ (2 M, 1.81 mL, 2.10 eq) were added to the mixture. The atmosphere of the reaction was vented and purged with nitrogen, and the reaction solution was stirred at 120° C. for 2 hours in microwave. LCMS monitored and showed a large amount of raw material remaining and the product was detected. The reaction solution was directly rotary concentrated to dryness. The residue was purified by column chromatography to afford a crude product. The crude product was purified by preparative high performance liquid chromatography to afford the desired product A-1.

The relevant characterization data was as follows: LCMS m/z: 371.3 [M+H].

$^1$H NMR (400 MHz, DMSO-d$_6$): δ 8.56 (s, 1H), 8.40-8.30 (brs, 2H), 7.54 (s, 1H), 7.43 (s, 1H), 7.37-7.33 (m, 5H), 2.46 (s, 3H).

The preparation of example compounds in Table 1 can be carried out by referring to the similar step and method in the above-mentioned route 1 for the preparation of Example A-1, except that in step 2 boric acids in the following table were used as starting materials to replace the raw material 1a.

TABLE 1

| Products No. | Structure of products | Raw materials No. and their chemical structures | LCMS of products, m/z: [M + H] | $^1$H NMR of products |
|---|---|---|---|---|
| Example A-2 | [structure: 5-amino-triazolopyrimidine with 3-fluorophenyl and 2-methyl-6-trifluoromethylpyridinyl substituents] | [structure: 3-fluorophenylboronic acid] 1b | 389.0 | $^1$H NMR (400 MHz, DMSO-d$_6$): δ 8.57 (s, 1H), 7.55 (s, 1H), 7.47 (s, 1H), 7.38-7.34 (m, 1H), 7.24-7.20 (m, 2H), 7.11 (d, J = 7.6 Hz, 1H), 2.43 (s, 3H). |
| Example A-3 | [structure: 5-amino-triazolopyrimidine with 2,3-difluorophenyl and 2-methyl-6-trifluoromethylpyridinyl substituents] | [structure: 2,3-difluorophenylboronic acid] 1c | 407.0 | $^1$H NMR (400 MHz, DMSO-d$_6$): δ 8.64 (s, 1H), 7.58-7.42 (m, 3H), 7.38-7.25 (m, 2H), 2.51 (s, 3H). |
| Example A-4 | [structure: 5-amino-triazolopyrimidine with 2-methoxyphenyl and 2-methyl-6-trifluoromethylpyridinyl substituents] | [structure: 2-methoxyphenylboronic acid] 1d | 401.0 | $^1$H NMR (400 MHz, DMSO-d$_6$): δ 8.58 (s, 1H), 7.45 (s, 1H), 7.41-7.34 (m, 3H), 7.02 (t, J = 7.2 Hz, 1H), 6.90 (d, J = 8.0 Hz, 1H), 3.33 (s, 3H), 2.43 (s, 3H). |

TABLE 1-continued

| Products No. | Structure of products | Raw materials No. and their chemical structures | LCMS of products, m/z: [M + H] | $^1$H NMR of products |
|---|---|---|---|---|
| Example A-5 | (structure shown) | 1e | 407.0 | $^1$H NMR (400 MHz, DMSO-$d_6$): δ 8.59 (s, 1H), 7.55 (s, 1H), 7.51 (s, 1H), 7.32-7.28 (m, 1H), 7.06-7.04 (m, 2H), 2.51(s, 3H). |

Synthesis of compound A-1 using (A-1-1a) as starting material and the detailed synthetic route 2 as follows

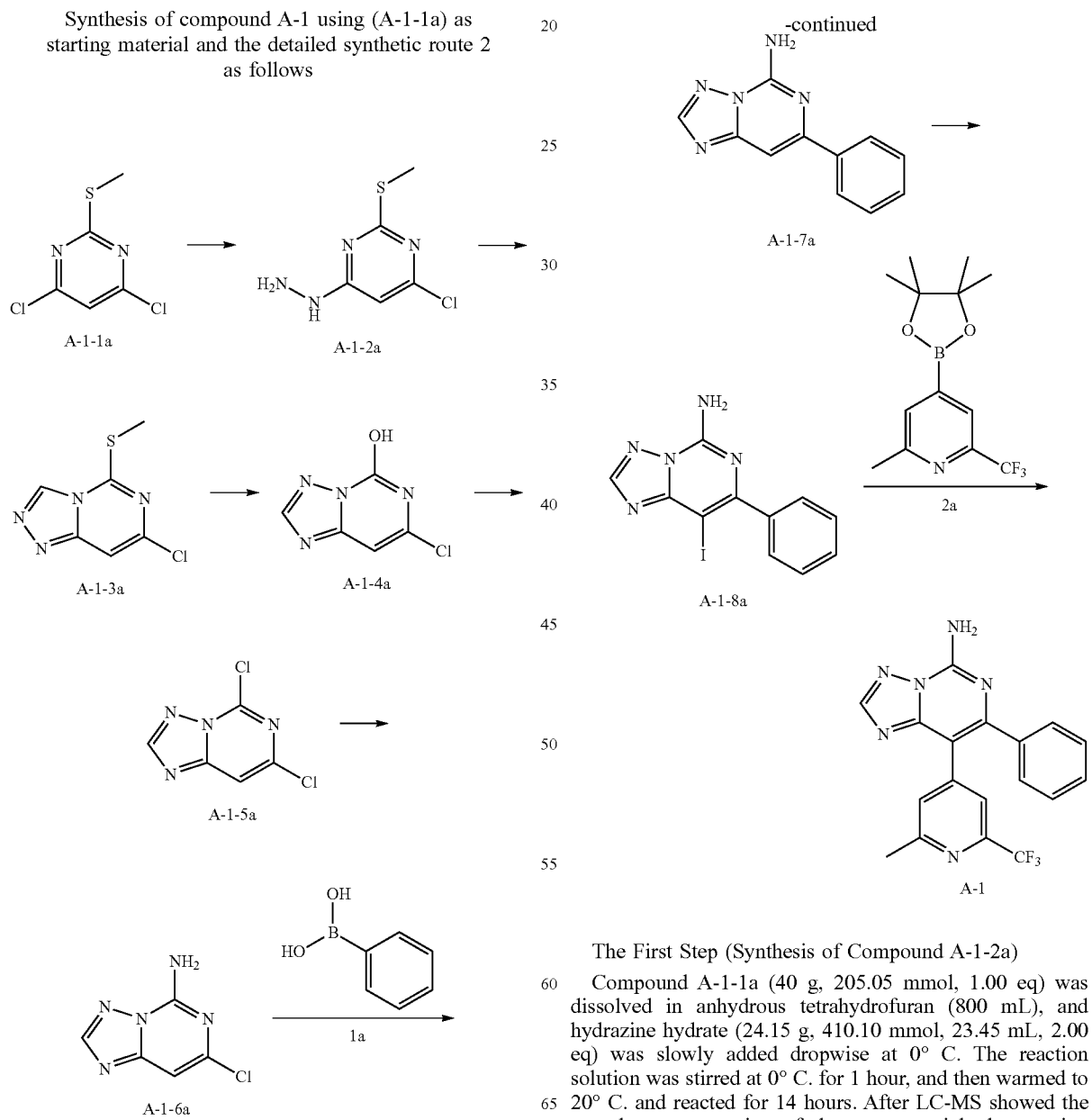

The First Step (Synthesis of Compound A-1-2a)

Compound A-1-1a (40 g, 205.05 mmol, 1.00 eq) was dissolved in anhydrous tetrahydrofuran (800 mL), and hydrazine hydrate (24.15 g, 410.10 mmol, 23.45 mL, 2.00 eq) was slowly added dropwise at 0° C. The reaction solution was stirred at 0° C. for 1 hour, and then warmed to 20° C. and reacted for 14 hours. After LC-MS showed the complete consumption of the raw material, the reaction solution was concentrated under reduced pressure. 500 mL of water was added to the crude product. The mixture was stirred for 30 minutes, filtered, and washed with water to afford the compound A-1-2a.

The relevant characterization data was as follows: LCMS m/z: 190.4 [M+H].

The Second Step (Synthesis of Compound A-1-3a)

Compound A-1-2a (41.00 g, 195.70 mmol, 1.00 eq), and triethyl orthoformate were dissolved in glacial acetic acid (800 mL) at 25° C. The mixture was stirred for 10 min, and then heated to 120° C. and stirred for 16 hours. After LC-MS showed the complete consumption of the raw material, the reaction solution was cooled to room temperature. The reaction solution was concentrated under reduced pressure at 60° C. 800 mL of water was added to the resulting crude product and stirred for 10 minutes. The pH was adjusted to 7-8 with sodium bicarbonate and the mixture was extracted with ethyl acetate. The organic phase was dried over anhydrous sodium sulfate, and concentrated under reduced pressure to afford the compound A-1-3a.

The relevant characterization data was as follows: LCMS m/z: 200.4 [M+H].

The Thrid Step (Synthesis of Compound A-1-4a)

Compound A-1-3a (38.00 g, 180.86 mmol, 1.00 eq), and sodium hydroxide (0.25 M, 217.03 mL, 0.30 eq) were dissolved in anhydrous tetrahydrofuran (450 mL) and stirred at 25° C. for 16 hours. After LC-MS showed the complete consumption of the raw material, the reaction solution was filtered and washed with tetrahydrofuran (50 mL*4). The residue was dried to afford the compound A-1-4a.

The relevant characterization data was as follows: LCMS m/z: 170.3 [M+H].

The Fourth Step (Synthesis of Compound A-1-5a)

Compound A-1-4a (5.50 g, 31.60 mmol, 1.00 eq) was dissolved in phosphorus oxychloride (165.00 g, 1.08 mol, 100.00 mL, 34.05 eq) at 25° C., and N,N-dimethylaniline (382.95 mg, 3.16 mmol, 398.91 µL, 0.10 eq) was slowly added to the reaction solution. The reaction solution was heated to 110° C. and stirred for 16 hours. After LC-MS showed the complete consumption of the raw material, the reaction solution was concentrated under reduced pressure at 50° C. Water (100 mL) was slowly added to the obtained crude product and the mixture was stirred for 20 minutes. The aqueous phase was extracted with ethyl acetate (50 mL*4). The organic phases were combined, washed sequentially with saturated aqueous solution of sodium bicarbonate (50 mL*3) and saturated brine (50 mL*2), dried over anhydrous sodium sulfate, filtered and concentrated under reduced pressure to afford the compound A-1-5a.

The relevant characterization data was as follows: LCMS m/z: 188.3 [M+H].

The Fifth Step (Synthesis of Compound A-1-6a)

Compound A-1-5a (3.05 g, 16.14 mmol, 1.00 eq) was dissolved in dioxane (50 mL), and ammonia gas was introduced to the reaction solution at 0° C. for 20 min. The reaction solution was poured into a 100 mL smoldering pot, heated to 90° C. and stirred for 12 hours. LC-MS showed complete consumption of compound 1-5 and 66% was the desired product. The reaction solution was concentrated under reduced pressure to afford the desired product A-1-6a.

The relevant characterization data was as follows: LCMS m/z: 169.4 [M].

The Sixth Step (Synthesis of Compound A-1-7a)

Compound A-1-6a (3.58 g, 15.20 mmol, 1.00 eq), phenylboric acid 1a (2.22 g, 18.24 mmol, 1.20 eq), and potassium carbonate (4.20 g, 30.40 mmol, 2.00 eq) were dissolved in dioxane (80 mL) and water (16 mL), and Pd(dppf)Cl$_2$.CH$_2$Cl$_2$ (1.24 g, 1.52 mmol, 0.10 eq) was added to the reaction solution. The reaction solution was vented and purged with nitrogen for 5 times and stirred under nitrogen at 90° C. for 12 hours. LC-MS showed complete consumption of the starting materials. The reaction solution was concentrated under reduced pressure at 50° C. The crude product was purified by a normal phase silica gel column (PE:EA=10:1 to 0:1) to afford the compound A-1-7a.

The relevant characterization data was as follows: LCMS m/z: 211.5 [M+H].

The Seventh Step (Synthesis of Compound A-1-8a)

Compound A-1-7a (2.80 g, 11.27 mmol, 1.00 eq) was dissolved in acetonitrile (50.00 mL) at 25° C., and N-iodo-succinimide (5.07 g, 22.54 mmol, 2.00 eq) was slowly added to the reaction solution. The reaction solution was heated to 90° C. and stirred for 12 hours. After LC-MS showed the complete consumption of the raw material, the reaction solution was concentrated under reduced pressure at 50° C. Sodium thiosulfate (100 mL) was added to the obtained crude product and the mixture was stirred for 5 min. The aqueous phase was extracted with ethyl acetate (100 mL*8). The organic phases were combined, washed with saturated brine (50 mL*2), dried over anhydrous sodium sulfate, filtered and concentrated under reduced pressure to afford the compound A-1-8a.

The relevant characterization data was as follows: LCMS m/z: 337.6 [M+H].

The Eighth Step (Synthesis of Example A-1)

Compound A-1-8a (2.00 g, 5.52 mmol, 1.00 eq), 2a (2.64 g, 8.28 mmol, 1.50 eq), and potassium carbonate (1.53 g, 11.04 mmol, 2.00 eq) were dissolved in dioxane (60 mL) and water (12 mL). To the reaction solution, Pd(dppf)Cl$_2$.CH$_2$Cl$_2$ (450.79 mg, 552.00 µmol, 0.10 eq) was added. The reaction solution was vented and purged with nitrogen for 5 times and stirred under nitrogen at 90° C. for 16 hours. LC-MS showed complete consumption of the starting materials. The reaction solution was concentrated under reduced pressure at 50° C. The crude product was purified by a normal phase silica gel column (PE:EA=10:1 to 0:1) and pre-HPLC to afford the desired compound A-1.

The relevant characterization data was as follows: LCMS m/z: 370.7 [M+H].

$^1$HNMR (400 MHz, DMSO-d$_6$): δ8.55 (s, 1H), 8.36-8.29 (m, 2H), 7.53 (s, 1H), 7.43 (s, 1H), 7.38-7.31 (m, 5H), 2.45 (s, 3H).

Example A-6

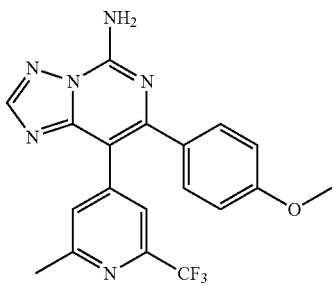

A-6

Synthesis of example compound A-6 using (A-1-6a) as starting material and the detailed synthetic route as follows:

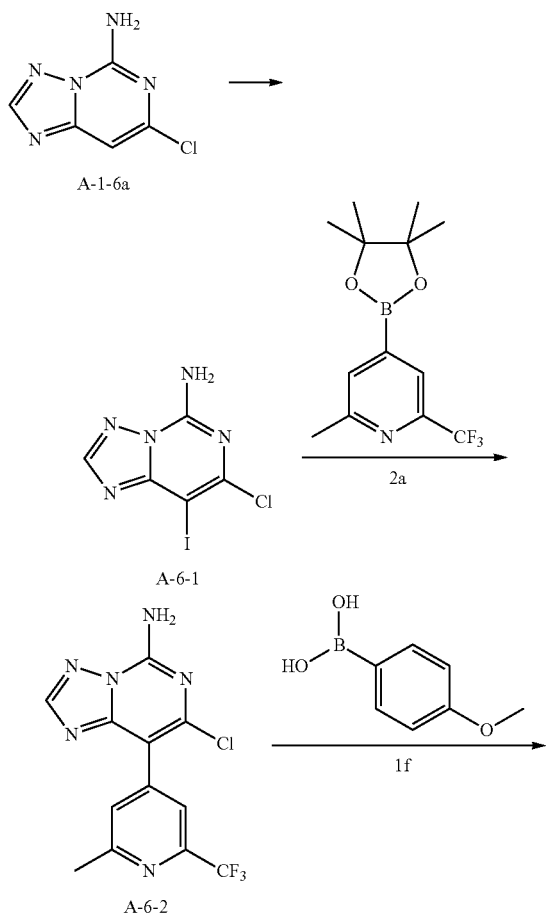

The First Step (Synthesis of Compound A-6-1)

Compound A-1-6a (4.00 g, 22.30 mmol, 1.00 eq), and NIS (10.04 g, 44.60 mmol, 2.00 eq) were dissolved in MeCN (40 mL) at 25° C. The reaction solution was heated to 90° C. and stirred for 14 hours. After LC-MS showed the complete consumption of the raw material, the reaction solution was cooled to room temperature. The reaction solution was concentrated under reduced pressure at 50° C. to afford the compound A-6-1.

The relevant characterization data was as follows: LCMS m/z: 295.8 [M+H].

$^1$H NMR (400 MHz, DMSO-d$_6$): δ 11.05 (brs, 2H), 8.48 (s, 1H).

The Second Step (Synthesis of Compound A-6-2)

Compound A-6-1 (2.00 g, 6.23 mmol, 1.00 eq), 2a (2.38 g, 7.48 mmol, 1.20 eq), potassium phosphate (2.64 g, 12.46 mmol, 2.00 eq), and DTBPF(PdCl$_2$) (406.04 mg, 623.00 μmol, 0.10 eq) were dissolved in dioxane/water (30 mL/6 mL) at 25° C. The mixture was vented and purged with nitrogen for three times and then heated to 110° C. and stirred for 14 hours. After LC-MS showed the complete consumption of the raw material, the reaction solution was cooled to room temperature. The reaction solution was concentrated under reduced pressure at 50° C. The crude product was isolated by column chromatography (100-200 mesh silica gel, petroleum ether/ethyl acetate=5:1, 1:1), and then subjected to neutral p-HPLC machine separation (mobile phase: water/acetonitrile) to afford the compound A-6-2.

The relevant characterization data for A-6-2 is as follows: LCMS m/z: 328.9 [M+H].

The Thrid Step (Synthesis of Compound A-6)

Compound A-6-2 (40.00 mg, 121.70 μmol, 1.00 eq), 1f (27.74 mg, 182.55 μmol, 1.50 eq), potassium carbonate (33.64 mg, 243.40 μmol, 2.00 eq), and Pd(dppf)Cl$_2$.CH$_2$Cl$_2$ (9.94 mg, 12.17 μmol, 0.10 eq) were dissolved in dioxane/water (3 mL/0.6 mL) at 25° C. The mixture was vented and purged with nitrogen for three times and then heated to 100° C. and stirred for 14 hours. After LC-MS showed the complete consumption of the raw material, the reaction solution was cooled to room temperature. The reaction solution was concentrated under reduced pressure at 50° C. The crude product was isolated by column chromatography (100-200 mesh silica gel, petroleum ether/ethyl acetate=5:1, 1:1), and then subjected to neutral machine separation (mobile phase: water/acetonitrile) to afford the compound A-6.

The relevant characterization data was as follows: LCMS m/z: 401.1 [M+H].

$^1$H NMR (400 MHz, DMSO-d$_6$): δ 8.52 (s, 1H), 7.54 (s, 1H), 7.47 (s, 1H), 7.29 (d, J=8.8 Hz, 2H), 6.89 (d, J=8.8 Hz, 2H), 6.05 (br s, 2H), 3.75 (s, 3H), 2.48 (s, 3H).

Example A-7

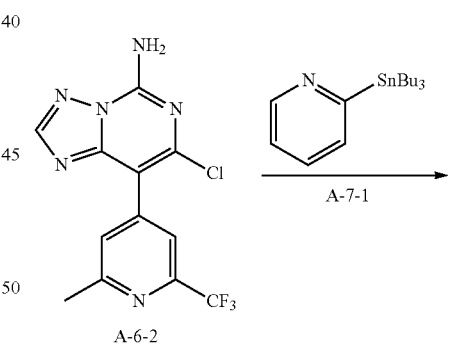

Compound A-6-2 (40.00 mg, 121.70 μmol, 1.00 eq), A-7-1 (145.46 mg, 304.25 μmol, 2.50 eq), LiCl (15.48 mg, 365.10 μmol, 7.48 uL, 3.00 eq), and Pd(dppf)Cl$_2$.CH$_2$Cl$_2$ (19.88 mg, 24.34 μmol, 0.20 eq) were dissolved in dioxane (4.00 mL) at 25° C. The mixture was vented and purged with nitrogen for three times, and then heated to 125° C. and stirred for 48 hours. After LC-MS showed the complete consumption of the raw material, the reaction solution was cooled to room temperature. The reaction solution was concentrated under reduced pressure at 50° C. The crude product was isolated by column chromatography (100-200 mesh silica gel, petroleum ether/ethyl acetate=5:1, 1:1), and then subjected to neutral machine separation (mobile phase: water/acetonitrile) to afford the compound A-7.

The relevant characterization data was as follows: LCMS m/z: 372.1 [M+H].

$^1$H NMR (400 MHz, DMSO-d$_6$): δ 8.59 (s, 1H), 8.41 (br s, 2H), 8.35 (d, J=4.0 Hz, 1H), 7.92 (dt, J=1.6, 8.0 Hz, 1H), 7.80 (d, J=8.0 Hz, 1H), 7.49 (s, 1H), 7.39 (ddd, 4.8, 7.6 Hz, 1H), 7.33 (s, 1H), 2.47 (s, 3H).

Example A-8

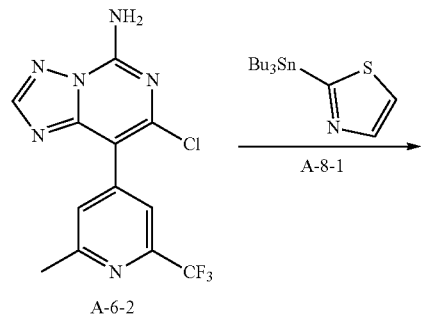

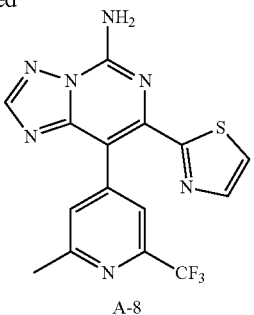

A-8

Example A-8: The preparation of the present example compound can be carried out by referring to the similar step and method in the above-mentioned route for the preparation of Example A-7, except that in step 2 starting material A-8-1 was used to replace the raw material A-7-1, and the crude product was isolated by TLC plate and then subjected to neutral machine separation (mobile phase: water/acetonitrile) to afford A-8.

The relevant characterization data was as follows: LCMS m/z: 378.0 [M+H].

$^1$H NMR (400 MHz, DMSO-d$_6$): δ 8.53 (s, 1H), 7.87 (d, J=3.2 Hz, 1H), 7.73 (d, J=3.2 Hz, 1H), 7.67 (s, 1H), 7.62 (s, 1H), 2.58 (s, 3H).

The preparation of example compounds in Table 2 can be carried out by referring to the similar step and method in the above-mentioned route for the preparation of Example A-6, except that in step 3 boric acids in the following table were used as starting materials to replace the raw material 1a.

TABLE 2

| Products No. | Structure of products | Raw materials No. and their chemical structures | LCMS of products, m/z: [M + H] | $^1$H NMR of products |
|---|---|---|---|---|
| Example A-9 | (structure shown) | 1g (structure shown) | 405.1 | $^1$H NMR (400 MHz, DMSO-d$_6$): δ 8.56 (s, 1H), 7.53 (s, 1H), 7.48 (s, 1H), 7.44-7.34 (m, 4H), 2.48 (s, 3H). |
| Example A-10 | (structure shown) | 1h (structure shown) | 387.0 | $^1$H NMR (400 MHz, DMSO-d$_6$): δ 9.76 (br s, 1H), 8.52 (s, 1H), 8.28 (br s, 2H), 7.57 (s, 1H), 7.47 (s, 1H), 7.19 (d, J = 8.8 Hz, 2H), 6.70 (d, J = 8.8 Hz, 2H), 2.49 (s, 3H). |

TABLE 2-continued

| Products No. | Structure of products | Raw materials No. and their chemical structures | LCMS of products, m/z: [M + H] | $^1$H NMR of products |
|---|---|---|---|---|
| Example A-11 | | 1i | 372.1 | $^1$H NMR (400 MHz, DMSO-d$_6$): δ 8.59 (s, 1H), 8.57-8.53 (m, 2H), 7.51 (d, J = 4.8 Hz, 2H), 7.37-7.27 (m, 2H), 2.47 (s, 3H) |
| Example A-12 | | 1j | 372.1 | $^1$H NMR (400 MHz, DMSO-d$_6$): δ 8.58 (s, 1H), 8.55 (d, J = 4.8 Hz, 1H), 8.49-8.42 (m, 3H), 7.77 (br d, J = 7.8 Hz, 1H), 7.52 (d, J = 9.0 Hz, 2H), 7.39 (dd, J = 4.9, 7.9 Hz, 1H), 2.47 (s, 3H) |
| Example A-13 | | 1k | 439.1 | $^1$H NMR (400 MHz, DMSO-d$_6$): δ 8.60 (s, 1H), 8.47 (br s, 2H), 7.73 (d, J = 8.2 Hz, 2H), 7.56 (d, J = 7.5 Hz, 3H), 7.40 (s, 1H), 2.47 (s, 3H) |
| Example A-14 | | 1l | 396.1 | $^1$H NMR (400 MHz, DMSO-d$_6$): δ 8.60 (s, 1H), 8.47 (br s, 2H), 7.83 (d, J = 8.4 Hz, 2H), 7.56-7.46 (m, 4H), 2.47 (s, 3H). |
| Example A-15 | | 1m | 389.1 | $^1$H NMR (400 MHz, DMSO-d$_6$): δ 8.55 (s, 1H), 8.36 (br s, 2H), 7.53 (s, 1H), 7.45 (s, 1H), 7.40-7.37 (m, 2H), 7.21-7.16 (m, 2H), 2.47 (s, 3H). |

TABLE 2-continued

| Products No. | Structure of products | Raw materials No. and their chemical structures | LCMS of products, m/z: [M + H] | $^1$H NMR of products |
|---|---|---|---|---|
| Example A-17 | | 1n | 389.1 | $^1$H NMR (400 MHz, DMSO-d$_6$): δ 8.60 (s, 1H), 8.43 (br s, 2H), 7.53-7.41 (m, 4H), 7.30-7.28 (m, 1H), 7.15-7.10 (m, 1H), 2.45 (s, 3H). |
| Example A-19 | | 1p | 361.0 | $^1$H NMR (400 MHz, DMSO-d$_6$): δ 8.49 (s, 1H), 7.63-7.61 (m, 3H), 6.85 (s, 1H), 6.61-6.59 (m, 1H), 2.59 (s, 3H). |
| Example A-21 | | 1r | 375.0 | $^1$H NMR (400 MHz, DMSO-d$_6$): δ 8.50 (s, 1H), 8.25 (brs, 2H), 7.69 (d, J = 2.0 Hz, 1H), 7.61 (s, 1H), 7.55 (s, 1H), 6.43 (d, J = 2.0 Hz, 1H), 3.68 (s, 3H), 2.55 (s, 3H). |
| Example A-23 | | 1t | 419.0 | $^1$H NMR (400 MHz, CDCl$_3$): δ 8.37 (s, 1H), 7.43 (s, 1H), 7.39-7.35 (m, 2H), 6.80-6.76 (td, J = 2.4, 8.4 Hz, 1H), 6.52-6.49 (dd, J = 2.4, 8.4 Hz, 1H), 6.30 (s, 2H), 3.40 (s, 3H), 2.57 (s, 3H) |

The preparation of example compounds in Table 3 can be carried out by referring to the similar step and method in the above-mentioned route 1 for the preparation of the example, except that in steps 6 and 8 boric acids in the following table were used as starting materials to replace the raw materials 1a and 2a to afford the corresponding compounds.

TABLE 3
| Products No. | Structure of products | Raw materials No. and their chemical structures | LCMS of products, m/z: [M + H] | $^1$H NMR of products |
|---|---|---|---|---|
| Example A-24 | 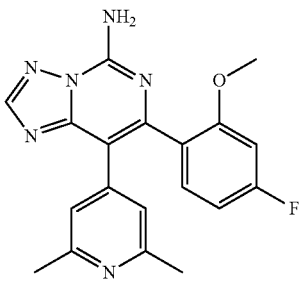 [SMILES: COc1cc(F)ccc1-c1nc(N)n2ncnc2c1-c1cc(C)nc(C)c1] | 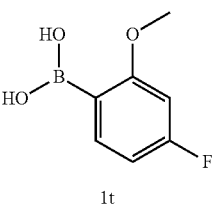<br>1t<br>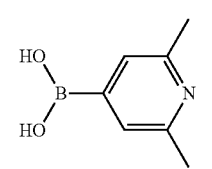<br>2e | 365.1 | $^1$H NMR (400 MHz, METHANOL-d$_4$): δ 8.37 (s, 1H), 7.38 (dd, J = 6.8, 8.4 Hz, 1H), 6.96 (s, 2H), 6.79-6.61 (m, 2H), 3.42 (s, 3H), 2.38 (s, 6H) |
| Example A-25 | 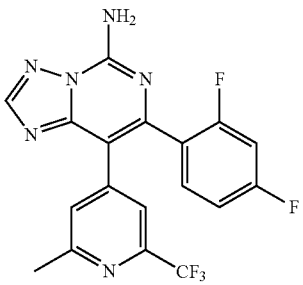 [SMILES: Cc1cc(-c2c(-c3ccc(F)cc3F)nc(N)n3ncnc23)cc(C(F)(F)F)n1] | 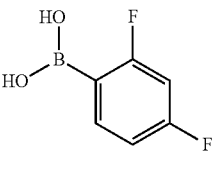<br>1u<br>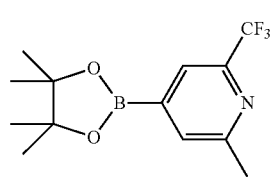<br>2a | 407.1 | $^1$H NMR (400 MHz, DMSO-d$_6$): δ 8.62 (s, 1H), 8.48 (br s, 2H), 7.67-7.57 (m, 1H), 7.52 (s, 1H), 7.45 (s, 1H), 7.27-7.18 (m, 2H), 2.48 (s, 3H) |
| Example A-26 | 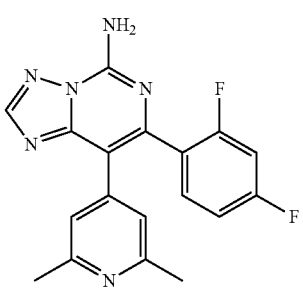 [SMILES: Cc1cc(-c2c(-c3ccc(F)cc3F)nc(N)n3ncnc23)cc(C)n1] | 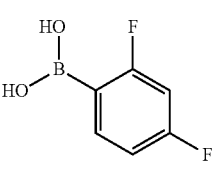<br>1u<br>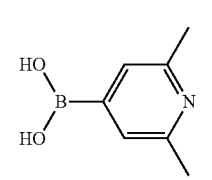<br>2e | 353.1 | $^1$H NMR (400 MHz, DMSO-d$_6$): δ 8.56 (s, 1H), 8.28 (br s, 2H), 7.62-7.44 (m, 1H), 7.27-7.07 (m, 2H), 6.90 (s, 2H), 2.31 (s, 6H) |

TABLE 3-continued

| Products No. | Structure of products | Raw materials No. and their chemical structures | LCMS of products, m/z: [M + H] | $^1$H NMR of products |
|---|---|---|---|---|
| Example A-27 | | 1d, 2e | 347.1 | $^1$H NMR (400 MHz, METHANOL-$d_4$): δ 8.40 (s, 1H), 7.42-7.34 (m, 2H), 7.07-6.96 (m, 3H), 6.89 (d, J = 8.7 Hz, 1H), 3.51-3.42 (m, 3H), 2.38 (s, 6H) |
| Example A-28 | | 1u, 2e | 351.1 | $^1$H NMR (400 MHz, METHANOL-$d_4$): δ 8.42 (s, 1H), 7.49-7.24 (m, 4H), 6.99 (s, 2H), 2.35 (s, 6H) |
| Example A-29 | | 1t | 377.1 | $^1$H NMR (400 MHz, DMSO-$d_6$): δ 8.48 (s, 1H), 7.96 (br s, 2H), 7.67-7.47 (m, 2H), 7.25 (t, J = 7.7 Hz, 1H), 7.05 (br d, J = 8.4 Hz, 1H), 6.85-6.58 (m, 2H), 3.40 (s, 3H) |

TABLE 3-continued
| Products No. | Structure of products | Raw materials No. and their chemical structures | LCMS of products, m/z: [M + H] | ¹H NMR of products |
|---|---|---|---|---|
| | 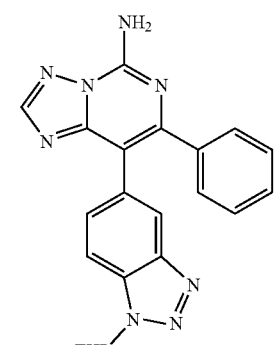<br>B-33-1 | | | |
| Example A-30 | 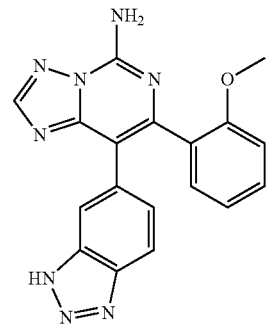 [SMILES: COc1ccccc1-c1nc(N)n2ncnc2c1-c1ccc2nn[nH]c2c1] | 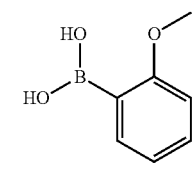<br>1d | 359.1 | ¹H NMR (400 MHz, METHANOL-d₄): δ 8.38 (s, 1H), 7.79-7.67 (m, 2H), 7.45-7.39 (m, 1H), 7.34 (dd, J = 1.6, 7.2 Hz, 1H), 7.31-7.24 (m, 1H), 6.94 (t, J = 7.4 Hz, 1H), 6.80 (d, J = 8.2 Hz, 1H), 3.41 (s, 3H). |
| | 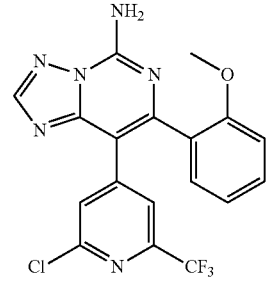 [SMILES: COc1ccccc1-c1nc(N)n2ncnc2c1-c1cc(Cl)nc(C(F)(F)F)c1]<br>B-33-1 | | | |
| Example A-31 | 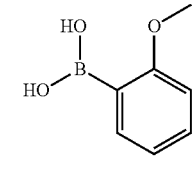 | 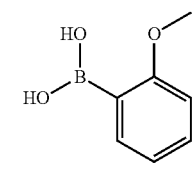<br>1d | 421.0 | ¹H NMR (400 MHz, DMSO-d₆): δ 8.61 (s, 1H), 8.48 (br s, 2H), 7.69 (s, 1H), 7.64 (s, 1H), 7.43 (m, 7.2 Hz, 2H), 7.07 (t, J = 7.6 Hz, 1H), 7.00-6.89 (m, 1H), 3.35 (s, 3H) |

TABLE 3-continued

| Products No. | Structure of products | Raw materials No. and their chemical structures | LCMS of products, m/z: [M + H] | $^1$H NMR of products |
|---|---|---|---|---|
| | | 2y | | |
| Example A-32 | | 1v | 439.0 | $^1$H NMR (400 MHz, DMSO-d$_6$): δ 8.62 (s, 1H), 8.53 (br s, 2H), 7.71 (d, J = 7.6 Hz, 2H), 7.42-7.16 (m, 2H), 6.95 (m, 1H), 3.32 (s, 3H) |
| | | 2y | | |
| Example A-33 | | 1w | 456.9 | $^1$H NMR (400 MHz, DMSO-d$_6$): δ 8.66 (s, 1H), 7.79 (s, 1H), 7.68 (s, 1H), 7.50 (m, 1H), 7.19 (m, 1H), 3.50 (s, 3H) |
| | | 2y | | |

The preparation of example compounds in Table 4 can be carried out by referring to the similar method in the above-mentioned route 1 for the preparation of Example A-1, except that in step 7 boric acids in the following table were used as starting materials to replace the raw material 2a to afford the corresponding compounds.

TABLE 4

| Products No. | Structure of products | Raw materials No. and their chemical structures | LCMS of products, m/z: [M + H] | $^1$H NMR of products |
| --- | --- | --- | --- | --- |
| Example B-2 | | 2c | 320.1 | $^1$H NMR (400 MHz, DMSO-d$_6$): δ 8.46-8.51 (m, 1H), 8.01-8.12 (m, 2H), 7.29 (m, 6H), 6.97-7.07 (m, 2H), 2.17 (s, 3H) |
| Example B-3 | | 2d | 352.2 | $^1$H NMR (400 MHz, DMSO-d$_6$): δ 8.49 (s, 1H), 8.06 (brs, 2H), 7.32-7.37 (m, 6H), 7.02-7.04 (m, 2H), 3.84 (s, 3H). |
| Example B-5 | | 2e | 317.0 | $^1$H NMR (400 MHz, DMSO-d$_6$): δ 8.50 (s, 1H), 8.19 (brs, 2H), 7.34 (m, 5H), 6.92 (m, 2H), 2.31 (s, 6H). |
| Example B-8 | | 2h | 328.0 | $^1$H NMR (400 MHz, DMSO-d$_6$): δ 12.41(m, 1H), 8.46 (s, 1H), 8.19 (s, 1H), 7.97(brs, 2H), 7.63-7.50 (m, 2H), 7.36-7.34 (m, 2H), 7.22-7.20 (m, 3H), 7.05-7.01 (m, 1H). |

TABLE 4-continued

| Products No. | Structure of products | Raw materials No. and their chemical structures | LCMS of products, m/z: [M + H] | ¹H NMR of products |
|---|---|---|---|---|
| Example B-9 | 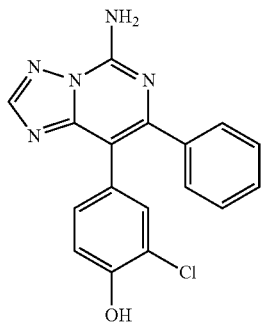 [SMILES: Cc1cc(-c2c(-c3ccccc3)nc(N)n3ncnc23)ccc1F] | 2i | 332.1 | ¹H NMR (400 MHz, DMSO-$d_6$): δ 8.45 (s, 1H), 7.98 (brs, 2H), 7.35-7.37 (m, 2H), 7.27-7.28 (m, 3H), 6.80-6.82 (m, 2H), 6.67-6.68 (m, 1H), 6.00 (s, 2H). |

Example B-4

Example B-7

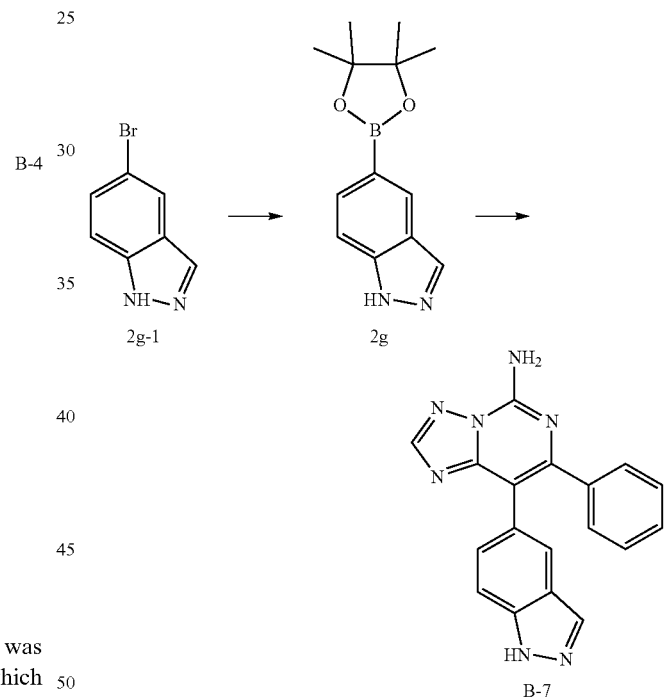

Compound B-3 (117.00 mg, 212.85 μmol, 1.00 eq) was dissolved in anhydrous dichloromethane (5 mL), to which boron tribromide (533.24 mg, 2.13 mmol, 205.09 μL, 10.00 eq) was slowly added under nitrogen at 0° C. The reaction solution was stirred at 0° C. for 2 hours and then warmed to 20° C. and stirred for 10 hours. When LC-MS showed the completion of the reaction, 10 mL of methanol was added to the reaction solution and stirred for 10 minutes. The pH of the reaction solution was adjusted to 8 with triethylamine. The reaction solution was concentrated under reduced pressure at 40° C. and purified by preparative HPLC to afford the product B-4.

The relevant characterization data was as follows: LCMS m/z: 338.0 [M+H].

¹H NMR (400 MHz, DMSO-$d_6$): δ 8.48 (s, 1H), 8.02 (s, 2H), 7.35-7.38 (m, 2H), 7.28-7.31 (m, 4H), 6.91-6.94 (d, J=8.4 Hz, 1H), 6.84-6.86 (d, J=8.4 Hz, 1H).

The First Step (Synthesis of Compound 2g)

Compound 2g-1 (500.00 mg, 2.54 mmol, 1.00 eq) and bis(pinacolato)diboron (1.10 g, 4.32 mmol, 1.70 eq) were dissolved in anhydrous dioxane (10 mL). Potassium acetate and Pd(dppf)Cl$_2$ (55.76 mg, 76.20 μmol, 0.03 eq) were added to the reaction solution. The reaction solution was stirred at 90° C. for 16 hours under nitrogen atmosphere. LC-MS showed 15% was compound 2g-1 and 51% was compound 2g. Bis(pinacolato)diboron (645.01 mg, 2.54 mmol, 1.00 eq) was added to the reaction solution. The reaction solution was stirred at 100° C. for 2 hours under nitrogen atmosphere. LC-MS showed 9% was compound 2g-1 and 62% was compound 2g. The reaction solution was concentrated under reduced pressure. The obtained crude product was purified by a normal phase silica gel column (PE:EA=1:0 to 5:1) to afford the compound 2g.

The relevant characterization data was as follows: LCMS m/z: 245.2 [M+H].

The Second Step (Synthesis of Compound B-7)

Example B-7: The preparation of the present example compound can be carried out by referring to the method in the above-mentioned route 1 for the preparation of Example A-1, except that in step 7 boric acid 2g was used as starting material to replace the raw material 2a. The product was purified by a normal phase silica gel column (PE:EA=10:1 to 0:1) and preparative HPLC to afford the desired product B-7.

The relevant characterization data was as follows: LCMS m/z: 328.1 [M+H].

$^1$HNMR (400 MHz, DMSO-d$_6$): δ 13.06 (brs, 1H), 8.47 (s, 1H), 8.02-7.99 (m, 3H), 7.73 (s, 1H), 7.43-7.15 (m, 7H).

Example B-10

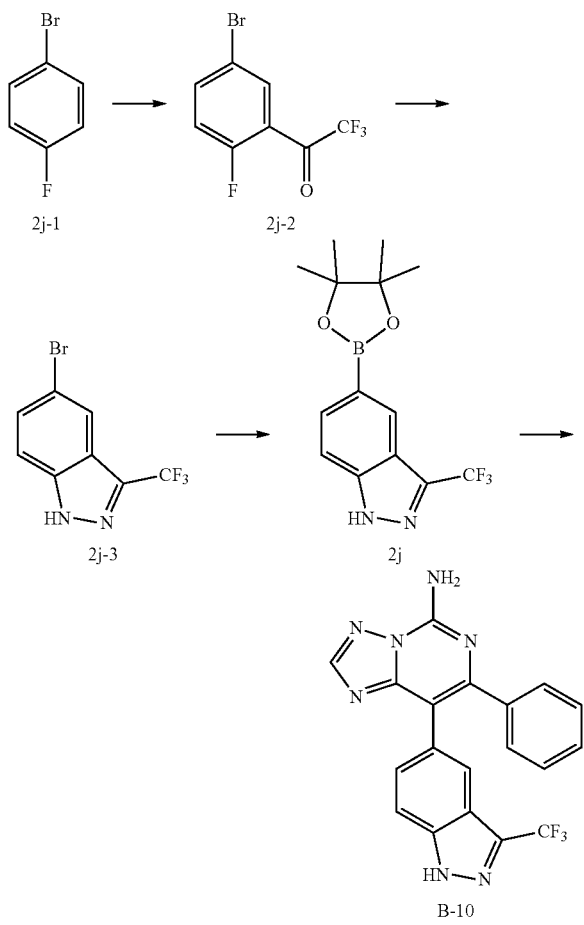

The First Step (Synthesis of Compound 2j-2)

Diisopropylamine (635.57 mg, 6.28 mmol, 882.74 uL, 1.10 eq) was dissolved in THF (20.00 mL), to which n-BuLi (2.5 M, 2.51 mL, 1.10 eq) was added dropwise at −78° C. The reaction was carried out at −78° C. for 1 hour, and then a solution of the compound 2j-1 (1.00 g, 5.71 mmol, 628.93 μL, 1.00 eq) in THF (10.00 mL) was added dropwise. The reaction solution was reacted at −78° C. for 1 hour, and then a solution of ethyl trifluoroacetate (893.07 mg, 6.28 mmol, 867.06 uL, 1.10 eq) in THF (10.00 mL) was added. The reaction solution was then allowed to react at 0° C. for 2 hours. TLC showed complete consumption of compound 2j-1, and production of a more polar spot. The reaction was quenched by the addition of 20 mL of an aqueous solution of ammonium chloride at 0° C. The mixture was extracted with ethyl acetate (20 mL*2). The organic layers were combined, washed with saturated brine (40 mL), dried over anhydrous sodium sulfate and filtered. The solvent was evaporated to dryness. The crude product was purified by a normal phase silica gel column (PE:EA=1:0 to 3:1) to afford the compound 2j-2, yield: 42.0%.

The relevant characterization data was as follows: $^1$H NMR (400 MHz, CHLOROFORM-d): δ 7.91 (dd, J=2.4, 6.0 Hz, 1H), 7.71 (ddd, J=2.4, 4.4, 8.8 Hz, 1H), 7.07 (dd, J=8.8, 10.2 Hz, 1H).

The Second Step (Synthesis of Compound 2j-3)

Compound 2j-2 (5.00 g, 18.45 mmol, 1.00 eq) was dissolved in n-butanol (70.00 mL). Hydrazine hydrate (18.47 g, 369.00 mmol, 17.93 mL, 20.00 eq) was added and the reaction solution was reacted at 120° C. for 6 hours. After the completion of the reaction, the reaction solution was cooled to room temperature, and then 100 mL of water was added. The mixture was extracted with ethyl acetate (100 mL*3). The organic layers were combined, washed with saturated brine (100 mL), dried over anhydrous sodium sulfate and filtered. The solvent was evaporated to dryness. The crude product was purified by a normal phase silica gel column (PE:EA=1:0 to 2:3) to afford the compound 2j-3.

The relevant characterization data was as follows: $^1$H NMR (400 MHz, CHLOROFORM-d): δ 10.28-10.89 (m, 1H), 8.04 (s, 1H), 7.60 (dd, J=1.6, 8.8 Hz, 1H), 7.47 (d, J=8.8 Hz, 1H)

The Thrid Step (Synthesis of Compound 2j)

Compound 2j-3 (630.00 mg, 2.38 mmol, 1.00 eq), bis(pinacolato)diboron (1.51 g, 5.95 mmol, 2.50 eq), potassium acetate (700.72 mg, 7.14 mmol, 3.00 eq), and Pd(dppf)Cl$_2$.CH$_2$Cl$_2$ (97.18 mg, 119.00 μmol, 0.05 eq) were mixed in dioxane (30.00 mL), and vented and purged with nitrogen for three times. The reaction solution was reacted at 90° C. for 16 hours. After TLC showed the completion of the reaction, the reaction was quenched by the addition of 30 mL of water. The mixture was extracted with ethyl acetate (30 mL*3). The organic layers were combined, washed with saturated brine (50 mL), dried over anhydrous sodium sulfate and filtered. The solvent was evaporated to dryness. The crude product was purified by a normal phase silica gel column (PE:EA=1:0 to 4:1) to afford the compound 2j.

The relevant characterization data was as follows: $^1$HNMR (400 MHz, CHLOROFORM-d): δ 10.97 (br s, 1H), 8.31 (s, 1H), 7.83 (d, J=8.8 Hz, 1H), 7.45-7.51 (m, 1H), 7.19 (s, 1H), 1.31 (s, 12H).

The Fourth Step (Synthesis of Compound B-10)

Example B-10: The preparation of the present example compound can be carried out by referring to the method in the above-mentioned route 2 for the preparation of Example A-1, except that in step 8 boric acid 2j was used as starting material to replace the raw material 2a. The crude product was purified to afford the desired product B-10.

The relevant characterization data was as follows: LCMS m/z: 396.2 [M+H].

$^1$H NMR (400 MHz, DMSO-d$_6$): δ 14.00 (br s, 1H), 8.51 (s, 1H), 8.08 (br s, 2H), 7.76 (s, 1H), 7.58 (d, J=8.78 Hz, 1H), 7.34 (br d, J=8.78 Hz, 3H), 7.20-7.27 (m, 3H).

The preparation of example compounds in Table 5 can be carried out by referring to the method in the above-mentioned route 2 for the preparation of Example A-1, except that in step 8 boric acids in the following table were used as starting materials to replace the raw material 2a to afford the corresponding compounds.

TABLE 5

| Products No. | Structure of products | Raw materials No. and their chemical structures | LCMS of products, m/z: [M + H] | $^1$H NMR of products |
|---|---|---|---|---|
| Example B-20 | (structure) 2s | (structure) | 343.1 | $^1$H NMR (400 MHz, DMSO-$d_6$): δ 10.41 (s, 1 H), 8.47 (s, 1H), 7.99 (br s, 2H), 7.35-7.40 (m, 2 H), 7.26-7.30 (m, 3H), 7.23 (s, 1H), 6.93 (s, 1 H), 6.69 (d, J = 8.0 Hz, 1 H), 3.44 (s, 2H). |
| Example B-24 | (structure) 2v | (structure) | 322.1 | $^1$H NMR (400 MHz, DMSO-$d_6$): δ 8.48 (s, 1H), 7.54-7.61 (m, 2H), 7.40-7.42 (m, 3H), 6.06 (br s, 2H), 5.36 (s, 1H), 4.15 (m, 1H), 3.67 (d, J = 3.2 Hz, 1H), 2.38-2.42 (m, 1H), 2.08-2.12 (m, 1H), 1.15 (d, J = 6.0 Hz, 3H), 0.90-0.94 (m, 3H) |
| Example B-26 | (structure) 2w | (structure) | 336.0 | $^1$H NMR (400 MHz, CDCl$_3$): δ 8.24 (s, 1H), 7.33-7.31 (m, 2H), 7.24-7.21 (m, 3H), 7.05-7.02 (m, 2H), 6.97 (s, 1H), 5.88 (brs, 2H), 2.19 (s, 3H). |

Example B-13

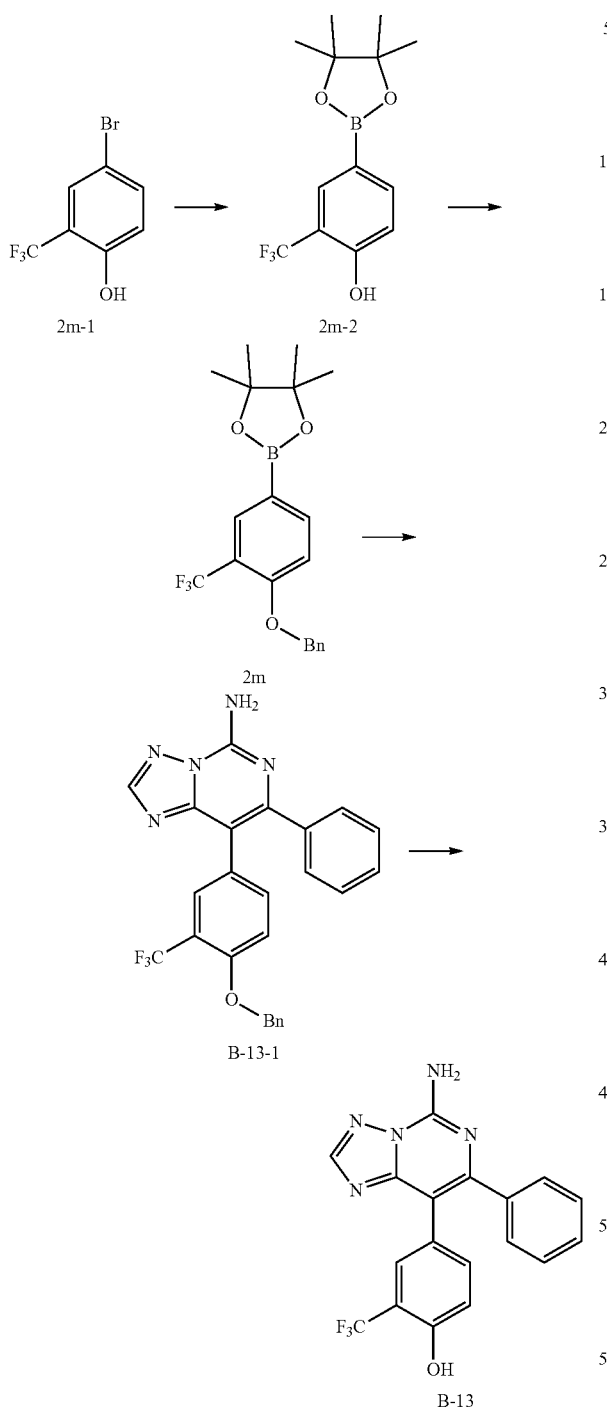

The First Step (Synthesis of Compound 2m-2)

The preparation of the present compound can be carried out by referring to the above-mentioned method for the preparation of Example B-10, except that in step 3 boric acid 2m-1 was used as starting material to replace the raw material. The crude product was purified by silica gel column chromatography (packing material: 100-200 mesh silica gel powder, mobile phase: petroleum ether/ethyl acetate=50/1, 10/1) to afford the compound 2m.

The relevant characterization data was as follows: LCMS m/z: 289.0 [M+H].

The Second Step (Synthesis of Compound 2m)

Compound 2m-2 (600.00 mg, 1.12 mmol, 1.00 eq), benzyl bromide (287.33 mg, 1.68 mmol, 199.53 uL, 1.50 eq), and potassium carbonate (309.59 mg, 2.24 mmol, 2.00 eq) were dissolved in acetonitrile (8 mL), which was heated to 90° C. and stirred for 10 hours. After LC-MS showed the complete consumption of the raw material, the reaction solution was cooled to room temperature. The reaction solution was concentrated under reduced pressure at 50° C. The crude product was purified by silica gel column chromatography (packing material: 100-200 mesh silica gel powder, mobile phase: petroleum ether/ethyl acetate=20/1, 10/1) to afford 2m.

The relevant characterization data was as follows: LCMS m/z: 379.0 [M+H].

The Thrid Step (Synthesis of Compound B-13-1)

The preparation of B-13-1 can be carried out by referring to the method in the above-mentioned route 2 for the preparation of Example A-1, except that in step 8 boric acid 2m was used as starting material to replace the raw material 2a. The crude product was purified by preparative TLC plate (petroleum ether/ethyl acetate=1:1) to afford the compound B-13-1.

The relevant characterization data was as follows: LCMS m/z: 461.4 [M+H].

The Fourth Step (Synthesis of Compound B-13)

Compound B-13-1 (50.00 mg, 78.02 μmol, 1.00 eq), and Pd/C (5.00 mg, 7.80 μmol, 10% purity) were dissolved in tetrahydrofuran/methanol (6 mL/8 mL) at 25° C. The mixture was vented and purged with hydrogen for three times and then stirred at 25° C. for 20 hours under hydrogen atmosphere. After LC-MS showed the complete consumption of the raw material, the reaction solution was concentrated under reduced pressure at 50° C. The crude product was purified by silica gel column chromatography (packing material: 100-200 mesh silica gel powder, mobile phase: petroleum ether/ethyl acetate=5/1, 1/1) to afford a crude product. The crude product was subjected to neutral Pre-HPLC machine separation (mobile phase: water/acetonitrile) to afford B-13.

The relevant characterization data was as follows: LCMS m/z: 372.0 [M+H].

$^1$H NMR (400 MHz, DMSO-d$_6$): δ 10.52 (br s, 1H), 8.49 (s, 1H), 8.03 (br s, 2H), 7.43 (d, J=2.0 Hz, 1H), 7.36-7.24 (m, 6H), 6.89 (d, J=8.4 Hz, 1H)

Example B-14

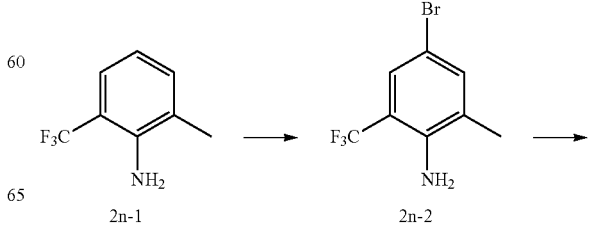

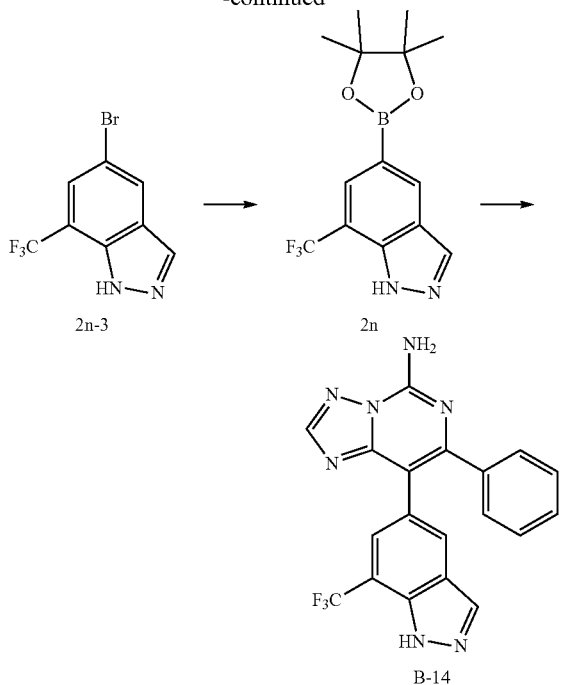

The Thrid Step (Synthesis of Compound 2n)

The preparation of the present compound can be carried out by referring to the above-mentioned method for the preparation of Example B-10, except that in step 3 boric acid 2n-3 was used as starting material to replace the raw material. The crude product was purified by silica gel column chromatography (packing material: 100-200 mesh silica gel powder, mobile phase: petroleum ether/ethyl acetate=1/0, 10/1) to afford the compound 2n.

The relevant characterization data was as follows: LCMS m/z: 313.1 [M+H].

$^1$H NMR (400 MHz, CDCl$_3$): δ 10.4 (brs, 1H), 8.46 (s, 1H), 8.18 (s, 1H), 8.08 (s, 1H), 1.38 (s, 12H).

The Fourth Step (Synthesis of Compound B-14)

Example B-14: The preparation of the present example compound can be carried out by referring to the method in the above-mentioned route 2 for the preparation of Example A-1, except that in step 8 boric acid 2n was used as starting material to replace the raw material 2a to afford the compound B-14.

The relevant characterization data was as follows: LCMS m/z: 396.0 [M+H].

$^1$H NMR (400 MHz, DMSO-d$_6$): δ 13.65 (s, 1H), 8.51 (s, 1H), 8.25 (m, 1H), 8.11 (br s, 2H), 8.07 (s, 1H), 7.53 (s, 1H), 7.38-7.31 (m, 2H), 7.29-7.21 (m, 3H).

Example B-15

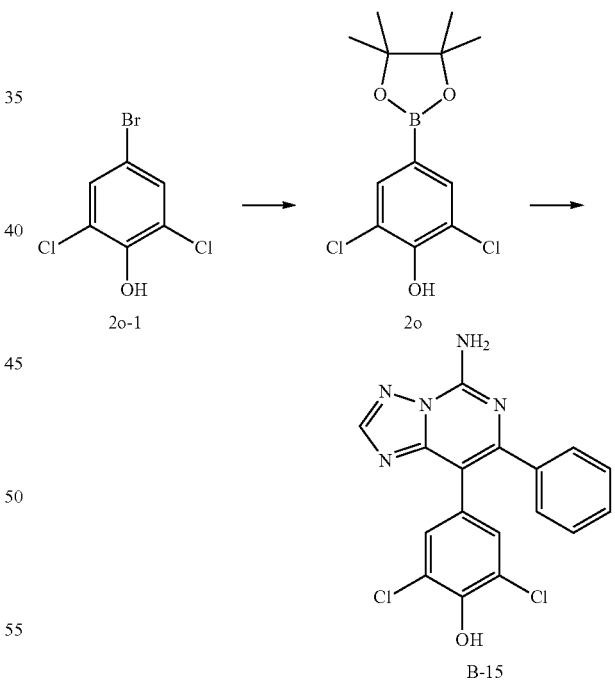

The First Step (Synthesis of Compound 2n-2)

Compound 2n-1 (2.00 g, 11.42 mmol, 1.00 eq) was dissolved in acetonitrile (55.00 mL) at 25° C., and N-bromosuccinimide (2.03 g, 11.42 mmol, 1.00 eq) was slowly added to the reaction solution. The reaction solution was heated to 25° C. and stirred for 1 hour. After LC-MS showed the complete consumption of the raw material, the reaction solution was concentrated under reduced pressure at 50° C. Saturated brine was added to the obtained crude product. The aqueous phase was extracted with ethyl acetate (50 mL*3). The organic phases were combined and concentrated under reduced pressure. The crude product was purified by a normal phase silica gel column (PE:EA=1:0) to afford the desired compound 2n-2.

The relevant characterization data was as follows: LCMS m/z: 253.9 [M+H].

$^1$H NMR (400 MHz, CDCl$_3$): δ 7.44 (s, 1H), 7.32 (s, 1H), 4.25 (brs, 1H), 2.18 (s, 3H).

The Second Step (Synthesis of Compound 2n-3)

Compound 2n-2 (2.00 g, 7.87 mmol, 1.00 eq) and acetic acid (7.09 g, 118.05 mmol, 6.75 mL, 15.00 eq) were dissolved in toluene (40.00 mL) at 25° C., and potassium acetate (6.18 g, 62.96 mmol, 8.00 eq) was added to the reaction solution. The reaction solution was stirred at 25° C. for 10 minutes to form a large amount of precipitate. The reaction solution was diluted with acetic acid (6 mL), and amyl nitrite (1.01 g, 8.66 mmol, 1.17 mL, 1.10 eq) was added dropwise to the reaction solution. The reaction solution was stirred at 25° C. for 3 hours. After LC-MS showed the complete consumption of the raw material, the reaction solution was diluted with water (10 mL) and extracted with ethyl acetate and saturated sodium bicarbonate. The organic phase was washed twice with brine. The organic phases were combined, dried over anhydrous sodium sulfate and concentrated under reduced pressure. The crude product was purified by normal phase silica gel column (PE:EA=20:1 to 10:1) to afford the desired compound 2n-3.

The relevant characterization data was as follows: LCMS m/z: 264.9 [M+H].

The First Step (Synthesis of Compound 2o)

The preparation of the present compound can be carried out by referring to the above-mentioned method for the preparation of Example B-10, except that in step 3 boric acid 2o-1 was used as starting material to replace the raw material. The crude product was purified by silica gel column chromatography (packing material: 100-200 mesh silica gel powder, mobile phase: petroleum ether/ethyl acetate=1/1) to afford the compound 2o.

The relevant characterization data was as follows: ¹H NMR (400 MHz, DMSO-d₆): δ 7.50 (s, 2H), 1.27 (s, 12H).

The Second Step (Synthesis of Compound B-15)

Example B-15: The preparation of the present example compound can be carried out by referring to the method in the above-mentioned route 2 for the preparation of Example A-1, except that in step 8 boric acid 2o was used as starting material to replace the raw material 2a to afford the compound B-15.

The relevant characterization data was as follows: LCMS m/z: 372.0 [M+H].

¹HNMR (400 MHz, DMSO-d₆): δ 8.48 (s, 1H), 8.01 (br s, 2H), 7.41-7.36 (m, 2H), 7.34-7.27 (m, 3H), 7.13 (s, 2H).

Example B-16

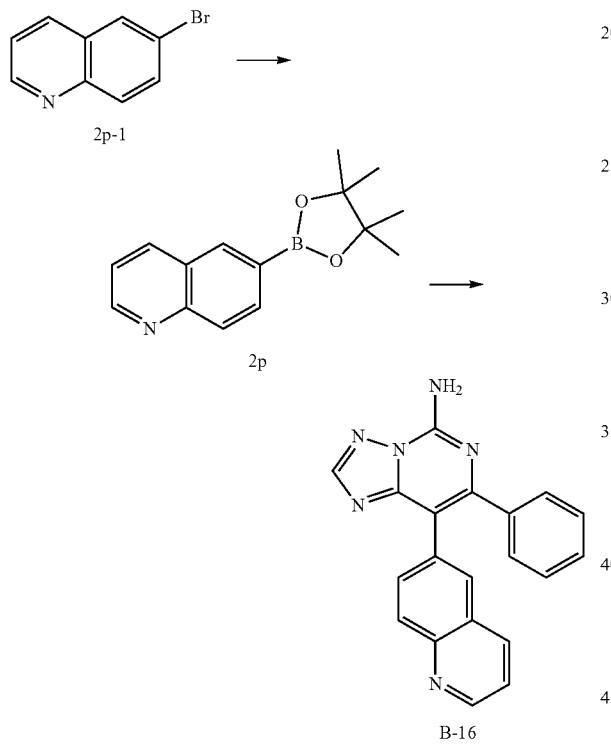

The First Step (Synthesis of Compound 2p)

The preparation of the present compound can be carried out by referring to the above-mentioned method for the preparation of Example B-10, except that in step 3 boric acid 2p-1 was used as starting material to replace the raw material. The crude product was purified by a normal phase silica gel column (PE:EA=1:0 to 10:1) to afford the compound 2p.

The relevant characterization data was as follows: ¹H NMR (400 MHz, CHLOROFORM-d): δ 8.95 (dd, J=1.6, 4.0 Hz, 1H), 8.35 (s, 1H), 8.20 (dd, J=1.6, 8.0 Hz, 1H), 8.09 (m, 2H), 7.42 (dd, J=4.0, 8.0 Hz, 1H), 1.40 (s, 12H).

The Second Step (Synthesis of Compound B-16)

Example B-16: The preparation of the present example compound can be carried out by referring to the method in the above-mentioned route 2 for the preparation of Example A-1, except that in step 8 boric acid 2p was used as starting material to replace the raw material 2a. The crude product was purified by pre-HPLC to afford the compound B-16.

The relevant characterization data was as follows: LCMS m/z: 339.2 [M+H].

¹H NMR (400 MHz, DMSO-d₆): δ 8.88 (dd, J=1.6, 4.0 Hz, 1H), 8.52 (s, 1H), 8.27 (d, J=8.0 Hz, 1H), 8.05-8.21 (m, 2H), 8.01 (d, J=1.6 Hz, 1H), 7.87 (d, J=8.4 Hz, 1H), 7.48-7.55 (m, 2H), 7.35-7.41 (m, 2H), 7.20-7.28 (m, 3H).

Example B-17

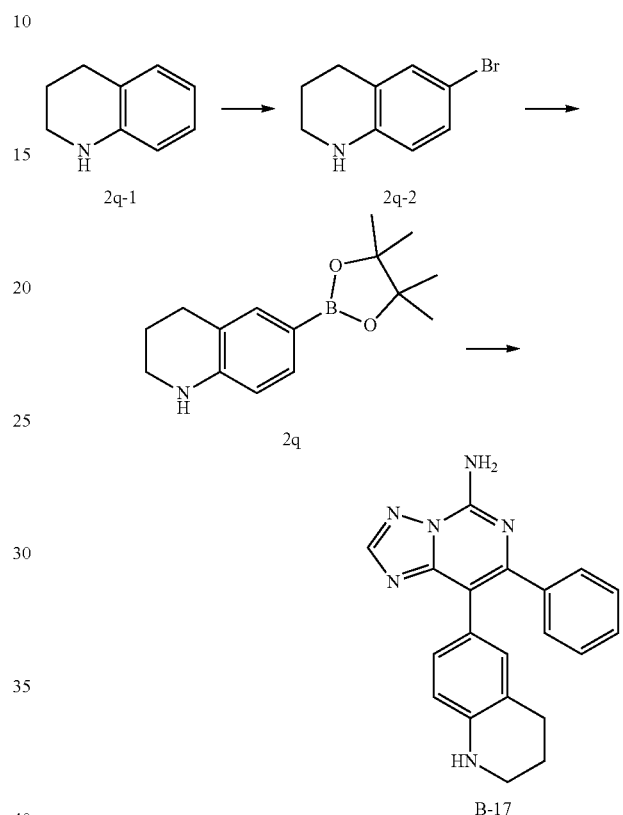

The First Step (Synthesis of Compound 2q-2)

Compound 2q-1 (3.00 g, 22.52 mmol, 1.00 eq) was dissolved in acetonitrile (50.00 mL), and NBS (3.81 g, 21.39 mmol, 0.95 eq) was added portionwise at 0° C. The reaction solution was reacted at 0° C. for 3 hours. The reaction was quenched by the addition of 50 mL of water at 0° C. The mixture was extracted with ethyl acetate (50 mL*3). The organic layers were combined, washed with saturated brine (50 mL), dried over anhydrous sodium sulfate and filtered. The solvent was evaporated to dryness. The crude product was purified by normal phase silica gel column (PE:EA=1:0 to 10:1) to afford the compound 2q-2.

The relevant characterization data was as follows: ¹H NMR (400 MHz, CHLOROFORM-d): δ 6.98-7.07 (m, 2H), 6.34 (d, J=8.0 Hz, 1H), 3.25-3.31 (m, 2H), 2.72 (t, J=6.40 Hz, 2H), 1.85-1.95 (m, 2H).

The Second Step (Synthesis of Compound 2q)

The preparation of the present compound can be carried out by referring to the above-mentioned method for the preparation of Example B-10, except that in step 3 boric acid 2q-2 was used as starting material to replace the raw material. The crude product was purified by normal phase silica gel column (PE:EA=1:0 to 10:1) to afford the compound 2q.

The relevant characterization data was as follows: ¹HNMR (400 MHz, CHLOROFORM-d): δ 7.40-7.46 (m, 2H), 6.45 (d, J=8.28 Hz, 1H), 3.30-3.38 (m, 2H), 2.78 (t, J=6.27 Hz, 2H), 1.89-1.98 (m, 2H), 1.33 (s, 12H).

The Thrid Step (Synthesis of Compound B-17)

Example B-17: The preparation of the present example compound can be carried out by referring to the method in the above-mentioned route 2 for the preparation of Example A-1, except that in step 8 boric acid 2q was used as starting material to replace the raw material 2a. The crude product was purified by pre-HPLC to afford the compound B-17.

The relevant characterization data was as follows: LCMS m/z: 343.2 [M+H].

$^1$H NMR (400 MHz, DMSO-d$_6$): δ 8.44 (s, 1H), 7.83 (br s, 2H), 7.35-7.41 (m, 2H), 7.24-7.30 (m, 3H), 6.86 (s, 1H), 6.63 (d, J=8.4 Hz, 1H), 6.27 (d, J=8.4 Hz, 1H), 5.69 (s, 1H), 3.17 (br d, J=4.8 Hz, 2H), 2.54-2.59 (m, 2H), 1.77 (br d, J=4.8 Hz, 2H).

Example B-19

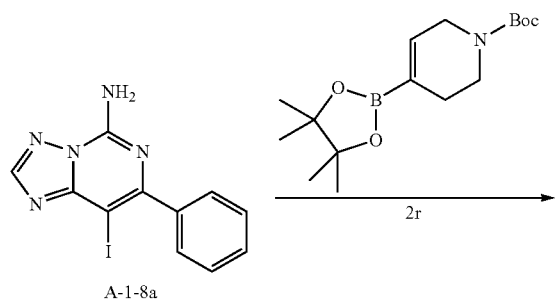

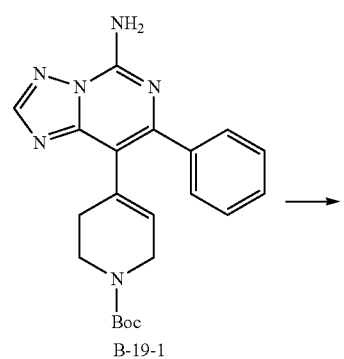

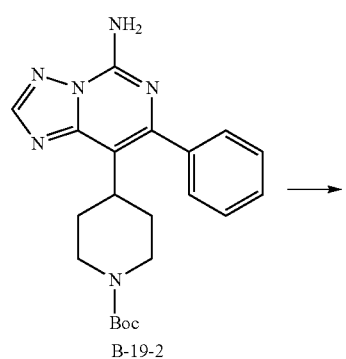

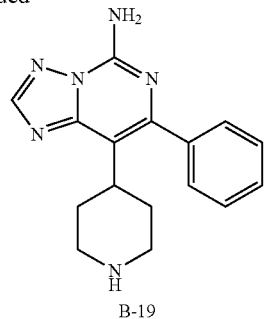

B-19

The First Step (Synthesis of Compound B-19-1)

The preparation of the present compound B-18-1 can be carried out by referring to the method in the above-mentioned route 2 for the preparation of Example A-1, except that in step 8 boric acid 2r was used as starting material to replace the raw material 2a. The crude product was purified by column chromatography (100-200 mesh silica gel, petroleum ether/ethyl acetate=5:1, 1:1) to afford the compound B-19-1.

The relevant characterization data was as follows: LCMS m/z: 377.1 [M+H].

$^1$H NMR (300 MHz, DMSO-d$_6$): δ 8.46 (s, 1H), 7.94 (br s, 2H), 7.58 (br d, J=3.2 Hz, 2H), 7.39 (br dd, 5.0 Hz, 3H), 5.60 (br s, 1H), 3.80 (br s, 2H), 3.45 (br s, 2H), 2.24 (br s, 2H), 1.40 (s, 9H).

The Second Step (Synthesis of Compound B-19-2)

Compound B-19-1 (100.00 mg, 249.71 μmol, 1.00 eq), and Pd/C (20.00 mg, 10% purity) were dissolved in (15.00 mL) at 20° C., and then the reaction solution was stirred at 20° C. under hydrogen pressure of 30 psi for 36 hours. After LC-MS showed the complete consumption of the raw material, the reaction solution was filtered and then concentrated under reduced pressure at 50° C. to afford the compound B-19-2.

The relevant characterization data was as follows: LCMS m/z: 339.1 [M+H].

The Thrid Step (Synthesis of Compound B-19)

Compound B-19-2 (74.00 mg, 166.58 μmol, 1.00 eq) was dissolved in EtOAc (2.00 mL) at 20° C., and then HCl/EtOAc (2.00 mL, 1.00 eq) was added dropwise to the reaction solution and stirred at 20° C. for 1 hour. After LC-MS showed the complete consumption of the raw material, the reaction solution was concentrated under reduced pressure at 50° C., and then dissolved with water. Then, a 2M NaOH solution (2 mL) was added dropwise. The mixture was filtered to afford the compound B-19.

The relevant characterization data was as follows: LCMS m/z: 295.1 [M+H].

$^1$H NMR (400 MHz, DMSO-d$_6$): δ 8.51 (s, 1H), 7.75 (br s, 2H), 7.54-7.38 (m, 5H), 2.95 (br d, J=10.8 Hz, 2H), 2.73-2.67 (m, 2H), 2.45-2.42 (m, 1H), 2.37-2.24 (m, 2H), 1.46 (br d, J=11.6 Hz, 2H).

Example B-22

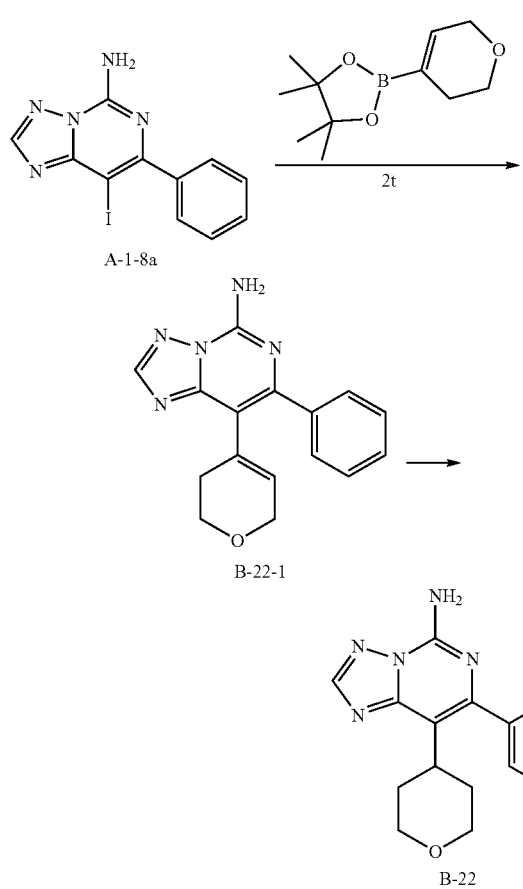

The First Step (Synthesis of Compound B-22-1)

Example B-22-1: The preparation of the present example compound can be carried out by referring to the method in the above-mentioned route 2 for the preparation of Example A-1, except that in step 8 the boric acid 2t was used as starting material to replace the raw material 2a.

The Second Step (Synthesis of Compound B-22)

Compound B-22-1 (30.00 mg, 101.25 μmol, 1.00 eq) was dissolved in methanol (10 mL), and Pd/C (30.00 mg, 10% purity) was added to the reaction solution. The reaction solution was vented and purged with nitrogen for three times, vented and pruged with hydrogen for three times, and stirred at 30° C. under hydrogen pressure of 30 psi for 12 hours. LC-MS showed that 87% of the starting material was not reacted. The reaction solution was filtered with Celite, and the filtrate was concentrated under reduced pressure at 50° C. Methanol (10 mL) was added, and Pd/C (30.00 mg, 10% purity) was added to the reaction solution. The reaction solution was vented and purged with nitrogen for three times, vented and pruged with hydrogen for three times, and stirred at 40° C. under hydrogen pressure of 50 psi for 12 hours. LC-MS showed complete consumption of the raw material. The reaction solution was filtered with Celite, and the filtrate was concentrated under reduced pressure at 50° C. The crude product was purified by prep HPLC to afford B-22.

The relevant characterization data was as follows: LCMS m/z: 296.1 [M+H].

$^1$H NMR (400 MHz, DMSO-d$_6$): δ 8.52 (s, 1H), 7.79 (br s, 2H), 7.53-7.42 (m, 5H), 3.91-3.86 (m, 2H), 3.20-3.17 (m, 2H), 2.90-2.81 (m, 1H), 2.71-2.58 (m, 2H), 1.46 (m, 2H).

Example B-25

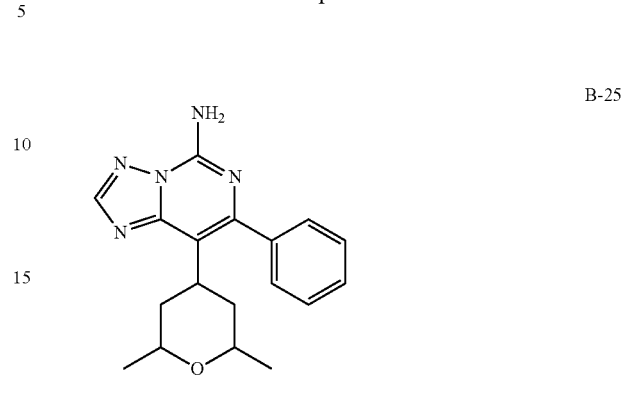

Compound B-24 (38.00 mg, 118.24 μmol, 1.00 eq) and wet palladium on carbon (20.00 mg) were dissolved in methanol (10 mL) at 25° C. The reaction solution was vented and purged with nitrogen for three times and placed in hydrogen atmosphere of 50 psi. The reaction solution was heated to 40° C. and stirred for 32 hours. After the completion of the reaction, the reaction solution was filtered with Celite, and the filtrate was rotary evaporated to dryness. The crude product was subjected to neutral machine separation (mobile phase: water/acetonitrile) to afford B-25.

The relevant characterization data was as follows: LCMS m/z: 324.1 [M+H].

$^1$H NMR (400 MHz, DMSO-d$_6$): δ 8.52 (s, 1H), 7.79 (br s, 2H), 7.44-7.48 (m, 5H), 3.30-3.25 (m, 2H), 2.94-2.96 (m, 1H), 2.17-2.23 (m, 2H), 1.49-1.52 (m, 2H), 1.08 (d, J=6.0 Hz, 6H).

Example B-23

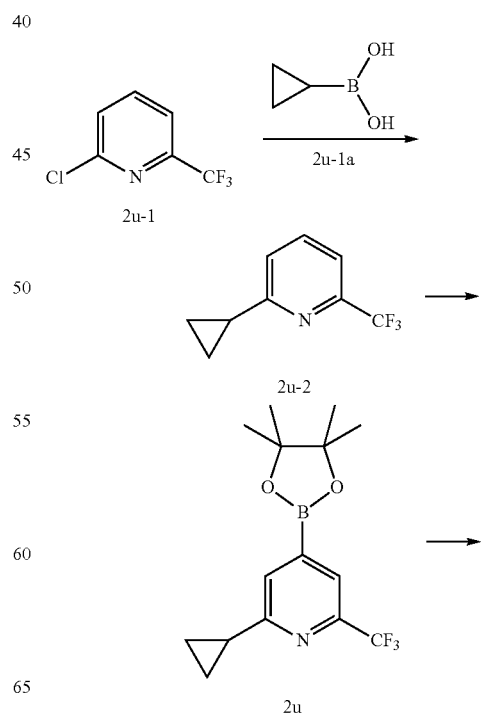

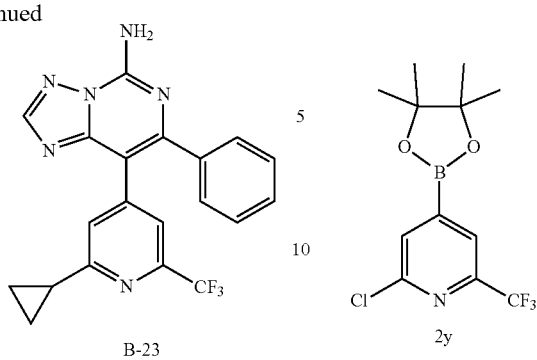

B-23

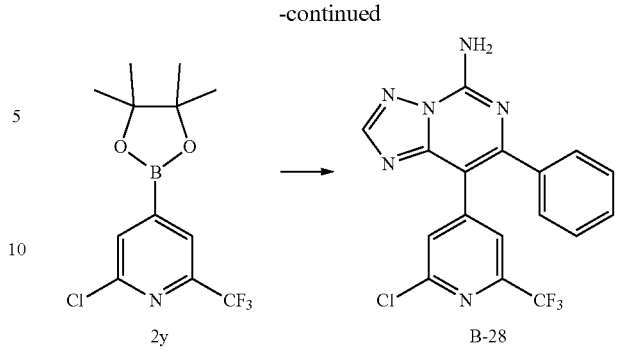

2y      B-28

The First Step (Synthesis of Compound 2u-2)

Compound 2u-1 (1.00 g, 5.51 mmol, 1.00 eq), cyclopropylboric acid 2u-1a (709.96 mg, 8.27 mmol, 1.50 eq), and potassium carbonate (1.52 g, 11.02 mmol, 2.00 eq) were dissolved in dioxane (20 mL) and water (4 mL) at 25° C., and then Pd(dppf)Cl$_2$.CH$_2$Cl$_2$ (449.97 mg, 551.00 μmol, 0.10 eq) was added to the reaction solution. The reaction solution was heated to 100° C. and stirred for 6 hours. After LC-MS showed the complete consumption of the raw material, the reaction solution was filtered with Celite, and the filtrate was concentrated under reduced pressure at 50° C. to afford the desired compound 2u-2.

The relevant characterization data was as follows: LCMS m/z: 188.0 [M+H].

The Second Step (Synthesis of Compound 2u)

The preparation of the present compound can be carried out by referring to the method in the above-mentioned route 1 for the preparation of Example A-1, except that in step 1 boric acid 2u-2 was used as starting material to replace the raw material. The reaction solution was concentrated to afford the crude product 2u, which was directly used in the next step.

The Thrid Step (Synthesis of Compound B-23)

Example B-23: The preparation of the present example compound can be carried out by referring to the method of step 8 of the above-mentioned route 2 for the preparation of Example A-1, except that in step 8 boric acid 2u was used as starting material to replace the raw material 2a to afford the compound B-23.

The relevant characterization data was as follows: LCMS m/z: 397.1 [M+H].

$^1$H NMR (400 MHz, DMSO-d$_6$): δ 8.56 (s, 1H), 8.34 (br s, 2H), 7.41 (d, J=5.2 Hz, 2H), 7.39-7.32 (m, 5H), 2.10-2.04 (m, 1H), 1.01-0.93 (m, 2H), 0.79-0.72 (m, 2H).

Example B-28

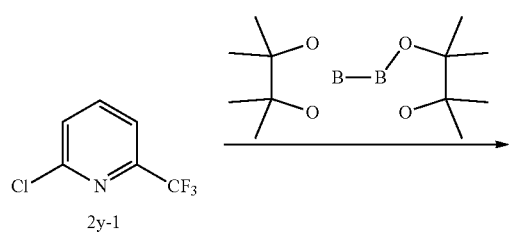

2y-1

The First Step (Synthesis of Compound 2y)

Methyl tert-butyl ether (10 mL) was added to (1,5-cyclooctadiene)(methoxy) iridium (I) dimer (54.69 mg, 82.50 μmol, 0.03 eq), 4,4'-di-tert-butyl-2,2'-bipyridine (44.29 mg, 165.00 μmol, 0.06 eq) and pinacol borate (698.33 mg, 2.75 mmol, 1.00 eq) under nitrogen atmosphere. After the addition, the mixture was stirred at 50° C. for 30 minutes until the solution became dark red. Compound 2y-1 (500.00 mg, 2.75 mmol, 1.00 eq) was then added to the mixture, and the reaction solution was stirred at 50° C. for further 12 hours. After the reaction was completed, the reaction solution was filtered with Celite, and the filtrate was concentrated to afford a crude product. The crude product was purified by silica gel column chromatography (packing material: 200-300 mesh silica gel powder, mobile phase: petroleum ether/ethyl acetate=100/0-10/1) to afford the compound 2y.

The relevant characterization data was as follows: $^1$H NMR (400 MHz, CDCl$_3$-d) δ ppm 7.85 (s, 1H), 7.79 (s, 1H), 1.29 (s, 12H).

The Second Step (Synthesis of Compound B-28)

Example B-28: The preparation of the present example compound can be carried out by referring to the method of step 8 of the above-mentioned route 2 for the preparation of Example A-1, except that in step 8 boric acid 2y was used as starting material to replace the raw material 2a to afford the compound B-28.

The relevant characterization data was as follows: LCMS m/z: 391.0 [M+H].

$^1$H NMR (400 MHz, DMSO-d$_6$): δ 8.61 (s, 1H), 7.79 (s, 1H), 7.66 (d, J=0.8 Hz, 1H), 7.37-7.44 (m, 5H).

The preparation of example compounds in Table 6 can be carried out by referring to the method in the above-mentioned route for the preparation of Example B-28, except that in step 1 starting materials were used to replace the raw material 2y-1 to afford corresponding compounds.

TABLE 6

| Products No. | Structure of products | Raw materials No. and their chemical structures | LCMS of products, m/z: [M + H] | ¹H NMR of products |
|---|---|---|---|---|
| Example B-27 | (structure, 2x) | (pyridine structure) | 319.0 | ¹H NMR (400 MHz, DMSO-d$_6$): δ 8.58-8.46 (m, 1H), 8.35-8.09 (m, 2H), 8.07-7.93 (m, 1H), 7.41-7.23 (m, 5H), 6.86-6.68 (m, 2H), 3.81 (s, 3H) |
| Example B-29 | (structure, 2z) | (pyridine structure) | 333.0 | ¹H NMR (400 MHz, DMSO-d$_6$): δ 8.51 (s, 1H), 8.20 (br s, 2H), 7.45-7.22 (m, 5H), 6.74 (s, 1H), 6.47 (s, 1H), 3.77 (s, 3H), 2.29 (s, 3H) |
| Example B-31 | (structure, 2aa) | (pyridine structure) | 337.0 | ¹H NMR (400 MHz, DMSO-d$_6$): δ 8.54 (s, 1H), 7.41-7.32 (m, 5H), 7.15 (d, J = 8.1 Hz, 2H), 2.34 (s, 3H) |

Example B-32

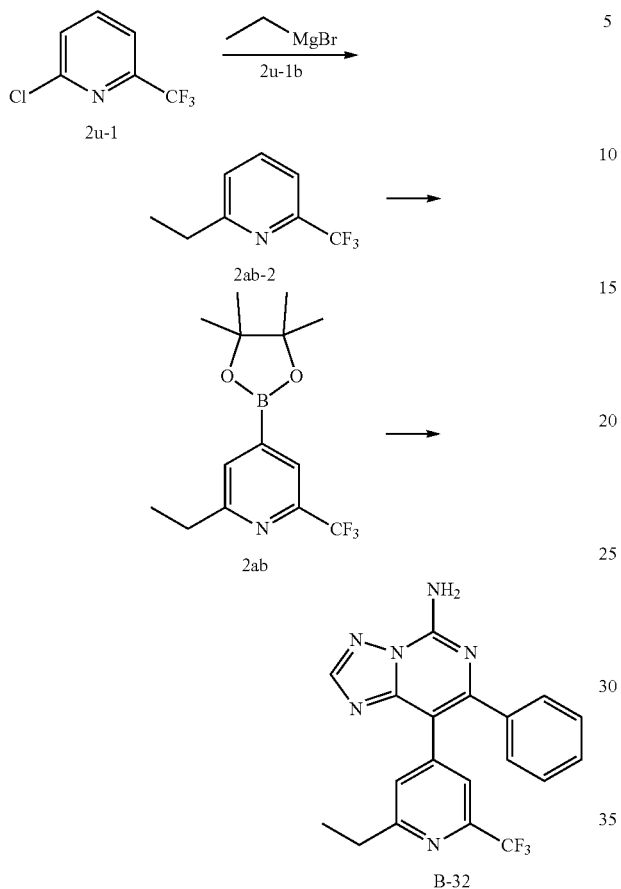

The First Step (Synthesis of Compound 2aB-2)

Compound 2u-1 (1.00 g, 5.51 mmol, 1.00 eq) and iron acetylacetonate (389.08 mg, 1.10 mmol, 0.20 eq) were added to anhydrous tetrahydrofuran (20.00 mL) and N-methylpyrrolidone (2.00 mL) in an ice bath (0° C.). Ethylmagnesium bromide (3 M, 3.67 mL, 2.00 eq) was then added to the reaction solution. This mixture was stirred at 0° C. for 0.5 hour. LCMS showed the completion of the reaction. The reaction was quenched by aqueous sodium bicarbonate solution (60 mL), and then extracted with ethyl acetate (60 mL*3). The organic phase was washed with saturated brine (40 mL*2), dried over anhydrous sodium sulfate and filtered. The filtrate was concentrated under reduced pressure. The residue was purified by column chromatography (silica gel, eluent: petroleum ether/ethyl acetate=100:1 to 20:1) to afford the desired compound 2ab-2.

The relevant characterization data was as follows: LCMS m/z: 176.0 [M+H].

The Second Step (Synthesis of Compound 2ab)

Bis(pinacolato)diboron (763.24 mg, 3.01 mmol, 1.04 eq) was dissolved in methyl tert-butyl ether (10.00 mL), and then bis(1,5-cyclooctadiene)di-μ-methoxy diiridium (I) (57.47 mg, 86.70 μmol, 0.03 eq) and 4,4'-di-tert-butyl-2,2'-bipyridine (23.27 mg, 86.70 μmol, 0.03 eq) were added to the reaction solution. This mixture was stirred at 70-80° C. for 15 minutes. The compound 2ab-2 (507.00 mg, 2.89 mmol, 1.00 eq) was then added to the reaction system. This mixture was stirred at 70-80° C. for 9 hours. LCMS indicated completion of the reaction and this mixture was concentrated under reduced pressure. The residue was purified by column chromatography (silica gel, eluent: petroleum ether/ethyl acetate=10:1 to 1:1) to afford the desired compound 2ab.

The relevant characterization data was as follows: LCMS m/z: 220.1 [M+H].

The Thrid Step (Synthesis of Compound B-32)

Example B-32: The preparation of the present example compound can be carried out by referring to the method of step 8 of the above-mentioned route 2 for the preparation of Example A-1, except that in step 8 boric acid 2ab was used as starting material to replace the raw material 2a to afford the compound B-32.

The relevant characterization data was as follows: LCMS m/z: 385.1 [M+H].

$^1$H NMR (400 MHz, DMSO-$d_6$): δ 8.58 (s, 1H), 8.38 (br s, 2H), 7.64 (s, 1H), 7.47-7.18 (m, 6H), 2.68 (q, J=7.6 Hz, 2H), 1.05 (t, J=7.6 Hz, 3H)

Example B-34

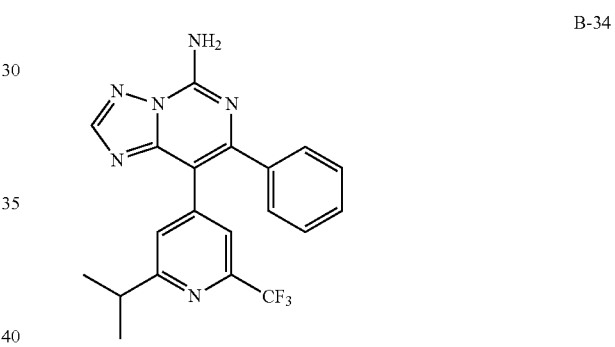

Example B-34: The preparation of the present example compound can be carried out by referring to the method in the above-mentioned route for the preparation of Example B-32, except that in step 1 isopropyl magnesium bromide was used as starting material to replace the raw material 2u-1b to afford compound B-34.

Example B-33

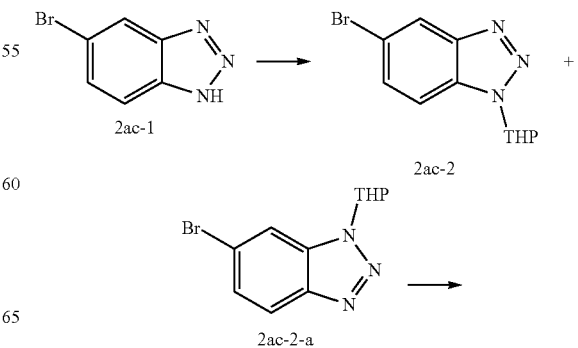

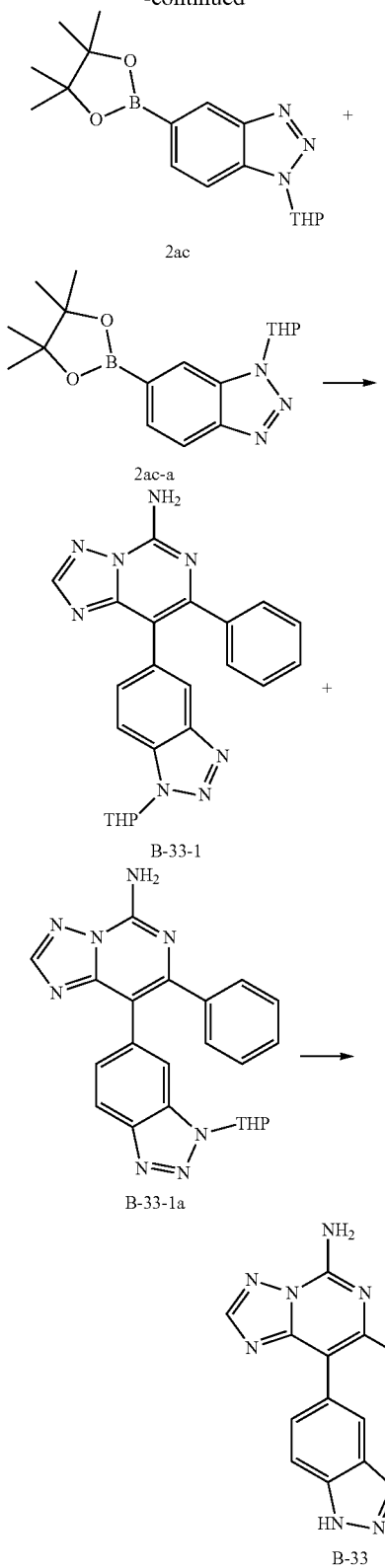

C. for 16 h. After the reaction was completed, the reaction solution was concentrated to afford a crude product. The crude product was purified by silica gel plate chromatography (eluent: petroleum ether/ethyl acetate=3/1) to afford a mixture of 2ac-2 and 2ac-2-a.

The second step (synthesis of compounds 2ac and 2ac-a)

A mixture of 2ac-2 and 2ac-2-1 (160.00 mg, 567.09 μmol, 1.00 eq), pinacol borate (158.41 mg, 623.80 μmol, 1.10 eq), Pd(dppf)Cl$_2$ (82.99 mg, 113.42 μmol, 0.20 eq), and potassium acetate (166.96 mg, 1.70 mmol, 3.00 eq) were dissolved in 1,4-dioxane (5 mL) at 25° C. The reaction solution was vented and purged with nitrogen for three times and then heated to 90° C. and further stirred for 16 hours under nitrogen. After the reaction was completed, the reaction solution was cooled to 25° C. The reaction solution was filtered with Celite, and the filtrate was concentrated. The crude product was purified by silica gel plate chromatography (eluent: petroleum ether/ethyl acetate=1/1) to afford a mixture of 2ac and 2ac-a.

The third step (synthesis of compounds B-33-1 and B-33-1a)

Example B-33-1 and B-33-1a: The preparation of the present example compounds can be carried out by referring to the method of step 8 of the above-mentioned route 2 for the preparation of Example A-1, except that in step 8 boric acid 2ac and 2ac-a were used as starting materials to replace the raw material 2a to afford the compounds B-33-1 and B-33-1a.

The relevant characterization data was as follows: LCMS m/z: 413.1 [M+H].

The Fourth Step (Synthesis of Compound B-33)

To a solution of the compounds B-33 and B-33-1a (50.00 mg, 121.23 μmol, 1.00 eq) in methanol (4 mL), a solution of hydrogen chloride in methanol (4 M, 2.00 mL, 65.99 eq) was added in one portion at 25° C., and the reaction solution was heated to 70° C. and stirred for 3 hours. After the reaction was completed, the reaction solution was rotary evaporated to dryness. The crude product was dissolved in methanol (5 mL), adjusted to pH=8 to 9 with sodium bicarbonate solids, and then subjected to neutral machine separation (mobile phase: water/acetonitrile) to afford B-33.

The relevant characterization data was as follows: LCMS m/z: 329.1 [M+H].

$^1$H NMR (400 MHz, DMSO-d$_6$): δ 8.50 (s, 1H), 8.12 (brs, 2H), 7.76-7.84 (m, 2H), 7.35 (m, 2H), 7.24 (m, 4H).

Example C-1

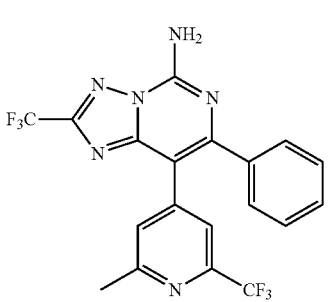

The first step (synthesis of compounds 2ac-2 and 2ac-2-a)

A solution of the mixture of 2ac-1 (250.00 mg, 1.26 mmol, 1.00 eq), 3,4-dihydro-2H-pyran (108.33 mg, 1.29 mmol, 117.75 μL, 1.02 eq) and DDQ (28.66 mg, 126.25 μmol, 0.10 eq) in acetonitrile (10.00 mL) was stirred at 20°

Synthesis of compound C-1 using (C-1-1) as starting material and the detailed synthetic route as follows:

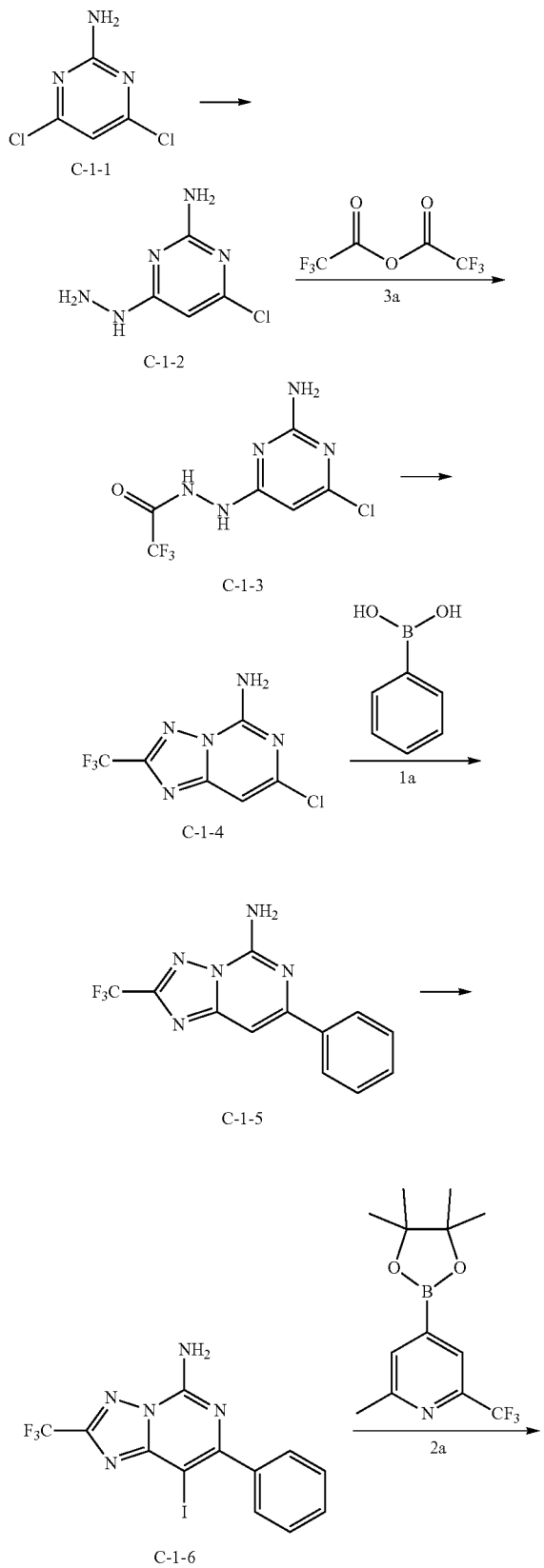

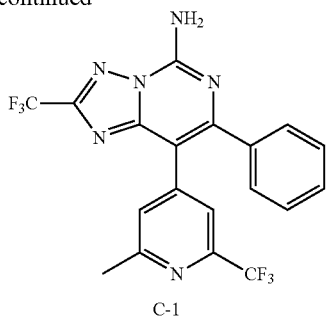

The First Step (Synthesis of Compound C-1-2)

Compound C-1-1 (20.00 g, 121.96 mmol, 1.00 eq.) was dissolved in methanol (1.40 L), and hydrazine hydrate (14.37 g, 243.92 mmol, 13.95 mL, 85% purity, 2.00 eq) was added dropwise to the solution. The reaction solution was stirred at room temperature for 20 hours. After completion of the reaction, most of the solvent was removed by rotary evaporation, and the crude compound C-1-2 was obtained by filtration.

The relevant characterization data was as follows: LCMS m/z: 159.8 [M+H]

The Second Step (Synthesis of Compound C-1-3)

Trifluoroacetic anhydride 3a (4.74 g, 22.56 mmol, 3.14 mL, 1.2 eq.) was added dropwise to a solution of compound C-1-2 (3.00 g, 18.80 mmol, 1.00 eq) in DMF (20.00 mL) at 0° C. The reaction solution was stirred for 4 hours at 0° C. The solvent was rotary evaporated under reduced pressure until solids precipitated. The crude compound C-1-3 was obtained by filtration.

The relevant characterization data was as follows: LCMS m/z: 255.9 [M+H]

The Thrid Step (Synthesis of Compound C-1-4)

Compound C-1-3 (1.09 g, 7.43 mmol, 1.00 eq) was dissolved in N,O-bistrimethylsilylacetamide (20 mL) and stirred at 80° C. for 15 hours. After completion of the reaction, the reaction solution was slowly added dropwise to methanol (50 mL), and then the methanol solution was concentrated to afford a solid. The solid was isolated by column chromatography to afford the compound 4.

The relevant characterization data was as follows: LCMS m/z: 237.9 [M+H]

$^1$H NMR (400 MHz, DMSO-$d_6$): δ 7.23 (s, 1H), 8.72 (br s, 2H)

The Fourth Step (Synthesis of Compound C-1-5)

Compound C-1-4 (100 mg, 421 μmol, 1.00 eq), phenylboric acid 1a (62 mg, 505 μmol, 1.20 eq), Pd(dppf)Cl$_2$.CH$_2$Cl$_2$ (34 mg, 42 μmol, 0.10 eq) and potassium carbonate (116 mg, 842 μmol, 2.00 eq) were dissolved in a mixed solvent of 1,4-dioxane (5 mL) and water (1 mL), vented and purged with nitrogen for three times, and then stirred at 90° C. for 2 hours under nitrogen atmosphere. After the reaction was completed, the reaction solution was cooled to room temperature, and the solvent was rotary evaporated to dryness under reduced pressure. The resulting solid was diluted with water (20 mL) and extracted with ethyl acetate (300 mL*3). The organic phases were combined, dried over anhydrous sodium sulfate and filtered. The filtrate was rotary evaporated to dryness and subjected to column chromatography to afford the compound C-1-5.

The relevant characterization data was as follows: LCMS m/z: 279.9 [M+H]

$^1$H NMR (400 MHz, DMSO-d$_6$): δ 8.33 (brs, 2H), 8.17-8.15 (m, 2H), 7.71 (s, 1H), 7.54-7.47 (m, 3H).

The Fifth Step (Synthesis of Compound C-1-6)

Compound C-1-5 (90 mg, 322.3 μmol, 1.00 eq), and NIS (145.0 mg, 664.6 μmol, 2 eq) were dissolved in acetonitrile (4 mL) and stirred at 80° C. for 2 hr. The reaction solution was cooled to room temperature, and the solvent was removed under reduced pressure. The resulting solid was diluted with aqueous sodium thiosulfate (20 mL) and extracted with ethyl acetate (30 mL*3). The organic phases were combined, dried over anhydrous sodium sulfate and filtered. The filtrate was rotary evaporated to dryness to afford the crude product C-1-6.

The relevant characterization data was as follows: LCMS m/z: 405.9 [M+H].

$^1$H NMR (400 MHz, DMSO-d$_6$): δ 8.42 (brs, 2H), 7.61-7.59 (m, 2H), 7.51-7.41 (m, 3H)

The Sixth Step (Synthesis of Compound C-1)

Compound C-1-6 (126.0 mg, 311 μmol, 1.00 eq), compound 2a (267.9 mg, 933 μmol, 3 eq), Pd(dppf)Cl$_2$·CH$_2$Cl$_2$ (45 mg, 55 μmol, 0.18 eq) and sodium carbonate (107 mg, 777 μmol, 2.50 eq) were dissolved in a mixed solvent of 1,4-dioxane (4 mL) and water (1 mL), vented and purged with nitrogen for three times, and then stirred at 90° C. for 16 hours under nitrogen. The reaction solution was cooled to room temperature, and the solvent was removed under reduced pressure. The resulting solid was diluted with methanol (20 mL) and filtered with suction. The filtrate was rotary evaporated to dryness to afford a solid. The solid was isolated by preparative liquid chromatography to afford the compound C-1.

The relevant characterization data was as follows: LCMS m/z: 439.3 [M+H]

$^1$H NMR (400 MHz, DMSO-d$_6$): δ 7.53 (s, 1H), 7.38-7.32 (m, 6H), 2.48 (s, 3 H).

The preparation of example compounds in Table 7 can be carried out by referring to the similar method in the above-mentioned route for the preparation of Example C-1, except that in steps 2, 4 and 6 raw materials in the following table were used as starting materials to afford the corresponding compounds.

TABLE 7

| Products No. | Structure of products | No. of reaction raw materials | LCMS of products, m/z: [M + H] | $^1$H NMR of products |
|---|---|---|---|---|
| Example C-2 | 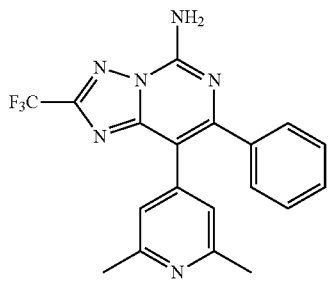 [SMILES: Cc1cc(-c2c(-c3ccccc3)nc(N)n3nc(C(F)(F)F)nc23)cc(C)n1] | 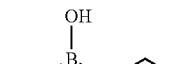 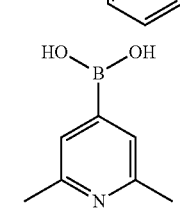 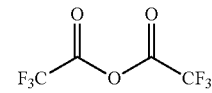 | 385.3 | $^1$H NMR (400 MHz, CDCl$_3$): δ 7.31-7.21 (m, 5H), 6.86 (s, 2H), 6.06 (brs, 2H), 2.38 (s, 6H) |
| Example C-5 | 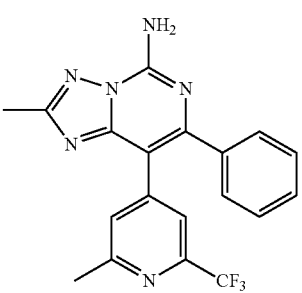 [SMILES: Cc1cc(-c2c(-c3ccccc3)nc(N)n3nc(C)nc23)cc(C(F)(F)F)n1] | 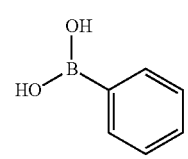 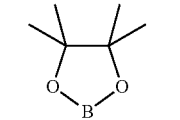 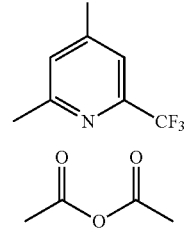 | 385.1 | $^1$H NMR (400 MHz, METHANOL-d$_4$): δ 7.54 (s, 1H), 7.42-7.36 (m, 4H), 7.36-7.29 (m, 2H), 2.56 (s, 3H), 2.54 (s, 3H) |

TABLE 7-continued

| Products No. | Structure of products | No. of reaction raw materials | LCMS of products, m/z: [M + H] | ¹H NMR of products |
|---|---|---|---|---|
| Example C-6 | | phenylboronic acid; (2,6-dimethylpyridin-4-yl)boronic acid; acetic anhydride | 331.1 | ¹H NMR (400 MHz, DMSO-d$_6$): δ 8.07 (br s, 2H), 7.37-7.25 (m, 5H), 6.90 (s, 2H), 2.47 (s, 3H), 2.31 (s, 6H) |
| Example C-7 | | phenylboronic acid; 2-methyl-6-(trifluoromethyl)pyridin-4-yl boronic acid pinacol ester; propionyl chloride | 399.1 | ¹H NMR (400 MHz, DMSO-d$_6$): δ 8.22 (br s, 2H), 7.54 (s, 1H), 7.40 (s, 1H), 7.37-7.29 (m, 5H), 2.85 (q, J = 7.6 Hz, 2H), 2.47 (s, 3H), 1.32 (t, J = 7.6 Hz, 3H) |
| Example C-8 | | phenylboronic acid; (2,6-dimethylpyridin-4-yl)boronic acid; propionyl chloride | 345.0 | ¹H NMR (400 MHz, DMSO-d$_6$): δ 8.06 (br s, 2H), 7.41-7.21 (m, 5H), 6.91 (s, 2H), 2.83 (q, J = 7.6 Hz, 2H), 2.32 (s, 6H), 1.30 (t, J = 7.6 Hz, 3H) |

TABLE 7-continued
| Products No. | Structure of products | No. of reaction raw materials | LCMS of products, m/z: [M + H] | ¹H NMR of products |
|---|---|---|---|---|
| Example C-10 | 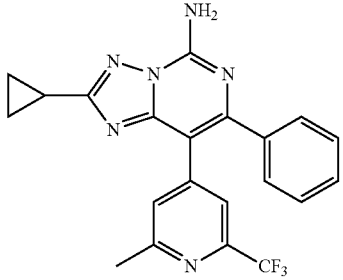 [SMILES: Cc1cc(-c2c(-c3ccccc3)nc(N)n3nc(C4CC4)nc23)cc(C(F)(F)F)n1] | 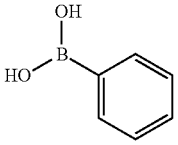 | 411.1 | ¹H NMR (400 MHz, DMSO-d₆): δ 8.18 (brs, 2H), 7.50 (s, 1H), 7.39-7.31 (m, 6H), 2.46 (s, 3H), 2.22-2.13 (m, 1H), 1.06-0.99 (m, 4H) |
| Example C-11 | 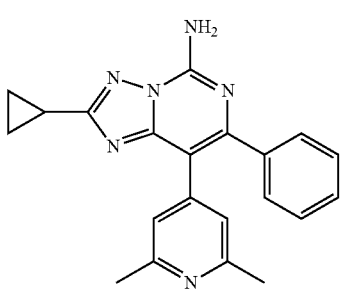 [SMILES: Cc1cc(-c2c(-c3ccccc3)nc(N)n3nc(C4CC4)nc23)cc(C)n1] | 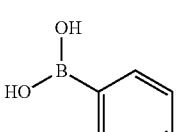 | 357.0 | ¹H NMR (400 MHz, DMSO-d₆): δ 8.01 (br s, 2H), 7.39-7.21 (m, 5H), 6.88 (s, 2H), 2.31 (s, 6H), 2.19-2.14 (m, 1H), 1.04 (m, 2H), 0.98 (m, 2H) |
| Example C-21 | 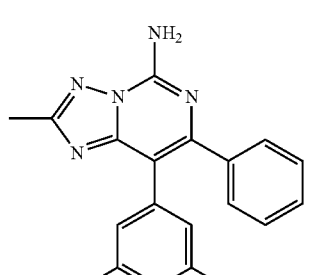 | 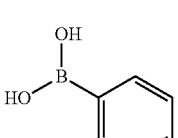 | 351.0 | ¹H NMR (400 MHz, DMSO-d₆): δ 7.30-7.42 (m, 5H), 7.13 (s, 2H), 2.49 (s, 3H), 2.35 (s, 3H). |

TABLE 7-continued
| Products No. | Structure of products | No. of reaction raw materials | LCMS of products, m/z: [M + H] | ¹H NMR of products |
|---|---|---|---|---|
| Example C-22 | 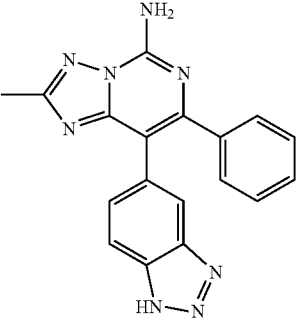 [SMILES: Cc1nc2c(-c3ccc4[nH]nnc4c3)c(-c3ccccc3)nc(N)n2n1] | 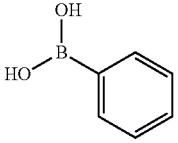 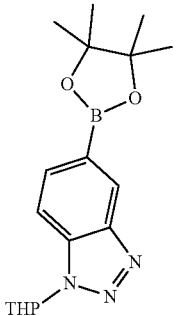 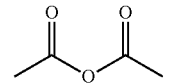 | 343.1 | ¹H NMR (400 MHz, DMSO-d₆): δ 7.96 (br s, 2 H), 7.79 (s, 1H), 7.75 (d, J = 8.4 Hz, 1H), 7.33-7.35 (m, 2H), 7.16-7.25 (m, 4H), 2.46 (s, 3H). |
| Example C-25 | 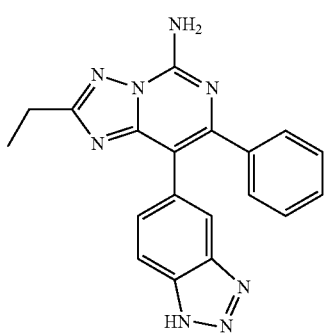 [SMILES: CCc1nc2c(-c3ccc4[nH]nnc4c3)c(-c3ccccc3)nc(N)n2n1] | 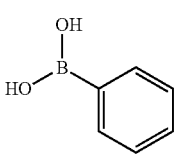 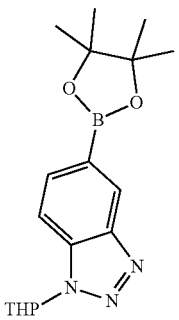 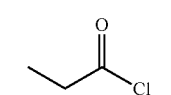 | 357.1 | ¹H NMR (400 MHz, DMSO-d₆): δ 7.90 (br s, 2 H), 7.74 (s, 1H), 7.67 (d, J = 8.4 Hz, 1H), 7.34 (m, 2H), 7.17-7.24 (m, 3H), 7.06 (d, J = 8.4 Hz, 1H), 6.07 (br s, 1H), 2.81 (q, J = 7.6 Hz, 2H), 1.29 (t, J = 7.6 Hz, 3H) |

TABLE 7-continued
| Products No. | Structure of products | No. of reaction raw materials | LCMS of products, m/z: [M + H] | ¹H NMR of products |
|---|---|---|---|---|
| Example C-26 | 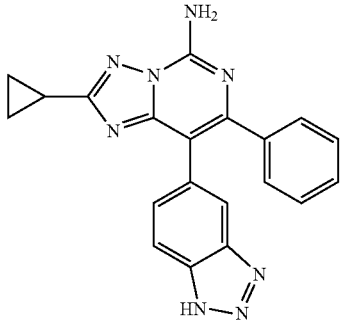 [SMILES: Nc1nc(-c2ccccc2)c(-c2ccc3[nH]nnc3c2)c2nc(C3CC3)nn12] | 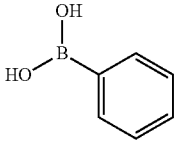 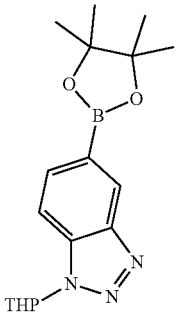 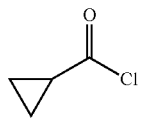 | 369.1 | ¹H NMR (400 MHz, DMSO-d$_6$): δ 7.91 (br s, 2H), 7.79 (s, 1H), 7.75 (d, J = 8.4 Hz, 1H), 7.31 (m, 2H), 7.19-7.25 (m, 4H), 2.12-2.18 (m, 1H), 1.01-1.04 (m, 2H), 0.94-0.96 (m, 2H). |
| Example C-27 | 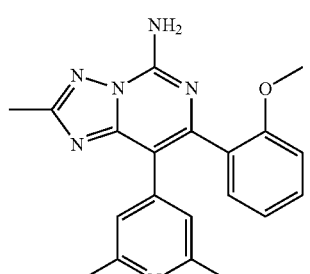 | 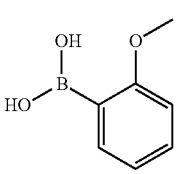 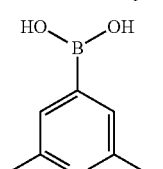 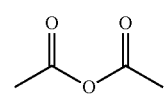 | 415.0 | ¹H NMR (400 MHz, METHANOL-d$_4$): δ 7.44-7.32 (m, 4H), 7.05-6.97 (m, 1H), 6.84 (d, J = 8.0 Hz, 1H), 3.38 (s, 3H), 2.53 (s, 3H), 2.46 (s, 3H). |

TABLE 7-continued
| Products No. | Structure of products | No. of reaction raw materials | LCMS of products, m/z: [M + H] | ¹H NMR of products |
|---|---|---|---|---|
| Example C-29 | 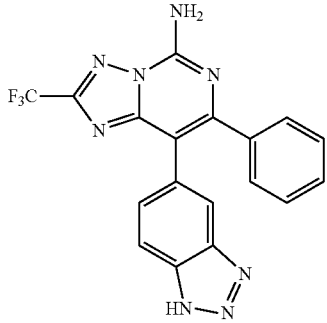 [SMILES: Nc1nc(-c2ccccc2)c(-c2ccc3[nH]nnc3c2)c2nc(C(F)(F)F)nn12] | 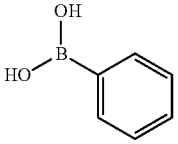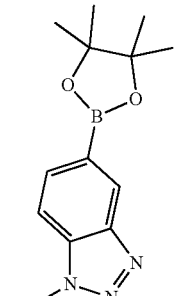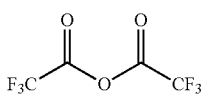 | 397.1 | ¹H NMR (400 MHz, DMSO-d₆): δ 8.44 (br s, 2 H), 7.86 (s, 1H), 7.82 (d, J = 8.8 Hz, 1H), 7.35-7.37 (m, 2H), 7.21-7.29 (m, 4H). |
| Example C-30 | 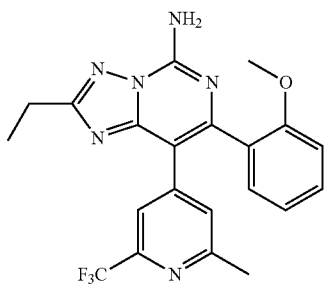 [SMILES: CCc1nc2c(-c3cc(C)nc(C(F)(F)F)c3)c(-c3ccccc3OC)nc(N)n2n1] | 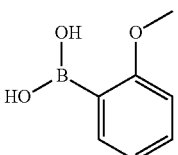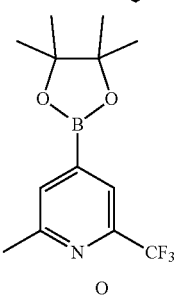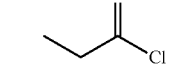 | 429.1 | 1H NMR (400 MHz, CDCl3): δ 7.43 (s, 1H), 7.41-7.35 (m, 3H), 7.06 (t, J = 7.6 Hz, 1H), 6.77 (d, J = 8.4 Hz, 1H), 6.20 (s, 2H), 3.40 (s, 3H), 2.97 (q, J = 7.6 Hz, 2H), 2.54 (s, 3H), 1.45 (t, J = 7.6 Hz, 3H) |

TABLE 7-continued
| Products No. | Structure of products | No. of reaction raw materials | LCMS of products, m/z: [M + H] | $^1$H NMR of products |
|---|---|---|---|---|
| Example C-31 | 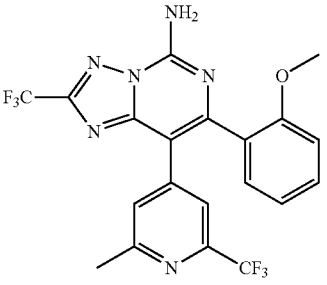 | 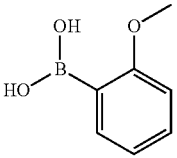 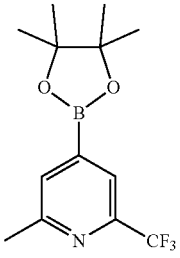 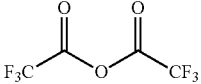 | 469.0 | 1H NMR (400 MHz, DMSO-d$_6$): δ 8.64 (br s, 2H), 7.45-7.36 (m, 4H), 7.05 (t, J = 7.6 Hz, 1H), 6.91-6.89 (d, J = 8.4 Hz, 1H), 3.34 (s, 3H), 2.47 (s, 3H) |
| Example C-32 | 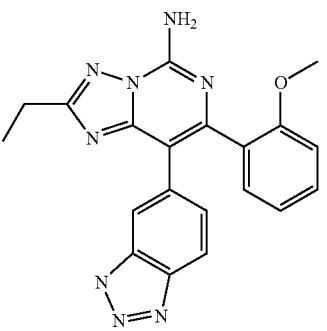 [SMILES: CCc1nc2c(-c3ccc4nn[nH]c4c3)c(-c3ccccc3OC)nc(N)n2n1] | 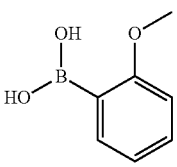 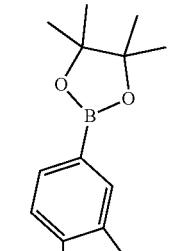 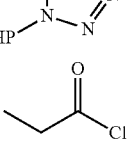 | 387.1 | 1H NMR (400 MHz, DMSO-d$_6$): δ 8.05-7.80 (m, 2H), 7.75-7.68 (m, 1H), 7.65 (s, 1H), 7.30-7.21 (m, 3H), 6.89 (t, J = 7.2 Hz, 1H), 6.82 (d, J = 8.0 Hz, 1H), 3.37 (s, 3H), 2.83 (q, J = 7.6 Hz, 2H), 1.30 (t, J = 7.6 Hz, 3H) |

TABLE 7-continued
| Products No. | Structure of products | No. of reaction raw materials | LCMS of products, m/z: [M + H] | ¹H NMR of products |
|---|---|---|---|---|
| Example C-34 | 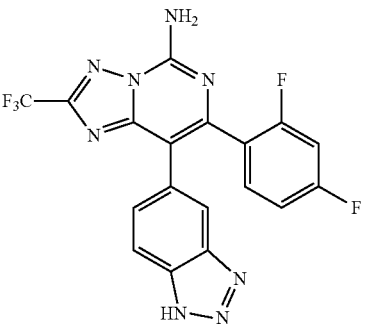 [SMILES: Nc1nc(-c2ccc(F)cc2F)c(-c2ccc3[nH]nnc3c2)c2nc(C(F)(F)F)nn12] | 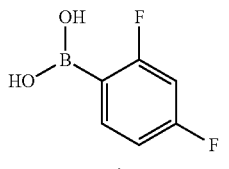 | 433.1 | ¹H NMR (400 MHz, DMSO-d$_6$): δ 8.51 (br s, 2H), 7.92-7.73 (m, 2H), 7.66-7.42 (m, 1H), 7.28 (br d, J = 8.4 Hz, 1H), 7.19-7.03 (m, 2H) |
| Example C-35 | 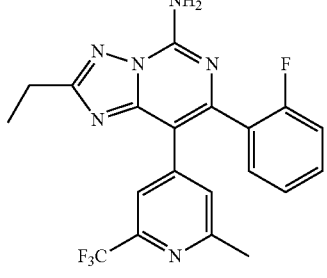 | 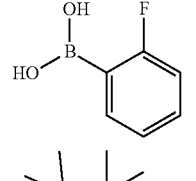 | 417.1 | 1H NMR (400 MHz, DMSO-d$_6$): δ 7.56-7.42 (m, 3H), 7.39 (s, 1H), 7.31-7.23 (m, 1H), 7.12 (t, J = 9.2 Hz, 1H), 2.87 (q, J = 7.5 Hz, 2H), 2.46 (s, 3H), 1.33 (t, J = 7.6 Hz, 3H) |
| Example C-36 | 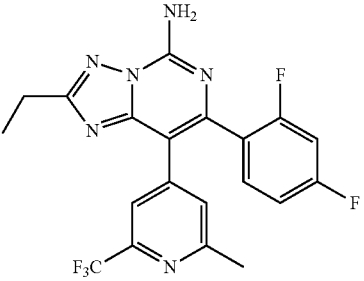 [SMILES: CCc1nc2c(-c3cc(C)nc(C(F)(F)F)c3)c(-c3ccc(F)cc3F)nc(N)n2n1] | 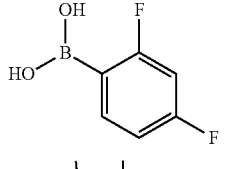 | 435.1 | ¹H NMR (400 MHz, DMSO-d$_6$): δ 8.32 (br s, 2H), 7.62-7.54 (m, 1H), 7.51 (s, 1H), 7.41 (s, 1H), 7.28-7.09 (m, 2H), 2.87 (q, J = 7.6 Hz, 2H), 2.48 (br s, 3H), 1.32 (t, J = 7.6 Hz, 3H) |

TABLE 7-continued
| Products No. | Structure of products | No. of reaction raw materials | LCMS of products, m/z: [M + H] | ¹H NMR of products |
|---|---|---|---|---|
| Example C-37 | 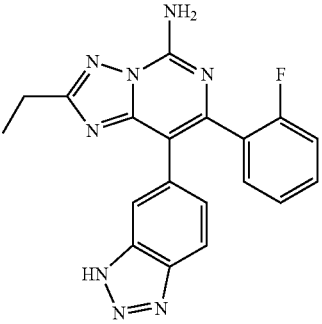 [SMILES: CCc1nc2c(-c3ccc4nn[nH]c4c3)c(-c3ccccc3F)nc(N)n2n1] | 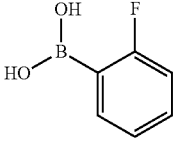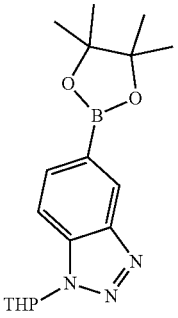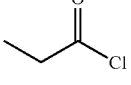 | 375.1 | ¹H NMR (400 MHz, DMSO-d₆): δ 8.00 (br s, 2H), 7.73-7.68 (m, 2H), 7.46-7.39 (m, 1H), 7.36-7.28 (m, 1H), 7.23-7.11 (m, 2H), 7.02 (t, J = 8.8 Hz, 1H), 2.84 (q, J = 7.6 Hz, 2H), 1.30 (t, J = 7.6 Hz, 3H) |
| Example C-38 | 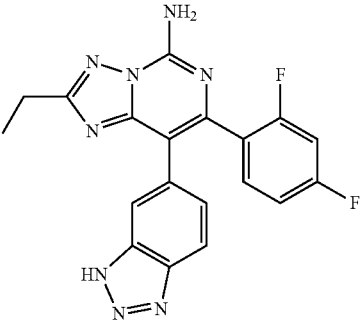 [SMILES: CCc1nc2c(-c3ccc4nn[nH]c4c3)c(-c3ccc(F)cc3F)nc(N)n2n1] | 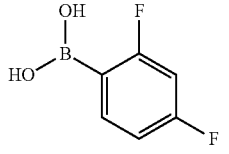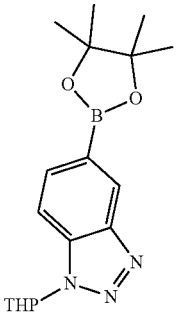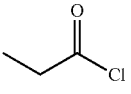 | 393.1 | ¹H NMR (400 MHz, METHANOL-d₄): δ 7.88-7.69 (m, 2H), 7.57-7.44 (m, 1H), 7.33 (m, 1H), 6.94 (m, 1H), 6.78 (m, 1H), 2.91 (q, J = 7.7 Hz, 2H), 1.41 (t, J = 7.6 Hz, 3H) |

TABLE 7-continued
| Products No. | Structure of products | No. of reaction raw materials | LCMS of products, m/z: [M + H] | ¹H NMR of products |
|---|---|---|---|---|
| Example C-39 | 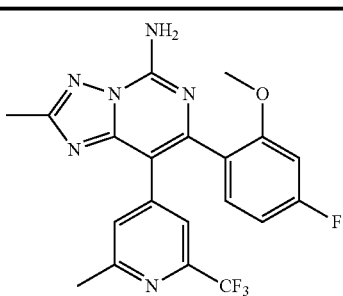 | 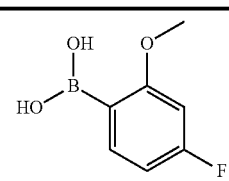 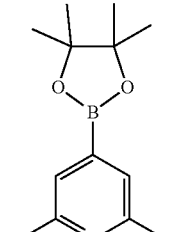 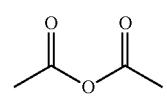 | 433.0 | ¹H NMR (400 MHz, METHANOL-d₄): δ 7.45-7.35 (m, 3H), 6.76 (m, 1H), 6.65 (m, 1H), 3.37 (s, 3H), 2.53 (s, 3H), 2.50 (s, 3H) |
| Example C-40 | 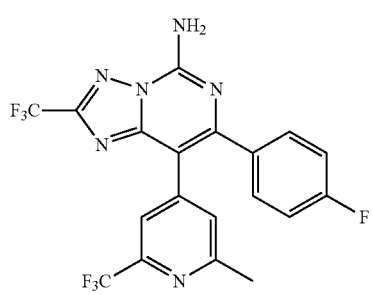 [SMILES: Cc1cc(-c2c(-c3ccc(F)cc3)nc(N)n3nc(C(F)(F)F)nc23)cc(C(F)(F)F)n1] | 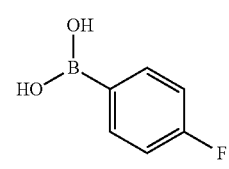 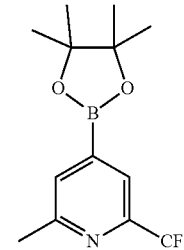 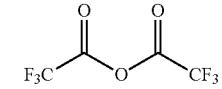 | 457.0 | ¹H NMR (400 MHz, DMSO-d₆): δ 8.68 (br s, 2H), 7.55 (s, 1H), 7.43 (s, 1H), 7.41-7.36 (m, 2H), 7.21 (t, J = 8.8 Hz, 2H), 2.54 (s, 3H) |
| Example C-41 | 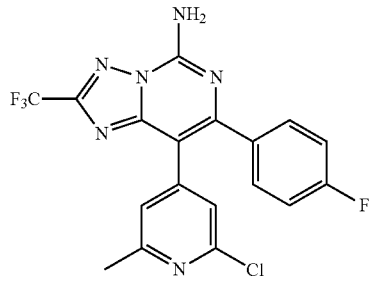 [SMILES: Cc1cc(-c2c(-c3ccc(F)cc3)nc(N)n3nc(C(F)(F)F)nc23)cc(Cl)n1] | 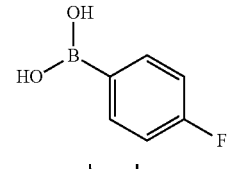 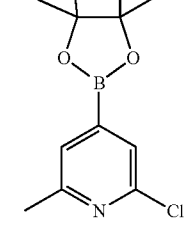 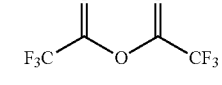 | 423.0 | ¹H NMR (400 MHz, DMSO-d₆): δ 8.63 (br s, 2H), 7.54-7.33 (m, 2H), 7.28-7.09 (m, 4H), 2.39 (s, 3H) |

TABLE 7-continued
| Products No. | Structure of products | No. of reaction raw materials | LCMS of products, m/z: [M + H] | ¹H NMR of products |
|---|---|---|---|---|
| Example C-42 | 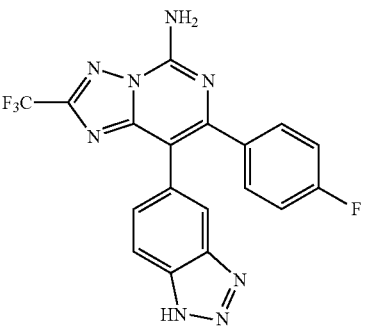 [SMILES: Nc1nc(-c2ccc(F)cc2)c(-c2ccc3[nH]nnc3c2)c2nc(C(F)(F)F)nn12] | 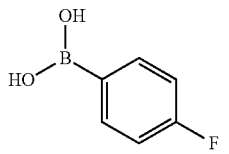 | 415.1 | ¹H NMR (400 MHz, DMSO-d₆): δ 8.45 (br s, 2H), 7.89 (s, 1H), 7.85 (br d, J = 8.4 Hz, 1H), 7.45-7.34 (m, 2H), 7.24 (d, J = 8.8 Hz, 1H), 7.10 (t, J = 8.8 Hz, 2H) |
| Example C-46 | 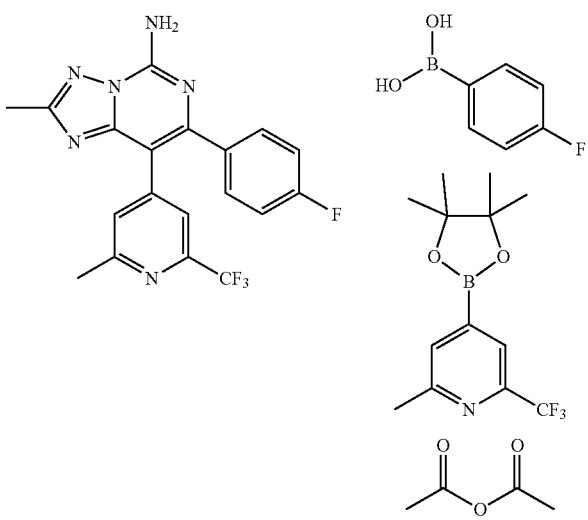 | 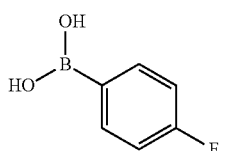 | 403.1 | ¹H NMR (400 MHz, DMSO-d₆): δ 8.25 (br s, 2H), 7.53 (s, 1H), 7.40 (s, 1H), 7.38-7.35 (m, 2H), 7.19-7.14 (t, J = 8.8 Hz, 2H), 2.48 (s, 6H) |
| Example C-47 | 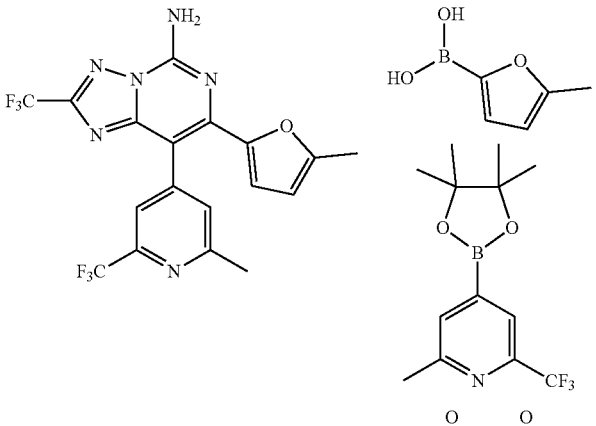 | 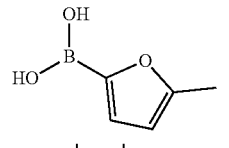 | 443.1 | ¹H NMR (400 MHz, CDCl₃): δ 7.45 (m, 2H), 6.73 (d, J = 3.2 Hz, 1H), 6.00 (m, 1H), 5.94 (br s, 2H), 2.64 (s, 3H), 2.16-1.94 (m, 3H) |

TABLE 7-continued
| Products No. | Structure of products | No. of reaction raw materials | LCMS of products, m/z: [M + H] | $^1$H NMR of products |
|---|---|---|---|---|
| Example C-48 | 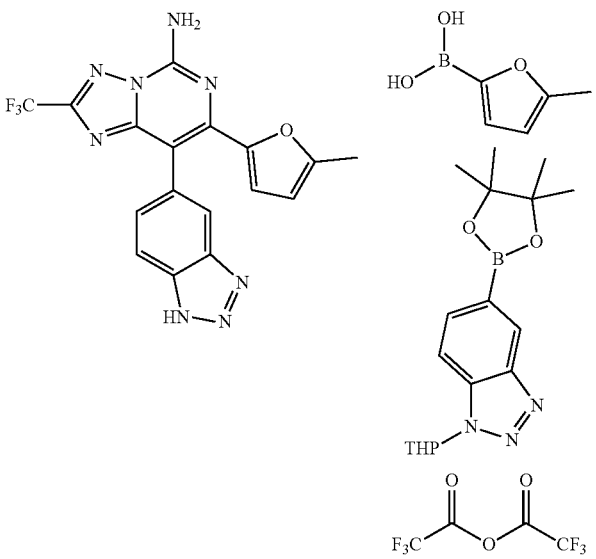 | 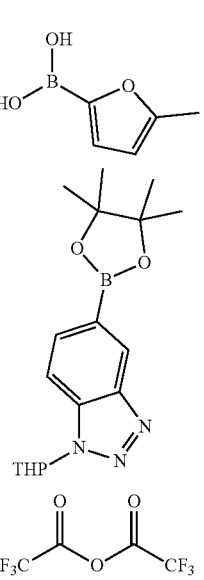 | 401.0 | $^1$H NMR (400 MHz, DMSO-$d_6$): δ 8.36 (br s, 2H), 7.99 (br d, J = 8.4 Hz, 1H), 7.94 (s, 1H), 7.37 (d, J = 8.4 Hz, 1H), 6.05 (m, 2H), 2.08 (s, 3H) |
| Example C-49 | 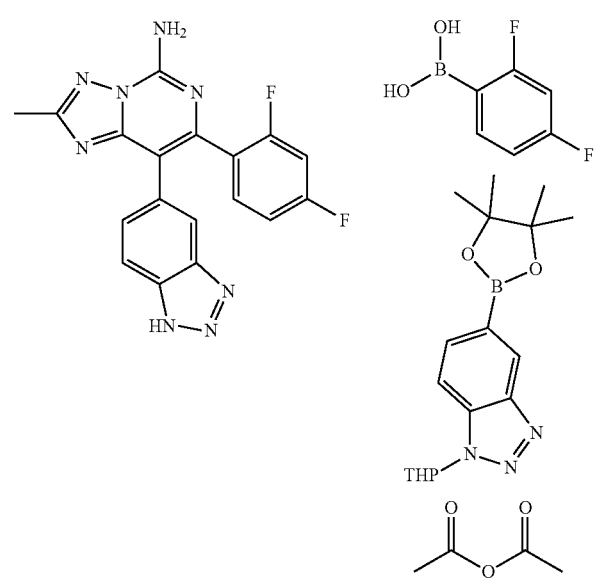 | 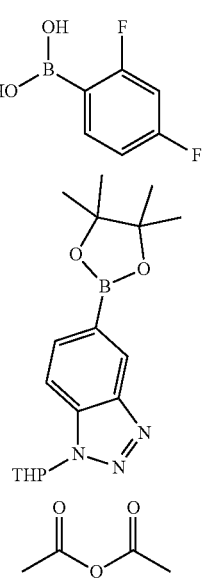 | 379.1 | $^1$H NMR (400 MHz, DMSO-$d_6$): δ 8.07 (br s, 2 H), 7.73-7.77 (m, 2H), 7.49-7.55 (m, 1H), 7.23 (d, J = 8.8 Hz, 1H), 7.05-7.10 (m, 2H), 2.48 (s, 3 H) |

TABLE 7-continued
| Products No. | Structure of products | No. of reaction raw materials | LCMS of products, m/z: [M + H] | ¹H NMR of products |
|---|---|---|---|---|
| Example C-51 | 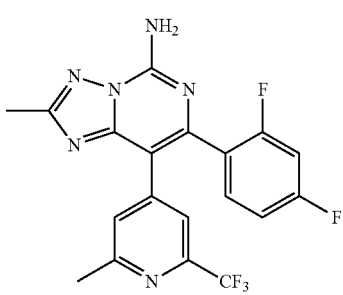 [SMILES: Cc1cc(-c2c(-c3ccc(F)cc3F)nc(N)n3nc(C)nc23)cc(C(F)(F)F)n1] | 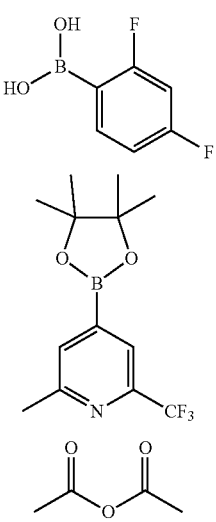 | 421.1 | ¹H NMR (400 MHz, DMSO-d$_6$): δ 7.56-7.62 (m, 1H), 7.51 (s, 1H), 7.40 (s, 1H), 7.17-7.23 (m, 2H), 2.50 (s, 3H), 2.48 (s, 3H) |
| Example C-54 | 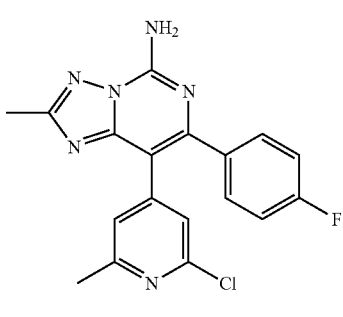 [SMILES: Cc1cc(-c2c(-c3ccc(F)cc3)nc(N)n3nc(C)nc23)cc(Cl)n1] | 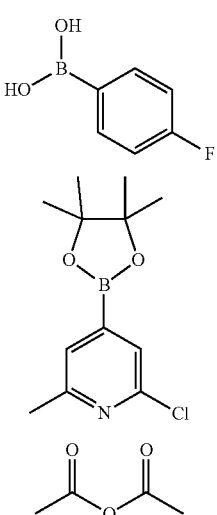 | 369.0 | ¹H NMR (400 MHz, DMSO-d$_6$): δ 8.21 (brs, 2H), 7.41-7.37 (m, 2H), 7.21-7.13 (m, 4H), 2.48 (s, 3H), 2.36 (s, 3H) |
| Example C-57 | 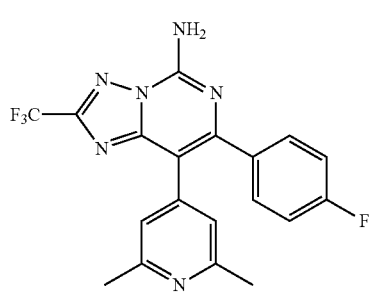 [SMILES: Cc1cc(-c2c(-c3ccc(F)cc3)nc(N)n3nc(C(F)(F)F)nc23)cc(C)n1] | 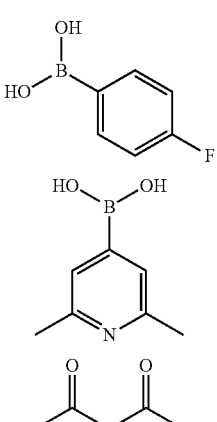 | 403.1 | ¹H NMR (400 MHz, DMSO-d$_6$): δ 8.51 (br s, 2H), 7.38-7.41 (m, 2H), 7.17 (t, J = 8.8 Hz, 2H), 6.93 (s, 2H), 2.35 (s, 6H) |

TABLE 7-continued
| Products No. | Structure of products | No. of reaction raw materials | LCMS of products, m/z: [M + H] | ¹H NMR of products |
|---|---|---|---|---|
| Example C-59 | 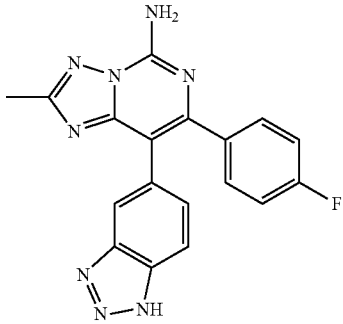 [SMILES: Cc1nc2c(-c3ccc4[nH]nnc4c3)c(-c3ccc(F)cc3)nc(N)n2n1] | 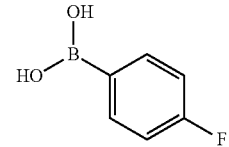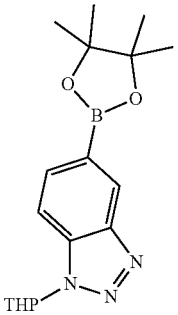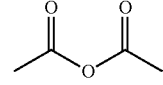 | 361.1 | ¹H NMR (400 MHz, DMSO-d$_6$): δ 8.05 (brs, 2H), 7.85 (s, 1H), 7.79 (m, 1H), 7.39-7.36 (m, 2H), 7.23 (m, 1H), 7.21-7.04 (m, 2H), 2.46 (s, 3H) |
| Example C-63 | 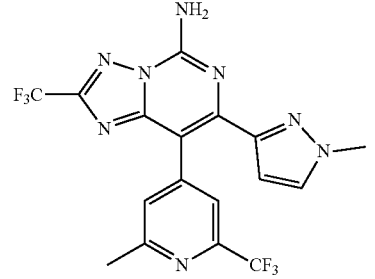 [SMILES: Cc1cc(-c2c(-c3ccn(C)n3)nc(N)n3nc(C(F)(F)F)nc23)cc(C(F)(F)F)n1] | 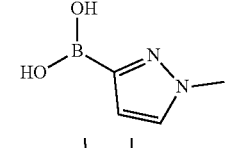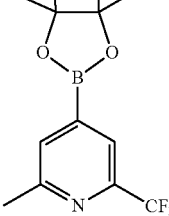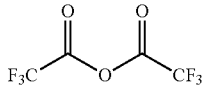 | 443.1 | ¹H NMR (400 MHz, DMSO-d$_6$): δ 8.49 (br s, 2H), 7.69 (d, J = 1.2 Hz, 1H), 7.60 (br s, 1H), 7.55 (s, 1H), 6.46 (d, J = 1.6 Hz, 1H), 3.67 (s, 3H), 2.58 (s, 3H) |
| Example C-64 | 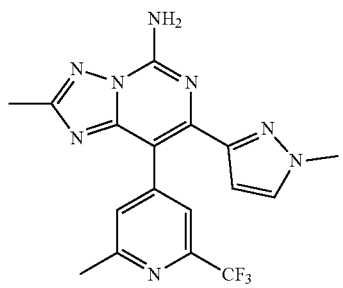 | 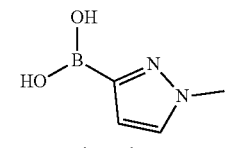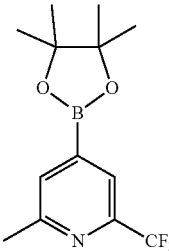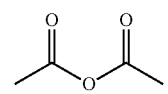 | 389.1 | ¹H NMR (400 MHz, DMSO-d$_6$): δ 8.11 (br s, 2H), 7.67 (d, J = 2.0 Hz, 1H), 7.59 (s, 1H), 7.51 (s, 1H), 6.40 (d, J = 2.0 Hz, 1H), 3.67 (s, 3H), 2.56 (s, 3H), 2.45 (s, 3H). |

Example C-12

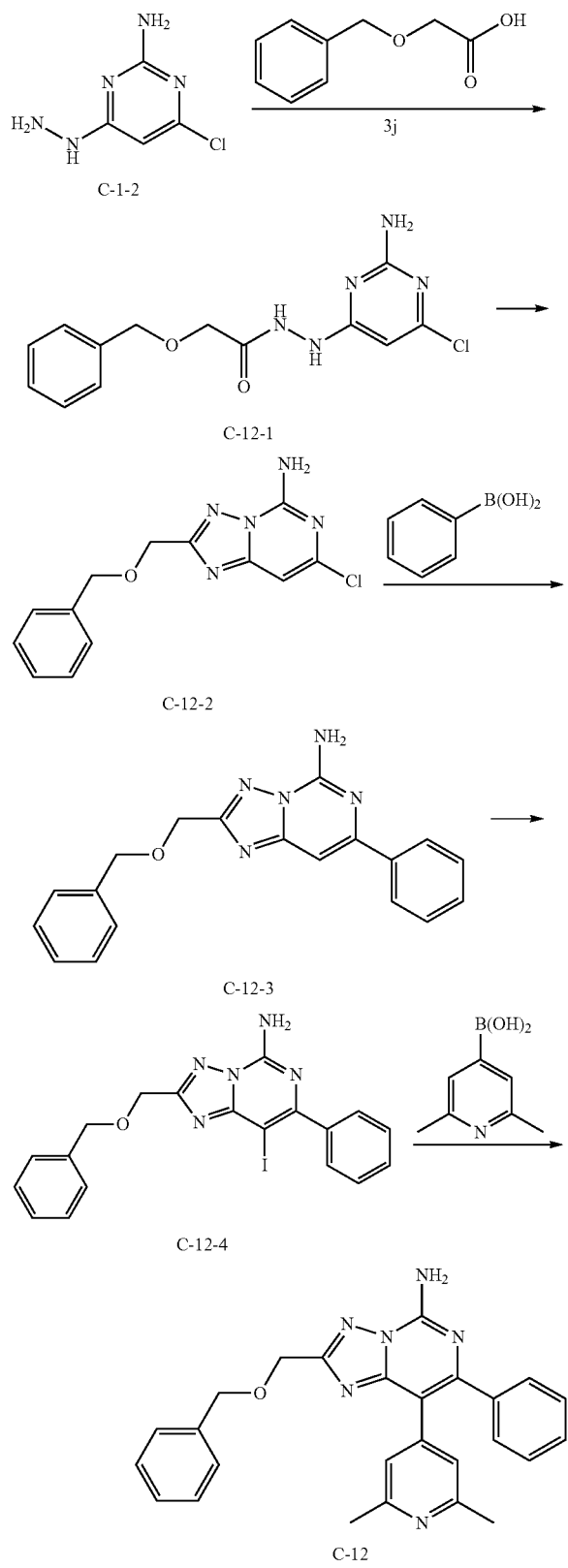

The First Step (Synthesis of Compound C-12-1)

CDI (5.85 g, 36.11 mmol, 1.2 eq) was added portionwise to a mixture of compound 3j (5.0 g, 30.09 mmol, 4.31 mL, 1 eq) and N,N-diisopropylethylamine (4.67 g, 36.11 mmol, 6.29 mL, 1.2 eq) in DMF (80 mL), and the mixture was stirred at 15° C. for 1 hour. 4-chloro-6-hydrazino-pyrimidin-2-amine C-1-2 (4.80 g, 30.09 mmol, 1 eq) was then added to the reaction solution. The reaction solution was stirred at 15° C. for 60 hours, poured into ice water (140 mL), stirred for 15 minutes, and extracted three times with ethyl acetate (75 mL). The extract was washed twice with water (40 mL), once with brine (50 mL), dried over sodium sulfate and filtered. The filtrate was concentrate to afford a crude product C-12-1.

The relevant characterization data was as follows: LCMS m/z: 308.2 [M+H]

The Second Step (Synthesis of Compound C-12-2)

A suspension of compound C-12-1 (10.00 g, 25.67 mmol, 1 eq) and N,O-bis(trimethylsilyl)acetamide (60.00 mL) was heated to 120° C. and stirred for 2 hours. After cooling, the reaction solution was slowly poured into cold methanol (200 mL) under vigorous stirring. The temperature was controlled at 5-10° C. The clarified mixture was concentrated. To the residue, ethyl acetate (30 mL) was added and the mixture was slurried twice. The filtrate was concentrated and purified by silica gel column (petroleum ether:ethyl acetate=3:1-2:1) to afford C-12-2.

The Thrid Step (Synthesis of Compound C-12-3)

Compound C-12-2 (1.35 g, 4.66 mmol, 1.0 eq) and phenylboric acid (852.29 mg, 6.99 mmol, 1.5 eq) were dissolved in 40 ml of dioxane and 8 ml of water. After vented and purged with nitrogen for three times, potassium carbonate (643.99 mg, 4.66 mmol, 1.0 eq) and catalyst Pd(dppf)Cl$_2$ (380.53 mg, 520.05 ummol, 0.112 eq) were added in sequence. The resulting mixture was then vented and purged with nitrogen for three times again, and then heated to 80-90° C. and stirred for 3 hours. LCMS showed the completion of the reaction and the desired compound. The reaction solution was cooled to room temperature and then concentrated to dryness, then diluted with about 200 ml of ethyl acetate and then washed 4 times with water (50 ml each time). The organics were concentrated and purified by silica gel column (200-300 mesh silica gel, petroleum ether/ethyl acetate=2:1) to afford product C-12-3.

The relevant characterization data was as follows: LCMS m/z: 332.0 [M+H]

$^1$H NMR (400 MHz, DMSO-d$_6$) δ 8.12 (t, J=5.6 Hz, 1H), 8.01 (m, 2H), 7.52 (s, 1H), 7.45-7.48 (m, 3H), 7.30-7.37 (m, 6H), 4.71 (s, 2H), 4.64 (s, 2H).

The Fourth Step (Synthesis of Compound C-12-4)

Compound C-12-3 (800 mg, 2.41 mmol, 1.0 eq) was dissolved in 20 mL of acetonitrile, and then iodosuccinimide (814.72 mg, 3.62 mmol, 1.5 eq) was added to the reaction solution. The reaction mixture was heated to 100° C. and stirred for 4 hours. Thin layer chromatography (petroleum ether/ethyl acetate=1:1, Rf=0.36) showed that the disappearance of the starting material and formation of a new point. The solvent acetonitrile was concentrated to dryness under reduced pressure. The residue was diluted with ethyl acetate (100 ml), and then washed twice with 20 ml of saturated aqueous sodium sulfite, twice with 20 ml of water, twice with 20 ml of saturated brine, dried over anhydrous sodium sulfate, and filtered to afford a crude product C-12-4, which was used directly in the next step.

The Fifth Step (Synthesis of C-12)

Compound C-12-4 (1.10 g, 2.41 mmol, 1.0 eq), 2,6-dimethylphenylboric acid (363.84 mg, 2.41 mmol, 1.0 eq)

and potassium carbonate (999.23 mg, 7.23 mmol, 3 eq) were dissolved in 20 ml of dioxane and 4 ml of water. After vented and purged with nitrogen for three times, catalyst Pd(dppf)Cl$_2$ (176.34 mg, 241.00 ummol, 0.10 eq) was added to the reaction solution. The reaction solution was then heated to 80-90° C. and stirred for 16 hours. Thin layer chromatography (petroleum ether/ethyl acetate=1:1) showed the completion of the reaction. The organic solvent was concentrated to dryness under reduced pressure, and then 150 ml of ethyl acetate was added to the residue. The mixture was washed twice with 20 ml of water and then 20 ml of saturated brine, respectively, and then concentrated to dryness. The residue was purified by silica gel column (200-300 mesh, petroleum ether/ethyl acetate=1:1) to afford a crude product. The crude product was further purified by preparative chromatography to afford pure C-12.

The relevant characterization data was as follows: LCMS m/z: 437.1 [M+H]

$^1$HNMR (400 MHz, CD$_3$OD): δ 7.42-7.30 (m, 10H), 7.03 (s, 2H), 4.79 (s, 2H), 4.70 (s, 2H), 2.41 (s, 6H).

The preparation of example compounds in Table 8 can be carried out by referring to the similar method in the above-mentioned route for the preparation of Example C-12, except that in steps 1, 3 and 5 raw materials in the following table were used as starting materials to afford the corresponding compounds.

TABLE 8

| Products No. | Structure of products | No. of reaction raw materials | LCMS of products, m/z: [M + H] | $^1$H NMR of products |
|---|---|---|---|---|
| Example C-9 | 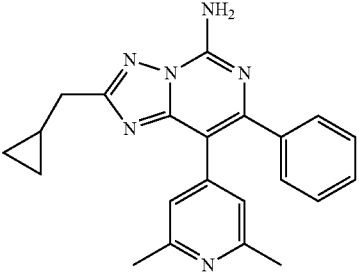 [SMILES: Cc1cc(-c2c(-c3ccccc3)nc(N)n3nc(CC4CC4)nc23)cc(C)n1] | 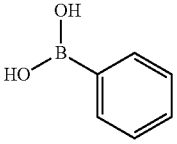<br>1a<br>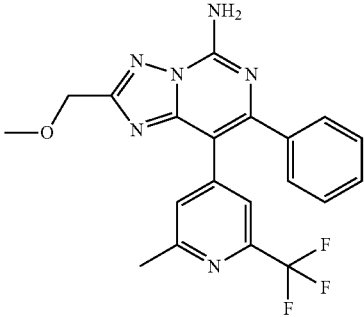 [SMILES: COCc1nc2c(-c3cc(C)nc(C(F)(F)F)c3)c(-c3ccccc3)nc(N)n2n1]<br>2e<br>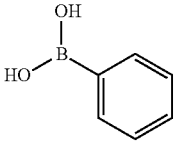<br>3f | 371.1 | $^1$H NMR (400 MHz, DMSO-d$_6$): 7.29-7.34 (m, 5H), 6.92 (s, 2H), 6.06 (br s, 1H), 2.74 (d, J = 6.8 Hz, 2H), 2.32 (s, 6H), 1.16-1.19 (m, 1H), 0.48-0.50 (m, 2H), 0.24-0.25 (m, 2H) |
| Example C-13 | 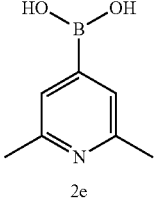 | 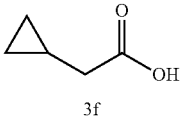 | 415.1 | $^1$H NMR (400 MHz, CDCl$_3$): δ 7.40 (m, 2H), 7.37-7.31 (m, 5H), 4.77 (s, 2H), 3.57 (s, 3H), 2.57 (s, 3H) |

TABLE 8-continued
| Products No. | Structure of products | No. of reaction raw materials | LCMS of products, m/z: [M + H] | ¹H NMR of products |
|---|---|---|---|---|
| Example C-14 | 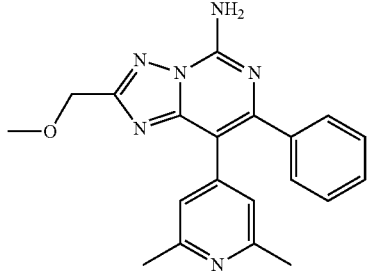 [SMILES: COCc1nc2c(-c3cc(C)nc(C)c3)c(-c3ccccc3)nc(N)n2n1] | 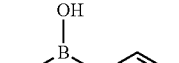 | 361.1 | ¹H NMR (400 MHz, CDCl₃): δ 7.27 (m, 5H), 6.89 (s, 2H), 6.37 (br s, 2H), 4.73 (s, 2H), 3.53 (s, 3H), 2.41 (s, 6H) |
| Example C-15 | 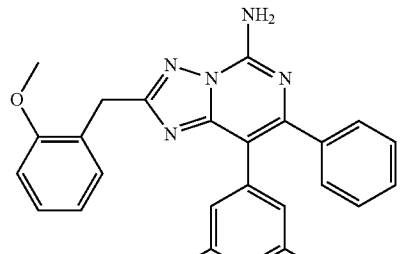 | 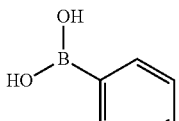 | 491.2 | ¹H NMR (400 MHz, CDCl₃): δ 7.45-7.21 (m, 9H), 6.96-6.87 (m, 2H), 6.40 (s, 2H), 4.29 (s, 2H), 3.85 (s, 3H), 2.55 (s, 3H) |
| Example C-16 | 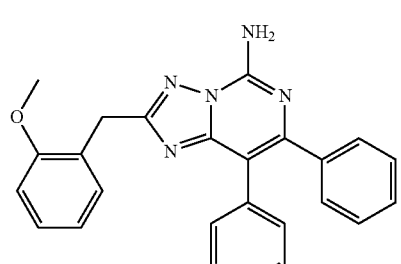 | 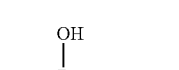 | 437.1 | ¹H NMR (400 MHz, CDCl₃): δ 7.39-7.19 (m, 7H), 6.99-6.83 (m, 4H), 6.35 (br s, 2H), 4.30 (s, 2H), 3.84 (s, 3H), 2.44 (s, 6H) |

TABLE 8-continued
| Products No. | Structure of products | No. of reaction raw materials | LCMS of products, m/z: [M + H] | ¹H NMR of products |
|---|---|---|---|---|
| Example C-17 | 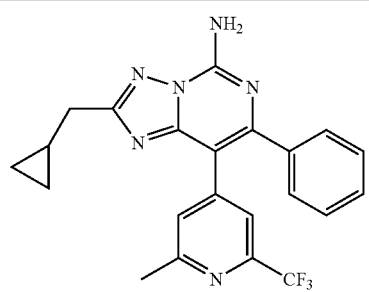 [SMILES: Cc1cc(-c2c(-c3ccccc3)nc(N)n3nc(CC4CC4)nc23)cc(C(F)(F)F)n1] | 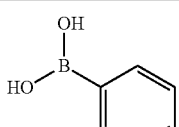 | 425.1 | ¹H NMR (400 MHz, DMSO-d$_6$): δ 7.54 (s, 1H), 7.37 (s, 1H), 7.32-7.35 (m, 5H), 2.75 (d, J = 6.8 Hz, 2 H), 2.46 (s, 3H), 1.15-2.24 (m, 1H), 0.48-0.52 (m, 2H), 0.26-0.28 (m, 2H) |
| Example C-23 | 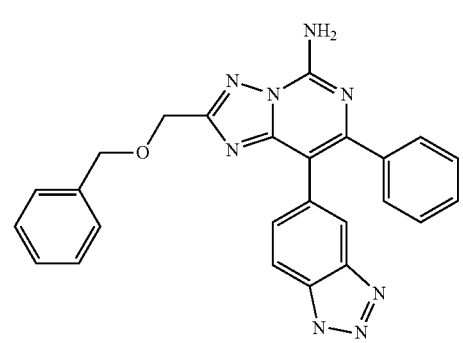 [SMILES: Nc1nc(-c2ccccc2)c(-c2ccc3[nH]nnc3c2)c2nc(COCc3ccccc3)nn12] | 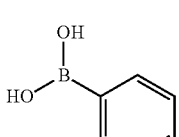 | 449.2 | ¹HNMR (400 MHz, DMSO-d$_6$): δ 8.08 (brs, 2H), 7.84 (s, 1H), 7.78 (d, J = 8.4 Hz, 1H), 7.36-7.31 (m, 7H), 7.24-7.21 (m, 4H), 4.71 (s, 2H), 4.62 (s, 2H) |

Example C-18

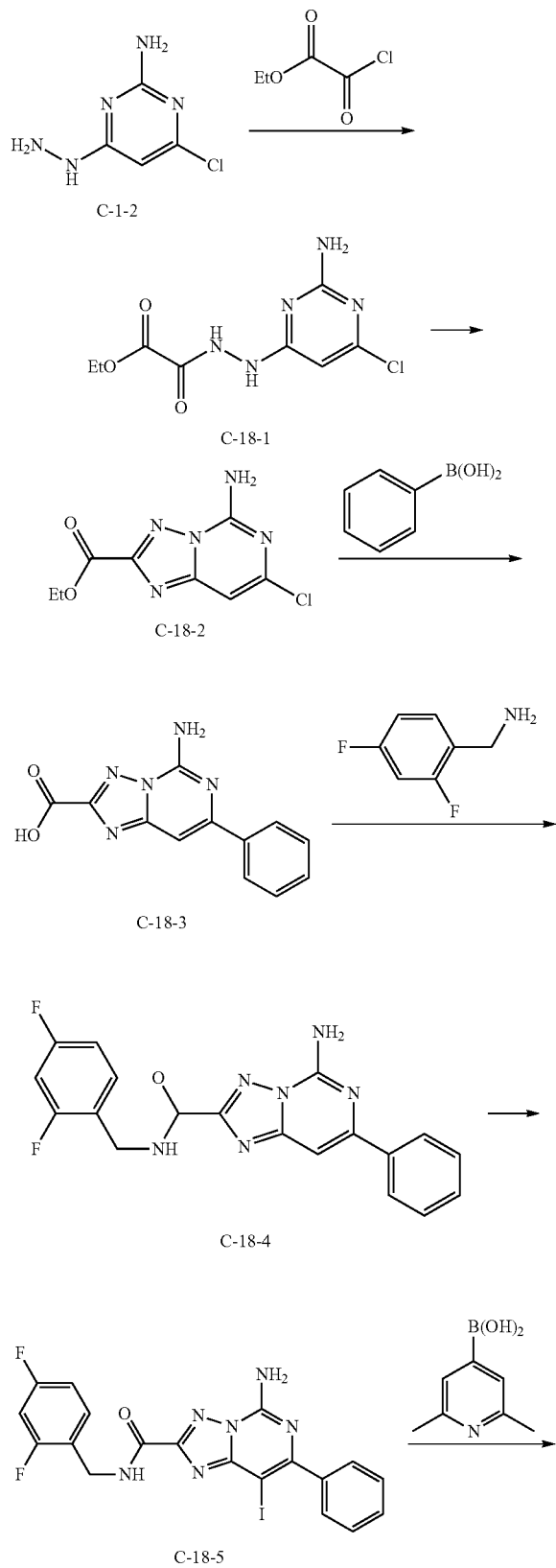

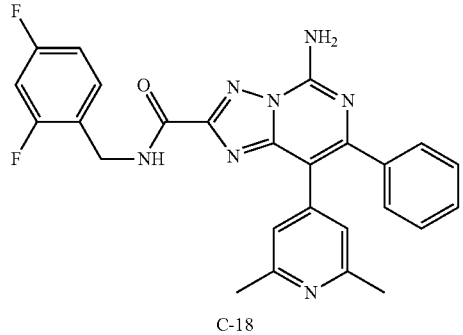

The First Step (Synthesis of Compound C-18-1)

A suspension of compound C-1-2 (2.00 g, 12.53 mmol, 1.00 eq) and diisopropylethylamine (2.43 g, 18.79 mmol, 3.28 mL, 1.50 eq) in dichloromethane (40.00 mL) was cooled to −40° C. To the suspension, a solution of oxalyl chloride monoethyl ester (1.63 g, 11.90 mmol, 1.33 mL, 0.95 eq) in dichloromethane (5.00 mL) was slowly added dropwise and the temperature of the reaction solution was controlled at −20° C. to −40° C. The addition was completed in 1 hour. The reaction solution was slowly warmed to 15° C. (room temperature) and stirred for 15 hours. After filtration, the solid was washed twice with dichloromethane (3 mL) and dried to afford C-18-1, which was used directly in the next step.

The relevant characterization data was as follows: LCMS m/z: 260.0 [M+H].

The Second Step (Synthesis of Compound C-18-2)

A suspension of compoun C-18-1 (8.00 g, 30.81 mmol, 1.00 eq) and N,O-bis(trimethylsilyl)acetamide (80.00 mL) was heated to 120° C. and stirred for 16 hours. After cooling, the reaction solution was slowly poured into methanol (100 mL) at 0° C. with vigorous stirring, and the mixture was stirred for 15 minutes. The clarified mixture was concentrated. Ethyl acetate (100 mL) was added to the residue, stirred for 30 min and filtered. The filtrate was concentrated and purified by silica gel column (petroleum ether:ethyl acetate=3:1-1:1) to afford C-18-2.

The Thrid Step (Synthesis of Compound C-18-3)

Compound C-18-2 (2.00 g, 8.28 mmol, 1.00 eq), phenylboric acid (1.11 g, 9.11 mmol, 1.10 eq), Pd(dppf)Cl₂ DCM complex (338.09 mg, 414.00 μmol, 0.05 eq) and potassium carbonate (2.29 g, 16.56 mmol, 2.00 eq) were added to 1,4-dioxane (20 mL) and water (4 mL), vented and purged with nitrogen several times, heated to 100° C. and stirred for 14 hours. The reaction solution was cooled to room temperature and filtered. The solid was washed with ethyl acetate (10 mL), slurried with water (40 mL) and filtered. Drying in vacuo gave a grey solid C-18-3.

The relevant characterization data was as follows: LCMS m/z: 256.2 [M+H].

¹H NMR (400 MHz, DMSO-d₆): δ 8.12 (s, 2H), 7.87 (s, 2H), 7.49-7.42 (s, 4H).

The Fourth Step (Synthesis of Compound C-18-4)

To a suspension of compound C-18-3 (200 mg, 0.783 mmol, 1.0 eq) and diisopropylethylamine (0.205 mL, 1.18 mmol) in DMF (5 mL) at room temperature (15-25° C.) was added HATU (327.75 mg, 0.862 mmol) portionwise. The reaction mixture was stirred at 10-25° C. for 10 min, and then 2,4-difluorobenzylamine (123.37 mg, 0.862 mmol) was added. The reaction mixture was stirred at 15-25° C. for 16 hours. LCMS showed that the desired product was obtained. The reaction mixture was poured into water, and solid was precipitated. The solid was collected, suspended in 100 ml of ethyl acetate, and then filtered. The filtrate was concentrated and purified by preparative thin layer chromatography (ethyl acetate/petroleum ether=1:1) to afford the compound C-18-4.

The relevant characterization data was as follows: LCMS m/z: 381.0 [M+H].

The fifth Step (Synthesis of Compound C-18-5)

Compound C-18-4 (36 mg, 94.65 μmol) was dissolved in 3 ml of acetonitrile. After nitrogen protection, NIS (25.55 mg, 113.58 ummol) was added. The mixture was stirred at 15-25° C. for 10 minutes, and then heated to 100° C. and stirred for 16 hours. LCMS showed the completion of the reaction and MS peak of the desired compound. The reaction solution was concentrated to remove the solvent to afford a crude product C-18-5.

The relevant characterization data was as follows: LCMS m/z: 506.9 [M+H].

The sixth Step (Synthesis of Compound C-18)

Compound C-18-5 (47.92 mg, 94.65 μmol, 1.00 eq), and 2,6-dimethylphenylboric acid (14.29 mg, 94.65 μmol, 1.00 eq) were dissolved in 2.5 ml of dioxane and 0.5 ml of water, and then potassium carbonate (39.24 mg, 283.95 μmol, 3.00 eq) and catalyst diphenylferrocene palladium chloride dichloromethane complex (15.46 mg, 18.93 μmol, 0.2 eq) were added in one portion. The mixture was vented three times with nitrogen, and slowly heated to 100° C. and stirred for 16 hours. LCMS showed the completion of the reaction and MS peak of the desired compound. The reaction mixture was directly concentrated under reduced pressure. The residue was purified by preparative thin layer chromatography (dichloromethane/methanol=10:1), followed by preparative thin layer chromatography (ethyl acetate/petroleum ether=2:1) to afford a crude product. The crude product was purified by preparative high-performance liquid chromatography to afford the desired compound C-18.

The relevant characterization data was as follows: LCMS m/z: 486.0 [M+H].

$^1$H NMR (400 MHz, DMSO-$d_6$): δ 9.16 (t, J=6.0 Hz, 1H), 8.32 (brs, 1H), 7.06-7.40 (m, 8H), 6.95 (s, 1H), 4.51 (d, J=6.0 Hz, 2H), 2.33 (s, 3H), 2.08 (s, 3H).

Example C-19

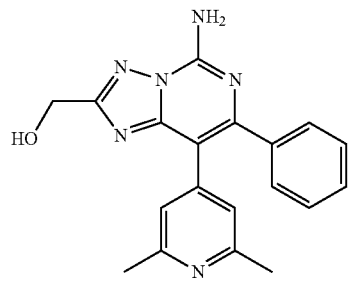

C-19

C12 (1.7 g, 3.89 mmol) was dissolved in 20 mL of trifluoroacetic acid, which was heated to 70° C. for 1 hour. LCMS showed complete debenzylation. The excess trifluoroacetic acid was removed by rotary evaporation under reduced pressure, and the residue was diluted with methanol (4 mL). The mixture was adjusted to pH 7.0 with NaHCO3 and filtered. The filtrate was concentrated to afford a crude product. The crude product was purified by reverse phase preparative chromatography to afford a pure product C-19.

The relevant characterization data was as follows: LCMS m/z: 347.2 [M+H].

$^1$HNMR (400 MHz, DMSO-$d_6$): δ 8.12 (brs, 2H), 8.36-7.29 (m, 5H), 6.92 (s, 2H), 5.54-5.51 (t, J=6.4 Hz, 1H), 4.64-4.62 (d, J=6.4 Hz, 2H), 2.32 (s, 6H).

The preparation of example compounds in Table 9 can be carried out by referring to the method in the above-mentioned route for the preparation of Example C-19.

TABLE 9

| Products No. | Structure of products | No. of reaction raw materials | LCMS of products, m/z: [M + H] | $^1$H NMR of products |
|---|---|---|---|---|
| Example C-24 | (structure shown) | (structure shown) | 359.1 | $^1$HNMR (400 MHz, DMSO-$d_6$): δ 8.03 (brs, 2H), 7.84 (s, 1H), 7.77 (d, J = 11.2 Hz, 1H), 7.35 (d, J = 7.2 Hz, 3H), 7.24-7.20 (m, 4H), 5.52 (brs, 1H), 4.62 (d, J = 5.2 Hz, 2H) |

TABLE 9-continued
| Products No. | Structure of products | No. of reaction raw materials | LCMS of products, m/z: [M + H] | ¹H NMR of products |
|---|---|---|---|---|
| Example C-33 | 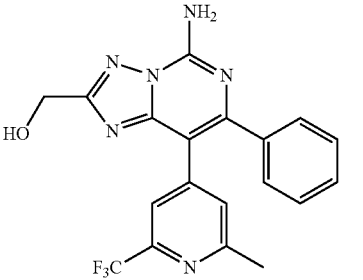 [SMILES: Cc1cc(-c2c(-c3ccccc3)nc(N)n3nc(CO)nc23)cc(C(F)(F)F)n1] | 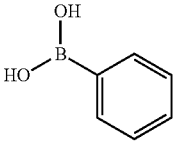 | 401.0 | ¹HNMR (400 MHz, DMSO-d$_6$): δ 8.26 (brs, 2H), 7.62 (s, 1H), 7.40-7.25 (m, 6H), 5.63 (m, 1H), 4.70 (s, 2H), 2.48 (s, 3H) |
| Example C-43 | 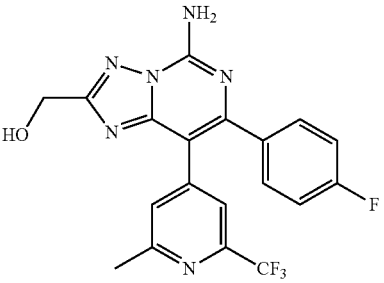 [SMILES: Cc1cc(-c2c(-c3ccc(F)cc3)nc(N)n3nc(CO)nc23)cc(C(F)(F)F)n1] | 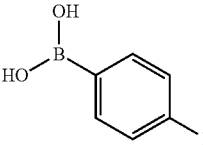 | 419.1 | ¹H NMR (400 MHz, CDCl$_3$): δ 7.43-7.36 (m, 2H), 7.16 (s, 1H), 7.08-7.00 (m, 3H), 6.06 (br s, 2H), 4.97 (s, 2H), 2.50 (s, 3H) |
| Example C-44 | 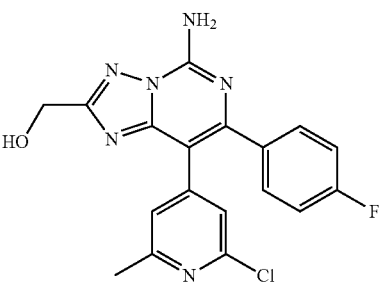 [SMILES: Cc1cc(-c2c(-c3ccc(F)cc3)nc(N)n3nc(CO)nc23)cc(Cl)n1] | 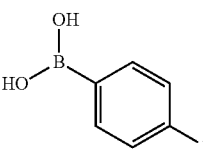 | 385.0 | ¹H NMR (400 MHz, CDCl$_3$): δ 7.49-7.35 (m, 2H), 7.24-7.16 (m, 3H), 7.14 (s, 1H), 4.65 (s, 2H), 2.39-2.33 (m, 3H) |

TABLE 9-continued

| Products No. | Structure of products | No. of reaction raw materials | LCMS of products, m/z: [M + H] | ¹H NMR of products |
|---|---|---|---|---|
| Example C-45 | (structure shown) | (4-fluorophenyl boronic acid; THP-protected benzotriazole pinacol boronate; BnOCH₂COOH) | 377.1 | ¹H NMR (400 MHz, DMSO-d₆): δ 8.07 (br s, 2H), 7.88 (s, 1H), 7.81 (d, J = 8.4 Hz, 1H), 7.45-7.33 (m, 2H), 7.23 (dd, J = 1.4, 8.7 Hz, 1H), 7.14-6.99 (m, 2H), 5.52 (t, J = 6.0 Hz, 1H), 4.62 (d, J = 5.6 Hz, 2H) |
| Example C-50 | (structure shown) | (2-methoxyphenyl boronic acid; 2-methyl-6-trifluoromethylpyridine-4-pinacol boronate; BnOCH₂COOH) | 431.1 | ¹H NMR (400 MHz, DMSO-d₆): δ 7.45 (s, 1H), 7.39-7.35 (m, 3H), 7.02-6.99 (t, J = 7.6 Hz, 1H), 6.89-6.87 (d, J = 8.0 Hz, 1H), 4.67 (s, 2H), 3.34 (s, 3H), 2.44 (s, 3H) |

TABLE 9-continued

| Products No. | Structure of products | No. of reaction raw materials | LCMS of products, m/z: [M + H] | ¹H NMR of products |
|---|---|---|---|---|
| Example C-52 | (structure) | (structures) | 419.1 | ¹H NMR (400 MHz, DMSO-d$_6$): δ 7.50-7.54 (m, 2H), 7.43-7.49 (m, 1H), 7.38 (s, 1H), 7.27 (m, 1H), 7.10-7.15 (m, 1H), 4.68 (s, 2H), 2.47 (s, 3H) |
| Example C-53 | (structure) | (structures) | 437.1 | ¹H NMR (400 MHz, DMSO-d$_6$): δ 7.56-7.64 (m, 1H), 7.52 (s, 1H), 7.41 (s, 1H), 7.17-7.24 (m, 2H), 7.07 (br s, 2H), 5.61 (br s, 1H), 4.67 (s, 2H), 2.49 (s, 3H) |
| Example C-55 | (structure) | (structures) | 365.1 | ¹H NMR (400 MHz, DMSO-d$_6$): δ 8.14 (br s, 2H), 7.39 (dd, J = 5.6, 8.7 Hz, 2H), 7.15 (t, J = 8.9 Hz, 2H), 6.93 (s, 2H), 5.54 (br s, 1H), 4.63 (s, 2H), 2.34 (s, 6H) |

TABLE 9-continued

| Products No. | Structure of products | No. of reaction raw materials | LCMS of products, m/z: [M + H] | ¹H NMR of products |
|---|---|---|---|---|
| Example C-58 | (structure shown) | (4-fluorophenylboronic acid; pinacol boronate of 2-chloro-6-(trifluoromethyl)pyridin-4-yl; BnOCH₂COOH) | 439.0 | ¹H NMR (400 MHz, DMSO-d₆): δ 8.47 (br s, 2H), 7.85 (s, 1H), 7.62 (s, 1H), 7.43 (dd, J = 5.6, 8.8 Hz, 2H), 7.23 (t, J = 8.8 Hz, 2H), 5.61 (t, J = 6.0 Hz, 1H), 4.67 (d, J = 6.0 Hz, 2H) |
| Example C-66 | (structure shown) | (5-methylfuran-2-boronic acid; pinacol boronate of 2-methyl-6-(trifluoromethyl)pyridin-4-yl; BnOCH₂COOH) | 405.1 | ¹H NMR (400 MHz, DMSO-d₆): δ 8.15 (br s, 2H), 7.65 (d, J = 4.4 Hz, 2H), 6.65 (d, J = 3.2 Hz, 1H), 6.20 (dd, J = 0.8 and 3.2 Hz, 1H), 5.52 (br s, 1H), 4.59 (s, 2H), 2.61 (s, 3H), 2.04 (s, 3H) |
| Example C-67 | (structure shown) | (5-methylfuran-2-boronic acid; pinacol boronate of 2-chloro-6-methylpyridin-4-yl; BnOCH₂COOH) | 371.1 | ¹H NMR (400 MHz, DMSO-d₆): δ 8.08 (br s, 2H), 7.32 (s, 1H), 7.28 (s, 1H), 6.55 (d, J = 3.2 Hz, 1H), 6.19 (dd, J = 1.2 and 3.2 Hz, 1H), 5.53 (br s, 1H), 4.59 (s, 2H), 2.49 (s, 3H), 2.12 (s, 3H) |

Example C-20

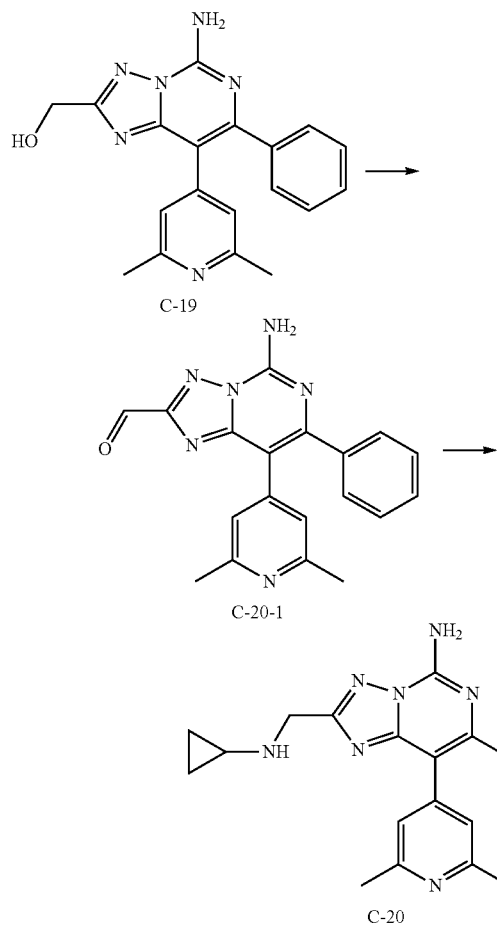

Example C-56

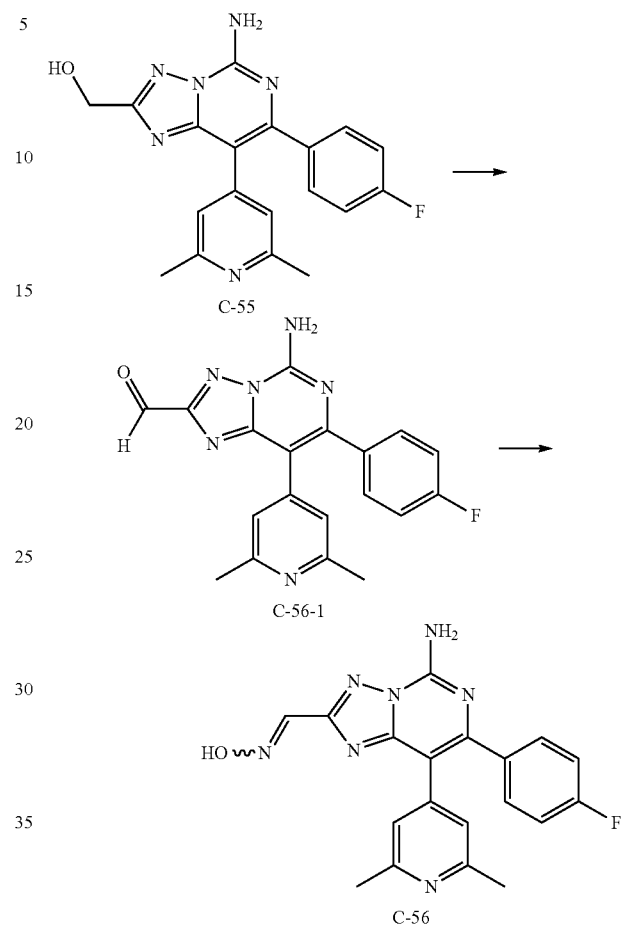

The First Step (Synthesis of Compound C-20-1)

DMP (95.91 mg, 1.17 mmol, 361.98 μL, 1.5 eq) was added to a solution of compound C-19 (270 mg, 779.48 μmol, 1 eq) in DCM (5 mL) at 20° C. The reaction solution was stirred at 20° C. for 12 hours, and then water (10 mL) was added. The reaction solution was filtered and washed with water. The filtrate was concentrated under reduced pressure to afford a crude product C-20-1.

The relevant characterization data was as follows: LCMS m/z: 345.0 [M+H]

The Second Step (Synthesis of Compound C-20)

To a solution of compound C-20-1 (100 mg, 290.39 μmol, 1 eq) in (3.00 mL) was added cyclopropylamine (24.87 mg, 435.58 μmol, 30.18 μL, 1.5 eq), and stirred at 20° C. for half an hour. Then, NaBH$_3$CN (36.50 mg, 580.77 μmol, 2 eq) was added, and the reaction solution was stirred at 20° C. for 1.5 hours. Water (20 mL) was added to the reaction solution. The mixture was extracted with ethyl acetate (20 mL*2). The organic phase was washed with saturated brine, dried over anhydrous sodium sulfate and concentrated. The residue was purified by preparative silica gel (DCM/=10/1) and preparative column chromatography to afford C-20.

The characterization data was as follows: LCMS m/z: 386.1 [M+H]

$^1$H NMR (400 MHz, CDCl$_3$): δ 7.37-7.27 (m, 5H), 6.94 (s, 2H), 6.03 (brs, 2H), 4.15 (s, 2H), 2.46 (s, 6H), 2.32-2.28 (m, 1H), 0.52-0.48 (m, 4H)

The First Step (Synthesis of Compound C-56-1)

Dess-Martin periodinane (275.51 mg, 649.56 μmol, 201.10 μL, 1.5 eq) was added to a solution of compound C-55 (150 mg, 433.04 μmol, 1.0 eq) in dichloromethane at room temperature. The reaction was carried out for three hours under nitrogen atmosphere. The mixture was filtered to give the filtrate, and the filter cake was washed with methanol (10 mL*3). The filtrate was combined and concentrated to afford compound C-56-1.

The relevant characterization data was as follows: LCMS m/z: 345.0 [M+H].

The Second Step (Synthesis of Compound C-56)

Compound C-56-1 (50 mg, 145.19 μmol, 1 eq) was dissolved in water (3 mL), ethanol (3 mL) and tetrahydrofuran (3 mL) at room temperature. Hydroxyamine hydrochloride (15.13 mg, 217.79 μmol, 1.5 eq) and sodium acetate (23.82 mg, 290.39 μmol, 2.0 eq) were added to the mixture. The mixture was heated to 80° C., stirred at 80° C. for two hours and then concentrated. The crude product was purified by reverse phase preparative chromatography (column: Phenomenex Gemini 150*25 mm*10 μm; mobile phase: [A: purified water (10 mM NH$_4$HCO$_3$), B: ACN]; B %: 18%-48%, 3 min) to afford C-56.

The relevant characterization data was as follows: LCMS m/z: 360.1 [M+H].

$^1$H NMR (400 MHz, METHANOL-d$_4$): δ 8.24 (s, 1H), 7.40-7.27 (m, 5H), 7.02 (m, 2H), 2.40 (s,6H).

Examples C-60 and C-61

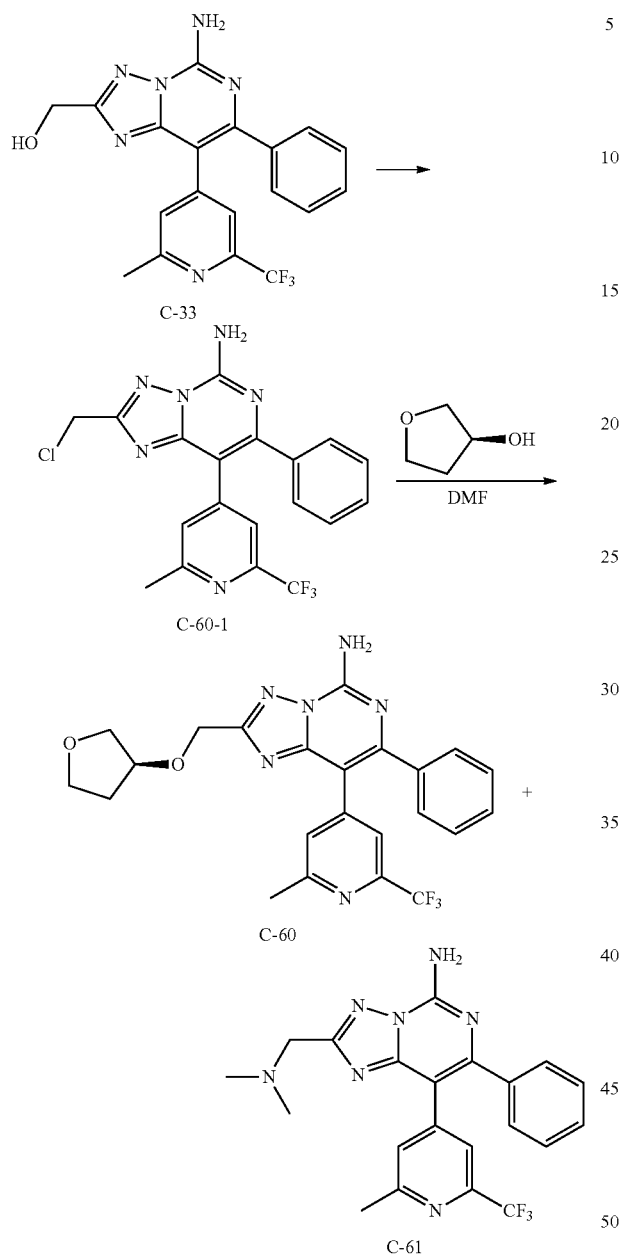

The First Step (Synthesis of Compound C-60-1)

Compound C-33 (200 mg, 499.55 μmol, 1 eq) was dissolved in anhydrous dichloromethane (5 mL) and then cooled to 0° C. To the solution was added thionyl chloride (297.16 mg, 2.50 mmol, 181.19 μL, 5 eq) in one portion, and the mixture was stirred at 20° C. for 2 hr. After completion of the reaction, the reaction solution was concentrated. The residue was slurried with dichloromethane (10 mL) and the formed suspension was filtered. The filter cake was washed with dichloromethane (10 mL) and dried to afford the compound C-60-1.

The relevant characterization data was as follows: LCMS (Ms+1): 419.0.

The Second Step (Synthesis of Compound C-60)

Compound C-60-1 (42.92 mg, 487.10 μmol, 1.2 eq) was dissolved in DMF (5 mL) and cooled to 0° C. To the solution was added NaH (24.36 mg, 608.88 μmol, 60% purity, 1.5 eq) in one portion. The mixture was stirred at 20° C. for 0.5 hour, and then to the mixture was added the compound 3-S-hydroxy-tetrahydrofuran (170 mg, 405.92 μmol, 1 eq). The reaction solution was stirred at 20° C. for 16 hours. After the reaction was completed, the reaction solution was quenched with saturated aqueous $NH_4Cl$ (50 mL), then diluted with ethyl acetate (20 mL) and extracted twice with ethyl acetate (20 mL). The combined organic phases were washed with saturated brine (50 mL), dried with anhydrous $Na_2SO_4$, filtered and then rotary evaporated to dryness. The resulting crude product was subjected to neutral machine separation (mobile phase: water/acetonitrile) to afford C-60 and C-61.

The relevant characterization data of C-60 was as follows: LCMS m/z: 471.2 [M+H].

$^1$H NMR (400 MHz, DMSO-$d_6$): δ 8.34 (br s, 2H), 7.54 (s, 1H), 7.41 (s, 1H), 7.33-7.39 (m, 5H), 4.69 (s, 2H), 4.36 (br d, J=3.2 Hz, 1H), 3.72-3.77 (m, 2H), 3.66-3.69 (m, 2H), 2.47 (s, 3H), 1.95-2.00 (m, 2H).

The relevant characterization data of C-61 was as follows: LCMS m/z: 428.2 [M+H].

$^1$H NMR (400 MHz, DMSO-$d_6$): δ 8.30 (br s, 2H), 7.54 (s, 1H), 7.41 (s, 1H), 7.32-7.39 (m, 5H), 3.67 (s, 2H), 2.47 (s, 3H), 2.25 (s, 6H).

Example C-62

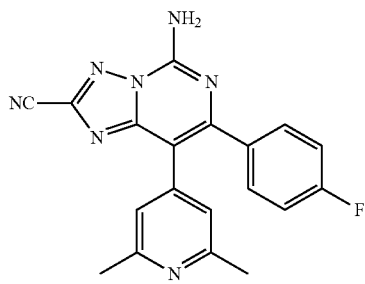 [SMILES: Cc1cc(-c2c(-c3ccc(F)cc3)nc(N)n3nc(C#N)nc23)cc(C)n1]

Compound C-56 was added to phosphorus oxychloride (5 mL) at room temperature. The system was heated to 70° C. and stirred at 70° C. for 2 hours. The mixture was concentrated, and to the residue was added methanol (3 mL). The mixture was adjusted to pH 7 with solid sodium bicarbonate and filtered to afford filtrate. The filtrate was purified by reverse phase preparative chromatography (column: Phenomenex Gemini 150*25 mm*10 μm; mobile phase: [A: purified water (10 mM $NH_4HCO_3$), B: ACN]; B %: 20%-50%, 3 min) to afford the compound C-62.

The relevant characterization data was as follows: LCMS m/z: 342.1 [M+H].

$^1$H NMR (400 MHz, METHANOL-$d_4$): δ 7.42~7.40 (m, 2H), 7.32-7.28 (m, 2H), 7.02 (s, 2H), 2.40 (s, 6H).

Example C-73

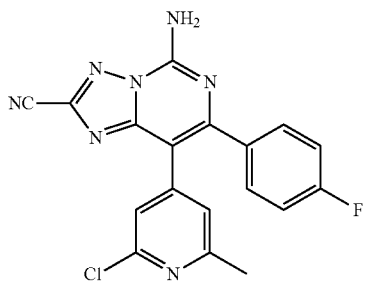

C-73

Example C-73: The preparation of the present example compound can be carried out by referring to the above-mentioned method for the preparation of Example C-62 to afford the compound C-73.

The relevant characterization data was as follows: LCMS m/z: 380.0 [M+H].

$^1$H NMR (400 MHz, DMSO-d$_6$): δ 8.73 (br s, 2H), 7.40-7.43 (m, 2H), 7.23 (t, J=8.8 Hz, 2H), 7.15 (d, J=5.2 Hz, 2H), 2.40 (s, 3H).

Example C-74

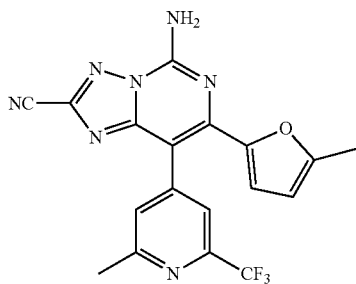

C-74

Example C-74: The preparation of the present example compound can be carried out by referring to the above-mentioned method for the preparation of Example C-62 to afford the compound C-74.

The relevant characterization data was as follows: LCMS m/z: 400.0 [M+H].

$^1$H NMR (400 MHz, DMSO-d$_6$): δ 8.58 (br s, 2H), 7.65 (d, J=2.0 Hz, 2H), 6.77 (d, J=3.2 Hz, 1H), 6.25 (d, J=2.8 Hz, 1H), 2.63 (s, 3H), 2.05 (s, 3H).

Example C-65

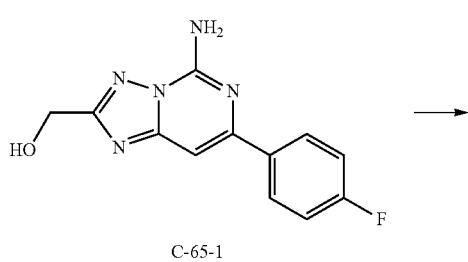

C-65-1

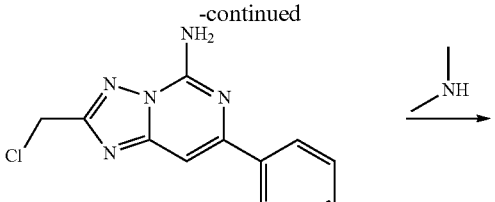

C-65-2

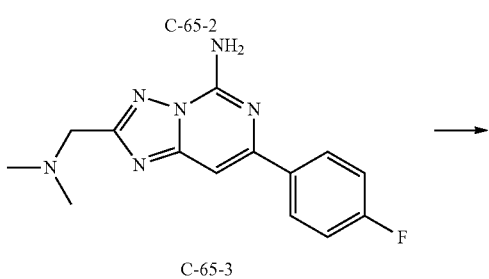

C-65-3

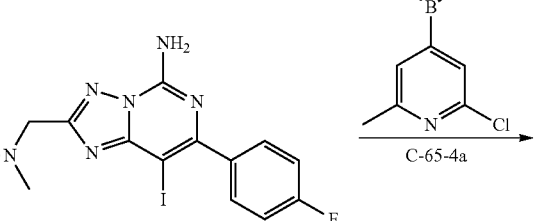

C-65-4

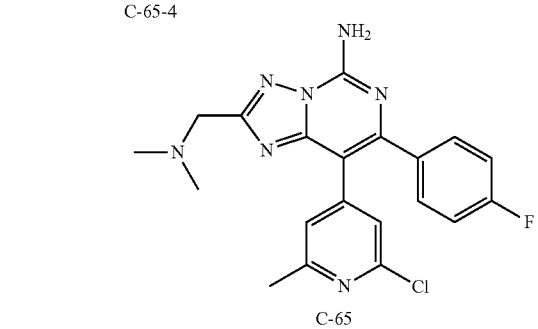

C-65

The First Step (Synthesis of Compound C65-2)

To a solution of compound C-65-1 (3.8 g, 14.66 mmol, 1 eq) in dichloromethane (60 mL) was added thionyl chloride (10.46 g, 87.95 mmol, 6.38 mL, 6 eq). The reaction solution was stirred at 50° C. for 5 hours under nitrogen. The reaction solution was filtered and washed with dichloromethane. The filtrate was concentrated to dryness under reduced pressure to afford C-65-2.

The relevant characterization data was as follows: LCMS m/z: 278.0 [M+H]

The Second Step (Synthesis of Compound C-65-3)

To a solution of compound C-65-2 (700 mg, 2.52 mmol, 1 eq) in dioxane (10 mL) was added dimethylamine (3.44 g, 25.21 mmol, 33%, 10 eq). The reaction solution was stirred at 60° C. for 12 hours in a 30 mL smoldering pot. The reaction solution was concentrated to dryness under reduced pressure. To the residue were added (20 mL) and H$_2$O (20 mL), and slurried to afford C-65-3.

The relevant characterization data was as follows: LCMS m/z: 287.1 [M+H]

The Thrid Step (Synthesis of Compound C-65-4)

To a solution of compound C-65-3 (600 mg, 2.10 mmol, 1 eq) in ACN (8 mL) was added NIS (942.97 mg, 4.19 mmol, 2 eq), and the reaction solution was stirred at 80° C. for 12 hours. Saturated Na$_2$SO$_3$ (20 mL) and H$_2$O (10 mL) were added to the reaction solution. The mixture was extracted with EA (20 mL*2). The organic phase was washed with saturated brine, dried over anhydrous sodium sulfate and filtered. The filtrate was concentrated to afford the compound C-65-4.

The relevant characterization data was as follows: LCMS m/z: 413.0 [M+H]

The Fourth Step (Synthesis of Compound C-65)

To a solution of compound C-65-4 (250 mg, 606.50 μmol, 1 eq) in 1,4-dioxane (5 mL) and H$_2$O (1 mL) were added Pd(dppf)Cl$_2$ (44.38 mg, 60.65 μmol, 0.1 eq), K$_2$CO$_3$ (167.65 mg, 1.21 mmol, 2 eq), and C-65-4a (184.52 mg, 727.79 μmol, 1.2 eq). The mixture was vented and purged with nitrogen for three times, stirred at 90° C. for 2 hours and concentrated. The residue was purified by silica gel column (PE/EA=5/1 to PE/EA/EtOH=2/3/1) and preparative silica gel plate (DCM/=10/1) and then preparative column chromatography to afford C-65.

The relevant characterization data was as follows: LCMS m/z: 412.1 [M+H]

$^1$H NMR (400 MHz, DMSO-d$_6$): δ 8.26 (br s, 2H), 7.40-7.37 (m, 2H), 7.20-7.12 (m, 4H), 3.64 (s, 2H), 2.36 (s, 3H), 2.24 (s, 6H).

Example C-68

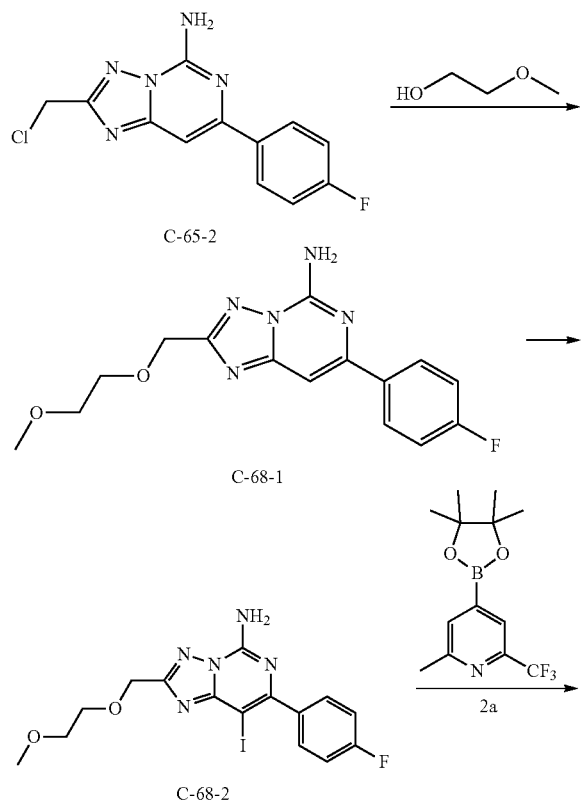

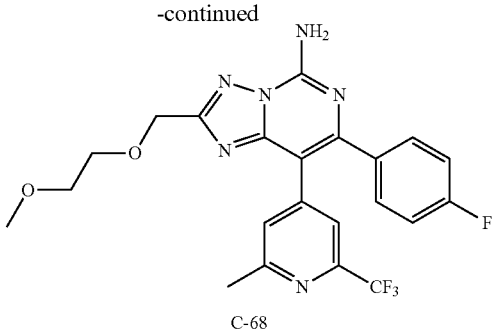

The First Step (Synthesis of Compound C-68-1)

Ethylene glycol monomethyl ether (89.38 mg, 1.17 mmol, 92.62 μL, 2.5 eq) was dissolved in tetrahydrofuran (3 mL), and then sodium hydride (46.98 mg, 1.17 mmol, 60% purity, 2.5 eq) was added. This mixture was stirred at 20° C. for 2 hours, and then compound C-65-2 (0.13 g, 469.83 μmol, 1 eq) was added. This mixture was stirred at 70-80° C. for 5 hours. LCMS showed the appearance of the MS peak of the desired compound. The reaction solution was quenched with 10 mL of water at 15° C. The mixture was stripped of the solvent tetrahydrofuran under a reduced pressure water pump, and then extracted three times with ethyl acetate (10 mL each time). The organic phases were combined, and then washed once with saturated brine (10 mL), dried over anhydrous sodium sulfate and filtered. The organic phase was concentrated under reduced pressure to give a residue, which was collected to afford the desired compound C-68-1.

The relevant characterization data was as follows: LCMS m/z: 318.0 [M+H].

The Second Step (Synthesis of Compound C-68-2)

Compound C-68-1 (0.12 g, 378.17 μmol, 1 eq) was dissolved in acetonitrile (5 mL), and then N-iodosuccinimide (170.16 mg, 756.34 μmol, 2 eq) was added to the reaction solution. The reaction solution was stirred at 70-80° C. for 5 hours. LCMS showed the appearance of the MS peak of the desired compound. The reaction solution was quenched with 20 mL aqueous sodium sulfite at 15° C., and then extracted twice with ethyl acetate (50 mL each time). The organic phases were combined, washed once with saturated brine (10 mL), dried over anhydrous sodium sulfate and filtered. The organic phase was concentrated under reduced pressure to afford a residue, which was collected to afford the desired compound C-68-2.

The relevant characterization data was as follows: LCMS m/z: 443.9 [M+H].

The Thrid Step (Synthesis of Compound C-68)

To compound C-68-2 (0.3 g, 676.87 μmol, 1 eq) was added 1,4-dioxane (20 mL) and water (5 mL), and then 2a (194.32 mg, 676.87 μmol, 1 eq), potassium phosphate (287.35 mg, 1.35 mmol, 2 eq), and 1,1'-bis(di-tert-butylphosphino)ferrocene palladium dichloride (88.23 mg, 135.37 μmol, 0.2 eq) were added. This mixture was vented and purged with nitrogen for three times and stirred at 100° C. for eight hours under nitrogen atmosphere. LCMS showed the appearance of the MS peak of the desired compound. The solvent was concentrated to dryness under reduced pressure. The residue was purified by silica gel column (silica gel, eluent: petroleum ether/ethyl acetate=3:1 to 1:1), and then by column: Phenomenex Gemini 150*25 mm*10 um; mobile phase: ([A: purified water (10 mM NH₄HCO₃), B: ACN]; B %: 40%-70%, 3 min) to afford the desired compound C-68.

The relevant characterization data was as follows: LCMS m/z: 477.1 [M+H].

¹H NMR (400 MHz, DMSO-d₆): δ 8.35 (br s, 2H), 7.54 (s, 1H), 7.44 (s, 1H), 7.39 (dd, J=5.7, 8.7 Hz, 2H), 7.18 (t, J=8.8 Hz, 2H), 4.70 (s, 2H), 3.72-3.66 (m, 2H), 3.50 (dd, J=3.8, 5.6 Hz, 2H), 3.25 (s, 3H), 2.48 (s, 3H).

The preparation of example compounds in Table 10 can be carried out by referring to the method in the above-mentioned route for the preparation of Example C-68.

TABLE 10

| Products No. | Structure of products | LCMS of products, m/z: [M + H] | ¹H NMR of products |
|---|---|---|---|
| Example C-68 | | 477.1 | ¹H NMR (400 MHz, DMSO-d₆): δ 8.35 (br s, 2H), 7.54 (s, 1H), 7.44 (s, 1H), 7.39 (dd, J = 5.6, 8.8 Hz, 2H), 7.18 (t, J = 8.8 Hz, 2H), 4.70 (s, 2H), 3.72-3.66 (m, 2H), 3.50 (dd, J = 3.6, 5.6 Hz, 2H), 3.25 (s, 3H), 2.48 (s, 3H) |
| Example C-69 | | 443.0 | ¹H NMR (400 MHz, DMSO-d₆): δ 8.32 (br s, 2H), 7.44-7.37 (m, 2H), 7.23-7.16 (m, 3H), 7.14 (s, 1H), 4.69 (s, 2H), 3.67 (dd, J = 3.6, 5.6 Hz, 2H), 3.49 (dd, J = 4.0, 5.2 Hz, 2H), 3.25 (s, 3H), 2.37 (s, 3H) |
| Example C-70 | | 455.1 | ¹H NMR (400 MHz, DMSO-d₆): δ 8.32 (br s, 2H), 7.40 (dd, J = 5.6, 8.8 Hz, 2H), 7.23-7.16 (m, 3H), 7.14 (s, 1H), 4.67 (s, 2H), 4.34 (m, 1H), 3.79-3.72 (m, 2H), 3.71-3.63 (m, 2H), 2.37 (s, 3H), 2.02-1.91 (m, 2H) |
| Example C-71 | | 489.1 | ¹H NMR (400 MHz, DMSO-d₆): δ 8.36 (br s, 2H), 7.53 (s, 1H), 7.45 (s, 1H), 7.38 (dd, J = 5.6, 8.8 Hz, 2H), 7.19 (t, J = 8.8 Hz, 2H), 4.68 (s, 2H), 4.36-4.35 (m, 1H), 3.75-3.66 (m, 4H), 2.48 (s, 3H), 2.01-1.95 (m, 2H) |

TABLE 10-continued

| Products No. | Structure of products | LCMS of products, m/z: [M + H] | $^1$H NMR of products |
|---|---|---|---|
| Example C-72 | | 475.1 | $^1$H NMR (400 MHz, DMSO-$d_6$): δ 8.18 (br s, 2H), 7.64 (s, 2H), 6.67 (d, J = 3.2 Hz, 1H), 6.19-6.20 (m, 1H), 4.61 (s, 2 H), 4.30-4.34 (m, 1H), 3.64-3.76 (m, 4H), 2.60 (s, 3H), 2.04 (s, 3H), 1.93-1.97 (m, 2 H) |

Example C-75

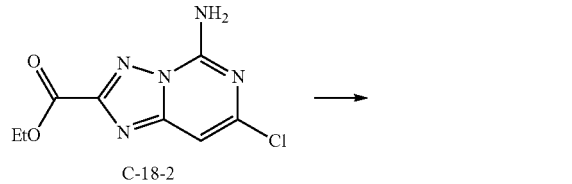

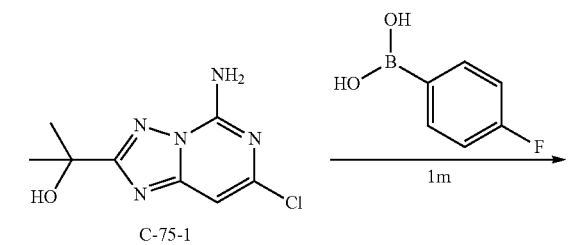

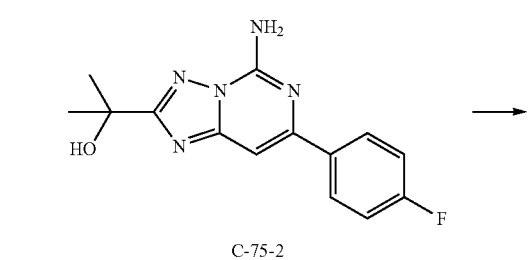

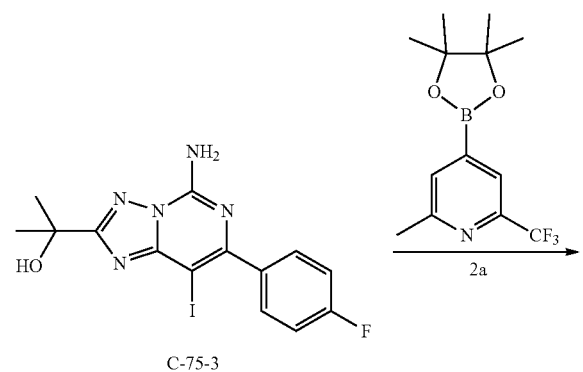

The First Step (Synthesis of Compound C-75-1)

Compound C-18-2 (500 mg, 2.07 mmol, 1 eq) was dissolved in anhydrous dichloromethane (20 mL), and then methylmagnesium bromide (3 M, 2.07 mL, 3 eq) was added to the reaction solution in one portion under nitrogen. The reaction solution was stirred at 25° C. for 0.5 h. After the reaction was completed, the reaction solution was quenched with saturated aqueous ammonium chloride (50 mL). The aqueous phase was extracted with dichloromethane (100 mL). The organic phase was dried over anhydrous sodium sulfate, filtered and rotary evaporated to dryness. Finally, the residue was purified by silica gel plate (eluent: petroleum ether/ethyl acetate=1/1) to afford C-75-1.

The relevant characterization data was as follows: LCMS m/z: 227.9 [M+H]

The Second Step (Synthesis of Compound C-75-2)

Compound C-75-1 (110 mg, 483.20 μmol, 1 eq), compound 1m (81.13 mg, 579.84 μmol, 1.2 eq), 1,1'-bis(di-tert-butylphosphino)ferrocene palladium dichloride (62.98 mg, 96.64 μmol, 0.20 eq) and potassium phosphate (205.14 mg, 966.39 μmol, 2.00 eq) were dissolved in a mixed solvent of 1,4-dioxane (10 mL) and water (1 mL). The mixture was vented and purged with nitrogen three times and then stirred at 100° C. for 12 hours under nitrogen atmosphere. After the completion of the reaction, the reaction solution was cooled to room temperature, filtered over Celite, and rotary evaporated to dryness. The obtained crude product was purified by silica gel plate (eluant: petroleum ether/ethyl acetate=1/1) to afford C-75-2.

The relevant characterization data was as follows: LCMS m/z: 288.0 [M+H].

The Thrid Step (Synthesis of Compound C-75-3)

Compound C-75-2 (110 mg, 382.89 μmol, 1.00 eq) and N-iodosuccinimide (172.28 mg, 765.77 μmol, 2 eq) were dissolved in acetonitrile (5 mL) and stirred at 80° C. for 3 hours. The reaction solution was cooled to room temperature, quenched with saturated aqueous sodium sulfite (20 mL), and extracted with ethyl acetate (20 mL*2). The organic phases were combined, washed with saturated brine (30 mL), dried over anhydrous sodium sulfate and filtered. The filtrate was rotary evaporated to dryness to afford C-75-3.

The relevant characterization data was as follows: LCMS m/z: 413.8 [M+H].

The Fourth Step (Synthesis of Compound C-75)

Compound C-75-3 (150 mg, 363.03 µmol, 1 eq), compound 2a (125.06 mg, 435.64 µmol, 1.2 eq), 1,1'-bis(di-tert-butylphosphino)ferrocene palladium dichloride (47.32 mg, 72.61 µmol, 0.20 eq) and potassium phosphate (154.12 mg, 726.06 µmol, 2 eq) were dissolved in a mixed solvent of 1,4-dioxane (5 mL) and water (1 mL). The mixture was vented and purged with nitrogen three times and then stirred at 100° C. for 12 hours under nitrogen atmosphere. The reaction solution was cooled to room temperature, and then filtered over Celite. The filtrate was rotary evaporated to dryness to give a crude product. The crude product was isolated by preparative liquid chromatography to afford C-75.

The relevant characterization data was as follows: LCMS m/z: 447.1 [M+H].

$^1$H NMR (400 MHz, DMSO-d$_6$): δ 8.22 (br s, 2H), 7.55 (s, 1H), 7.46 (s, 1H), 7.38 (dd, J=1.2, 8.8 Hz, 2H), 7.18 (t, J=8.8 Hz, 2H), 5.32 (s, 1H), 2.49 (s, 3H), 1.59 (s, 6H).

Example C-77

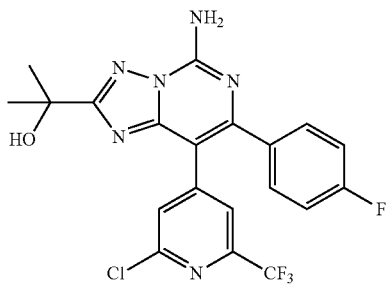

C-77

Example C-77: The preparation of the present example compound can be carried out by referring to the above-mentioned method for the preparation of Example C-75 to afford the compound C-77.

The relevant characterization data was as follows: LCMS m/z: 467.1 [M+H].

$^1$H NMR (400 MHz, DMSO-d$_6$): δ 8.37 (br s, 2H), 7.83 (s, 1H), 7.66 (s, 1H), 7.43 (dd, J=6.0, 8.4 Hz, 2H), 7.23 (t, J=8.8 Hz, 2H), 5.38 (s, 1H), 1.60 (s, 6H).

Example C-78

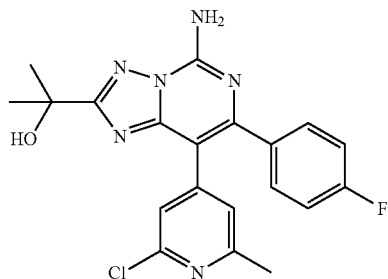

C-78

Example C-78: The preparation of the present example compound can be carried out by referring to the above-mentioned method for the preparation of Example C-75 to afford the compound C-78.

The relevant characterization data was as follows: LCMS m/z: 413.1 [M+H].

$^1$H NMR (400 MHz, DMSO-d$_6$): δ 8.16 (br s, 2H), 7.41-7.34 (m, 2H), 7.21-7.15 (m, 4H), 5.35 (s, 1H), 2.36 (s, 3H), 1.58 (s, 6H).

Example C-76

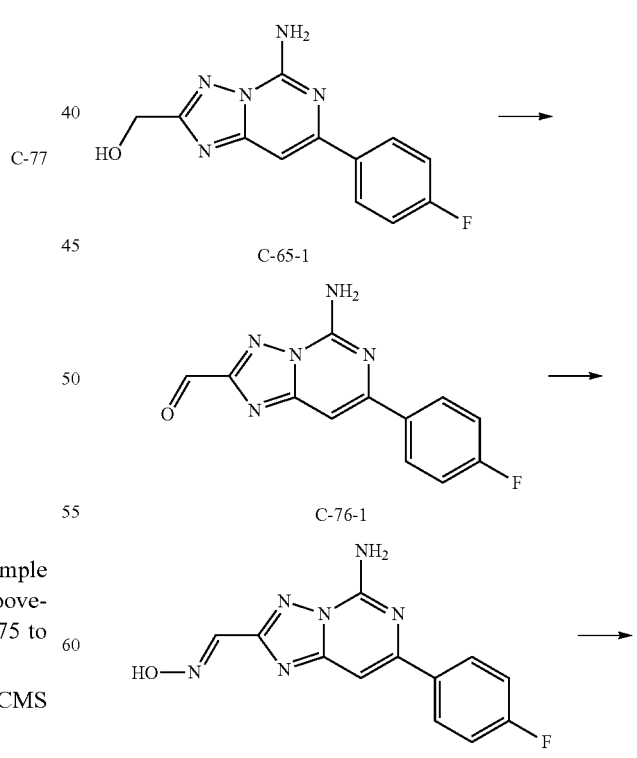

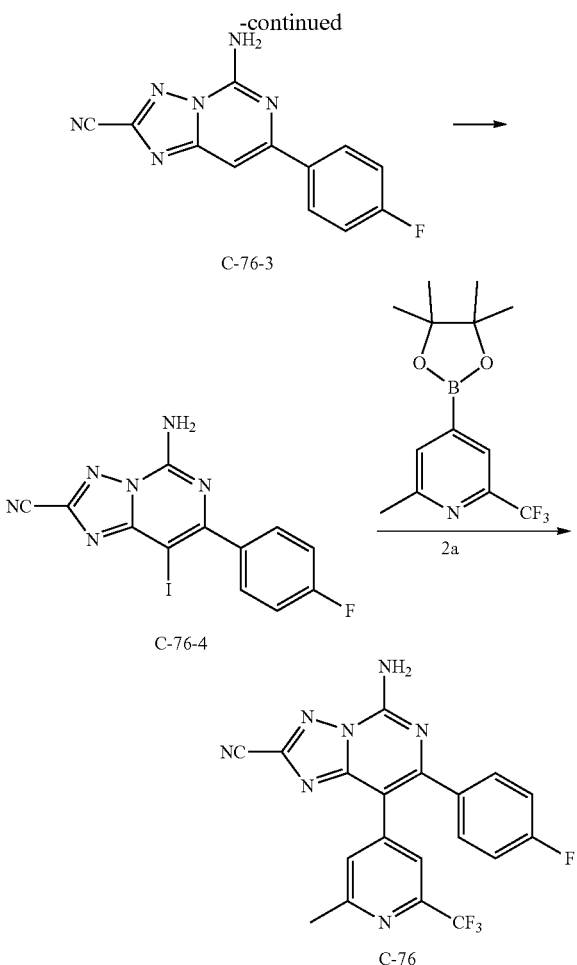

The First Step (Synthesis of Compound C-76-1)

To a suspension of compound C-65-1 (1.3 g, 5.01 mmol, 1 eq) in dichloromethane (50 mL) was added Dess-Martin periodinane (3.19 g, 7.52 mmol, 2.33 mL, 1.5 eq), and the reaction solution was stirred at 25° C. for 12 hours. After completion of the reaction, the reaction solution was quenched with saturated aqueous sodium bicarbonate (40 mL) and saturated aqueous sodium thiosulfate (40 mL), and stirred at room temperature for 30 min. The aqueous solution was extracted three times with ethyl acetate (100 mL). The organic phases were combined, washed with saturated brine (200 mL), dried over anhydrous sodium sulfate and filtered. The filtrate was concentrated under reduced pressure to afford the compound C-76-1.

The relevant characterization data was as follows: LCMS (Ms+1): 257.9.

$^1$H NMR (400 MHz, DMSO-d$_6$): δ 10.13 (s, 1H), 8.32 (br s, 2H), 8.21-8.24 (m, 2H), 7.68 (s, 1H), 7.32-7.37 (m, 2H).

The Second Step (Synthesis of Compound C-76-2)

To a solution of the compound C-76-1 (1 g, 3.89 mmol, 1 eq) in a mixed solvent of water (6 mL), ethanol (6 mL) and THF (6 mL) were added hydroxyamine hydrochloride (405.24 mg, 5.83 mmol, 1.5 eq) and sodium acetate (637.81 mg, 7.78 mmol, 2 eq), and the reaction solution was heated to 80° C. and stirred for 2 h. After the raw material was completely reacted, the reaction solution was concentrated under reduced pressure, and the obtained solid was washed three times with water (20 mL) and dried in vacuo to afford the compound C-76-2.

The relevant characterization data was as follows: LCMS (Ms+1): 273.0.

The Thrid Step (Synthesis of Compound C-76-3)

Compound C-76-2 (0.65 g, 2.39 mmol, 1 eq) was dissolved in phosphorus oxychloride (10 mL) at 25° C., and the reaction solution was stirred at 70° C. for 2 hr. The reaction solution was concentrated, and a saturated aqueous sodium bicarbonate solution was added to the residue to adjust the pH of the reaction solution to 7-8. The formed solution was extracted three times with ethyl acetate (50 mL). The organic phases were combined, washed with saturated brine (100 mL), dried over anhydrous sodium sulfate, and filtered. The filtrate was concentrated under reduced pressure to afford the compound C-76-3.

The relevant characterization data was as follows: LCMS m/z: 254.9 [M+H].

The Fourth Step (Synthesis of Compound C-76-4)

Compound C-76-3 (100 mg, 393.36 μmol, 1.00 eq) and N-iodosuccinimide (176.99 mg, 786.71 μmol, 2 eq) were dissolved in acetonitrile (5 mL). The reaction solution was heated to 80° C. and stirred for 2 hours. After the raw material was completely reacted, the reaction solution was cooled to room temperature, quenched with a saturated aqueous solution of sodium sulfite (20 mL) and extracted with ethyl acetate (20 mL*2). The organic phases were combined, washed with saturated brine (30 mL), dried over anhydrous sodium sulfate, and filtered. The filtrate was concentrated under reduced pressure to afford the compound C-76-4.

The relevant characterization data was as follows: LCMS m/z: 380.6 [M+H]

The fifth Step (Synthesis of Compound C-76)

Compound C-76-4 (180 mg, 473.54 μmol, 1 eq), 6 (163.13 mg, 568.24 μmol, 1.2 eq), 1,1'-bis(di-tert-butylphosphino)ferrocene palladium dichloride (61.73 mg, 94.71 μmol, 0.20 eq) and potassium phosphate (201.04 mg, 947.07 μmol, 2.00 eq) were dissolved in dioxane/water (10 mL/2 mL) at 25° C. The reaction solution was vented and purged with nitrogen for three times, heated to 100° C. and stirred for further 12 hours under nitrogen. After completion of the reaction, the reaction solution was filtered with Celite, and the filtrate was rotary evaporated to dryness. The crude product was subjected to neutral machine separation (mobile phase: water/acetonitrile) to afford the compound C-76.

The relevant characterization data was as follows: LCMS m/z: 414.1 [M+H].

$^1$H NMR (400 MHz, DMSO-d$_6$): δ 8.77 (br s, 2H), 7.54 (s, 1H), 7.38-7.41 (m, 3H), 7.21 (t, J=8.8 Hz, 2H), 2.51 (br s, 3H).

Example C-79

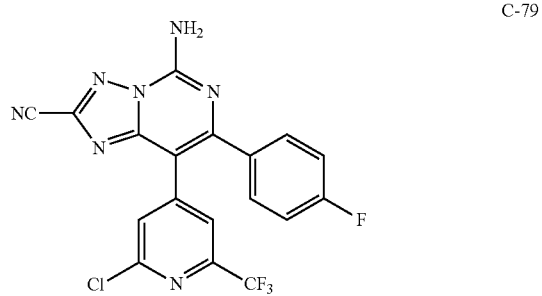 [SMILES: N#Cc1nc2c(-c3cc(Cl)nc(C(F)(F)F)c3)c(-c3ccc(F)cc3)nc(N)n2n1]

195

Example C-79: The preparation of the present example compound can be carried out by referring to the above-mentioned method for the preparation of the present compound C-77 to afford the compound C-79.

The relevant characterization data was as follows: LCMS m/z: 434.0 [M+H].

$^1$H NMR (400 MHz, DMSO-$d_6$): δ 8.93 (br s, 2H), 7.78 (s, 1H), 7.62 (s, 1H), 7.44 (dd, J=5.6, 8.8 Hz, 2H), 7.25 (t, J=8.8 Hz, 2H).

Example C-80

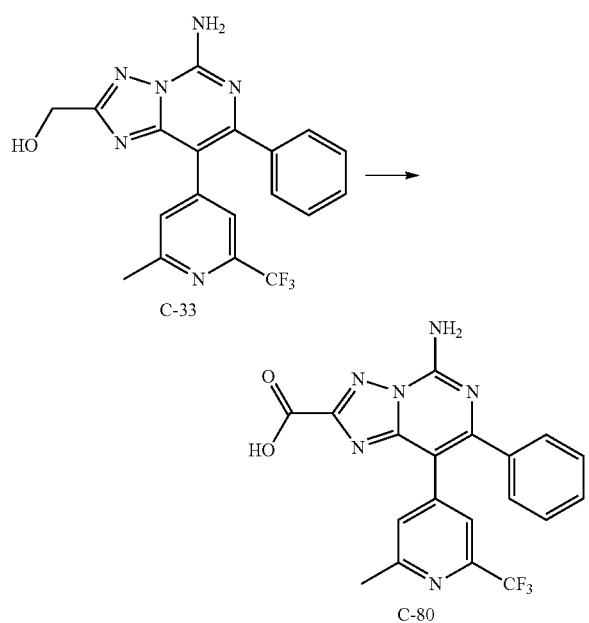

The First Step (Synthesis of Compound C-80)

Compound C-33 (0.5 g, 1.25 mmol, 1 eq) was added to water (25 mL), and then potassium permanganate (394.73 mg, 2.50 mmol, 2 eq) and sodium hydroxide (99.90 mg, 2.50 mmol, 2 eq) were added to the reaction solution. This mixture was stirred at 40° C. for 8 hours. LCMS and HPLC showed the appearance of the MS peak of the desired compound. The reaction was quenched by adding 1 g of sodium sulfite solid to the reaction solution, and then the pH was adjusted to 5-6 with 2M hydrochloric acid. The mixture was extracted three times with ethyl acetate (60 mL each time). The organic phases were combined, washed twice with saturated brine (30 mL), dried over anhydrous sodium sulfate, and filtered. The organic phase was concentrated under reduced pressure to give a residue. The residue was purified by preparative column chromatography: Phenomenex Gemini 150*25 mm*10 μm; mobile phase: [H$_2$O (10 mM NH$_4$HCO$_3$)-ACN]; B %: 10%-40%, 10 min. The desired compound C-80 was collected.

The relevant characterization data was as follows: LCMS m/z: 415.2 [M+H].

$^1$H NMR (400 MHz, METHANOL-$d_4$): δ 7.72 (s, 1H), 7.45-7.27 (m, 6H), 2.56 (s, 3H).

The pharmacological activity of the compounds disclosed herein is determined by the following in vitro assay for detecting A$_{2A}$ receptor activity.

196

ASSAY EXAMPLE 1

In Vitro Activity Assay

Human adenosine A$_{2A}$ receptor calcium flux assay
Cell Source:
A$_{2A}$ stable cell strain was constructed by Shanghai WuXi PharmaTech, and the host cell was CHO.
Detection Kit:
Fluo-4 Direct Kit (Invitrogen, Cat. No. F10471). After the fluorescent detection reagent (specifically binding to calcium ions and causing an increase in fluorescence signal) in the kit was incubated with the cells for a suitable period of time, the compound was added to stimulate the cells to cause changes in intracellular calcium flux, thereby causing changes in the fluorescent signal, which can reflect the strength of the agonistic or inhibitory activity of the compound.
Cell Culture Medium:
F12+10% fetal bovine serum+geneticin 300 ug/ml+blasticidin 2 ug/ml Compound dilution buffer:
Hanks Balanced Salt Buffer (Invitrogen)+20 mM HEPES, configured before each use
Agonist:
NECA (Sigma-E2387)
Reference compound (antagonist):
CGS-15943 (Sigma-C199)
Compound dilution:
The test compounds were dissolved in DMSO to prepare 10 mM stock solutions. The test compounds were diluted to 0.2 mM with DMSO, and the reference compound CGS-15943 was diluted to 0.015 mM with DMSO. Next, 10 points of three-fold serial dilutions were made with ECHO. 900 nl was transferred to the compound plate (Greiner-781280), and 30 ul of compound dilution buffer was added. The final starting concentration of the test compounds was 1 uM and CGS-15943 was 0.075 uM.
Assay method:
Cell preparation:
Cryopreserved A$_{2A}$ cells were resuscitated, and then resuspended in culture medium to 1×10$^6$ cells/ml. The suspension was seeded into 384-well polylysine-coated cell plates (Greiner-781946) at 20 μl/well and incubated overnight in a 5% CO$_2$ incubator at 37° C.
The cell plate prepared the day before was taken out from the incubator, and 20 ul of 2× Fluo-4 Direct™ buffer was added to each well. The plate was incubated for 50 minutes in a 5% CO$_2$ incubator at 37° C. and allowed to stand at room temperature for 10 minutes.
Determination of the EC80 of the agonist NECA:
Dilution of agonist NECA: 10 points of three-fold serial dilutions were made with Echo for NECA from a starting concentration of 0.15 mM. 900 nL was then transferred to the corresponding compound plate; and then 30 μl of compound dilution buffer was added to the corresponding compound plate. The final starting concentration was 750 nM.
FLIPR instrument software was run. According to the programmed procedure, 10 ul of compound dilution buffer was added to the cell plate and the fluorescence signal was read. 10 ul of the agonist reference compound at the indicated concentration was then added to the cell plate and the fluorescent signal was read. After reading, the data was exported by the "Max-Min", "Read 90 to Maximum allowed" method in the software, and the EC80 of the A$_{2A}$ cell line was calculated. The agonist was prepared at a concentration of 6× EC80. A 6× EC80 concentration of a reference compound agonist of the corresponding cells was prepared with a buffer solution, and added at 30 ul/well to the corresponding compound plate for use.

Determination of IC50 of the Test Compounds:

FLIPR instrument software was run. According to the programmed procedure, 10 μl of the test compounds and reference compound at an indicated concentration was added to the cell plate and the fluorescence signal was read. 10 ul of the reference compound agonist at a concentration of 6× EC80 was then added to the cell plate and the fluorescent signal was read. For the agonist detection of the compounds, the data was exported by the "Max-Min", "Read 1 to 90" method in the software. For the antagonist detection of the compound, the data was exported by the "Max-Min", "Read 90 to Maximum allowed" method in the software. Data were analyzed by GraphPad Prism 5.0 and the IC50 values of the test compounds were calculated.

TABLE 11

Results of in vitro screening assays of the compounds disclosed herein

| Compound No. | $IC_{50}$ value (nM) | Compound No. | $IC_{50}$ value (nM) | Compound No. | $IC_{50}$ value (nM) |
|---|---|---|---|---|---|
| A-1 | 0.23 | B-2 | 7.82 | C-1 | 1.65 |
| A-2 | 0.38 | B-3 | 9.92 | C-2 | 2.97 |
| A-3 | 0.32 | B-4 | 0.14 | C-5 | 0.53 |
| A-4 | 1.08 | B-5 | 0.28 | C-6 | 0.74 |
| A-5 | 0.83 | B-7 | 0.17 | C-7 | 1.35 |
| A-6 | 1.04 | B-8 | 0.44 | C-8 | 0.45 |
| A-7 | 5.83 | B-9 | 48.0 | C-9 | 1.4 |
| A-8 | 23.9 | B-10 | 1.98 | C-10 | 3.68 |
| A-9 | 1.13 | B-13 | 0.71 | C-11 | 0.78 |
| A-10 | 0.88 | B-14 | 0.47 | C-12 | 0.82 |
| A-11 | 3.87 | B-15 | 0.44 | C-13 | 1.02 |
| A-12 | 11.44 | B-16 | 0.14 | C-14 | 0.68 |
| A-13 | 13.82 | B-17 | 1.89 | C-15 | 20.4 |
| A-14 | 4.07 | C-74 | 1.72 | C-18 | 2.39 |
| A-15 | 0.38 | C-75 | 2.03 | C-19 | 0.40 |
| A-17 | 1.30 | B-20 | 71.29 | C-20 | 1.20 |
| A-19 | 1.16 | B-23 | 50.51 | C-21 | 0.80 |
| A-21 | 0.90 | B-24 | 1.18 | C-22 | 2.96 |
| A-23 | 1.15 | B-26 | 14.85 | C-23 | 2.63 |
| A-24 | 4.90 | B-27 | 0.28 | C-24 | 0.95 |
| A-25 | 1.14 | B-28 | 1.55 | C-25 | 3.16 |
| A-26 | 0.87 | B-29 | 0.11 | C-26 | 4.34 |
| A-27 | 4.38 | B-31 | 0.28 | C-27 | 4.93 |
| A-28 | 37.4 | B-32 | 2.83 | C-28 | 0.77 |
| A-29 | 37.2 | B-33 | 0.12 | C-29 | 1.50 |
| A-30 | 20.41 | B-34 | 19.02 | C-30 | 2.99 |
| A-31 | 1.25 | C-47 | 13.6 | C-31 | 14.1 |
| A-32 | 1.21 | C-48 | 11.3 | C-32 | 38.9 |
| A-33 | 15.3 | C-49 | 50.0 | C-60 | 3.13 |
| C-33 | 0.65 | C-50 | 5.36 | C-61 | 3.47 |
| C-34 | 73.8 | C-51 | 13.6 | C-62 | 0.83 |
| C-35 | 4.13 | C-52 | 1.75 | C-63 | 7.22 |
| C-36 | 7.92 | C-53 | 7.73 | C-64 | 0.36 |
| C-37 | 4.68 | C-54 | 1.08 | C-65 | 0.84 |
| C-38 | 15.3 | C-55 | 0.86 | C-66 | 0.79 |
| C-39 | 10.9 | C-56 | 1.50 | C-67 | 0.26 |
| C-40 | 44.5 | C-57 | 4.49 | C-68 | 0.64 |
| C-41 | 4.99 | C-58 | 1.72 | C-69 | 54.3 |
| C-42 | 10.1 | C-59 | 9.95 | C-70 | 0.59 |
| C-43 | 1.36 | C-76 | 5.61 | C-71 | 0.82 |
| C-44 | 0.67 | C-77 | 6.84 | C-72 | 0.16 |
| C-45 | 2.06 | C-78 | 0.77 | C-79 | 16.9 |
| C-46 | 3.08 | C-16 | 1.77 | C-80 | 1.82 |
| C-73 | 1.73 | C-17 | 10.4 | | |

Conclusion: As shown in Table 11, the compounds disclosed herein exhibited excellent adenosine $A_{2A}$ receptor antagonistic activity.

ASSAY EXAMPLE 2

Determination of Kinetic Solubility

The test compounds were dissolved in DMSO to prepare 10 mmol/L stock solutions. The stock solutions were diluted with 50% ACN/50 mM phosphate buffer (pH 7.4) to prepare standard solutions (1 μM, 20 μM, 200 04).

490 μL of dissolution medium (50 mM phosphate buffer solution, pH 7.4) was pipetted into a 96-well plate with a single-well volume of 2 mL using a pipette (Eppendorf Research Inc.). 10 μL of the stock solution of each test compounds and QC sample (10 mmol/L DMSO stock solution) were added to the dissolution medium, respectively, and the sample plate was sealed with a sealing film. The final concentration of the test compounds and DMSO in the sample solution were 200 μM and 2%, respectively. The mixture was shaken at 600 rpm for 24 hours at room temperature. 200 μL of the sample solution was transferred into a 96-well filter plate using a pipette and filtered with suction. The filtrate and the standard solution were detected by high performance liquid chromatography (HPLC-DAD). The concentration of the test compounds in the filtrate was calculated by an external standard method, which was the kinetic solubility of the compounds.

TABLE 12

| Compound | Solubility (μM) pH 7.4 |
|---|---|
| Compound A | 29.2 |
| Example A-1 | 185.0 |
| Example A-3 | 92.5 |
| Example A-4 | 160.0 |
| Example B-5 | 197.0 |
| Example B-28 | 54.5 |
| Example B-31 | 56.0 |
| Example C-19 | 194.0 |
| Example C-33 | >200 |
| Example C-43 | 168.0 |
| Example C-46 | 172.0 |
| Example C-58 | 78.9 |

Conclusion: As shown in Table 12, the compounds disclosed herein exhibited excellent water solubility (at pH=7.4) as compared with Compound A.

ASSAY EXAMPLE 3

Evaluation of Compounds' Pharmacokinetics

Objective: To test the pharmacokinetics of compounds in female Balb/c mice in vivo Assay Materials:

Balb/c mice (female, 15-30 g, 7-9 weeks old, Shanghai Lingchang)

Assay Procedures:

The pharmacokinetics profile of the compounds in rodent after intravenous injection and oral administrations was tested using a standard protocol. In the assay, the candidate compound was formulated into a clear solution and administrated to the mice through a single intravenous injection, and formulated into a uniform suspension and administrated to the mice through a single oral administration. Intravenous vehicle was 5% DMSO/95% 10% Cremophor EL, and oral vehicle was 1% tween 80, 9% PEG 400, and 90% water. The whole blood samples were collected within 24 hours, centrifuged at 3000 g at 4° C. for 15 minutes, and plasma samples were obtained by separating the supernatant. 20 times volume of acetonitrile solution containing an internal standard was added to precipitate proteins. After centrifugation, the supernatant was collected, to which an equal volume of water was added, and further centrifuged to collect the supernatant. The LC-MS/MS method was used to quantitatively analyze the plasma concentration, and the pharmacokinetics parameters, such as peak concentration, peak time, clearance rate, half-life, area under the curve, and bioavailability were calculated.

Assay Results:

TABLE 13

Pharmacokinetic assay results

| Test samples (compounds prepared in each example) | Clearance (mL/min/kg) | Half-life $T_{1/2}$ (h) | Concentration integral AUC (nM · hr) | Bioavailability F (%) |
|---|---|---|---|---|
| Compound A | 208 | 0.28 | 501 | 21.6 |
| Example A-1 | 51.2 | 0.47 | 3330 | 41.1 |
| Example A-2 | 44.9 | 0.80 | 5928 | 62.1 |
| Example B-5 | 24.0 | 0.33 | 19640 | 91.0 |
| Example B-31 | 44.3 | 0.25 | 1727 | 17.4 |
| Example C-1 | 11.7 | 3.95 | 13150 | 40.5 |
| Example C-2 | 8.76 | 2.00 | 24931 | 50.4 |
| Example C-19 | 38.7 | 0.92 | 8787 | 70.7 |
| Example C-33 | 18 | 1.2 | 22005 | 95.2 |
| Example C-41 | 5.53 | 8.04 | 25068 | 41.2 |
| Example C-43 | 7.51 | 1.99 | 43891 | 82.9 |
| Example C-46 | 0.54 | 1.92 | 20136 | 44.0 |
| Example C-57 | 3.94 | 3.2 | 71682 | 69.3 |
| Example C-58 | 2.5 | 7.26 | 157241 | 123 |

Conclusion: The compounds disclosed herein have significantly increased pharmacokinetic index in mice.

The invention claimed is:
1. A compound represented by formula (I), or a pharmaceutically acceptable salt thereof,

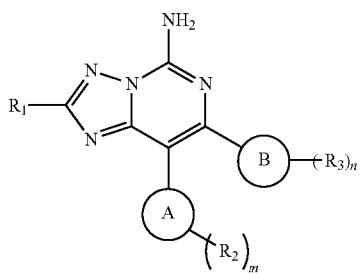

wherein
$R_1$ is selected from the group consisting of H, CN, COOH, and

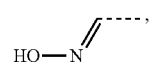

or is selected from the group consisting of $C_{1-3}$ alkyl, $C_{1-3}$ alkyl-O—$C_{1-3}$ alkyl-, $C_{1-3}$ alkyl-C(=O)NH-, and $C_{3-6}$ cycloalkyl, each of which is optionally substituted by 1, 2 or 3 R;
$R_2$ is each independently selected from the group consisting of H, F, Cl, Br, I, OH, $NH_2$, and CN, or is independently selected from the group consisting of $C_{3-6}$ cycloalkyl, $C_{1-6}$ alkyl, and $C_{1-6}$ heteroalkyl, each of which is optionally substituted by 1, 2 or 3 R;
$R_3$ is each independently selected from the group consisting of H, F, Cl, Br, I, OH, $NH_2$, and CN, or is independently selected from the group consisting of $C_{1-6}$ alkyl or $C_{1-6}$ heteroalkyl, each of which is optionally substituted by 1, 2 or 3 R;
n is 0, 1, 2 or 3;
m is 0, 1, 2 or 3;
ring A is selected from the group consisting of 6- to 10-membered aryl, 5- to 10-membered heteroaryl, 5- to 10-membered heterocycloalkyl and 5- to 10-membered heterocycloalkenyl;
ring B is selected from the group consisting of phenyl and 5- to 6-membered heteroaryl;
R is selected from the group consisting of F, Cl, Br, I, OH, $NH_2$, and CN, or is selected from the group consisting of $C_{1-3}$ alkyl, $C_{3-6}$ cycloalkyl, $C_{3-6}$ cycloalkyl-NH—, 3- to 6-membered heterocycloalkyl, 3- to 6-membered heterocycloalkyl-O-, and phenyl, each of which is optionally substituted by 1, 2 or 3 R';
R' is selected from the group consisting of F, Cl, Br, I, OH, $NH_2$, Me, and

the heteroatom or the heteroatom group of the C1-6 heteroalkyl, 5- to 10-membered heteroaryl, 5- to 10-membered heterocycloalkyl, 3- to 6-membered heterocycloalkyl and 5- to 10-membered heterocycloalkenyl is each independently selected from the group consisting of N, O, S, NH, —C(=O)—, —C(=O)O- and —C(=O)NH—;
the number of the heteroatom or the heteroatom group is each independently 1, 2, 3 or 4.

2. The compound, or a pharmaceutically acceptable salt thereof according to claim 1, wherein R is selected from the group consisting of F, Cl, Br, I, OH, $NH_2$, and CN, or is selected from the group consisting of Me, Et,

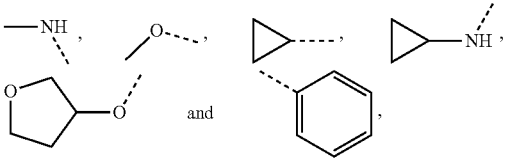

each of which is optionally substituted by 1, 2 or 3 R'.

3. The compound, or a pharmaceutically acceptable salt thereof according to claim 2, wherein R is selected from the group consisting of F, Cl, Br, I, OH, $NH_2$, CN, Me, Et,

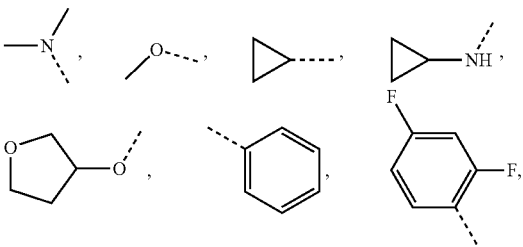

-continued

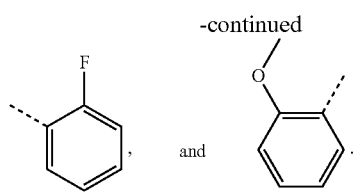
and

4. The compound, or a pharmaceutically acceptable salt thereof according to claim 1, wherein R₁ is selected from the group consisting of H, CN, COOH, and

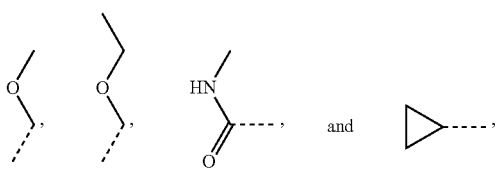

or is selected from the group consisting of Me, Et,

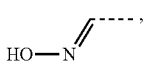

each of which is optionally substituted by 1, 2 or 3 R.

5. The compound, or a pharmaceutically acceptable salt thereof according to claim 4, wherein R₁ is selected from the group consisting of H, CN, COOH, Me, Et,

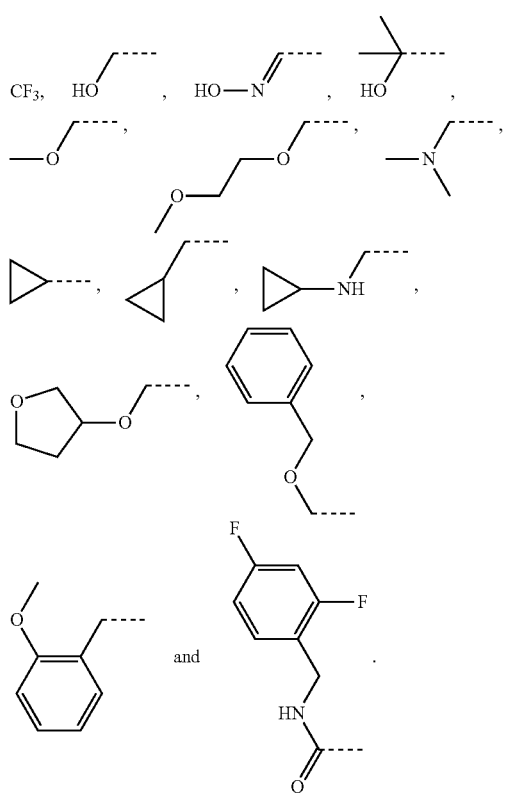

and

6. The compound, or a pharmaceutically acceptable salt thereof according to claim 1, wherein R₂ is each independently selected from the group consisting of H, F, Cl, Br, I, OH NH₂, and CN, or is independently selected from the group consisting of $C_{3-6}$ cycloalkyl, $C_{1-3}$ alkyl and $C_{1-3}$ alkoxy, each of which is optionally substituted by 1, 2 or 3 R.

7. The compound, or a pharmaceutically acceptable salt thereof according to claim 6, wherein R₂ is each independently selected from the group consisting of H, F, Cl, Br, I, OH, NH₂, CN, Me, Et, CF₃,

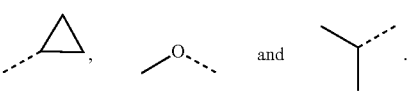

8. The compound, or a pharmaceutically acceptable salt thereof according to claim 1, wherein R₃ is each independently selected from the group consisting of H, F, Cl, Br, I, OH, NH₂, and CN, or is independently selected from the group consisting of $C_{1-3}$ alkyl and $C_{1-3}$ alkoxy, each of which is optionally substituted by 1, 2 or 3 R.

9. The compound, or a pharmaceutically acceptable salt thereof according to claim 8, wherein R₃ is each independently selected from the group consisting of H, F, Cl, Br, I, OH, NH₂, CN, Me, Et, CF₃ and

10. The compound, or a pharmaceutically acceptable salt thereof according to claim 1, wherein ring A is selected from the group consisting of phenyl, pyridyl, tetrahydropyranyl, 3,6-dihydro-2H-pyranyl, piperidinyl, 1,2,3,6-tetrahydropyridyl, 1H-indolyl, 1H-indazolyl, 1H-benzo[d]imidazolyl, benzo[d][1,3 dioxolyl, indolin-2-onyl, 1H-benzo[d][1,2,3]triazolyl, quinolinyl and 1,2,3,4-tetrahydroquinolinyl.

11. The compound, or a pharmaceutically acceptable salt thereof according to claim 10, wherein the moiety

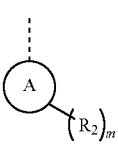

is selected from the group consisting of

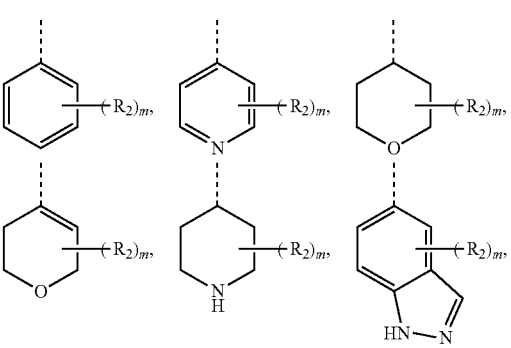

-continued
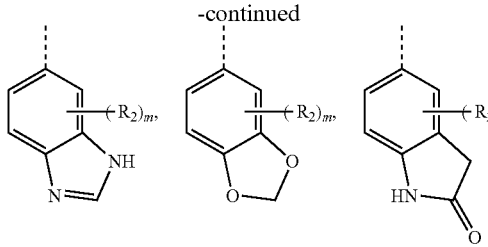
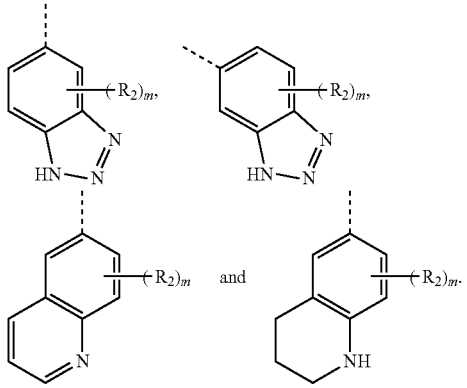
12. The compound, or a pharmaceutically acceptable salt thereof according to claim 11, wherein the moiety
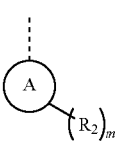
is selected from the group consisting of
-continued
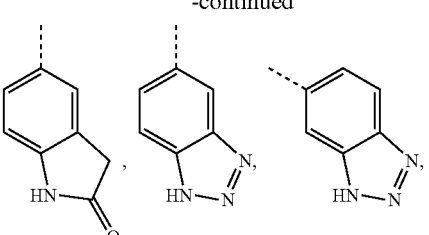
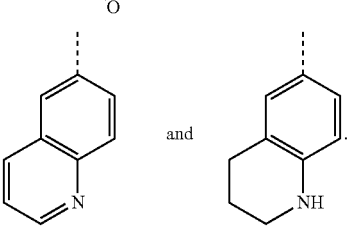
13. The compound, or a pharmaceutically acceptable salt thereof according to claim 12, wherein the moiety
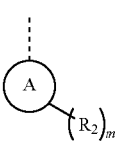
is selected from the group consisting of

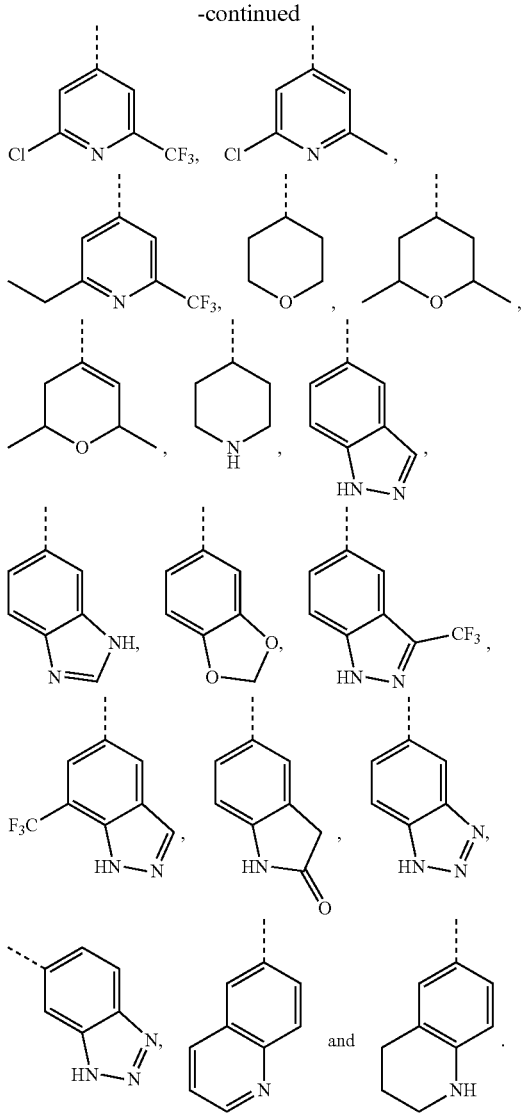

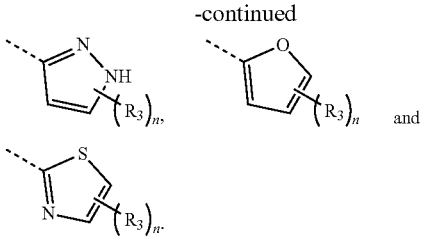

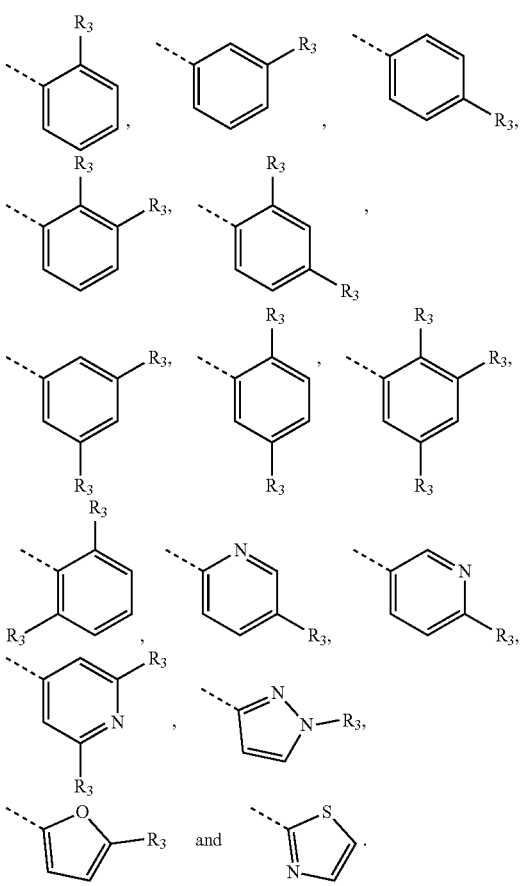

14. The compound, or a pharmaceutically acceptable salt thereof according to claim 1, wherein ring B is selected from the group consisting of phenyl, pyridyl, imidazolyl, pyrazolyl, furyl, thienyl, and thiazolyl.

15. The compound, or a pharmaceutically acceptable salt thereof according to claim 14, wherein the moiety

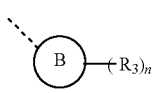

is selected from the group consisting of

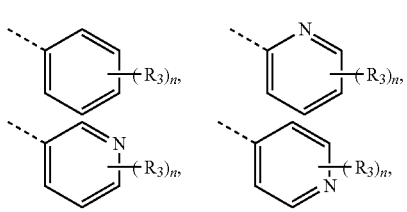

16. The compound, or a pharmaceutically acceptable salt thereof according to claim 15, wherein the moiety

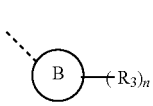

is selected from the group consisting of

17. The compound, or a pharmaceutically acceptable salt thereof according to claim 16, wherein the moiety

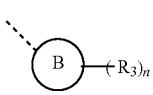

is selected from the group consisting of

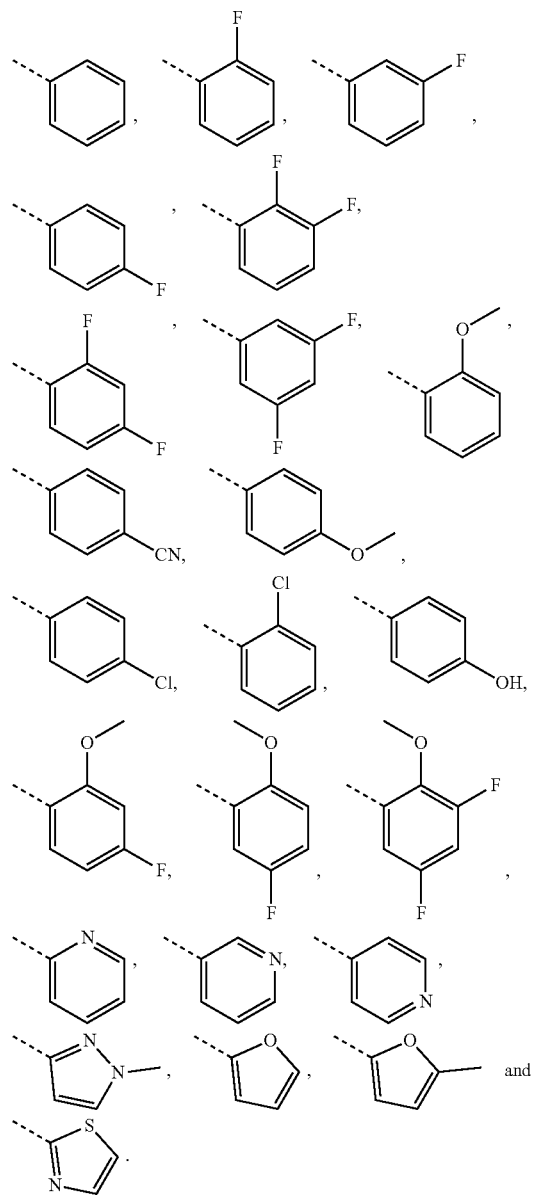

18. The compound, or a pharmaceutically acceptable salt thereof according to claim 1, which is selected from the group consisting of

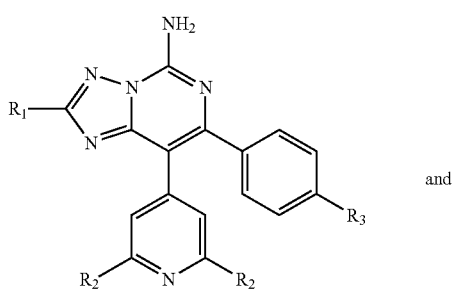

(I-1)

and

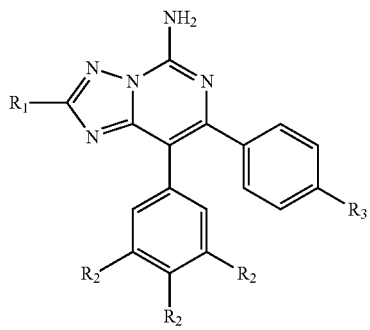

(I-2)

wherein $R_1$, $R_2$, and $R_3$ are as defined in claim 1.

19. The compound or a pharmaceutically acceptable salt thereof according to claim 1, wherein the compound is selected from the group consisting of

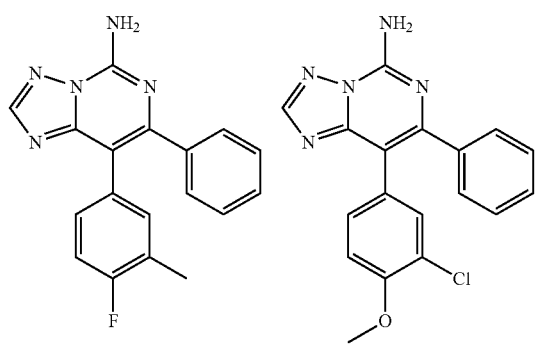

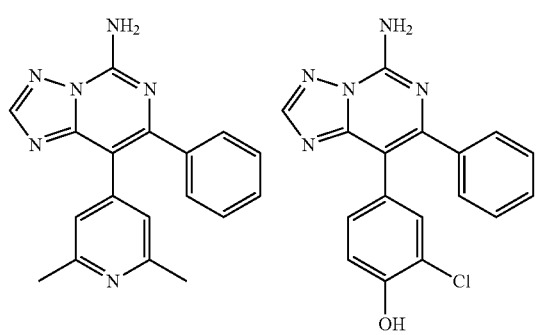

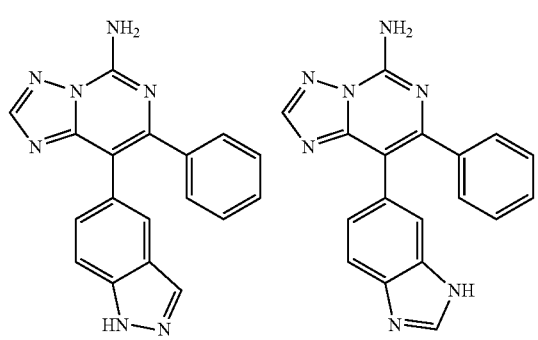

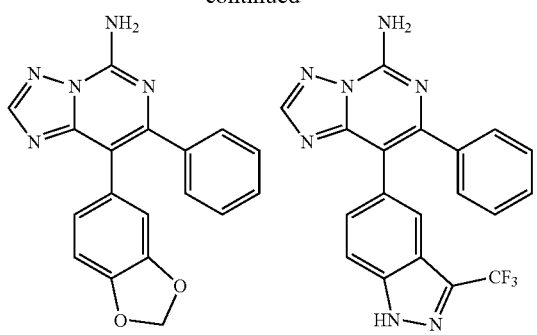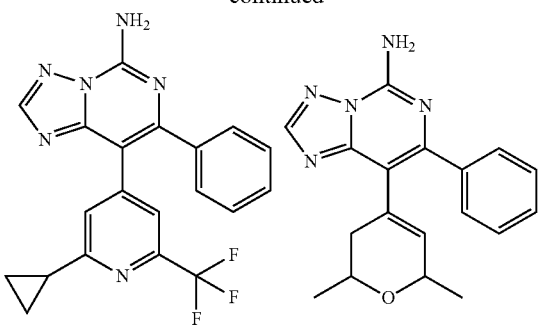

211
-continued
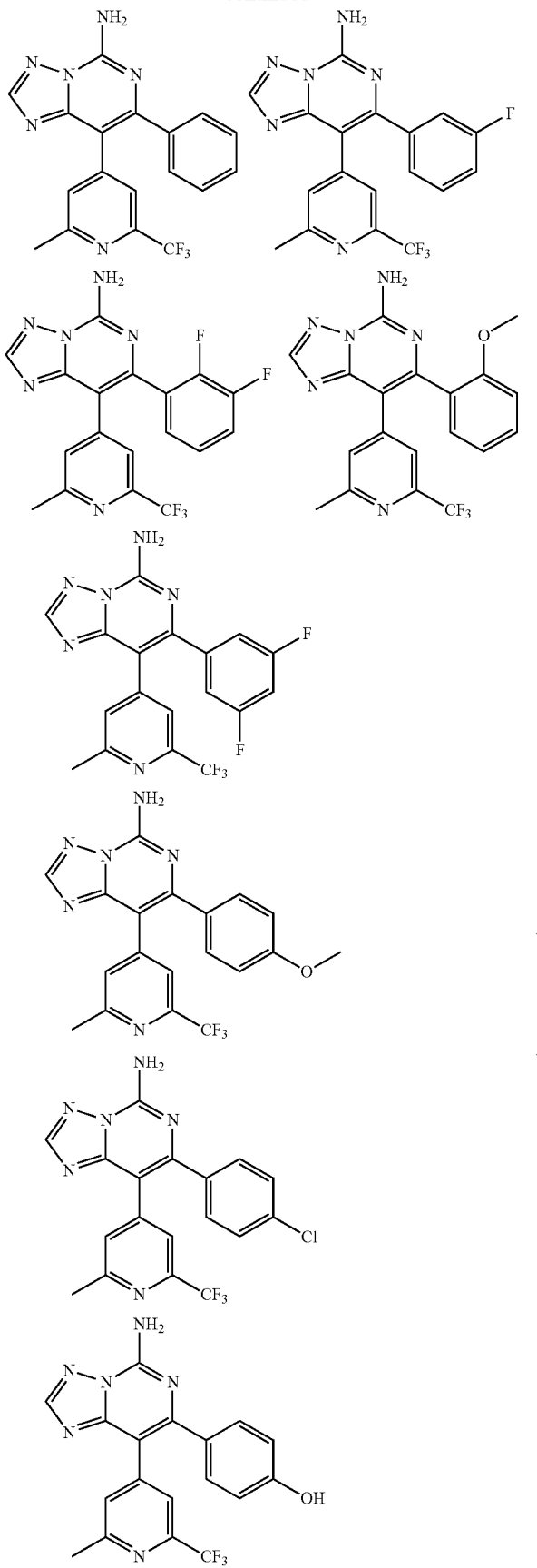
212
-continued
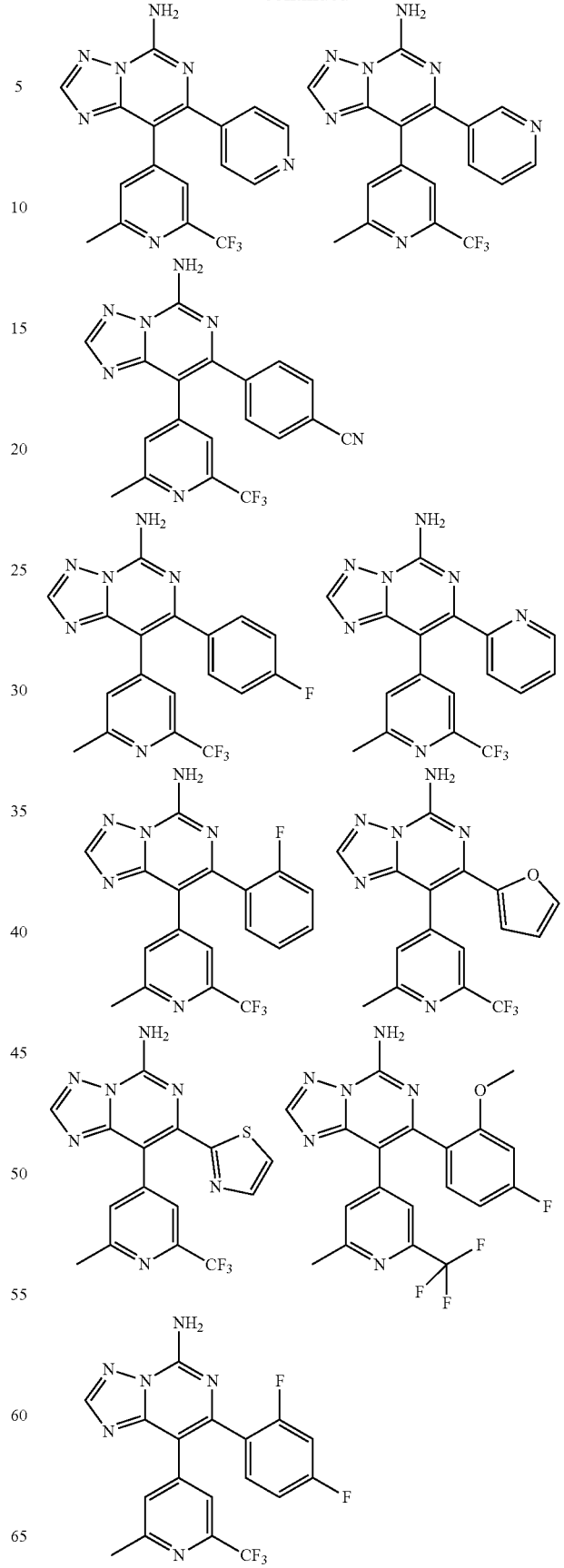

213
-continued
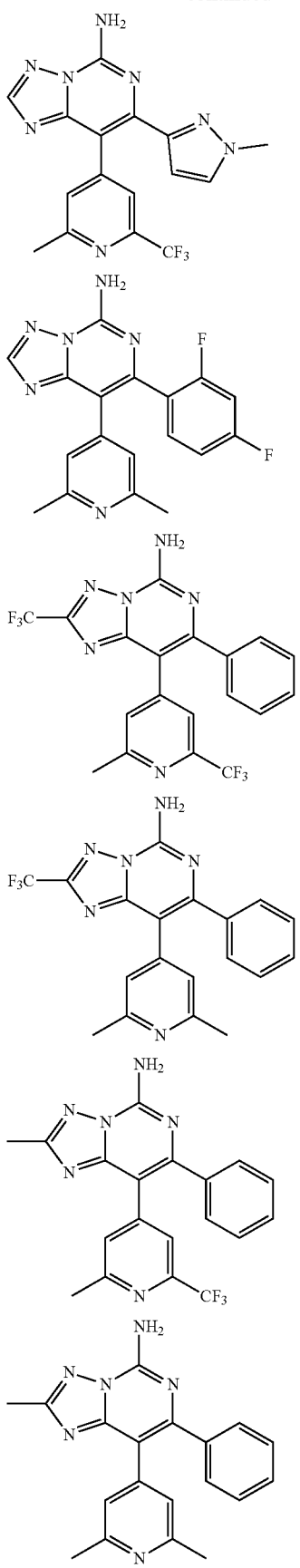
214
-continued
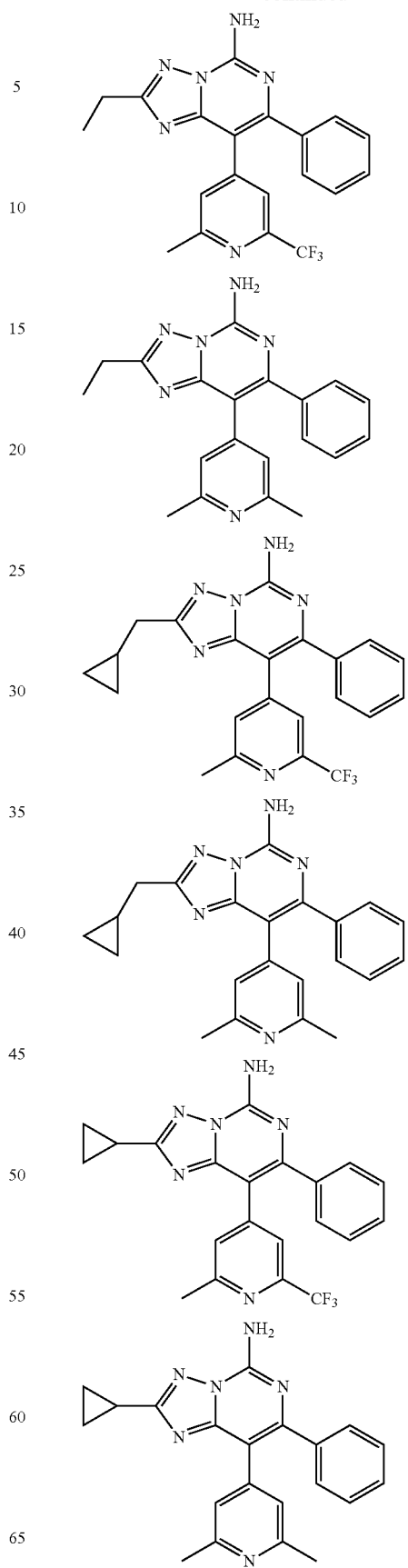

215
-continued
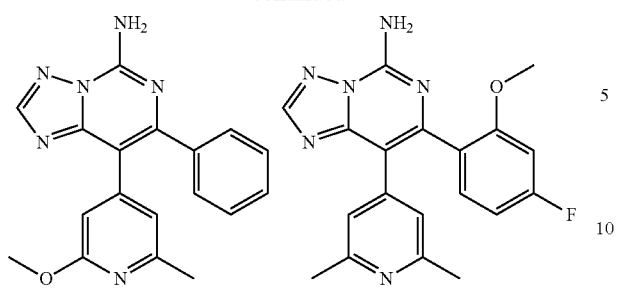
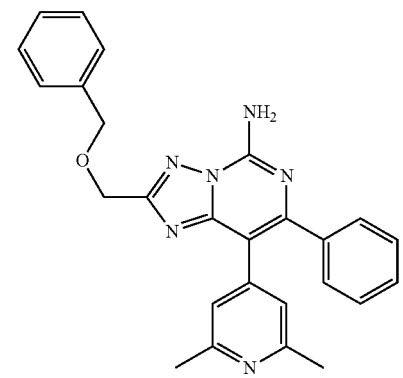
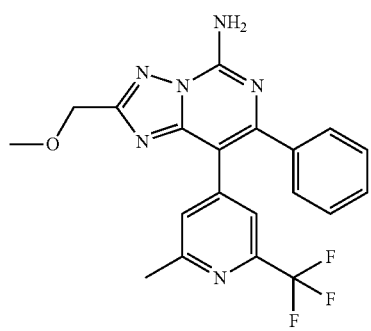
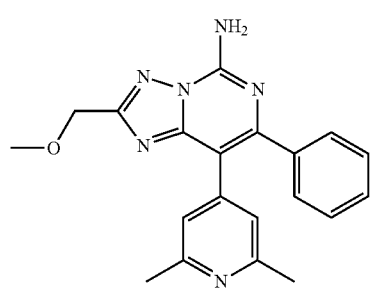
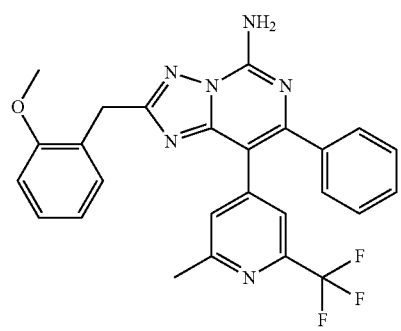
216
-continued
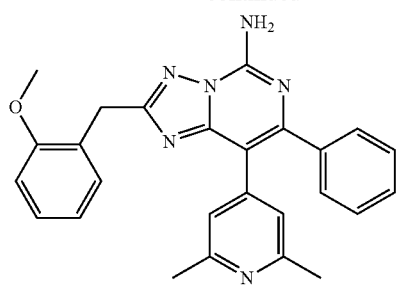
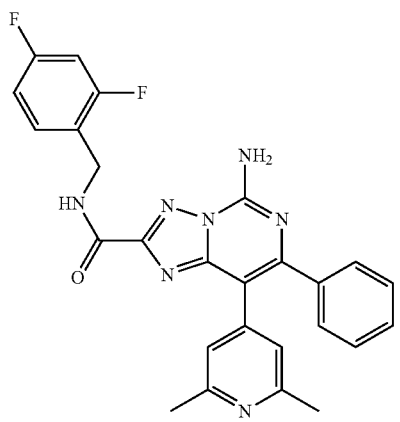
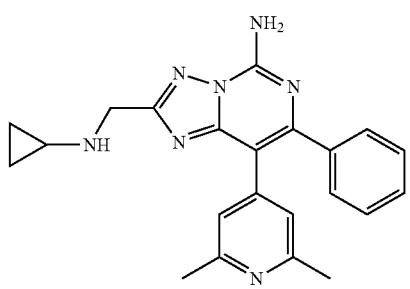
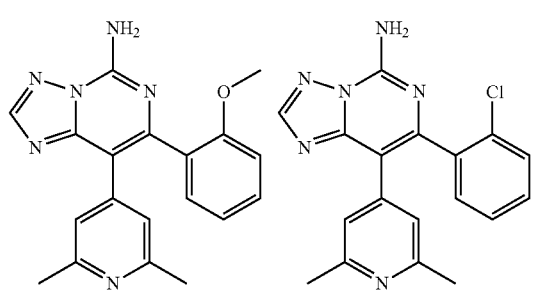
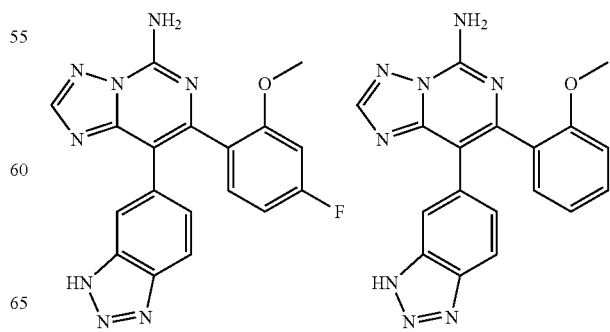

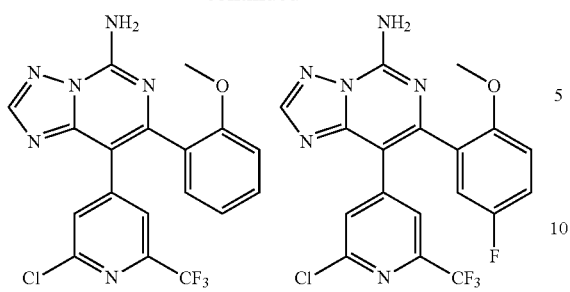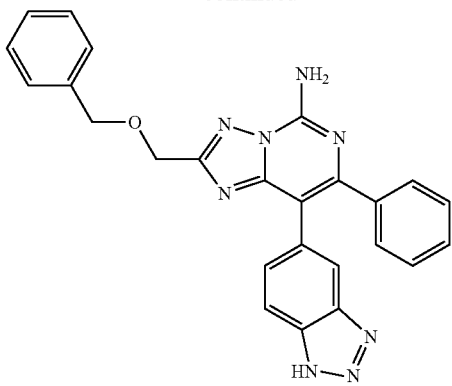

219
-continued
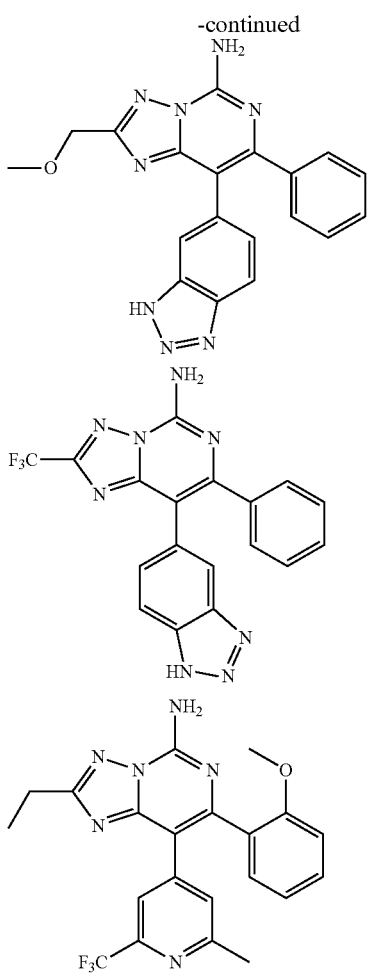
220
-continued
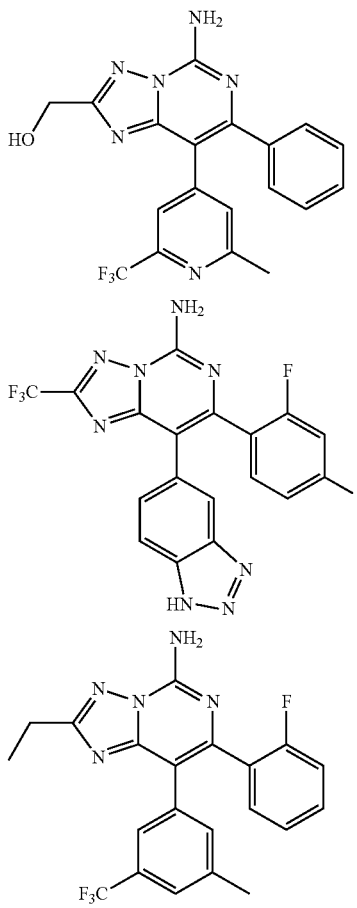
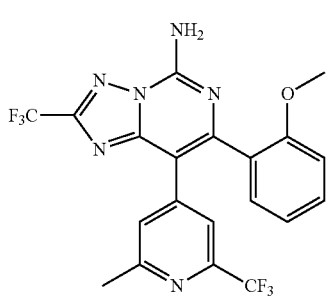
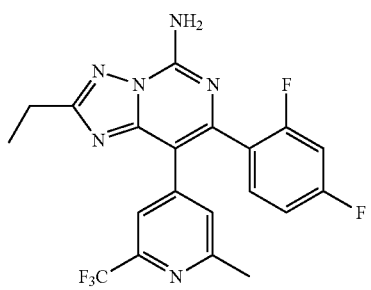
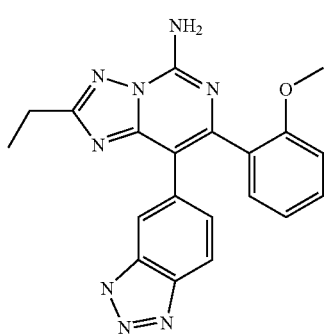
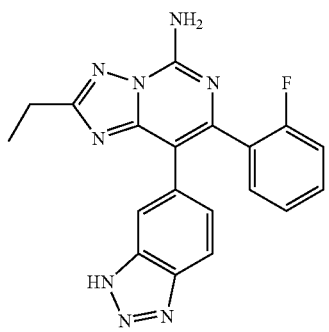

221
-continued
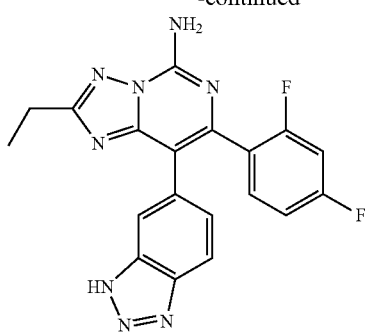
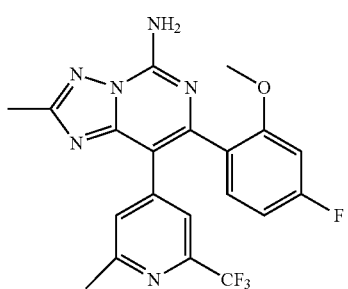
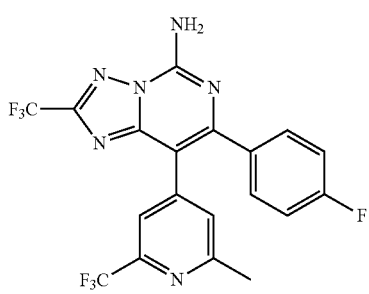
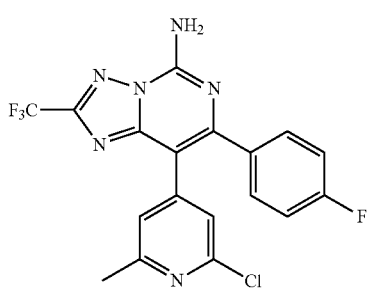
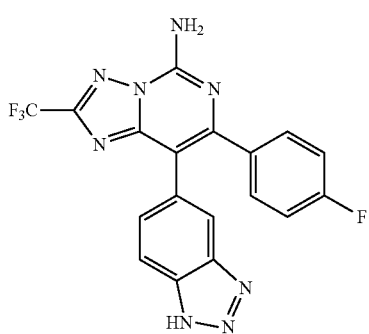
222
-continued
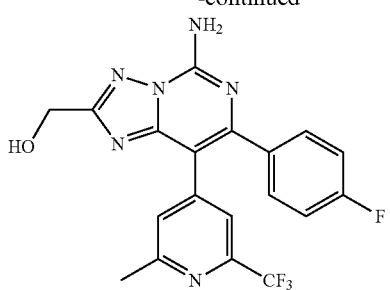
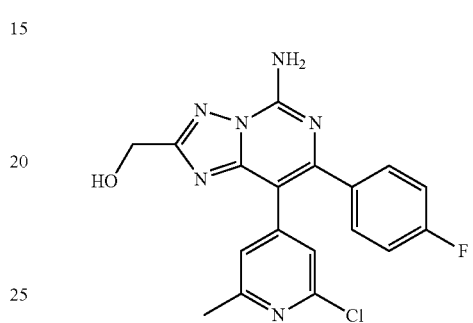
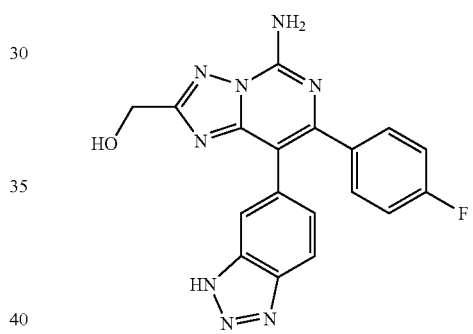
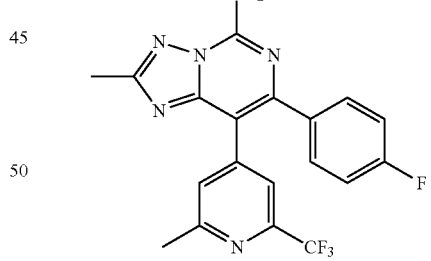
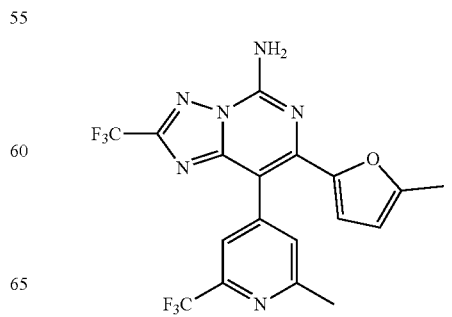

223
-continued
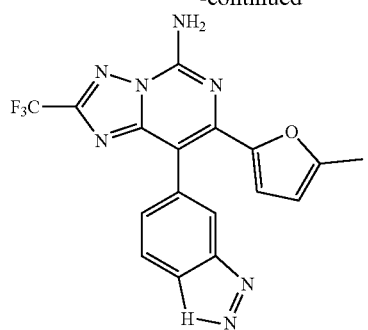
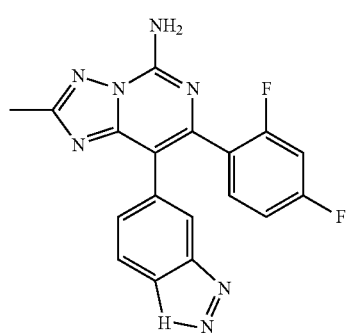
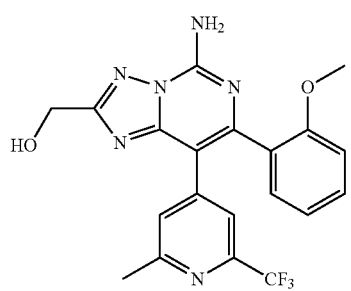
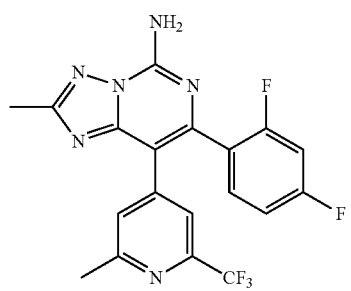
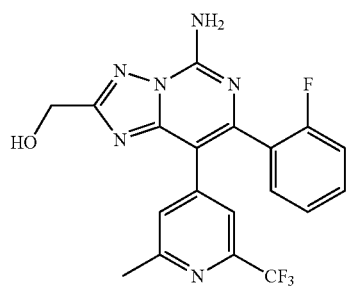
224
-continued
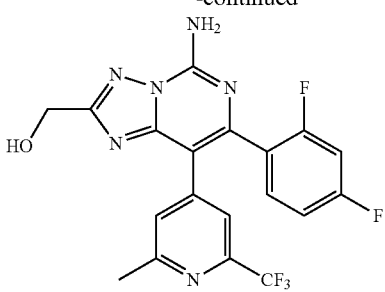
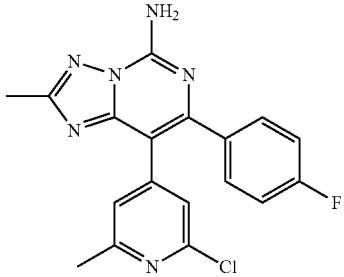
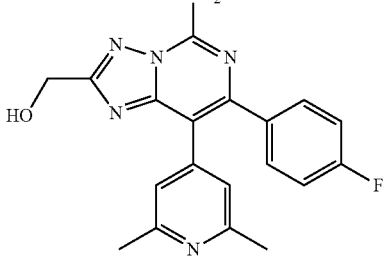
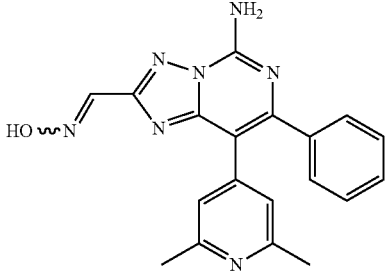
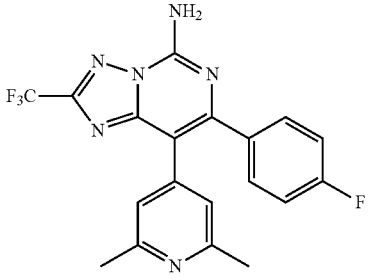
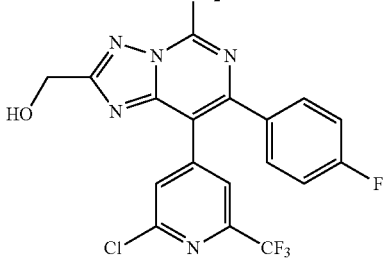

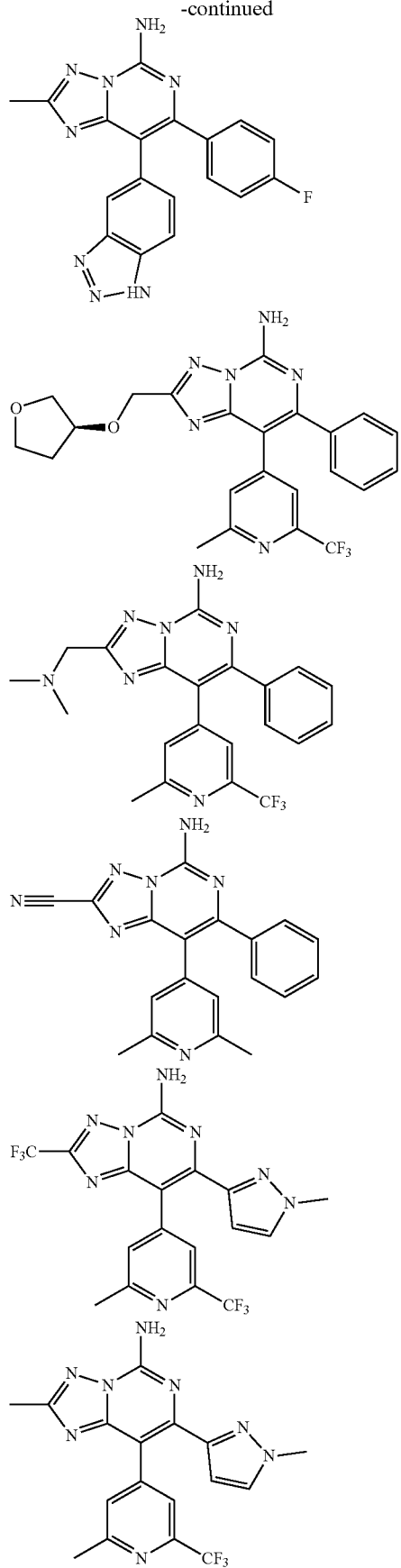
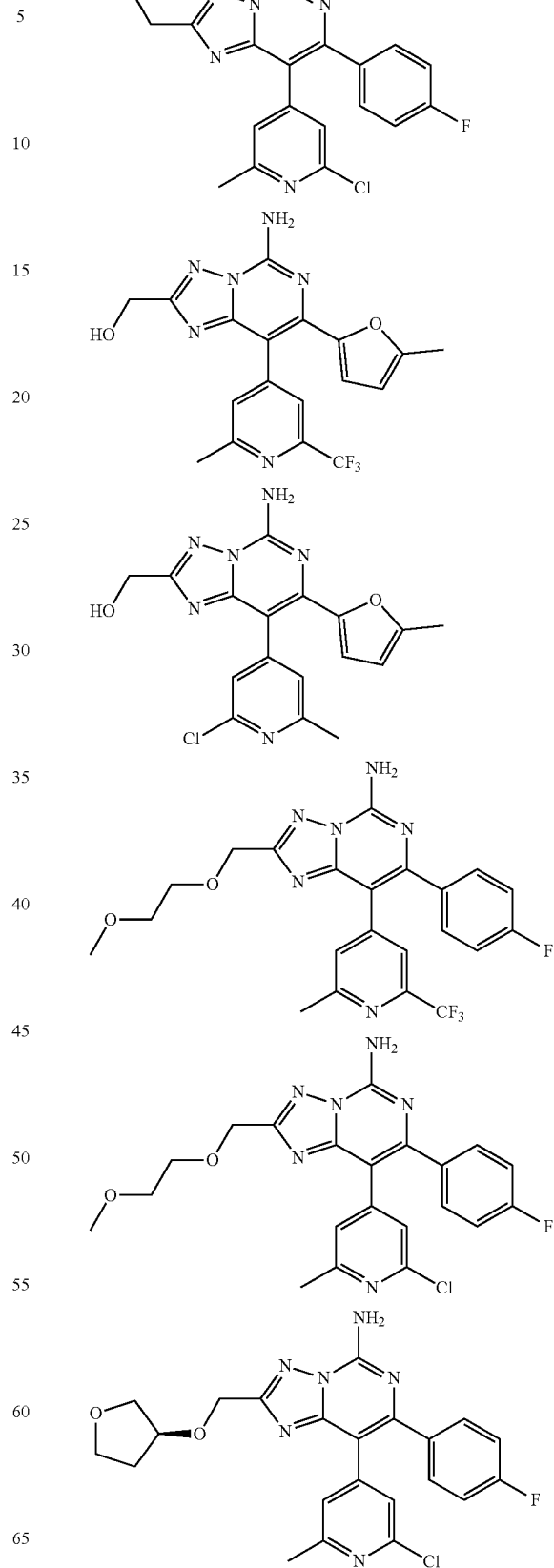

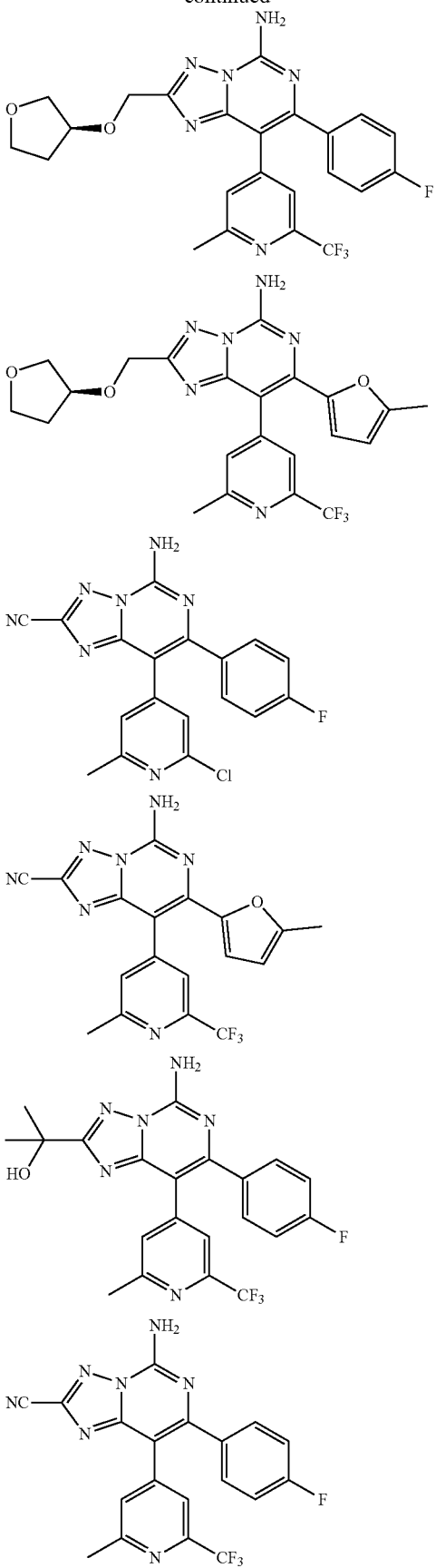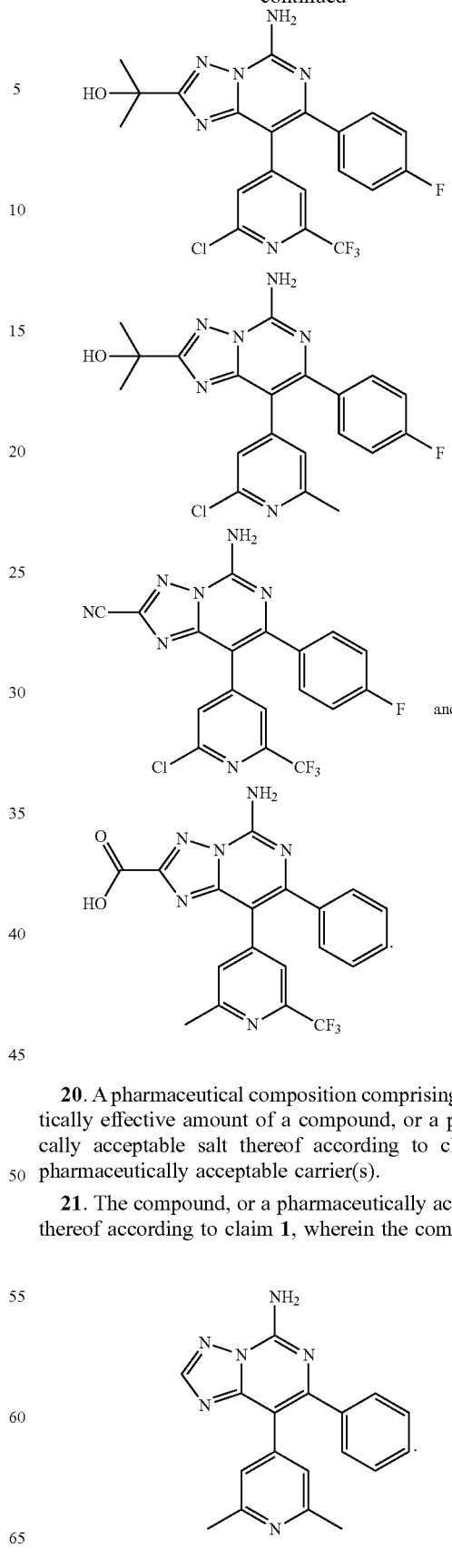
20. A pharmaceutical composition comprising a therapeutically effective amount of a compound, or a pharmaceutically acceptable salt thereof according to claim 1, and pharmaceutically acceptable carrier(s).
21. The compound, or a pharmaceutically acceptable salt thereof according to claim 1, wherein the compound is:
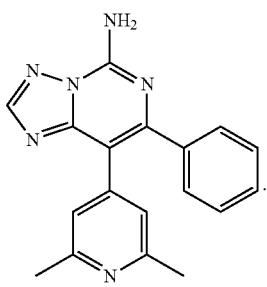 [SMILES: Cc1cc(-c2c(-c3ccccc3)nc(N)n3ncnc23)cc(C)n1]

22. The compound, or a pharmaceutically acceptable salt thereof according to claim 1, wherein the compound is:
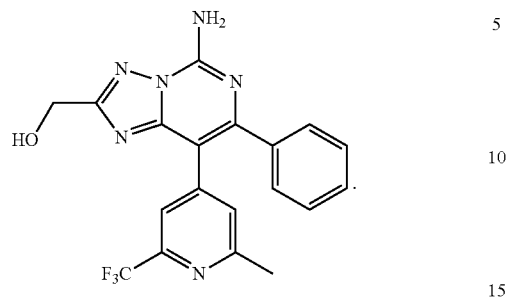
23. The compound, or a pharmaceutically acceptable salt thereof according to claim 1, wherein the compound is:
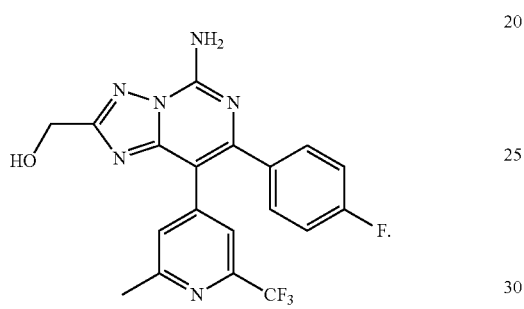
* * * * *